US007101875B2

(12) United States Patent
McKew et al.

(10) Patent No.: US 7,101,875 B2
(45) Date of Patent: *Sep. 5, 2006

(54) METHODS FOR TREATING ARTHRITIC DISORDERS

(75) Inventors: John C. McKew, Arlington, MA (US); Steve Y. Tam, Wellesley, MA (US); Katherine L. Lee, West Newton, MA (US); Lihren Chen, Cambridge, MA (US); Paresh Thakker, Boston, MA (US); Fuk-Wah Sum, Pomona, NY (US); Mark Behnke, Sommerville, MA (US); Baihua Hu, Audubon, PA (US); James D. Clark, Acton, MA (US)

(73) Assignee: Wyeth, Madison, NJ (US)

( * ) Notice: Subject to any disclaimer, the term of this patent is extended or adjusted under 35 U.S.C. 154(b) by 423 days.

This patent is subject to a terminal disclaimer.

(21) Appl. No.: 10/302,087

(22) Filed: Nov. 22, 2002

(65) Prior Publication Data

US 2003/0166649 A1 Sep. 4, 2003

Related U.S. Application Data

(60) Provisional application No. 60/334,591, filed on Dec. 3, 2001.

(51) Int. Cl.
*A61K 31/404* (2006.01)
*A61K 31/54* (2006.01)
*A61K 31/42* (2006.01)
*A61K 31/41* (2006.01)
*A61K 31/40* (2006.01)

(52) U.S. Cl. .................. 514/228.2; 514/374; 514/375; 514/381; 514/386; 514/406; 514/414; 514/233.5; 514/254.09; 514/256; 514/365; 514/278; 514/364; 514/326; 514/357; 514/327; 514/350; 514/339; 514/345

(58) Field of Classification Search ............ 514/228.2, 514/374, 375, 381, 386, 406, 414, 233.5, 514/254.09, 256, 365, 248, 314, 345
See application file for complete search history.

(56) References Cited

U.S. PATENT DOCUMENTS

| | | | |
|---|---|---|---|
| 3,505,354 | A | 4/1970 | Doebel et al. |
| 3,629,284 | A | 12/1971 | Yamamoto et al. |
| 4,271,263 | A | 6/1981 | Goettert |
| 4,654,360 | A | 3/1987 | Greenhouse et al. |
| 4,894,386 | A | 1/1990 | Brown et al. |
| 5,081,145 | A | 1/1992 | Guindon et al. |
| 5,166,170 | A | 11/1992 | Tegeler et al. |
| 5,212,195 | A | 5/1993 | Clark et al. |
| 5,229,516 | A | 7/1993 | Musser et al. |
| 5,288,743 | A | 2/1994 | Brooks et al. |
| 5,290,798 | A | 3/1994 | Guillard et al. |
| 5,322,776 | A | 6/1994 | Knopf et al. |
| 5,332,755 | A | 7/1994 | Butler et al. |
| 5,354,677 | A | 10/1994 | Knopf et al. |
| 5,380,739 | A | 1/1995 | Clark et al. |
| 5,420,289 | A | 5/1995 | Musser et al. |
| 5,424,329 | A | 6/1995 | Boschelli et al. |
| 5,482,960 | A | 1/1996 | Berryman et al. |
| 5,641,800 | A | 6/1997 | Bach et al. |
| 6,797,708 | B1 * | 9/2004 | McKew et al. .......... 514/228.2 |

FOREIGN PATENT DOCUMENTS

| | | |
|---|---|---|
| CH | 484111 | 1/1970 |
| DE | 18 16 335 A | 7/1970 |
| DE | 43 38 770 A1 | 5/1995 |
| EP | 0 337 766 A1 | 10/1989 |
| EP | 0 337 767 A1 | 10/1989 |
| EP | 0 620 215 A1 | 10/1994 |
| FR | 1 492 929 | 7/1967 |
| WO | WO 91/06537 A2 | 5/1991 |
| WO | WO 93/23391 A1 | 11/1993 |
| WO | WO 95/13266 A1 | 5/1995 |

(Continued)

OTHER PUBLICATIONS

Roy et al., Further Studies on Anti-Inflammatory Activity of Two Potent Indian-1-Acetic Acids, Ind. J. Physiol. Pharmac., Jul.-Sep. 1982, vol. 28, No. 3, pp. 207-214.

(Continued)

*Primary Examiner*—Shengjun Wang
*Assistant Examiner*—Jennifer Kim
(74) *Attorney, Agent, or Firm*—Michael P. Straher; Cozen O'Connor

(57) ABSTRACT

This invention provides methods for treating in mammals arthritic or rheumatic disorders using substituted indole compounds of the general formula:

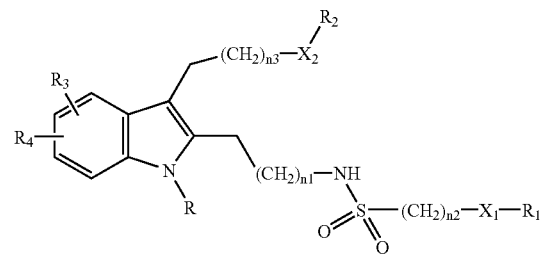

(I)

and pharmaceutically acceptable salt forms thereof, and methods for using the compounds as inhibitors of the activity of various phospholipase enzymes, particularly phospholipase $A_2$ enzymes, and for the medical treatment, prevention and inhibition of pain and inflammation.

48 Claims, No Drawings

FOREIGN PATENT DOCUMENTS

| WO | WO 98/05637 A1 | 2/1998 |
| WO | WO 98/08818 A1 | 3/1998 |
| WO | WO 99/43651 A2 | 9/1999 |
| WO | WO 99/43654 A2 | 9/1999 |
| WO | WO 99/43672 A1 | 9/1999 |

OTHER PUBLICATIONS

Draheim et al., Indole Inhibitors of Human Nonpancreatic Secretory Phospholipase $A_2$. 3 Indole-3-glyoxamides, J. Med. Chem 1996, vol. 39, No. 26, pp. 5159-5175.

Dillard et al., Indole Inhibitors of Human Nonpancreatic Secretory Phospholipase $A_2$. 2. Indole-3-acetamides with Additional Functionality, J. Med.chem. 1996, vol. 39, No. 26, pp. 5137-5158.

Dillard et al, Indole Inhibitors of Human Nonpancreatic Secretory Phospholipase $A_2$. 1. Indole-3-acetamides, J. Med. Chem., 1996, vol. 39, No. 26, pp. 5119-5136.

Schevitz et al., Nature Structural Biology, vol. 2, No. 2, Jun. 1995, pp. 458-465.

Doebel et al., J. Med. Chem., 1972, vol. 15, No. 10, pp. 1081-1082.

* cited by examiner

METHODS FOR TREATING ARTHRITIC DISORDERS

CROSS-REFERENCE TO RELATED APPLICATIONS

This application claims priority benefit of U.S. Provisional Application Ser. No. 60/334,591, filed on Dec. 3, 2001.

The present invention relates to methods of treating or alleviating the symptoms of arthritic and rheumatic disorders in mammals, including humans, the methods utilizing chemical inhibitors of the activity of various phospholipase enzymes, particularly cytosolic phospholipase $A_2$ enzymes ($cPLA_2$), more particularly including inhibitors of cytosolic phospholipase $A_2$ alpha enzymes ($cPLA_{2\alpha}$).

BACKGROUND OF THE INVENTION

Leukotrienes and prostaglandins are important mediators of inflammation, each of which contributes to the development of an inflammatory response in a different way. Leukotrienes recruit inflammatory cells such as neutrophils to an inflamed site, promote the extravasation of these cells and stimulate release of superoxide and proteases which damage the tissue. Leukotrienes also play a pathophysiological role in the hypersensitivity experienced by asthmatics [See, e.g. B. Samuelson et al., Science, 237:1171–76 (1987)]. Prostaglandins enhance inflammation by increasing blood flow and therefore infiltration of leukocytes to inflamed sites. Prostaglandins also potentiate the pain response induced by stimuli.

Prostaglandins and leukotrienes are unstable and are not stored in cells, but are instead synthesized [W. L. Smith, Biochem. J., 259:315–324 (1989)] from arachidonic acid in response to stimuli. Prostaglandins are produced from arachidonic acid by the action of COX-1 and COX-2 enzymes. Arachidonic acid is also the substrate for the distinct enzyme pathway leading to the production of leukotrienes.

Arachidonic acid which is fed into these two distinct inflammatory pathways is released from the sn-2 position of membrane phospholipids by phospholipase $A_2$ enzymes (hereinafter $PLA_2$). The reaction catalyzed by $PLA_2$ is believed to represent the rate-limiting step in the process of lipid mediated biosynthesis and the production of inflammatory prostaglandins and leukotrienes. When the phospholipid substrate of $PLA_2$ is of the phosphotidyl choline class with an ether linkage in the sn-1 position, the lysophospholipid produced is the immediate precursor of platelet activating factor (hereafter called PAF), another potent mediator of inflammation [S. I. Wasserman, Hospital Practice, 15:49–58 (1988)].

Most anti-inflammatory therapies have focused on preventing production of either prostglandins or leukotrienes from these distinct pathways, but not on all of them. For example, ibuprofen, aspirin, and indomethacin are all NSAIDs which inhibit the production of prostaglandins by COX-1/COX-2 inhibition, but have no effect on the inflammatory production of leukotrienes from arachidonic acid in the other pathways. Conversely, zileuton inhibits only the pathway of conversion of arachidonic acid to leukotrienes, without affecting the production of prostaglandins. None of these widely-used anti-inflammatory agents affects the production of PAF.

Consequently the direct inhibition of the activity of $PLA_2$ has been suggested as a useful mechanism for a therapeutic agent, i.e., to interfere with the inflammatory response. [See, e.g., J. Chang et al, Biochem. Pharmacol., 36:2429–2436 (1987)].

A family of $PLA_2$ enzymes characterized by the presence of a secretion signal sequenced and ultimately secreted from the cell have been sequenced and structurally defined. These secreted $PLA_2$s have an approximately 14 kD molecular weight and contain seven disulfide bonds which are necessary for activity. These $PLA_2$s are found in large quantities in mammalian pancreas, bee venom, and various snake venom. [See, e.g., references 13–15 in Chang et al, cited above; and E. A. Dennis, Drug Devel. Res., 10:205–220 (1987).] However, the pancreatic enzyme is believed to serve a digestive function and, as such, should not be important in the production of the inflammatory mediators whose production must be tightly regulated.

The primary structure of the first human non-pancreatic $PLA_2$ has been determined. This non-pancreatic $PLA_2$ is found in platelets, synovial fluid, and spleen and is also a secreted enzyme. This enzyme is a member of the aforementioned family. [See, J. J. Seilhamer et al, J. Biol. Chem., 264:5335–5338 (1989); R. M. Kramer et al, J. Biol. Chem., 264:5768–5775 (1989); and A. Kando et al, Biochem. Biophys. Res. Comm., 163:42–48 (1989)]. However, it is doubtful that this enzyme is important in the synthesis of prostaglandins, leukotrienes and PAF, since the non-pancreatic $PLA_2$ is an extracellular protein which would be difficult to regulate, and the next enzymes in the biosynthetic pathways for these compounds are intracellular proteins. Moreover, there is evidence that $PLA_2$ is regulated by protein kinase C and G proteins [R. Burch and J. Axelrod, Proc. Natl. Acad. Sci. U.S.A., 84:6374–6378 (1989)] which are cytosolic proteins which must act on intracellular proteins. It would be impossible for the non-pancreatic $PLA_2$ to function in the cytosol, since the high reduction potential would reduce the disulfide bonds and inactivate the enzyme.

A murine $PLA_2$ has been identified in the murine macrophage cell line, designated RAW 264.7. A specific activity of 2 mols/min/mg, resistant to reducing conditions, was reported to be associated with the approximately 60 kD molecule. However, this protein was not purified to homogeneity. [See, C. C. Leslie et al, Biochem. Biophys. Acta., 963:476–492 (1988)]. The references cited above are incorporated by reference herein for information pertaining to the function of the phospholipase enzymes, particularly $PLA_2$.

A cytosolic phospholipase $A_2$ alpha (hereinafter "$cPLA_{2\alpha}$") has also been identified and cloned. See, U.S. Pat. Nos. 5,322,776 and 5,354,677, which are incorporated herein by reference as if fully set forth. The enzyme of these patents is an intracellular $PLA_2$ enzyme, purified from its natural source or otherwise produced in purified form, which functions intracellularly to produce arachidonic acid in response to inflammatory stimuli.

Now that several phospholipase enzymes have been identified, it would be desirable to identify chemical inhibitors of the action of specific phospholipase enzymes, which inhibitors could be used to treat inflammatory conditions, particularly where inhibition of production of prostaglandins, leukotrienes and PAF are all desired results. There remains a need in the art for an identification of such anti-inflammatory agents for therapeutic use in a variety of disease states.

DETAILED DESCRIPTION OF THE INVENTION

This invention comprises a method of treatment of arthritic and/or rheumatic disorders in a mammal, preferably in a human, the method comprising administering to a mammal in need thereof a pharmaceutically effective amount of a compound of the formula:

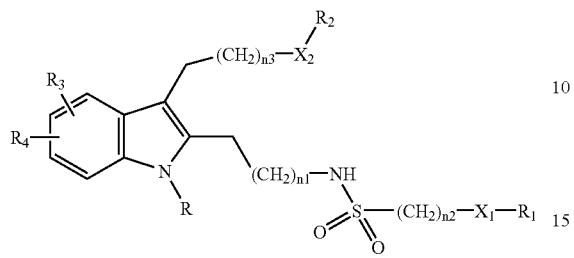

(I)

wherein:

R is selected from the formulae —$(CH_2)_n$-A, —$(CH_2)_n$—S-A, or —$(CH_2)_n$—O-A, wherein A is selected from the moieties:

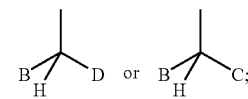

wherein

D is $C_1$–$C_6$ lower alkyl, $C_1$–$C_6$ lower alkoxy, $C_3$–$C_6$ cycloaklyl —$CF_3$ or —$(CH_2)_{1-3}$—$CF_3$;

B and C are independently selected from phenyl, pyridinyl, pyrimidinyl, furanyl, thiophenyl or pyrrolyl groups, each optionally substituted by from 1 to 3, preferably 1 to 2, substituents selected independently from H, halogen, —CN, —CHO, —$CF_3$, —$OCF_3$, —OH, —$C_1$–$C_6$ alkyl, $C_1$–$C_6$ alkoxy, —$NH_2$, —$N(C_1$–$C_6)_2$, —$NH(C_1$–$C_6)$, —N—C(O)—$(C_1$–$C_6)$, —$NO_2$, or by a 5- or 6-membered heterocyclic or heteroaromatic ring containing 1 or 2 heteroatoms selected from O, N or S; or n is an integer from 0 to 3;
$n_1$ is an integer from 1 to 3;
$n_2$ is an integer from 0 to 4;
$n_3$ is an integer from 0 to 3;
$n_4$ is an integer from 0 to 2;
$X_1$ is selected from a chemical bond, —S—, —O—, —S(O)—, —S(O)$_2$—, —NH—, —NHC(O)—, —C=C—,

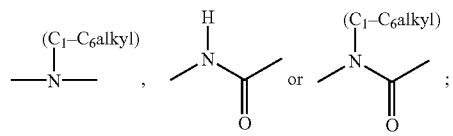

$R_1$ is a moiety selected from $C_1$–$C_6$ alkyl, $C_1$–$C_6$ fluorinated alkyl, $C_3$–$C_6$ cycloalkyl, tetrahydropyranyl, camphoryl, adamantyl, CN, —$N(C_1$–$C_6$ alkyl)$_2$, phenyl, pyridinyl, pyrimidinyl, furyl, thienyl, napthyl, morpholinyl, triazolyl, pyrazolyl, piperidinyl, pyrrolidinyl, imidazolyl, piperizinyl, thiazolidinyl, thiomorpholinyl, tetrazole, indole, benzoxazole, benzofuran, imidazolidine-2-thione, 7,7,dimethyl-bicyclo[2.2.1]heptan-2-one, Benzo[1,2,5]oxadiazole, 2-Oxa-5-aza-bicyclo[2.2.1]heptane, Piperazin-2-one or pyrrolyl groups, each optionally substituted by from 1 to 3, preferably 1 to 2, substituents independently selected from H, halogen, —CN, —CHO, —$CF_3$, $OCF_3$, —OH, —$C_1$–$C_6$ alkyl, $C_1$–$C_6$ alkoxy, —$NH_2$, —$N(C_1$–$C_6)_2$, —$NH(C_1$–$C_6)$, —N—C(O)—$(C_1$–$C_6)$, —$NO_2$, —$SO_2(C_1$–$C_3$ alkyl), —$SO_2NH_2$, —$SO_2NH(C_1$–$C_3$ alkyl), —$SO_2N(C_1$–$C_3$ alkyl)$_2$, —COOH, —$CH_2$—COOH, —$CH_2$—$N(C_1$–$C_6$ alkyl), —$CH_2$—$N(C_1$–$C_6$ alkyl)$_2$, —$CH_2$—$NH_2$, pyridine, 2-Methyl-thiazole, morpholino, 1-Chloro-2-methyl-propyl, —$C_1$–$C_6$thioalkyl, phenyl (further optionally substituted with halogens), benzyloxy, $(C_1$–$C_3$ alkyl)$C(O)CH_3$, $(C_1$–$C_3$ alkyl)$OCH_3$, $C(O)NH_2$, or

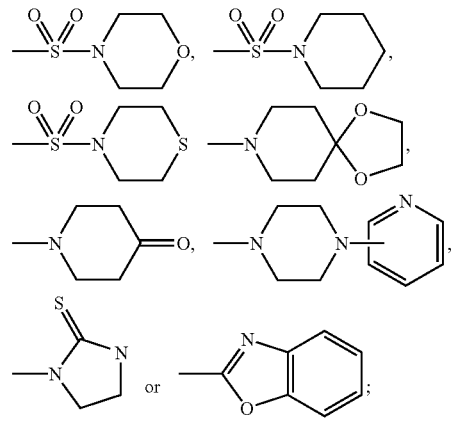

$X_2$ is selected from —O—, —$CH_2$—, —S—, —SO—, —$SO_2$—, —NH—, —C(O)—,

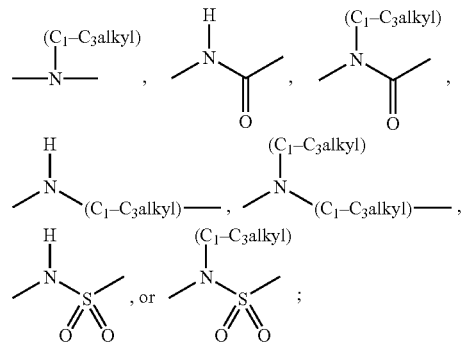

$R_2$ is a ring moiety selected from phenyl, pyridinyl, pyrimidinyl, furyl, thienyl or pyrrolyl groups, the ring moiety being substituted by a group of the formula —$(CH_2)_{n4}$—$CO_2H$ or a pharmaceutically acceptable acid mimic or mimetic; and also optionally substituted by 1 or 2 additional substituents independently selected from H, halogen, —CN, —CHO, —$CF_3$, —$OCF_3$, —OH, —$C_1$–$C_6$ alkyl, $C_1$–$C_6$ alkoxy, $C_1$–$C_6$ thioalkyl, —$NH_2$, —$N(C_1$–$C_6)_2$, —$NH(C_1$–$C_6)$, —N—C(O)—$(C_1$–$C_6)$, or —$NO_2$;

$R_3$ is selected from H, halogen, —CN, —CHO, —$CF_3$, —$OCF_3$, —OH, —$C_1$–$C_6$ alkyl, $C_1$–$C_6$ alkoxy, $C_1$–$C_6$ thioalkyl, —$NH_2$, —$N(C_1$–$C_6)_2$, —$NH(C_1$–$C_6)$, —N—C(O)—$(C_1$–$C_6)$, or —$NO_2$;

$R_4$ is selected from H, halogen, —CN, —CHO, —$CF_3$, —$OCF_3$, —OH, —$C_1$–$C_6$ alkyl, $C_1$–$C_6$ alkoxy, $C_1$–$C_6$ thioalkyl, —$NH_2$, —$N(C_1$–$C_6)_2$, —$NH(C_1$–$C_6)$, —N—C(O)—$(C_1$–$C_6)$, —$NO_2$, —N—C(O)—$N(C_1$–$C_3$ alkyl)$_2$, —N—C(O)—$NH(C_1$–$C_3$ alkyl), —N—C(O)—O—$(C_1$–$C_3$ alkyl), —SO$_2$—C$_1$–C$_6$ alkyl, —S—C$_3$–C$_6$ cycloalkyl, —S—CH$_2$—C$_3$–C$_6$ cycloalkyl, —SO$_2$—C$_3$–C$_6$ cycloalkyl, —SO$_2$—CH$_2$—C$_3$–C$_6$ cycloalkyl, C$_3$–C$_6$ cycloalkyl, —CH$_2$—C$_3$–C$_6$ cycloalkyl, —O—C$_3$–C$_6$ cycloalkyl, —O—CH$_2$—C$_3$–C$_6$ cycloalkyl, phenyl, benzyl, benzyloxy, morpholino or other heterocycles such as pyrrolidino, piperidine, piperizine furan, thiophene, imidazole, tetrazole, pyrazine, pyrazolone, pyrazole, imidazole, oxazole or isoxazole, the rings of each of these R$_4$ groups each being optionally substituted by from 1 to 3 substituents selected from the group of H, halogen, —CN, —CHO, —CF$_3$, —OH, —C$_1$–C$_6$ alkyl, C$_1$–C$_6$ alkoxy, —NH$_2$, —N(C$_1$–C$_6$)$_2$, —NH(C$_1$–C$_6$), —N—C(O)—(C$_1$–C$_6$), —NO$_2$, —SO$_2$(C$_1$–C$_3$ alkyl), —SO$_2$NH(C$_1$–C$_3$ alkyl), —SO$_2$N(C$_1$–C$_3$ alkyl)$_2$, or OCF$_3$;

or a pharmaceutically acceptable salt form thereof.

It will be understood that the C$_1$–C$_6$ fluorinated alkyl groups in the definition of R$_1$ may be any alkyl group of 1 to 6 carbon atoms with any amount of fluorine substitution including, but not limited to, —CF$_3$, alkyl chains of 1 to 6 carbon atoms terminated by a trifluoromethyl group, —CF$_2$CF$_3$, etc.

Ester forms of the present compounds include the pharmaceutically acceptable ester forms known in the art including those which can be metabolized into the free acid form, such as a free carboxylic acid form, in the animal body, such as the corresponding alkyl esters, cycloalkyl esters, aryl esters and heterocyclic analogues thereof can be used according to the invention, where alkyl esters, cycloalkyl esters and aryl esters are preferred and the alcoholic residue can carry further substituents. C$_1$–C$_8$ alkyl esters, preferably C$_1$–C$_6$ alkyl esters, such as the methyl ester, ethyl ester, propyl ester, isopropyl ester, butyl ester, isobutyl ester, t-butyl ester, pentyl ester, isopentyl ester, neopentyl ester, hexyl ester, cyclopropyl ester, cyclopropylmethyl ester, cyclobutyl ester, cyclopentyl ester, cyclohexyl ester, or aryl esters such as the phenyl ester, benzyl ester or tolyl ester are particularly preferred.

In the definition of X$_1$, the alkenyl bridging group —C=C— is understood to indicate either the cis or trans orientation of the indicated compound(s).

Pharmaceutically acceptable acid mimics or mimetics useful in the compounds of this invention include those wherein R$_2$ is selected from the group of:

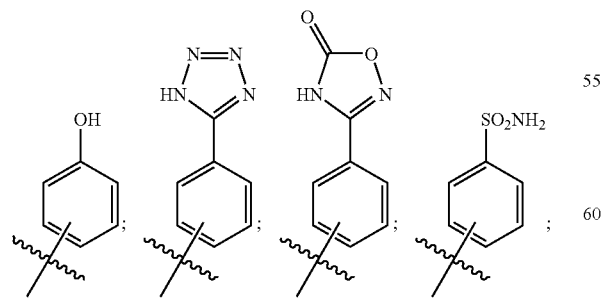

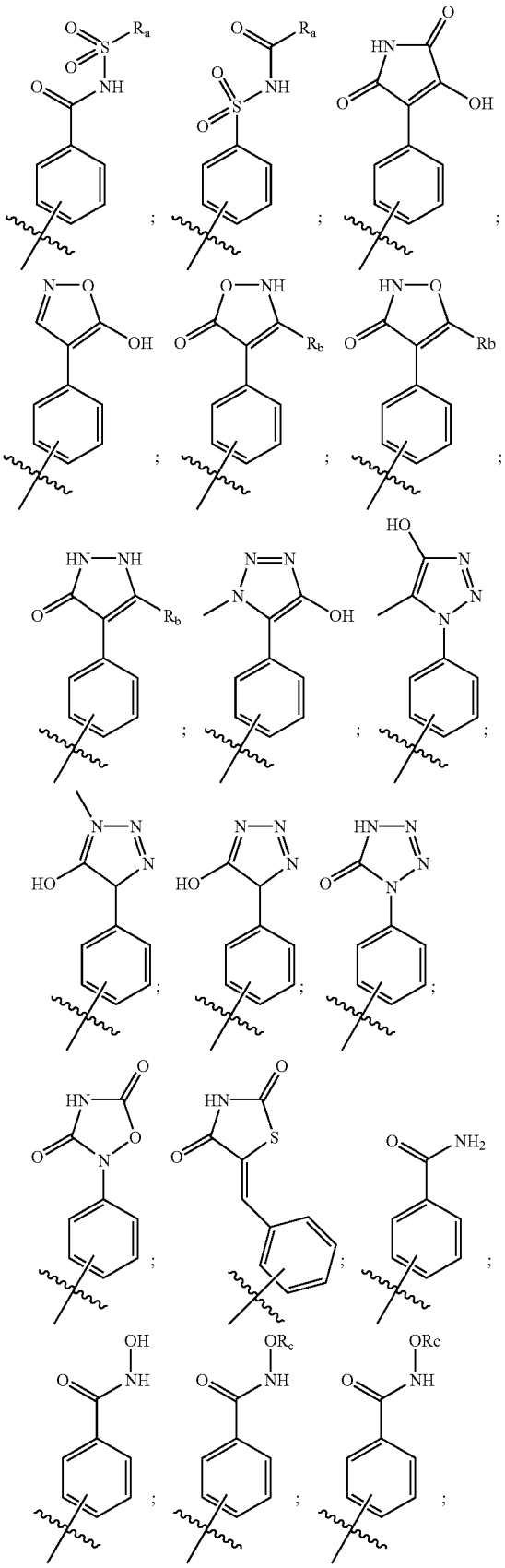

-continued

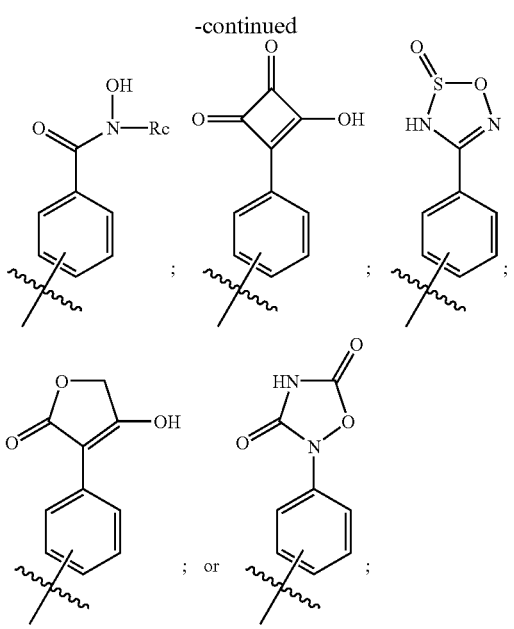

wherein $R_a$ is selected from —$CF_3$, —$CH_3$, phenyl, or benzyl, with the phenyl or benzyl groups being optionally substituted by from 1 to 3 groups selected from $C_1$–$C_6$ alkyl, $C_1$–$C_6$ alkoxy, $C_1$–$C_6$ thioalkyl, —$CF_3$, halogen, —OH, or —COOH; $R_b$ is selected from —$CF_3$, —$CH_3$, —$NH_2$, phenyl, or benzyl, with the phenyl or benzyl groups being optionally substituted by from 1 to 3 groups selected from $C_1$–$C_6$ alkyl, $C_1$–$C_6$ alkoxy, $C_1$–$C_6$ thioalkyl, —$CF_3$, halogen, —OH, or —COOH; and $R_c$ is selected from —$CF_3$ or $C_1$–$C_6$ alkyl.

The methods of this invention include alleviation, inhibition, relief and treatment in a mammal of arthritic disorders including, but not limited to, rheumatoid arthritis, spondyloarthropathies, gouty arthritis, infectious arthritis, osteoarthritis (which includes erosive osteoarthritis and is also known as osteoarthrosis or degenerative joint disease or DJD), systemic lupus erythematosus and juvenile arthritis. Each of these methods comprises administering to a mammal in need of such action a pharmaceutically effective amount of a substituted indole of this invention, as described herein, or a pharmaceutically acceptable salt or ester form thereof.

The methods of this invention include those for arthritic conditions associated with spondylitis, including ankylosing spondylitis, reactive arthritis (Reiter's syndrome), psoriatic arthritis, arthritis associated with chronic inflammatory bowel disease and AIDS-related seronegative spondyloarthropathy.

This invention also provides methods for treating, alleviating or inhibiting rheumatic disease and disorders. These methods are useful for treatment of systemic lupus erythematosus, systemic sclerosis and forms of scleroderma, polymyositis, dermatomyositis, necrotizing vasculitis and other vasculopathies, hypersensitivity vasculitis (including Henoch-Schönlein purpura), Wegener's granulomatosis, Giant cell arteritis, mucocutaneous lymph node syndrome (Kawasaki disease), Behcet's syndrome, Cryoglobulinemia, juvenile dermatomyositis, Sjögren's syndrome, overlap syndromes (includes mixed connective tissue disease), polymyalgia rheumaticqa, erythema nodosum, relapsing polychondritis, tendonitis (tenosynovitis), Bicipital tendenitis, bursitis, Olecranon bursitis, adhesive capsulitis of the shoulder (frozen shoulder) trigger finger, and Whipple's disease.

The methods of this invention are also useful for treatment, alleviation or inhibition of metabolic and endocrine diseases with rheumatic states, including gout, pseudogout, chondrocalcinosis, amyloidosis, scurvy, speicific enzyme deficiency states (including Fabry's disease, alkaptonuria, ochonosisi, Lesch-Nyhan syndrome, and Gaucher's disease), hyperlipoproteinemias (types II, IIa, IV), Ehlers-Danlos syndrome, Marfan's syndrome, pseudoxanthoma elasticum, Wilson's disease. Also treatable with the present methods are the rheumatic states associated with endocrine diseases, such as diabetes mellitus, acromegaly, hyperparathyroidism, myositis ossificans progressiva, hypermobility syndromes, arthrogryposis multiplex congenita, and thyroid diseases such as thyroiditis, hypothyroidism and hyperthyroidism. These methods may also be used for rheumatic conditions associated with neoplasms such as primary neoplasms (synovioma), metastatic neoplasms, multiple myeloma, leukemia and lymphomas, pigmented villonodular synovitis, osteochondromatosis and others. Also included among the methods of this invention are relief from the rheumatic conditions associated with neuropathic disorders including, Charcot's joints, hand-arm vibration syndrome (also known as vibration-induced white finger or Raynaud's phenomenon), repetitive stress syndromes, reflex sympathetic dystrophy and compression neuropathies, such as peripheral entrapment (including carpal tunnel syndrome, pronator syndrome, thoracic outlet syndromes and tarsal tunnel syndrome), radiculopathy and spinal stenosis.

The compounds and methods of this invention are useful in treating, alleviating and inhibiting these conditions and the pain and inflammation with which they are associated. Methods for treating, relieving, inhibiting or alleviating each of these conditions in a mammal, comprises administering to a mammal in need of such activity a pharmaceutically effective amount of a compound of this invention, alone or in combination with another agent, such as an anti-rheumatic, anti-inflammatory or analgesic pharmaceutical agent.

A first subgroup of compounds useful in the methods of this invention, or a pharmaceutically acceptable salt thereof, include those of the group above wherein A is the moiety:

and B, C, n, n1, n2, n3, n4, R, $X_1$, $X_2$, $R_1$, $R_2$, $R_3$, and $R_4$ are as defined above.

A second subgroup of compounds useful in the methods of this invention comprises those of the first subgroup, above, wherein B and C are unsubstituted phenyl, pyridinyl, pyrimidinyl, furyl, thienyl or pyrrolyl groups and R, n, n1, n2, n3, n4, $R_1$, $X_1$, $X_2$, $R_2$, $R_3$, and $R_4$ are as defined above.

A third subgroup of compounds and pharmaceutically acceptable salt forms useful in the methods of this invention comprise those of the second subgroup, above, wherein A is the moiety:

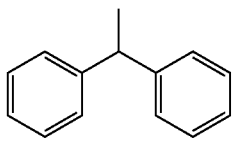

and n, n1, n2, n3, n4, R, $X_1$, $X_2$, $R_1$, $R_2$, $R_3$, and $R_4$ are as defined above.

A fourth subgroup of compounds useful in the methods of this invention comprises those of the formulae (II) or (III):

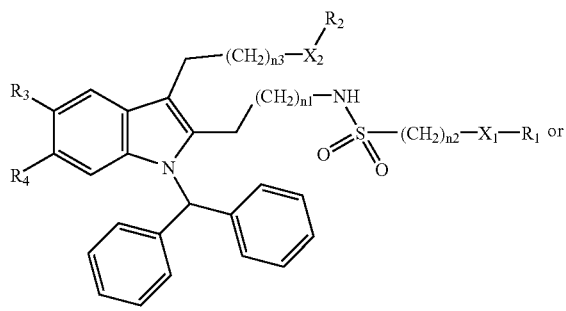

(II)

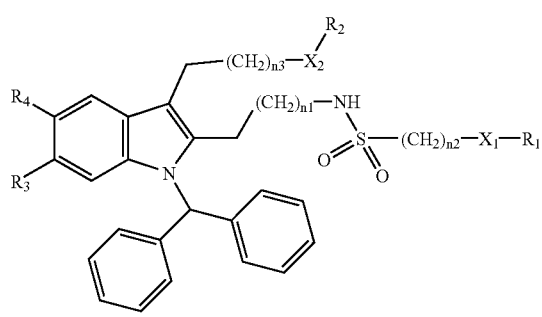

(III)

wherein n1, n2, n3, n4, $X_1$, $X_2$, $R_1$, $R_2$, $R_3$, and $R_4$ are as defined above, or a pharmaceutically acceptable salt thereof.

A fifth subgroup of compounds useful in the methods of this invention includes those of formulae (II) or (III) wherein n3=1, and n1, n2, n4, $X_1$, $X_2$, $R_1$, $R_2$, $R_3$, and $R_4$ are as defined above, or a pharmaceutically acceptable salt thereof.

A sixth subgroup of compounds useful in the methods of this invention includes those of the fifth subgroup, above, wherein $R_2$ is phenyl substituted by a group of the formula —$(CH_2)_{n4}$—$CO_2H$; and optionally substituted by 1 or 2 additional substituents independently selected from H, halogen, —CN, —CHO, —CF$_3$, —OH, —C$_1$–C$_6$ alkyl, C$_1$–C$_6$ alkoxy, C$_1$–C$_6$ thioalkyl, —NH$_2$, —N(C$_1$–C$_6$)$_2$, —NH (C$_1$–C$_6$), —N—C(O)—(C$_1$–C$_6$), or —NO; and n1, n2, n4, $R_1$, $X_1$, $X_2$, $R_2$, $R_3$, and $R_4$ are as defined above, or a pharmaceutically acceptable salt thereof.

A seventh subgroup of compounds useful in the methods of this invention comprises those of the formulae (IV) or (V):

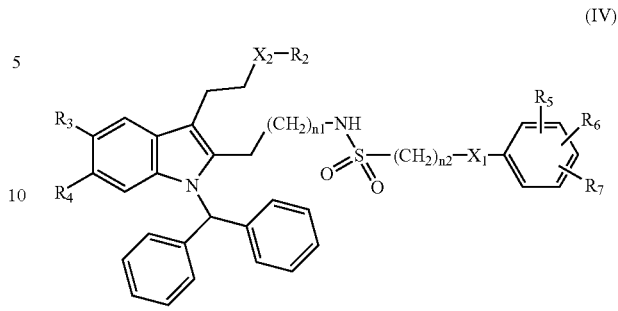

(IV)

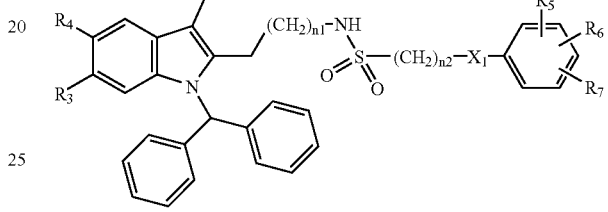

(V)

wherein:
$n_1$ is an integer from 1 to 3;
$n_2$ is an integer from 1 to 3;
$R_5$, $R_6$ and $R_7$ are independently selected from H, halogen, —CN, —CHO, —CF$_3$, —OCF$_3$, —OH, —C$_1$–C$_6$ alkyl, C$_1$–C$_6$ alkoxy, —NH$_2$, —N(C$_1$–C$_6$)$_2$, —NH(C$_1$–C$_6$), —N—C(O)—(C$_1$–C$_6$), or —NO$_2$;
$X_1$ is selected from a chemical bond, —S—, —O—, —NH— or —N(C$_1$–C$_3$ alkyl)-;
$X_2$ is selected from —O—, —SO$_2$— or —CH$_2$—;
$R_2$ is a moiety selected from the group of:

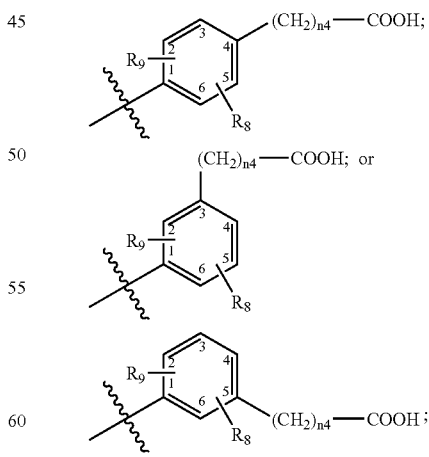

$R_8$ and $R_9$ are independently selected from H, halogen, —CN, —CHO, —CF$_3$, —OH, —C$_1$–C$_6$ alkyl, C$_1$–C$_6$ alkoxy, —NH$_2$, —N(C$_1$–C$_6$)$_2$, —NH(C$_1$–C$_6$), —N—C(O)—(C$_1$–C$_6$), or —NO$_2$;

$n_4$ is an integer from 0 to 2;

$R_3$ is selected from H, halogen, —CN, —CHO, —CF$_3$, —OH, —C$_1$–C$_6$ alkyl, C$_1$–C$_6$ alkoxy, C$_1$–C$_6$ thioalkyl, —NH$_2$, —N(C$_1$–C$_6$)$_2$, —NH(C$_1$–C$_6$), —N—C(O)—(C$_1$–C$_6$), or —NO$_2$; and $R_4$ is selected from H, halogen, —CN, —CHO, —CF$_3$, —OH, —C$_1$–C$_6$ alkyl, C$_1$–C$_6$ alkoxy, C$_1$–C$_6$ thioalkyl, —NH$_2$, —N(C$_1$–C$_6$)$_2$, —NH(C$_1$–C$_6$), —N—C(O)—(C$_1$–C$_6$), —NO$_2$, morpholino or other heterocycles such as pyrrolidino, piperidine, piperizine, furan, thiophene, imidazole, tetrazole, pyrazine, pyrazolone, pyrazole, imidazole, oxazole or isoxazole;

or a pharmaceutically acceptable salt form thereof.

An eighth subgroup of compounds useful in the methods of this invention include those of the formulae (VI) or (VII):

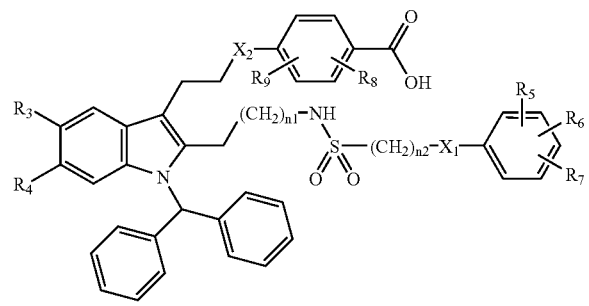

(VI)

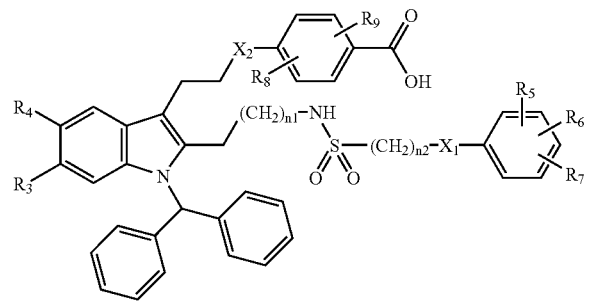

(VII)

wherein:

$X_1$ is selected from a chemical bond, —S—, —O—, —NH— or —N(C$_1$–C$_3$ alkyl)-;

$X_2$ is selected from —O—, —SO$_2$—, or —CH$_2$—;

$R_3$ is selected from H, halogen, —CN, —CHO, —CF$_3$, —OH, —C$_1$–C$_6$ alkyl, C$_1$–C$_6$ alkoxy, C$_1$–C$_6$ thioalkyl, —NH$_2$, —N(C$_1$–C$_6$)$_2$, —NH(C$_1$–C$_6$), —N—C(O)—(C$_1$–C$_6$), or —NO$_2$; and $R_4$ is selected from H, halogen, —CN, —CHO, —CF$_3$, —OH, —C$_1$–C$_6$ alkyl, C$_1$–C$_6$ alkoxy, C$_1$–C$_6$ thioalkyl, —NH$_2$, —N(C$_1$–C$_6$)$_2$, —NH(C$_1$–C$_6$), —N—C(O)—(C$_1$–C$_6$), —NO$_2$, morpholino or other heterocycles such as pyrrolidino, piperidine, piperizine, furan, thiophene, imidazole, tetrazole, pyrazine, pyrazolone, pyrazole, imidazole, oxazole or isoxazole;

$n_1$ is an integer from 1 to 2;

$n_2$ is an integer from 1 to 2;

$R_5$, $R_6$ and $R_7$ are independently selected from H, halogen, —CN, —CHO, —CF$_3$, —OCF$_3$, —OH, —C$_1$–C$_6$ alkyl, C$_1$–C$_6$ alkoxy, —NH$_2$, —N(C$_1$–C$_6$)$_2$, —NH(C$_1$–C$_6$), —N—C(O)—(C$_1$–C$_6$), or —NO$_2$;

$R_8$ and $R_9$ are independently selected from H, halogen, —CN, —CHO, —CF$_3$, —OH, —C$_1$–C$_6$ alkyl, C$_1$–C$_6$ alkoxy, —NH$_2$, —N(C$_1$–C$_6$)$_2$, —NH(C$_1$–C$_6$), —N—C(O)—(C$_1$–C$_6$), or —NO$_2$;

or a pharmaceutically acceptable salt form thereof.

A ninth subgroup of compounds useful in the methods of this invention include those of formulae (VI) or (VII) wherein: $n_1$ is 1; $n_2$ is 1; and $X_1$, $X_2$, $R_3$, $R_4$, $R_5$, $R_6$, $R_7$, $R_8$ and $R_9$ are as defined in the eighth subgroup, above, or a pharmaceutically acceptable salt form thereof.

A tenth subgroup useful in the methods of this invention comprises the compounds of the ninth subgroup, above, wherein $X_1$ is a chemical bond and $n_1$, $n_2$, $X_2$, $R_3$, $R_4$, $R_5$, $R_6$, $R_7$, $R_8$ and $R_9$ are as defined in the ninth subgroup, above, or a pharmaceutically acceptable salt form thereof.

This invention also provides pharmaceutical compositions useful in the methods herein comprising a pharmaceutically effective amount of a compound of this invention, or a pharmaceutically acceptable salt form thereof, and one or more pharmaceutically acceptable carriers or excipients.

Compounds of the present invention may be used in a pharmaceutical composition when combined with a pharmaceutically acceptable carrier. Such a composition may also contain (in addition to a compound or compounds of the present invention and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition may further contain other anti-inflammatory agents. Such additional factors and/or agents may be included in the pharmaceutical composition to produce a synergistic effect with compounds of the present invention, or to minimize side effects caused by the compound of the present invention.

The pharmaceutical composition of the invention may be in the form of a liposome in which compounds of the present invention are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

The terms "pharmaceutically effective amount" or "therapeutically effective amount" as used herein mean the total amount of each active component of the pharmaceutical composition or method that is sufficient to show a meaningful patient benefit, i.e., treatment, healing, prevention, inhibition or amelioration of a physiological response or condition, such as an inflammatory condition or pain, or an increase in rate of treatment, healing, prevention, inhibition or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

This invention further provides methods of alleviation, inhibition, relief or treatment of arthritic and rheumatic disorders in a mammal, the method comprising administering to a mammal in need thereof a pharmaceutically effective amount of a chemical inhibitor of phospholipase enzymes, particularly phospholipase $A_2$ enzymes, as defined herein and a pharmaceutically effective amount of an anti-rheumatic agent.

Combinations for the treatment of arthritic and rheumatic disorders may include commercially available anti-rheumatic agents such as, but not limited to, naproxen, which is commercially available in the form of EC-NAPROSYN® delayed release tablets, NAPROSYN®, ANAPROX® and ANAPROX® DS tablets and NAPROSYN® suspension from Roche Labs, CELEBREX® brand of celecoxib tablets, VIOXX® brand of rofecoxib, CELESTONE® brand of betamethasone, CUPRAMINE® brand penicillamine capsules, DEPEN® brand titratable penicillamine tablets, DEPO-MEDROL brand of methylprednisolone acetate injectable suspension, ARAVA™ leflunomide tablets, AZULFIDIINE EN-tabs® brand of sulfasalazine delayed release tablets, FELDENE® brand piroxicam capsules, CATAFLAM® diclofenac potassium tablets, VOLTAREN® diclofenac sodium delayed release tablets, VOLTAREN®-XR diclofenac sodium extended release tablets, ENBREL® etanerecept products, and other commercially available anti-rheumatic agents.

Also useful are GENGRAF™ brand cyclosporine capsules, RAPAMUNE® brand sirolimus products, NEORAL® brand cyclosprine capsules or oral solution, IMURAN® brand azathioprine tablets or IV injection, INDOCIN® brand indomethacin capsules, oral suspension and suppositories, PEDIAPED® prednisolone sodium phosphate oral solution, PLAQUENIL® brand hydroxychloroquine sulfate, PRELONE® brand prednisolone syrup, REMICADE® infliximab recombinant for IV injection, and SOLU-MEDROL® methylprednisolone sodium succinate for injection.

Also useful in the combinations of this invention are gold compounds and products useful in the treatment of arthritis and rheumatic conditions, such as auranofin or MYOCHRISYINE® gold sodium thiomalate injection.

Each of the methods of treatment or use of the present invention, as described herein, comprises administering to a mammal in need of such treatment or use a pharmaceutically or therapeutically effective amount of a compound of the present invention, or a pharmaceutically acceptable salt form thereof. Compounds of the present invention may be administered in accordance with the method of the invention either alone or in combination with other therapies such as treatments employing other anti-inflammatory agents, cytokines, lymphokines or other hematopoietic factors. When co-administered with one or more other anti-inflammatory agents, cytokines, lymphokines or other hematopoietic factors, compounds of the present invention may be administered either simultaneously with the other anti-inflammatory agent(s), cytokine(s), lymphokine(s), other hematopoietic factor(s), thrombolytic or anti-thrombotic factors, or sequentially. If administered sequentially, the attending physician will decide on the appropriate sequence of administering compounds of the present invention in combination with other anti-inflammatory agent(s), cytokine(s), lymphokine(s), other hematopoietic factor(s), thrombolytic or anti-thrombotic factors.

Administration of compounds of the present invention used in the pharmaceutical composition or to practice the method of the present invention can be carried out in a variety of conventional ways, such as oral ingestion, inhalation, or cutaneous, subcutaneous, or intravenous injection.

When a therapeutically effective amount of compounds of the present invention is administered orally, compounds of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% compound of the present invention, and preferably from about 25 to 90% compound of the present invention. When administered in liquid form, a liquid carrier such as water, petroleum, oils of animal or plant origin such as peanut oil, mineral oils, phospholipids, tweens, triglycerides, including medium chain triglycerides, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of compound of the present invention, and preferably from about 1 to 50% compound of the present invention.

When a therapeutically effective amount of compounds of the present invention is administered by intravenous, cutaneous or subcutaneous injection, compounds of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to compounds of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of compound(s) of the present invention in the pharmaceutical composition of the present invention will depend upon the nature and severity of the condition being treated, and on the nature of prior treatments the patient has undergone. Ultimately, the attending physician will decide the amount of compound of the present invention with which to treat each individual patient. Initially, the attending physician will administer low doses of compound of the present invention and observe the patient's response. Larger doses of compounds of the present invention may be administered until the optimal therapeutic effect is obtained for the patient, and at that point the dosage is not increased further. It is contemplated that the various pharmaceutical compositions used to practice the method of the present invention should contain about 0.1 μg to about 100 mg (preferably about 0.1 mg to about 50 mg, more preferably about 1 mg to about 2 mg) of compound of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the compounds of the present invention will be in the range of 12 to 24 hours of continuous intravenous administration. Ultimately the attending physician will decide on the appropriate duration of intravenous therapy using the pharmaceutical composition of the present invention.

A preferred lipid based oral formulation of this invention has been prepared by blending 50% PHOSOL® 53MCT (American Lecithin Company), 5% Polysorbate 80, 15% LABRASOL® Caprylocaproyl macrogol-8 glycerides (Gattefosse Corp.), 15% Propylene Carbonate and 15% active cPLA2 inhibiting compound(s) of this invention, each percentage listed being by weight.

This invention can be further understood by the following non-limiting specific examples.

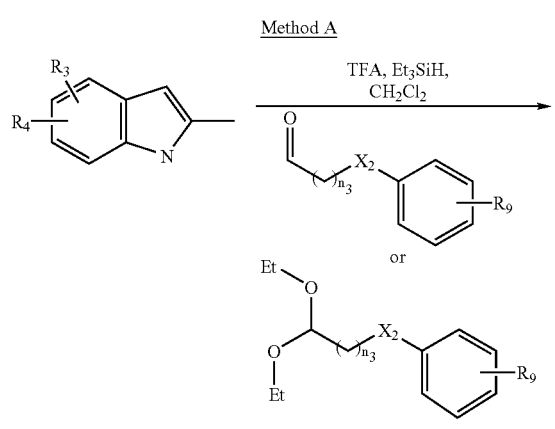

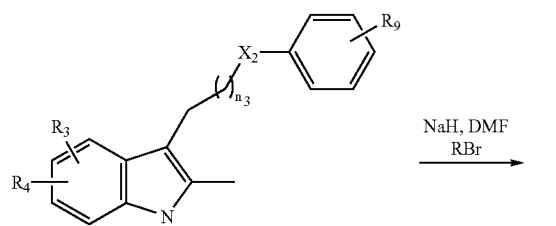

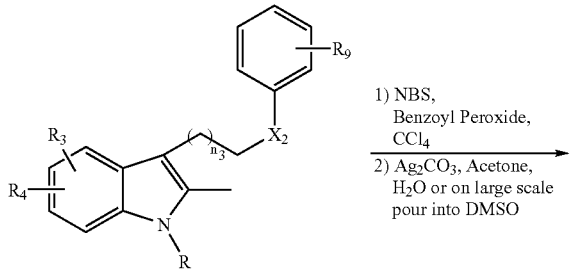

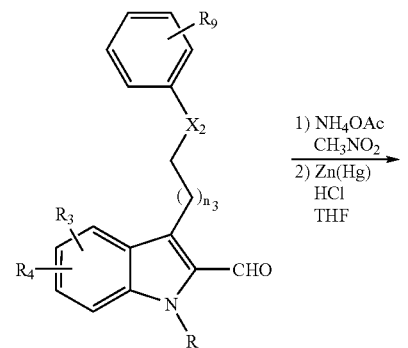

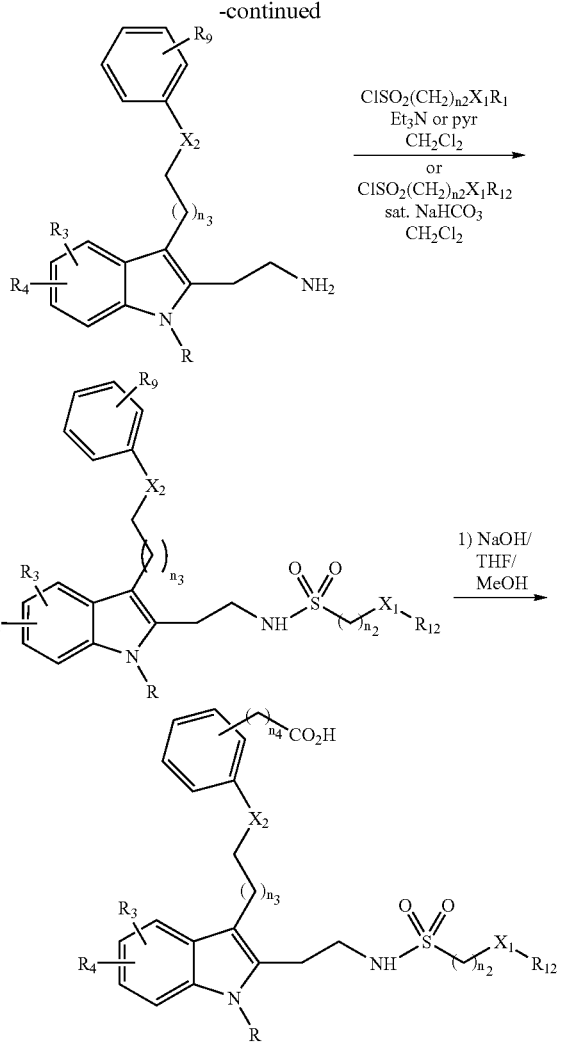

Method A

The initial indole of Method A may be alkylated at the C3 position (the carbon atom at the 3-position of the indole moiety) with aldehydes or the corresponding acetals in the presence of a Lewis or Bronsted acid, such as boron trifluoride etherate or trifluoroacetic acid. The indole nitrogen may then be alkylated by treatment with a strong base such as sodium bis(trimethylsilyl) amide, n-BuLi, sodium hydride or potassium hydride in a solvent such as DMF, DMSO or THF followed by exposure to the appropriate alkyl halide. The resulting product can be treated with carbon tetrabromide in carbon tetrachloride and a catalytic amount of benzoyl peroxide to effect dibromination of the C2 methyl group. The dibromide can then either be stirred with silver carbonate in acetone water or poured into DMSO and stirred. Both of these procedures generate the aldehyde which is then subjected to the nitro aldol reaction with nitromethane and a catalytic amount of ammonium acetate at reflux. The resulting vinyl nitro intermediate is reduced to the amine upon treatment with zinc mercury amalgam in a mixture of THF and conc. HCL at reflux. This amine can then be treated with the requisite sulfonyl chloride under biphasic conditions, aqueous sodium bicarbonate/dichloromethane, or in organic solvent with the addition of a hindered organic amine base. The final hydrolysis was accomplished under basic conditions with sodium hydroxide in water and methanol and THF at room temperature or at elevated temperature. Alternatively it may be cleaved by treatment with sodium thiomethoxide in a solvent such as THF or DMF at elevated temperatures (50° C.–100° C.). This method was used in the synthesis of Examples 1–88, 108–112, and 126–128.

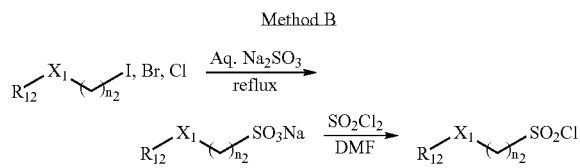

Method B

The initial halide of Method B is refluxed in aqueous sodium sulfite and a suitable cosolvent if necessary, such as alcohol, dioxane etc, for the required amount of time to form the desired sodium sulfonate. This intermediate was treated with thionyl chloride, phosphorous pentachloride or oxalyl chloride, in dichloromethane with a small amount of DMF and stirred for several hours at room temperature until the sulfonyl chloride is formed. The thus formed sulfonyl chloride is then used crude in Method A. This method was used in the synthesis of Examples 1–88, 108–112 and 126–128 when the sulfonyl chloride was not commercially available.

EXAMPLE 1

4-[2-(1-Benzhydryl-2-{2-[(benzylsulfonyl)amino]ethyl}-5-chloro-1H-indol-3-yl)ethoxy]benzoic acid This synthesis is depicted in Method A.

Step 1: To 4-hydroxy-benzoic acid methyl ester (1.0 eq) in DMF (0.83 M) was added $K_2CO_3$ (2.0 eq) followed by 2-bromo-1,1-diethoxy-ethane and the reaction mixture was stirred at 110° C. for 2 days. TLC showed a new spot. The reaction mixture was diluted with ethyl acetate, washed with 1N NaOH, water, and brine, dried over sodium sulfate, and solvent was removed to afford desired product in 84% yield. This material was used in the next step without further purification.

Step 2: To the above product (1.0 eq) and 5-chloro-2-methyl indole (1.0 eq) in $CH_2Cl_2$ (0.12 M) was added triethylsilane (3.0 eq) followed by trifluoroacetic acid (3.0 eq). After being stirred overnight at room temperature, added water and trifluroacetic acid (1.0 eq) to the reaction mixture, stirred at room temperature for two days, diluted with $CH_2Cl_2$, washed with 1N NaOH, water, brine, dried over sodium sulfate. Trituration of the material with $CH_2Cl_2$ and hexanes afforded the C3 alkylated indole in 92% yield Step 3: To the indole from above (1.0 eq) in DMF (0.36 M) at 25° C. was added NaH (1.2 eq, 60% dispersion in oil), and the brown solution was stirred at 0 to –5° C. for 1 h and then compound bromodiphenylmethane was added (1.1 eq), and then the reaction mixture was stirred overnight. It was then quenched with water, diluted with ethyl acetate, washed with water and brine, dried over sodium sulfate and purified by column chromatography to yield 72% of the desired product.

Step 4: To the N-alkylated indole from above (1.0 eq) in $CCl_4$ (0.2 M) was added N-bromosuccinimide (2.0 eq) and a catalytic amount of benzoyl peroxide. The solution was heated to reflux for 3 h, cooled to 25° C., filtered, and the solid was washed with $CCl_4$. The filtrate was concentrated to a foam, which was dried. The foam was dissolved in acetone, and $Ag_2CO_3$ (1.1 eq.) was added followed by water and the reaction mixture was stirred overnight at room temperature. It was filtered and washed with acetone. The filtrate was concentrated to a residue, to which was added water. This mixture was extracted with ethyl acetate, washed with brine, dried over sodium sulfate and then chromatographic purification on the residue gave the desired product in 85% yield. Alternatively the dibromide from the reaction with NBS could be poured into DMSO (10–20% concentration by weight) stirred for 30 minutes at room temperature. When the reaction was deemed complete it was poured into water and the resulting precipitate was isolated by filtration, the cake was washed with water and dried to yield an essentially quantitative yield.

Step 5: To the above aldehyde (1.0 equiv) in $CH_3NO_2$ (0.2 M) was added ammonium acetate (4 equiv) and the resulting mixture was heated to reflux for 4 h. The reaction mixture was then diluted with EtOAc and washed with brine. The aqueous phase was extracted with EtOAc. The combined organic extracts were washed with brine, dried over sodium sulfate, and concentrated until an orange crystalline solid precipitated. The mixture was refrigerated overnight and the nitroolefin (76% yield) was collected by filtration. Evaporation of the solution phase and purification of the residue by column chromatography (gradient elution 100% toluene→1% EtOAc-toluene) afforded an additional amount of the nitroolefin (23% yield).

Step 6: Zinc dust (20 equiv) was suspended in 5% aqueous HCl solution (8 M Zn/5% HCl). To this mixture was added $HgCl_2$ (0.28 equiv). The mixture was shaken for 10 min, the aqueous phase was decanted and replaced with fresh 5% HCl, and again the mixture was shaken for 5 min and the aqueous phase was removed. The zinc-mercury amalgam thus generated was then added to a mixture of the nitroolefin (1.0 equiv) and conc. HCl (80 equiv) in THF (0.04 M nitroolefin/THF). The mixture was maintained at a gentle reflux for 1 h. The formation of product was followed by TLC analysis. The mixture was cooled to room temperature and the solids were removed by filtration through Celite. Conc. $NH_4OH$ was added to the solution phase and the mixture was concentrated on the rotary evaporator. The residue was dissolved in $CH_2Cl_2$ and conc. $NH_4OH$. The aqueous phase was extracted with $CH_2Cl_2$, and the organic phase was washed with brine, dried over sodium sulfate, and concentrated. Purification by column chromatography afforded the desired product (65% yield).

Step 7: To methyl 4-{2-[2-(2-aminoethyl)-1-benzhydryl-5-chloro-1H-indol-3-yl]ethoxy}benzoate (1.0 equiv) and sat. $NaHCO_3$ (0.14 M) in $CH_2Cl_2$ (0.07 M) was added ▢-toluenesulfonyl chloride (1.0 equiv). After 1 h the mixture was poured into saturated sodium bicarbonate and extracted with $CH_2Cl_2$. The combined organic phase was washed with brine, dried over sodium sulfate and purified by column chromatography (gradient elution using 20% EtOAc-hexanes→50% EtOAc-hexanes) to afford 86% of the desired product.

Step 8: The resulting ester was hydrolyzed by stirring with 1N NaOH (5 equiv) in THF (0.07 M) and enough MeOH to produce a clear solution. The reaction was monitored by TLC (10% MeOH—$CH_2Cl_2$) for the disappearance of starting material. The mixture was heated in a 60 degrees C. oil bath for 2 hour. The mixture was concentrated, diluted with H$_2$O, and acidified to pH 2–4 using 1 M HCl. The aqueous phase was extracted with EtOAc and the organic phase was washed with brine, dried over sodium sulfate, and concentrated to afford the desired product in 92% yield. HRMS calc for [C$_{39}$H$_{35}$ClN$_2$O$_5$.S+H] 679.2028. found 679.2031.

EXAMPLE 2

4-[2-(1-Benzhydryl-5-chloro-2-{2-[(isopropylsulfonyl)amino]ethyl}-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and isopropylsulfonyl chloride according to the procedure in Example 1 Step 7 in 55% yield.

Step 2: The ester intermediate was hydrolyzed according to Step 8 Example 1 to afford the title acid in 81% yield. HRMS calc for [C$_{35}$H$_{35}$ClN$_2$O$_5$.S+H] 631.2028. found 631.2029.

EXAMPLE 3

4-[2-(1-Benzhydryl-2-{2-[(butylsulfonyl)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 1-butanesulfonyl chloride according to the procedure in Example 1 Step 7 in 61% yield.

Step 2: The ester intermediate was hydrolyzed according to Step 8 Example 1 to afford the title acid in 90% yield. HRMS calc for [C$_{36}$H$_{37}$ClN$_2$O$_5$.S+H] 645.2185. found 645.2185.

EXAMPLE 4

4-{2-[1-Benzhydryl-5-chloro-2-(2-{[(1-methyl-1H-imidazol-4-yl)sulfonyl]amino}ethyl)-1H-indol-3-yl]ethoxy}benzoic acid Step 1: To methyl 4-{2-[2-(2-aminoethyl)-1-benzhydryl-5-chloro-1H-indol-3-yl]ethoxy}benzoate (Step 6, Example 1) (1.0 equiv) and Et$_3$N (3.0 equiv) or pyridine (3.0 equiv) in CH$_2$Cl$_2$ (0.05 M) was added 1-methylimidazole-4-sulfonyl chloride (1.2 equiv). The reaction was monitored by TLC (10% MeOH—CH$_2$Cl$_2$) and was heated if necessary. After 30 min the mixture was poured into saturated sodium bicarbonate and extracted with CH$_2$Cl$_2$. The combined organic phase was washed with brine, dried over sodium sulfate and purified by column chromatography to afford 92% of the desired product.

Step 2: The ester intermediate was hydrolyzed according to Step 8 Example 1 to afford the title acid in 89% yield. HRMS calc for [C$_{36}$H$_{33}$ClN$_4$O$_5$.S+H] 669.1933. found 669.1932.

EXAMPLE 5

4-{2-[1-Benzhydryl-2-(2-{[(5-bromo-6-chloro-3-pyridinyl)sulfonyl]amino}ethyl)-5-chloro-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 3-bromo-2-chloropyridine-5-sulfonyl chloride according to the procedure in Example 1 Step 7 in 74% yield.

Step 2: The ester intermediate was hydrolyzed according to Step 8 Example 1 to afford the title acid in 98% yield. HRMS calc for [C$_{37}$H$_{30}$BrCl$_2$N$_3$O$_5$.S+H] 778.0539. found 778.0544.

EXAMPLE 6

4-[2-(1-Benzhydryl-5-chloro-2-{2-[({[(1R)-7,7-dimethyl-2-oxobicyclo[2.2.1]hept-1-yl]methyl}sulfonyl)amino]ethyl}-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and (1R)-(−)-10-camphorsulfonyl chloride according to the procedure in Example 1 Step 7 in 77% yield.

Step 2: The ester intermediate was hydrolyzed according to Step 8 Example 1 to afford the title acid in 94% yield. HRMS calc for [C$_{42}$H$_{43}$ClN$_2$O$_6$.S+H] 739.2603. found 739.26.

EXAMPLE 7

4-(2-{1-Benzhydryl-5-chloro-2-[2-({[(methylsulfonyl)methyl]sulfonyl}amino)ethyl]-1H-indol-3-yl}ethoxy)benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and (methanesulfonyl)methanesulfonyl chloride according to the procedure in Example 4 Step 1 in 43% yield.

Step 2: The ester intermediate was hydrolyzed according to Example 117 Step 2 to afford the title acid in 95% yield. HRMS calc for [C$_{34}$H$_{33}$ClN$_2$O$_7$.S$_2$+H] 681.1491. found 681.1489.

EXAMPLE 8

4-(2-{1-Benzhydryl-5-chloro-2-[2-({[(2-(1-naphthyl)ethyl]sulfonyl}amino)ethyl]-1H-indol-3-yl}ethoxy)benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-(1-naphthyl)ethanesulfonyl chloride according to the procedure Example 1 Step 7 in 60% yield.

Step 2: The ester intermediate was hydrolyzed according to Step 8 Example 1 to afford the title acid in 100% yield. HRMS calc for [C$_{44}$H$_{39}$ClN$_2$O$_5$.S+H] 743.2341. found 743.2338.

EXAMPLE 9

4-{2-[1-Benzhydryl-5-chloro-2-{2-[({2-nitrobenzyl}-sulfonyl)amino]ethyl}-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-nitro-□-toluenesulfonyl chloride according to the procedure in Example 1 Step 7 in 82% yield.

Step 2: The ester intermediate was hydrolyzed according to Step 8 Example 1 to afford the title acid in 85% yield. HRMS calc for [$C_{39}H_{34}ClN_3O_7.S+H$] 724.1879. found 724.1877.

EXAMPLE 10

4-(2-[1-Benzhydryl-5-chloro-2-(2-{[(3,4-dichlorobenzyl)sulfonyl]amino}-ethyl)-1H-indol-3-yl] ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and [(3,4-dichlorophenyl)-methyl]sulfonyl chloride according to the procedure in Example 1 Step 7 in 82% yield.

Step 2: The ester intermediate was hydrolyzed according to Step 8 Example 1 to afford the title acid in 86% yield. HRMS calc for [$C_{39}H_{33}Cl_3N_2O_5.S+H$] 747.1249. found 747.1249.

EXAMPLE 11

4-{2-[1-Benzhydryl-5-chloro-2-(2-{[(3,5-dichlorobenzyl)sulfonyl]amino}-ethyl)-1H-indol-3-yl] ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and [(3,5-dichlorophenyl)-methyl]sulfonyl chloride according to the procedure in Example 1 Step 7 in 100% yield.

Step 2: The ester intermediate was hydrolyzed according to Step 8 Example 1 to afford the title acid in 98% yield. HRMS calc for [$C_{39}H_{33}Cl_3N_2O_5.S+H$] 747.1249. found 747.1249.

EXAMPLE 12

4-(2-(1-Benzhydryl-5-chloro-2-(2-({[(3-(trifluoromethyl)benzyl]sulfonyl}-amino)ethyl]-1H-indol-3-yl}ethoxy)benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and [[3-(trifluoromethyl)-phenyl]methyl]sulfonyl chloride according to the procedure in Example 1 Step 7 in 74% yield.

Step 2: The ester intermediate was hydrolyzed according to Step 8 Example 1 to afford the title acid in 86% yield. HRMS calc for [$C_{40}H_{34}ClF_3N_2O_5S+H$] 747.1902. found 747.1904.

EXAMPLE 13

4-(2-{1-Benzhydryl-5-chloro-2-(2-({[(4-(trifluoromethyl)benzyl]sulfonyl}-amino)ethyl]-1H-indol-3-yl}ethoxy)benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and [[4-(trifluoromethyl)phenyl]methyl]sulfonyl chloride according to the procedure in Example 1 Step 7 in 77% yield.

Step 2: The ester intermediate was hydrolyzed according to Step 8 Example 1 to afford the title acid in 83% yield. HRMS calc for [$C_{40}H_{34}ClF_3N_2O_5S+H$] 747.1902. found 747.1901.

EXAMPLE 14

4-{2-[1-Benzhydryl-5-chloro-2-(2-{[(4-fluorobenzyl)sulfonyl]amino}-ethyl)-1H-indol-3-yl] ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and [(4-fluorophenyl)methyl]sulfonyl chloride according to the procedure in Example 1 Step 7 Step 1 in 86% yield.

Step 2: The ester intermediate was hydrolyzed according to Step 8 Example 1 to afford the title acid in 94% yield. HRMS calc for [$C_{39}H_{34}ClFN_2O_5S+H$] 697.1934. found 697.1938.

EXAMPLE 15

4-{2-[1-Benzhydryl-5-chloro-2-(2-{[(4-chlorobenzyl)sulfonyl]amino}-ethyl)-1H-indol-3-yl] ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and [(4-chlorophenyl-)methyl]sulfonyl chloride according to the procedure in Example 1 Step 7 in 73% yield.

Step 2: The ester intermediate was hydrolyzed according to Step 8 Example 1 to afford the title acid in 99% yield. HRMS calc for [$C_{39}H_{34}Cl_2N_2O_5S+H$] 713.1638. found 713.1643.

EXAMPLE 16

2-(2-{[(2-Aminobenzyl)sulfonyl]amino}ethyl)-4-{2-[1-benzhydryl-5-chloro-1H-indol-3-yl] ethoxy}benzoic acid Step 1: To methyl 4-{2-[1-benzhydryl-5-chloro-2-{2-[2-nitrobenzyl]benzyl}-sulfonyl)amino]ethyl}-1H-indol-3-yl)ethoxy]benzoate, Example 9, step 1, (1.0 equiv) in $CH_2Cl_2$ (0.014 M) was added a mixture of tin(II) chloride dihydrate (3.0 equiv) dissolved in concentrated HCl. After 16 h the mixture was basified (pH 10) with 3 N NaOH and extracted with $CH_2Cl_2$. The combined organic phase was washed with brine, dried over sodium sulfate and purified by column chromatography (gradient elution using 20% EtOAc-hexanes→50% EtOAc-hexanes) to afford 83% of the desired product.

Step 2: The ester intermediate was hydrolyzed according to Step 8 Example 1 to afford the title acid in 83% yield. HRMS calc for [$C_{39}H_{36}ClN_3O_5S+H$] 694.2137. found 694.2136.

EXAMPLE 17

4-{2-[1-Benzhydryl-5-chloro-2-(2-{[(dimethylamino)sulfonyl]amino}ethyl)-1H-indol-3-yl] ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and dimethylsulfamoyl chloride according to the procedure in Example 1 Step 7 in 49% yield.

Step 2: The ester intermediate was hydrolyzed according to Step 8 Example 1 to afford the title acid in 95% yield. HRMS calc for [$C_{34}H_{34}ClN_3O_5S+H$] 632.1981. found 632.1984.

EXAMPLE 18

4-{2-[1-Benzhydryl-5-chloro-2-(2-{[(3,4-difluorobenzyl)sulfonyl]amino}-ethyl)-1H-indol-3-yl]ethoxy}benzoic acid Step 1: To 3,4-difluorobenzyl bromide (1.0 equiv) in $H_2O$ (0.74 M) was added sodium sulfite (1.1 equiv). The mixture was heated to reflux for 16 hours then cooled to room temperature. The white precipitate was filtered and dried to afford 95% of the sodium sulfonate intermediate.

Step 2: To 3,4-difluorobenzyl sodium sulfonate (7.6 equiv) in $CH_2Cl_2$ (0.76 M) was added DMF (5.6 equiv) and $SOCl_2$ (30 equiv). After 1 h the mixture was concentrated and azeotroped with toluene. The residue was suspended in $CH_2Cl_2$ (0.38 M) and methyl 4-{2-[2-(2-aminoethyl)-1-benzhydryl-5-chloro-1H-indol-3-yl]ethoxy}benzoate (Step 6, Example 1) (1.0 equiv) and sat. $NaHCO_3$ (0.76 M) were added. After 1 h the mixture was poured into $H_2O$ and extracted with $CH_2Cl_2$. The combined organic phase was washed with brine, dried over sodium sulfate and purified by column chromatography (gradient elution using 20% EtOAc-hexanes→40% EtOAc-hexanes) to afford 94% of the methyl ester intermediate.

Step 3: The methyl ester was hydrolyzed according to Step 8 Example 1 to afford the title acid in 93% yield. HRMS calc for [$C_{39}H_{33}ClF_2N_2O_5S+H$] 715.184. found 715.1843.

EXAMPLE 19

4-{2-[1-benzhydryl-5-chloro-2-(2-{[(2-naphthylmethyl)sulfonyl]amino}ethyl)-1H-indol-3-yl]ethoxy}benzoic acid Step 1: The sulfonyl chloride intermediate was prepared from 2-(bromomethyl)naphthalene according to the procedure in Example 18 Step 1–2 in 34% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7 in 58% yield.

Step 2: The ester intermediate was hydrolyzed according to Step 8 Example 1 to afford the title acid in 74% yield. HRMS calc for [$C_{43}H_{37}ClN_2O_5S+H$] 729.2185. found 729.2189.

EXAMPLE 20

3-({[(2-[1-benzhydryl-3-[2-(4-carboxyphenoxy)ethyl]-5-chloro-1H-indol-2-yl)ethyl)amino]sulfonyl}methyl)benzoic acid Step 1: The sulfonyl chloride intermediate was prepared from methyl 3-(bromomethyl)benzoate according to the procedure in Example 18 Step 1–2.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7 in 23% yield.

Step 2: The ester intermediate was hydrolyzed according to Step 8 Example 1 to afford the title diacid in 93% yield. HRMS calc for [$C_{40}H_{35}ClN_2O_7S+H$] 723.1926. found 723.1932.

EXAMPLE 21

4-(2-{1-benzhydryl-5-chloro-2-[2-({[(E)-2-phenylethenyl]sulfonyl}amino)ethyl'1H-indol-3-yl}ethoxy)benzoic acid Step 1: To the methyl 4-{2-(2-(2-aminoethyl)-1-benzhydryl-5-chloro-1H-indol-3-yl]ethoxy}benzoate (Step 6, Example 1) was added trans-α-styrenesulfonyl chloride according to the procedure in Example 1 Step 7 to generate the product in 66% yield.

Step 2—The ester intermediate was hydrolyzed according to Step 8 Example 1 to afford the title acid in 98% yield. HRMS calc for [$C_{40}H_{35}ClN_2O_5S+H$] 691.2028. found 691.2034.

EXAMPLE 22

4-{2-[1-benzhydryl-5-chloro-2-(2-{[(trifluoromethyl)sulfonyl]amino)ethyl)-1H-indol-3-yl]ethoxy)benzoic acid Step 1: To the methyl 4-{2-[2-(2-aminoethyl)-1-benzhydryl-5-chloro-1H-indol-3-yl]ethoxy}benzoate (Step 6, Example 1) was added trifluoromethylsulfonyl chloride according to the procedure in Example 1 Step 7 to generate the product in 49% yield.

Step 2—The ester intermediate was hydrolyzed according to Step 8 Example 1 to afford the title acid in 100% yield. HRMS calc for [$C_{33}H_{28}ClF_3N_2O_5S+H$] 657.1432. found 657.1435.

EXAMPLE 23

4-[2-(1-benzhydryl-5-chloro-2-(2-[(cyclopropylsulfonyl)amino]ethyl}-1H-indol-3-yl)ethoxy]benzoic acid Step 1: To the methyl 4-{2-[2-(2-aminoethyl)-1-benzhydryl-5-chloro-1H-indol-3-yl]ethoxy)benzoate (Step 6, Example 1) was added cyclopropanesulfonyl chloride according to the procedure in Example 1 Step 7 to generate the product in 75% yield.

Step 2—The ester intermediate was hydrolyzed according to Step 8 Example 1 to afford the title acid in 84% yield. HRMS calc for [$C_{35}H_{33}ClN_2O_5S+H$] 629.1872. found 629.1874.

EXAMPLE 24

4-(2-{1-benzhydryl-2-[(2-({[3,5-bis(trifluoromethyl)benzyl]sulfonyl}amino)ethyl]-5-chloro-1H-indol-3-yl}ethoxy)benzoic acid Step 1: To the methyl 4-{2-[2-(2-aminoethyl)-1-benzhydryl-5-chloro-1H-indol-3-yl]ethoxy}benzoate (Step 6, Example 1) was added 3,5-bis(trifluoromethyl)benzylsulfonyl according to the procedure in Example 1 Step 7 to generate the product in 79% yield.

Step 2—The ester intermediate was hydrolyzed according to Step 8 Example 1 to afford the title acid in 81% yield. HRMS calc for [$C_{41}H_{33}ClF_6N_2O_5S+H$] 815.1776. found 815.1776.

EXAMPLE 25

2-{[(2-{1-benzhydryl-3-[2-(4-carboxyphenoxy)ethyl]-5-chloro-1H-indol-2-yl}ethyl)amino]sulfonyl}benzoic acid Step 1: To the methyl 4-{2-[2-(2-aminoethyl)-1-benzhydryl-5-chloro-1H-indol-3-yl]ethoxy}benzoate (Step 6, Example 1) was added methyl (2-chlorosulfonyl)benzoate according to the procedure in Example 1 Step 7 to generate the product in 100% yield.

Step 2—The ester intermediate was hydrolyzed according to Step 8 Example 1 to afford the title acid in 61% yield. HRMS calc for $[C_{39}H_{33}ClN_2O_7S+H]$ 709.177. found 709.1772.

EXAMPLE 26

4-[2-(1-benzhydryl-5-chloro-2-{2-[(2-naphthylsulfonyl)amino]ethyl}-1H-indol-3-yl)ethoxy]benzoic acid Step 1: To the methyl 4-{2-[2-(2-aminoethyl)-1-benzhydryl-5-chloro-1H-indol-3-yl]ethoxy}benzoate (Step 6, Example 1) was added 2-naphthalenesulfonyl chloride according to the procedure in Example 1 Step 7 to generate the product in 53% yield.

Step 2—The ester intermediate was hydrolyzed according to Step 8 Example 1 to afford the title acid in 100% yield. HRMS calc for $[C_{42}H_{35}ClN_2O_5S+H]$ 715.2028. found 715.2034.

EXAMPLE 27

4-(2-[1-benzhydryl-5-chloro-2-(2-{[(3,5-dichlorophenyl)sulfonyl]amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 6, Example 1) was added 3,5-dichlorobenzenesulfonyl chloride according to the procedure in Example 1 Step 7 to generate the product in 60% yield.

Step 2—The ester intermediate was hydrolyzed according to Step 8 Example 1 to afford the title acid in 88% yield. HRMS calc for $[C_{38}H_{31}Cl_3N_2O_5S+H]$ 733.1092. found 733.1096.

EXAMPLE 28

4-{2-[1-benzhydryl-5-chloro-2-(2-{[(3,4-dichlorophenyl)sulfonyl]amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 6, Example 1) was added 3,4-dichlorobenzenesulfonyl chloride according to the procedure in Example 1 Step 7 to generate the product in 60% yield.

Step 2—The ester intermediate was hydrolyzed according to Step 8 Example 1 to afford the title acid in 80% yield. HRMS calc for $[C_{38}H_{31}Cl_3N_2O_5S+H]$ 733.1092. found 733.1094.

EXAMPLE 29

4-{2-[1-benzhydryl-5-chloro-2-(2-{[(2,3-dichlorobenzyl)sulfonyl]amino}ethyl)-1H indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 6, Example 1) was added (2,3-dichlorophenyl)-methyl]sulfonyl chloride according to the procedure in Example 1 Step 7 to generate the product in 50% yield.

Step 2—The resulting ester was hydrolyzed by stirring with KOH (67 mg, 5 equiv.) in THF (5 mL) MeOH (5 mL) and H$_2$O (2 mL). The reaction was monitored by TLC (10% MeOH—CH$_2$Cl$_2$) for the disappearance of starting material. The mixture was stirred overnight at room temperature and then concentrated, diluted with H$_2$O, and acidified to pH 2–4 using 1 M HCl. The aqueous phase was extracted with EtOAc and the organic phase was washed with brine, dried over sodium sulfate, and concentrated to afford the desired product in 98% yield. HRMS calc for $[C_{39}H_{33}Cl_3N_2O_5S+H]$ 747.1249. found 747.1254.

EXAMPLE 30

4-{2-[1-benzhydryl-5-chloro-2-(2-{[(2,4-dichlorobenzyl)sulfonyl]amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 6, Example 1) was added (2,4-dichlorophenyl)-methyl]sulfonyl chloride according to the procedure in Example 1 Step 7 to generate the product in 98% yield.

Step 2—The ester intermediate was hydrolyzed according to Step 2 Example 29 to afford the title acid in 90% yield. HRMS calc for $[C_{39}H_{33}Cl_3N_2O_5S+H]$ 747.1249. found 747.1255.

EXAMPLE 31

4-{2-[1-benzhydryl-5-chloro-2-(2-{[(2,4-dichlorobenzyl)sulfonyl]amino}ethyl)-1H indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 6, Example 1) was added (2-chlorophenyl)-methyl]sulfonyl chloride according to the procedure in Example 1 Step 7 to generate the product in 86% yield.

Step 2—The ester intermediate was hydrolyzed according to Step 2 Example 29 to afford the title acid in 90% yield. HRMS calc for $[C_{39}H_{34}Cl_2N_2O_5S+H]$ 713.1638. found 713.1644.

EXAMPLE 32

4-(2-[1-benzhydryl-5-chloro-2-(2-{[(4-chloro-2-nitrobenzyl)sulfonyl]amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 6, Example 1) was added [(4-chloro-2-nitro)-methyl]sulfonyl chloride according to the procedure in Example 1 Step 7 to generate the product in 74% yield.

Step 2—The ester intermediate was hydrolyzed according to Step 2 Example 29 to afford the title acid in 90% yield. HRMS calc for [$C_{39}H_{33}Cl_2N_3O_7S+H$] 758.1489. found 758.1494.

Method I

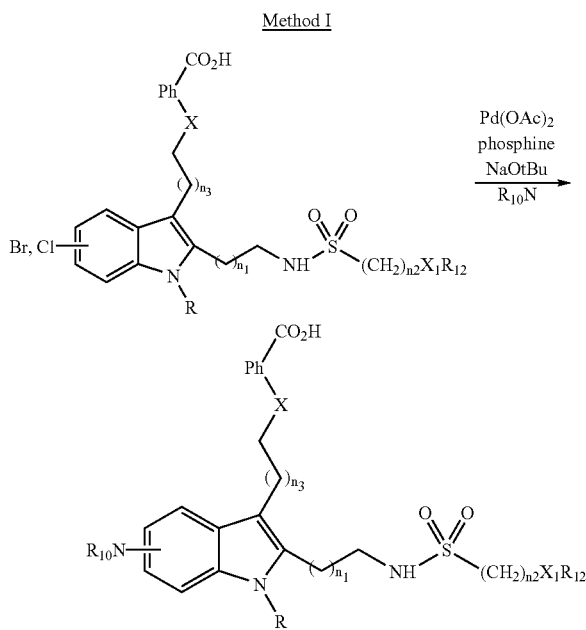

The acid resulting from Method A, or any subsequent method could be used as a subtrate for palladium catalyzed amination reaction using a base, an amine, a phosphine ligand and palladium reagent.

EXAMPLE 33

4-[2-(1-benzhydryl-2-{2-[(benzylsulfonyl)amino] ethyl}-5-morpholin-4-yl-1H-indol-'3-yl)ethoxy]benzoic acid Step 1—A flask was charged with tris(dibenzylideneacetone) dipalladium(0) (0.01 eq.), 2-(di-t-butylphosphino)biphenyl (0.04 eq.), sodium t-butoxide (2.4 eq.) and the acid from step 8 (1.0 eq.). 1.5 ml toluene (1.0 M) was added to the flask followed by morpholine (1.2 eq.) The reaction was heated to reflux for five hours. The reaction mixture was partitioned between 5% hydrochloric acid and dietheyl ether. The organic layer was washed with distilled water, followed by brine, dried over sodium sulfate and concentrated. The product was purified by preparatory LC-MS to afford 7.8% of the desired product. HRMS calc for [$C_{43}H_{43}N_3O_6S+H$] 730.2945. found 730.2945.

EXAMPLE 34

4-{2-[1-Benzhydryl-5-chloro-2-(2-{[(2-cyanobenzyl)sulfonyl]amino}ethyl)-1H-indol-3-yl] ethoxy}benzoic acid Step 1: (2-Cyano-phenyl)-methanesulfonyl chloride was prepared according to Example 18 Step 1–2 (crude yield 100%).
Step 2: The title compound was prepared from 4-{2-[2-(2-amino-ethyl)-1-benzhydryl-5-chloro-1H-indol-3-yl]-ethoxy}-benzoic acid methyl ester (Step 6, Example 1) and (2-cyano-phenyl)-methanesulfonyl chloride according to Example 1 Step 7 as a white solid in 72% yield.
Step 3—The ester intermediate was hydrolyzed according to Step 8 Example to afford the title acid in 74% yield. MS (ES) m/z (M−1) 702.0; HRMS Calcd. for $C_{40}H_{35}ClN_3O_5S$ (M+1): 704.1980. Found: 704.1984. Anal. Calcd. for $C_{40}H_{34}ClN_3O_5S$: C, 68.22; H, 4.87; N, 5.97. Found: C, 67.92; H, 5.11; N, 5.54.

EXAMPLE 35

4-{2-[1-benzhydryl-5-chloro-2-(2-{[(3,5-difluorobenzyl)sulfonyl]amino}ethyl)-1H-indol-3-yl] ethoxy}benzoic acid Step 1: The sulfonyl chloride intermediate was prepared from 3,5-difluorobenzyl bromide according to the procedure in Example 18 Step 1–2 in 95% yield.
Step 2: The methyl ester was prepared from the sulfonyl chloride and methyl 4-{2-[2-(2-aminoethyl)-1-benzhydryl-5-chloro-1H-indol-3-yl]ethoxy)benzoate (Step 6, Example 1) according to the procedure in Example 1 Step 7 in 78% yield.
Step 2: The ester intermediate was hydrolyzed according to Step 8 Example 1 to afford the title diacid in 83% yield. HRMS calc for [$C_{39}H_{33}ClF_2N_2O_5S+H$] 715.184. found 715.1842.

EXAMPLE 36

4-{2-[1-Benzhydryl-5-chloro-2-(2-{[(3-cyanobenzyl)sulfonyl]amino}ethyl)-1H-indol-3-yl] ethoxy}benzoic acid Step 1: (3-Cyano-phenyl)-methanesulfonyl chloride was prepared according to Example 18 Step 1–2 (crude yield 100%).
Step 2: The title compound was prepared from 4-{2-[2-(2-amino-ethyl)-1-benzhydryl-5-chloro-1H-indol-3-yl]-ethoxy}-benzoic acid methyl ester (Step 6, Example 1) and (3-cyano-phenyl)-methanesulfonyl chloride according to Example 1 Step 7.
Step 3—The ester intermediate was hydrolyzed according to Step 8 Example 1 to afford the title acid in 81% yield. MS (ES) m/z (M−1) 702.1; HRMS Calcd. for $C_{40}H_{33}ClN_3O_5S$ (M−1): 702.1834. Found: 702.1833. Anal. Calcd. for $C_{40}H_{34}ClN_3O_5S \cdot 0.8H_2O$: C, 67.00; H, 5.00; N, 5.86. Found: C, 67.22; H, 5.19; N, 5.44.

EXAMPLE 37

4-{2-[1-Benzhydryl-5-chloro-2-(2-{[(4-cyanobenzyl)sulfonyl]amino}ethyl)-1H-indol-3-yl] ethoxy}benzoic acid Step 1 (4-Cyano-phenyl)-methanesulfonyl chloride was prepared according to Example 18 Step 1–2 (crude yield 100%).
Step 2: The title compound was prepared from 4-{2-[2-(2-amino-ethyl)-1-benzhydryl-5-chloro-1H-indol-3-yl]-ethoxy}-benzoic acid methyl ester (Step 6, Example 1) and (4-cyano-phenyl)-methanesulfonyl chloride according to Example 1 Step 7.
Step 3—The ester intermediate was hydrolyzed according to Step 8 Example 1 to afford the title acid in 77% yield. MS (ES) m/z (M−1) 702.1; HRMS Calcd. for $C_{40}H_{35}ClN_3O_5S$ (M+1): 704.1980. Found: 704.1981. Anal. Calcd. for $C_{40}H_{34}ClN_3O_5S$: C, 68.22; H, 4.87; N, 5.97. Found: C, 68.09; H, 4.97; N, 5.73.

EXAMPLE 38

4-(2-{1-Benzhydryl-5-chloro-2-[2-({[4-(1piperidinylsulfonyl)benzyl]sulfonyl}amino)ethyl]-1H-indol-3-yl}ethoxy)benzoic acid Step 1: [4-(Piperidine-1-sulfonyl)-phenyl]-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy}-benzoic acid methyl ester (Step 6, Example 1) and 4-(Piperidine-1-sulfonyl)-phenyl]-methanesulfonyl according to Example 1 Step 7.

Step 3—The ester intermediate was hydrolyzed according to Step 8 Example 1 to afford the title acid in 73% yield. MS (ES) m/z (M−1) 824.2; HRMS Calcd. for $C_{44}H_{43}ClN_3O_7S_2$ (M−1): 824.2236. Found: 824.2246. Anal. Calcd. for $C_{44}H_{44}ClN_3O_7S_2.0.5H_2O$: C, 63.25; H, 5.43; N, 5.03. Found: C, 62.85; H, 5.64; N, 4.64.

EXAMPLE 39

4-(2-{2-[2-({[4-(Aminosulfonyl)benzyl]sulfonyl}-amino)ethyl]-1-benzhydryl-5-chloro-1H-indol-3-yl}ethoxy)benzoic acid Step 1: (4-Sulfamoyl-phenyl)-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy}-benzoic acid methyl ester (Step 6, Example 1) and (4-Sulfamoyl-phenyl)-methanesulfonyl chloride according to Example 1 Step 7.

Step 3—The ester intermediate was hydrolyzed according to Step 8 Example 1 to afford the title acid in 69% yield. MS (ES) m/z (M−1) 755.9; HRMS Calcd. for $C_{39}H_{35}ClN_3O_7S_2$ (M−1): 756.1613. Found: 756.1612. Anal. Calcd. for $C_{39}H_{36}ClN_3O_7S_2$: C, 61.77; H, 4.79; N, 5.54. Found: C, 61.93; H, 5.12; N, 5.19.

EXAMPLE 40

4-(2-{1-Benzhydryl-5-chloro-2-[2-(4-methanesulfonyl-phenylmethanesulfonylamino)-ethyl]-1H-indol-3-yl}-ethoxy)-benzoic acid Step 1: ((4-Methanesulfonyl-phenyl)-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy}-benzoic acid methyl ester (Step 6, Example 1) ((4-Methanesulfonyl-phenyl)-methanesulfonyl chloride according to Example 1 Step 7.

Step 3—The ester intermediate was hydrolyzed according to Step 8 Example 1 to afford the title acid in 75% yield. MS (ES) m/z (M−1) 755.0; HRMS Calcd. for $C_{40}H_{38}ClN_2O_7S_2$ (M+1): 757.1804. Found: 757.1804. Anal. Calcd. for $C_{40}H_{37}ClN_2O_7S_2.H_2O$: C, 61.96; H, 5.07; N, 3.61. Found: C, 61.82; H, 5.10; N, 3.48.

EXAMPLE 41

4-(2-{1-Benzhydryl-5-chloro-2-[2-(4-diethylsulfamoyl-phenylmethanesulfonylamino)-ethyl]-1H-indol-3-yl}-ethoxy)-benzoic acid Step 1: (4-Diethylsulfamoyl-phenyl)-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy}-benzoic acid methyl ester (Step 6, Example 1) and (4-Diethylsulfamoyl-phenyl)-methanesulfonyl chloride according to Example 1 Step 7.

Step 3—The ester intermediate was hydrolyzed according to Step 8 Example 1 to afford the title acid in 66% yield. MS (ES) m/z (M−1) 812.1; HRMS Calcd. for $C_{43}H_{45}ClN_3O_7S_2$ (M+1): 814.2382. Found: 814.2385. Anal. Calcd. for $C_{43}H_{44}ClN_3O_7S_2.0.3H_2O$: C, 62.99; H, 5.48; N, 5.14. Found: C, 62.91; H, 5.67; N, 4.79.

EXAMPLE 42

4-{3-[1-Benzhydryl-5-chloro-2-(2-phenylmethane-sulfonylamino-ethyl)-1H-indol-3-yl]-propyl}-benzoic acid Step 1: A mixture of methyl-4-iodobenzoate (5.3 g, 20.2 mmol), allyl alcohol (1.78 g, 30.3 mmol), $NaHCO_3$ (4.24 g, 50.5 mmol), $Pd(OAc)_2$ (0.14 g, 0.60 mmol), (n-Bu)$_4$NBr (6.55 g, 20.2 mmol) and 4-A molecular Sieves (4.1 g) in anhydrous DMF (69 mL) was stirred at room temperature for 4 days. The reaction mixture was filtered through celite and the filtrate poured onto water and extracted with EtOAc. Organic layer was washed with brine, dried ($Na_2SO_4$), and concentrated under vacuum. Flash chromatography (silica gel, 10–20% EtOAc-hexanes) gave 2.11 g (85% based on the recovered starting material) of the desired 4-(3-Oxo-propyl)-benzoic acid methyl ester as a clear oil.

Step 2: To a solution of 5-chloro-2-methylindole (0.86 g, 5.2 mmol) and 4-(3-Oxo-propyl)-benzoic acid methyl ester (1.0 g, 5.2 mmol) in methylene chloride (50 mL), was added TFA (1.78 g, 15.6 mmol), followed by triethylsilane (1.81 g, 15.6 mmol). The reaction mixture was stirred overnight, quenched with sat. $NaHCO_3$ solution (50 mL), and the organic layer was washed with sat. $NaHCO_3$ solution, water, brine, and dried ($Na_2SO_4$). Solvent was removed under reduced pressure, and the residue was purified by flash column chromatography with 10–20% EtOAc/hexanes to yield the desired product in 94% (1.67 g) yield.

Step 3: To a solution of the product from step 2 (1.66 g, 4.86 mmol) in DMF (20 mL) was added NaH (60% in mineral oil, 0.24 g, 5.83 mmol) under $N_2$ atmosphere. The mixture was stirred for 1 h at room temperature, followed by the dropwise addition of benzhydryl bromide (1.8 g, 7.29 mmol) in DMF (5 mL). This reaction mixture was stirred overnight at room temperature. Water (500 mL) was added to reaction mixture, it was extracted with EtOAc, washed with brine, dried ($Na_2SO_4$), and concentrated under reduced pressure to a brown syrup, which was purified by silica-gel chromatography using 10% EtOAc/hexanes as eluent to isolate 4 as a white solid in 59% (1.47 g) yield.

Step 4: The product from above (1.46 g, 2.87 mmol) was dissolved in $CCl_4$ (14.5 mL), followed by the addition of NBS (1.02 g, 5.73 mmol) and benzoyl peroxide (2 mg). The reaction mixture was heated to reflux for 1 h (until all the starting material disappeared). This mixture was cooled to room temperature, filtered and the solid was washed with CCl$_4$. The filtrate was evaporated to a brown residue, which was dissolved in acetone (40 mL) and water (4 mL), Ag$_2$CO$_3$ (1.75 g, 3.16 mmol) was then added to this solution and after being stirred overnight at room temperature, it was filtered through celite, the solvent was evaporated under reduced pressure, and water was added to the residue. It was extracted with EtOAc, washed with brine, dried (Na$_2$SO$_4$), and evaporated to a syrup, which was purified by 10% EtOAc/hexanes to isolate the 2-formyl indole (1.13 g) in 75% yield. Alternatively the dibromide from the reaction with NBS could be poured into DMSO (10–20% concentration by weight) and stirred for 30 minutes at room temperature. When the reaction was deemed complete it was poured into water and the resulting precipitate was isolated by filtration, the cake was washed with water and dried to yield an essentially quantitative yield.

Step 5: To a solution of the 2 formyl indole from above (0.52 g, 1 mmol) in CH$_3$NO$_2$ (6.2 mL) was added NH$_4$OAC (0.077 g, 1 mmol), the mixture was heated to reflux for 1 h, NH$_4$OAc (0.077 g, 1 mmol) was then added, heating at reflux was continued for an additional 1 h, NH$_4$Oac (0.077 g, 1 mmol) was added again and the heating continued for further 1 h. The reaction mixture was allowed to attain room temperature, EtOAc (50 mL) was added, followed by the addition of 100 mL water. The aqueous layer was extracted with EtOAc, and the combined organic layers were washed with brine, dried (Na$_2$SO$_4$), and evaporated to a yellow foam, which was subjected to chromatographic purification using 10% EtOAc/hexanes as an eluent to yield 6 as a yellow foam in 68% yield (0.38 g).

Step 6: Zn(Hg) was made by adding HgCl$_2$ (3.4 g, 7.2 mmol) to a mixture of Zn-dust (34.68 g, 530.35 mmol) and 5% HCl (38 mL) in a 100 mL beaker, this mixture was stirred vigorously for 10 min. Aqueous phase was decanted and added 38 mL of 5% HCl again and the mixture was stirred for 10 min. Aqueous phase was decanted. This solid was added to the vinyl nitro compound 6 (15 g, 26.57 mmol) in THF (660 mL) and conc. HCl (64.5 mL). This mixture was stirred at room temperature for 1 h, then at reflux for 15 min. The reaction mixture was cooled to room temperature and filtered through celite. Aq. NH$_4$OH solution (200 mL) was added to the filtrate, stirred for 15 min and THF was removed under reduced pressure. The aqueous layer was extracted with CH$_2$Cl$_2$, combined organic layer was washed with brine, dried (Na2SO4) and concentrated to a brown foam, which was purified by column chromatography by eluting the column with CHCl$_3$ in the beginning to remove non-polar impurities then with 2% MeOH/CHCl$_3$ to isolate the desired amine in 46% yield (6.1 g)

Step 7: To the amine (1.0 equiv.) and sat. NaHCO$_3$ (0.14 M) in CH$_2$Cl$_2$ (0.07 M) was added □-toluenesulfonyl chloride (1.0 equiv.). After 1 h the mixture was poured into saturated sodium bicarbonate and extracted with CH$_2$Cl$_2$. The combined organic phase was washed with brine, dried over sodium sulfate and purified by column chromatography to afford 84% of the desired product.

Step 8: The resulting ester was hydrolyzed by stirring with 1N NaOH (5 equiv.) in THF (0.07 M) and enough MeOH to produce a clear solution. The reaction was monitored by TLC (10% MeOH—CH$_2$Cl$_2$) for the disappearance of starting material. The mixture was stirred overnight at room temperature and then concentrated, diluted with H$_2$O, and acidified to pH 2–4 using 1 M HCl. The aqueous phase was extracted with EtOAc and the organic phase was washed with brine, dried over sodium sulfate, and concentrated to afford the desired product in 100% yield. HRMS calc for [C$_{40}$H$_{37}$ClN$_2$O$_4$S+H] 677.2235. found 677.224.

EXAMPLE 43

4-{3-[1-benzhydryl-5-chloro-2-(2-{[(3,5-dichlorobenzyl)sulfonyl]amino}ethyl)-1H-indol-3-yl]propyl}benzoic acid Step 1: This compound was prepared from the intermediate in Example 42 step 6 and (3,5-dichlorophenyl)-methyl]sulfonyl chloride according to the procedure in Example 43 Step 7 which yielded 98% of the desired product.

Step 2: The ester intermediate was hydrolyzed according to Step 8 Example 42 to afford the title acid in 100% yield. HRMS calc for [C$_{40}$H$_{35}$Cl$_3$N$_2$O$_4$S+H] 745.1456. found 745.1458.

EXAMPLE 44

4-{3-[1-benzhydryl-5-chloro-2-(2-{[(3,4-dichlorobenzyl)sulfonyl]amino}ethyl)-1H-indol-3-yl]propyl)benzoic acid Step 1: This compound was prepared from the intermediate in Example 42 step 6 and (3,4-dichlorophenyl)-methyl]sulfonyl chloride according to the procedure in Example 43 Step 7 which yielded 96% of the desired product.

Step 2: The ester intermediate was hydrolyzed according to Step 8 Example 42 to afford the title acid in 98% yield. HRMS calc for [C$_{40}$H$_{35}$Cl$_3$N$_2$O$_4$S+H] 745.1456. found 745.1458.

EXAMPLE 45

4-[2-(1-benzhydryl-5-chloro-2-(2-[(methylsulfonyl)amino]ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 6, Example 1) was added methanesulfonyl chloride according to the procedure in Example 4 Step 1 to generate the product in 92% yield.

Step 2: The ester intermediate was hydrolyzed according to Step 8 Example 1 to afford the title acid in 100% yield. HRMS calc for [C$_{33}$H$_{31}$ClN$_2$O$_5$S+H] 603.1715. found 603.1717.

EXAMPLE 46

4-[2-(1-benzhydryl-5-chloro-2-{2-[(phenylsulfonyl)amino]ethyl}-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 6, Example 1) was added benzenesulfonyl chloride according to the procedure in Example 4 Step 1 to generate the product in 90% yield.

Step 2: The ester intermediate was hydrolyzed according to Step 8 Example 1 to afford the title acid in 90% yield. HRMS calc for [C$_{38}$H$_{33}$ClN$_2$O$_5$S+H] 665.1872. found 665.1869.

EXAMPLE 47

4-(2-{1-benzhydryl-5-chloro-2-[2-({[3-(trifluorom-ethyl)benzyl]sulfonyl}amino)ethyl]-1H-indol-3-yl}ethoxy)benzoic acid Step 1: To the methyl 4-{2-[2-(2-aminoethyl)-1-benzhydryl-5-chloro-1H-indol-3-yl]ethoxy}benzoate (Step 6, Example 1) was added {[3-(trifluoromethyl)phenyl]methyl}sulfonyl chloride according to the procedure in Example 1 Step 7 to generate the product in 74% yield.

Step 2: The ester intermediate was hydrolyzed according to Step 8 Example 1 to afford the title acid in 86% yield. HRMS calc for $[C_{40}H_{34}ClF_3N_2O_5S+H]$ 747.1902. found 747.1904.

EXAMPLE 48

2-{[(2-{[(2-{1-benzhydryl-3-[2-(4-carboxyphenoxy)ethyl]-5-chloro-1H-indol-2-yl}ethyl)amino]sulfonyl}ethyl)amino]carbonyl}benzoic acid Step 1: To the methyl 4-{2-[2-(2-aminoethyl)-1-benzhydryl-5-chloro-1H-indol-3-yl]ethoxy}benzoate (Step 6, Example 1) was added 2-phthalimidoethanesulfonyl chloride according to the procedure in Example 1 Step 7 to generate the product in 78% yield.

Step 2: The ester intermediate was hydrolyzed according to Step 8 Example 1 to afford the title acid in 99% yield. HRMS calc for $[C_{42}H_{38}ClN_3O_8S+H]$ 780.2141. found 780.2148.

EXAMPLE 49

4-{2-[{1-benzhydryl-5-chloro-2-(2-{[(3-(pyridinyl-methyl)sulfonyl]amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 6, Example 1) was added (3-pyridylmethyl)sulfonyl chloride according to the procedure in Example 1 Step 7 to generate the product in 52% yield.

Step 2: The ester intermediate was hydrolyzed according to Step 8 Example 1 to afford the title acid in 94% yield. HRMS calc for $[C_{38}H_{34}ClN_3O_5S-H]$ 678.18349. found 678.18277.

EXAMPLE 50

4-{2-[{1-benzhydryl-5-chloro-2-(2-{[(4-(pyridinyl-methyl)sulfonyl]amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 6, Example 1) was added (4-pyridylmethyl)sulfonyl chloride according to the procedure in Example 1 Step 7 to generate the product in 57% yield.

Step 2: The ester intermediate was hydrolyzed according to Step 8 Example 1 to afford the title acid in 100% yield. m/z (M−1) HRMS calc for $[C_{38}H_{34}ClN_3O_5S-H]$ 678.18349. found 678.18249.

EXAMPLE 51

4-{2-[{1-benzhydryl-5-chloro-2-(2-{[(2-(pyridinyl-methyl)sulfonyl]amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 6, Example 1) was added (2-pyridylmethyl)sulfonyl chloride according to the procedure in Example 1 Step 7 to generate the product in 42% yield.

Step 2: The ester intermediate was hydrolyzed according to Step 8 Example 1 to afford the title acid in 56% yield. HRMS calc for $[C_{38}H_{34}ClN_3O_5S-H]$ 678.18349. found 678.18312.

EXAMPLE 52

4-{3-[1-benzhydryl-5-chloro-2-(2-{[(2,6-dimethyl-benzyl)sulfonyl]amino}ethyl)-1H-indoly-3-yl]propyl}benzoic acid Step 1: The sulfonyl chloride intermediate was prepared from 2,6-dimethylbenzyl chloride according to the procedure in Example 18 Step 1–2 in 100% yield.

Step 2: The methyl ester was prepared from the sulfonyl chloride and the intermediate in Example 42 step 6 according to the procedure in Example 42 Step 7 in 30% yield.

Step 3: The ester intermediate was hydrolyzed according to Step 8 Example 42 to afford the title acid in 100% yield. HRMS calc for $[C_{42}H_{41}ClN_2O_4S-H]$ 703.24028. found 703.23973.

EXAMPLE 53

4-{2-[1-benzhydryl-5-chloro-2-(2-{[(cyclohexylm-ethyl)sulfonyl]amino}ethyl)-1H-indol-3-yl]ethoxy}benzoic acid Step 1: The sulfonyl chloride intermediate was prepared from (bromomethyl)cyclohexane according to the procedure in Example 18 Step 1–2 in 100% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7 in 20% yield.

Step 3: The ester intermediate was hydrolyzed according to Step 8 Example 1 to afford the title acid in 73% yield. HRMS calc for $[C_{39}H_{41}ClN_2O_5S-H]$ 683.23519. found 683.23474.

EXAMPLE 54

4-{2-[1-benzhydryl-5-chloro-2-(2-{[(4-nitrobenzyl)sulfonyl]amino}ethyl)-1H-indol-3-yl]ethoxy}benzoic acid Step 1: The sulfonyl chloride intermediate was prepared from 4-nitrobenzyl bromide according to the procedure in Example 18 Step 1–2 in 95% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7 in 80% yield.

Step 3: The ester intermediate was hydrolyzed according to Step 8 Example 1 to afford the title compound in 90% yield. HRMS calc for $[C_{39}H_{34}ClN_3O_7S+H]$ 724.1879. found 724.1884.

EXAMPLE 55

4-{2-[1-benzhydryl-5-chloro-2-(2-{[(3-nitrobenzyl)sulfonyl]amino}ethyl)-1H-indol-3-yl]ethoxy}benzoic acid Step 1: The sulfonyl chloride intermediate was prepared from 3-nitrobenzyl bromide according to the procedure in Example 18 Step 1–2 in 95% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7 in 85% yield.

Step 3: The ester intermediate was hydrolyzed according to Step 8 Example 1 to afford the title compound in 85% yield. HRMS calc for $[C_{39}H_{34}ClN_3O_7S+H]$ 724.1879. found 724.1885.

EXAMPLE 56

4-{2-[1-Benzhydryl-5-chloro-2-{2-[({2-nitrobenzyl}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 2-nitro-□-toluenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for $[C_{40}H_{36}ClN_3O_6S+H]$ 722.2086. found 722.2088.

EXAMPLE 57

4-{3-[1-benzhydryl-5-chloro-2-(2-{[(4-fluorobenzyl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 42) was added and (4-Fluoro-phenyl)-methanesulfonyl chloride according to the procedure in Example 1 Step 7 to generate the product in 77% yield.

Step 2: The ester intermediate was hydrolyzed according to Step 8 Example 1 to afford the title acid in 68% yield. HRMS calc for $[C_{40}H_{36}ClFN_2O_4S+H]$ 695.2141. found 695.2145.

EXAMPLE 58

4-(3-[1-benzhydryl-5-chloro-2-[2-({[4-(trifluoromethyl)benzyl]sulfonyl}amino)ethyl]-1H-indol-3-yl}propyl)benzoic acid Step 1: To the methyl 4-{2-[2-(2-aminoethyl)-1-benzhydryl-5-chloro-1H-indol-3-yl]propyl}benzoate (Step 6, Example 42) was added and (4-Trifluoromethyl-phenyl)-methanesulfonyl chloride according to the procedure in Example 1 Step 7 to generate the product in 50% yield.

Step 2: The ester intermediate was hydrolyzed according to Step 8 Example 1 to afford the title acid in 100% yield. HRMS calc for $[C_{41}H_{36}ClF_3N_2O_4S+H]$ 745.2109. found 745.2114.

EXAMPLE 59

4-(3-{1-benzhydryl-5-chloro-2-[2-({[3-(trifluoromethyl)benzyl]sulfonyl}amino)ethyl]-1H-indol-3-yl}propyl)benzoic acid Step 1: To methyl 4-{2-[2-(2-aminoethyl)-1-benzhydryl-5-chloro-1H-indol-3-yl]propyl}benzoate (Step 6, Example 42) was added and (3-Trifluoromethyl-phenyl)-methanesulfonyl chloride according to the procedure in Example 1 Step 7 to generate the product in 56% yield.

Step 2: The ester intermediate was hydrolyzed according to Step 8 Example 1 to afford the title acid in 82% yield. HRMS calc for $[C_{41}H_{36}ClF_3N_2O_4S+H]$ 745.2109. found 745.211.

EXAMPLE 60

4-{3-[1-benzhydryl-5-chloro-2-(2-{[(4-chlorobenzyl)sulfonyl]amino}ethyl)-1H-indol-3-yl]propyl}benzoic acid Step 1: To the methyl methyl 4-{2-[2-(2-aminoethyl)-1-benzhydryl-5-chloro-1H-indol-3-yl]propyl}benzoate (Step 6, Example 42) was added and (4-chlorophenyl)-methanesulfonyl chloride according to the procedure in Example 1 Step 7 to generate the product in 74% yield.

Step 2: The ester intermediate was hydrolyzed according to Step 8 Example 1 to afford the title acid in 79% yield. HRMS calc for $[C_{40}H_{36}Cl_2N_2O_4S+H]$ 711.1846. found 711.1847.

EXAMPLE 61

4-{3-[1-benzhydryl-5-chloro-2-(2-{[(2-pyridinylmethyl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 42) was added pyridin-2-yl-methanesulfonyl chloride chloride according to the procedure in Example 4 Step 1 to generate the product in 75% yield.

Step 2: The ester intermediate was hydrolyzed according to Step 8 Example 1 to afford the title acid in 96% yield. HRMS calc for $[C_{39}H_{36}ClN_3O_4S+H]$ 678.2188. found 678.2187.

EXAMPLE 62

4-{3-[1-benzhydryl-5-chloro-2-(2-{[(3-pyridinylmethyl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 42) was added pyridin-3-yl-methanesulfonyl chloride chloride according to the procedure in Example 4 Step 1 to generate the product in 75% yield.

Step 2: The ester intermediate was hydrolyzed according to Step 8 Example 1 to afford the title acid in 88% yield.

EXAMPLE 63

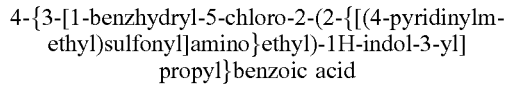
4-{3-[1-benzhydryl-5-chloro-2-(2-{[(4-pyridinylmethyl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 42) was added pyridin-4-yl-methanesulfonyl chloride chloride according to the procedure in Example 4 Step 1 to generate the product in 75% yield.

Step 2: The ester intermediate was hydrolyzed according to Step 8 Example 1 to afford the title acid in 77% yield. HRMS calc for $[C_{39}H_{36}ClN_3O_4S-H]$ 676.20423. found 676.20405.

EXAMPLE 64

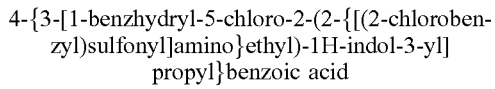
4-{3-[1-benzhydryl-5-chloro-2-(2-{[(2-chlorobenzyl)sulfonyl]amino}ethyl)-1H-indol-3-yl]propyl}benzoic acid Step 1: The sulfonyl chloride intermediate was prepared from 3-chlorobenzyl bromide according to the procedure in Example 18 Step 1–2.

Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 10% yield.

Step 3: The ester intermediate was hydrolyzed according to Step 8 Example 1 to afford the title compound in 100% yield. HRMS calc for $[C_{40}H_{36}Cl_2N_2O_4S-H]$ 709.17000. found 709.16961.

EXAMPLE 65

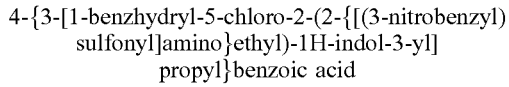
4-{3-[1-benzhydryl-5-chloro-2-(2-{[(3-nitrobenzyl)sulfonyl]amino}ethyl)-1H-indol-3-yl]propyl}benzoic acid Step 1: The sulfonyl chloride intermediate was prepared from 3-nitrobenzyl bromide according to the procedure in Example 18 Step 1–2.

Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 43% yield.

Step 3: The ester intermediate was hydrolyzed according to Step 8 Example 1 to afford the title compound in 88% yield. HRMS calc for $[C_{40}H_{36}ClN_3O_6S-H]$ 720.19405. found 720.19398.

EXAMPLE 66

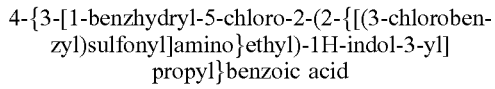
4-{3-[1-benzhydryl-5-chloro-2-(2-{[(3-chlorobenzyl)sulfonyl]amino}ethyl)-1H-indol-3-yl]propyl}benzoic acid Step 1: The sulfonyl chloride intermediate was prepared from 3-chlorobenzyl bromide according to the procedure in Example 18 Step 1–2.

Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 27% yield.

Step 3: The ester intermediate was hydrolyzed according to Step 8 Example 1 to afford the title compound in 93% yield. HRMS calc for $[C_{40}H_{36}Cl_2N_2O_4S-H]$ 709.17000. found 709.16963.

EXAMPLE 67

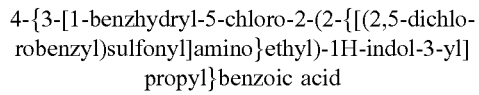
4-{3-[1-benzhydryl-5-chloro-2-(2-{[(2,5-dichlorobenzyl)sulfonyl]amino}ethyl)-1H-indol-3-yl]propyl}benzoic acid Step 1: The sulfonyl chloride intermediate was prepared from 2,5-dichlorobenzyl bromide according to the procedure in Example 18 Step 1–2.

Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 59% yield.

Step 3: The ester intermediate was hydrolyzed according to Step 8 Example 1 to afford the title compound in 100% yield. HRMS calc for $[C_{40}H_{35}Cl_3N_2O_4S-H]$ 743.13103. found 743.13079.

EXAMPLE 68

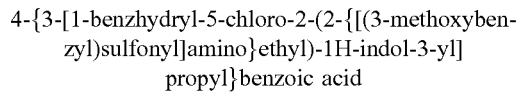
4-{3-[1-benzhydryl-5-chloro-2-(2-{[(3-methoxybenzyl)sulfonyl]amino}ethyl)-1H-indol-3-yl]propyl}benzoic acid Step 1: The sulfonyl chloride intermediate was prepared from 3-methoxybenzyl bromide according to the procedure in Example 18 Step 1–2.

Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 20% yield.

Step 3: The ester intermediate was hydrolyzed according to Step 8 Example 1 to afford the title compound in 100% yield. HRMS calc for $[C_{41}H_{39}ClN_2O_5S-H]$ 705.21954. found 705.21909.

EXAMPLE 69

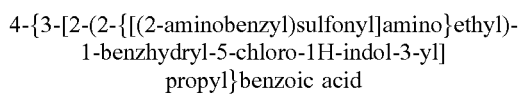
4-{3-[2-(2-{[(2-aminobenzyl)sulfonyl]amino}ethyl)-1-benzhydryl-5-chloro-1H-indol-3-yl]propyl}benzoic acid Step 1: The intermediate from Step 1 Example 56 was treated with $SnCl_2$ according to the procedure in Step 1 Example 16 to yield the amino ester in 99% yield.

Step 2: The ester intermediate was hydrolyzed according to Step 8 Example 1 to afford the title acid in 100% yield. HRMS calc for $[C_{40}H_{38}ClN_3O_4S-H]$ 690.21988. found 690.21941.

EXAMPLE 70

4-{3-[1-Benzhydryl-5-chloro-2-(2-{[(2-methylbenzyl)sulfonyl]amino}ethyl)-1H-indol-3-yl]propyl}benzoic acid Step 1: The sulfonyl chloride intermediate was prepared from 2-Methylbenzyl bromide according to the procedure in Example 18 Step 1–2 in quantitative yield.

Step 2: The methyl ester was prepared from the sulfonyl chloride and the intermediate in Example 42 step 6 according to the procedure in Example 42 Step 7 in 50% yield.

Step 2: The ester intermediate was hydrolyzed according to Step 8 Example 42 to afford the title acid in 93% yield. HRMS calc for $[C_{41}H_{39}ClN_2O_4S-H]$ 689.22463. found 689.22421.

EXAMPLE 71

4-{2-[1-Benzhydryl-5-chloro-2-(2-{[(4-trifluoromethoxybenzyl)sulfonyl]amino}ethyl)-1H-indol-3-yl]ethoxy}benzoic acid Step 1: The sulfonyl chloride intermediate was prepared from 4-Trifluorometoxybenzyl bromide according to the procedure in Example 18 Step 1–2 in quantitative yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7 in 48% yield.

Step 2: The ester intermediate was hydrolyzed according to Step 8 Example 1 to afford the title acid in 85% yield. HRMS calc for $[C_{40}H_{34}ClF_3N_2O_6S-H]$ 761.17054. found 761.17031.

EXAMPLE 72

4-{2-[1-Benzhydryl-5-chloro-2-(2-{[(2-fluoro-6-nitrobenzyl)sulfonyl]amino}ethyl)-1H-indol-3-yl]ethoxy}benzoic acid Step 1: The sulfonyl chloride intermediate was prepared from 2-Fluoro, 6-nitrobenzyl bromide according to the procedure in Example 18 Step 1–2 in quantitative yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7 in 91% yield.

Step 2: The ester intermediate was hydrolyzed according to Step 8 Example 1 to afford the title acid in 100% yield. m/z (M−1) 740.05

EXAMPLE 73

4-{2-[1-Benzhydryl-5-chloro-2-(2-{[(2-dichlorobenzyl)sulfonyl]amino}ethyl)-1H-indol-3-yl]ethoxy}benzoic acid Step 1: The c chloride intermediate was prepared from 3,5-dichlorobenzyl bromide according to the procedure in Example 18 Step 1–2 in theoretical yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7 in 100% yield.

Step 2: The ester intermediate was hydrolyzed according to Step 8 Example 1 to afford the title acid in 81% yield. m/z (M−1) 747.2. HRMS calc for $[C_{39}H_{33}Cl_3N_2O_5S-H]$ 745.11030. found 745.10954.

EXAMPLE 74

4-{2-[1-Benzhydryl-5-chloro-2-(2-{[(2,6-difluorobenzyl)sulfonyl]amino}ethyl)-1H-indol-3-yl]ethoxy}benzoic acid Step 1: The sulfonyl chloride intermediate was prepared from 2,6-difluorobenzyl bromide according to the procedure in Example 18 Step 1–2 in 95% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7 in 86% yield.

Step 2: The ester intermediate was hydrolyzed according to Step 8 Example 1 to afford the title acid in 71% yield. m/z (M−1) 714. HRMS calc for $[C_{39}H_{33}ClF_2N_2O_5S-H]$ 713.16940. found 713.16906.

EXAMPLE 75

4-(2-{1-benzhydryl-5-chloro-2-[2-({[(6-chloro-3-pyridinyl)methyl]sulfonyl}amino)ethyl]-1H-indol-3-yl}ethoxy)benzoic acid Step 1: (6-chloro-3-pyridinyl)-methanol (1.0 eq.) was taken up in dichloromethane and stirred overnight with carbon tetrabromide (1.5 eq.) and 1,3-bis(diphenylphosphino)propane (0.75 eq.) Ether was added to the solution and filtration followed by concentration of the filtrate afforded (6-chloro-3-bromomethyl)pyridine in 62% yield.

Step 2: The sulfonyl chloride intermediate was prepared from the product of Step 1 according to the procedure in Example 18 steps 1–2.

Step 3: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7 in 78% yield Step 4: The ester intermediate was hydrolyzed according to Step 8 Example 1 to afford the title acid in 89% yield. HRMS calc for $[C_{38}H_{33}Cl_2N_3O_5S-H]$ 712.14452. found 712.14420.

EXAMPLE 76

4-(2-{1-benzhydryl-5-chloro-2-[2-({[(5,6-dichloro-2-[pyridinyl)methyl]sulfonyl}amino)ethyl]-1H-indol-3-yl}ethoxy)benzoic acid Step 1: 5,6-dichloro-3-pyridinemethanol (1.0 eq.) was taken up in dichloromethane and stirred overnight with carbon tetrabromide (1.5 eq.) and 1,3-bis(diphenylphosphino)propane (0.75 eq.) Ether was added to the solution and filtration followed by concentration of the filtrate afforded the 5,6-dichloro-3-bromomethylpyridine in 130% yield.

Step 2: The sulfonyl chloride intermediate was prepared from the product of Step 1 according to the procedure in Example 18 steps 1–2 in 81% yield Step 3: The methyl ester was prepared from the sulfonyl chloride and methyl 4-{2-[2-(2-aminoethl)-1-benzhydryl-5-chloro-1H-indol-3-yl]ethoxy}benzoate (Step 6, Example 1) according to the procedure in Example 1 Step 7 in 79% yield Step 4: The ester intermediate was hydrolyzed according to Step 8 Example 1 to afford the title acid in 109% yield. HRMS calc for $[C_{38}H_{32}Cl_3N_3O_5S-H]$ 746.10554. found 746.10549.

EXAMPLE 77

4-{2-[1-Benzhydryl-5-chloro-2-(2-{[(3-methoxybenzyl)sulfonyl]amino}ethyl)-1H-indol-3-yl]ethoxy}benzoic acid Step 1: The sulfonyl chloride intermediate was prepared from 3-methoxybenzyl bromide according to the procedure in Example 18 Step 1–2 in 68% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7 in 68% yield.

Step 2: The ester intermediate was hydrolyzed according to Step 8 Example 1 to afford the title diacid in 93% yield. HRMS calc for $[C_{39}H_{33}Cl_3N_2O_5S+Na]$ 731.1953. found 731.1947.

EXAMPLE 78

4-{2-[1-Benzhydryl-5-chloro-2-(2-{[(3,5-dimethylbenzyl)sulfonyl]amino}ethyl)-1H-indol-3-yl]ethoxy}benzoic acid Step 1: The sulfonyl chloride intermediate was prepared from 3,5-dimethylbenzyl bromide according to the procedure in Example 18 Step 1–2 in 38% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7 in 38% yield.

Step 2: The ester intermediate was hydrolyzed according to Step 8 Example 1 to afford the title diacid in 88% yield. m/z (M–1) 705.0 HRMS calc for $[C_{41}H_{39}ClN_2O_5S-H]$ 705.21954. found 705.21916.

EXAMPLE 79

4-{2-[1-Benzhydryl-5-chloro-2-(2-{[(2-methylbenzyl)sulfonyl]amino}ethyl)-1H-indol-3-yl]ethoxy}benzoic acid Step 1: The sulfonyl chloride intermediate was prepared from 2-methylbenzyl bromide according to the procedure in Example 18 Step 1–2 in 35% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7 in 35% yield.

Step 2: The ester intermediate was hydrolyzed according to Step 8 Example 1 to afford the title diacid in 90% yield. m/z (M–1) 691.0. HRMS calc for $[C_{401}H_{37}ClN_2O_5S-H]$ 691.20389. found 691.20350.

EXAMPLE 80

4-{2-[1-Benzhydryl-5-chloro-2-(2-{[(2,6-dichlorobenzyl)sulfonyl]amino}ethyl)-1H-indol-3-yl]ethoxy}benzoic acid Step 1: The sulfonyl chloride intermediate was prepared from 2,6-dichlorobenzyl bromide according to the procedure in Example 18 Step 1–2 in 3% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7 in 3% yield.

Step 2: The ester intermediate was hydrolyzed according to Step 8 Example 1 to afford the title diacid in 92% yield. m/z (M–1) 745.0

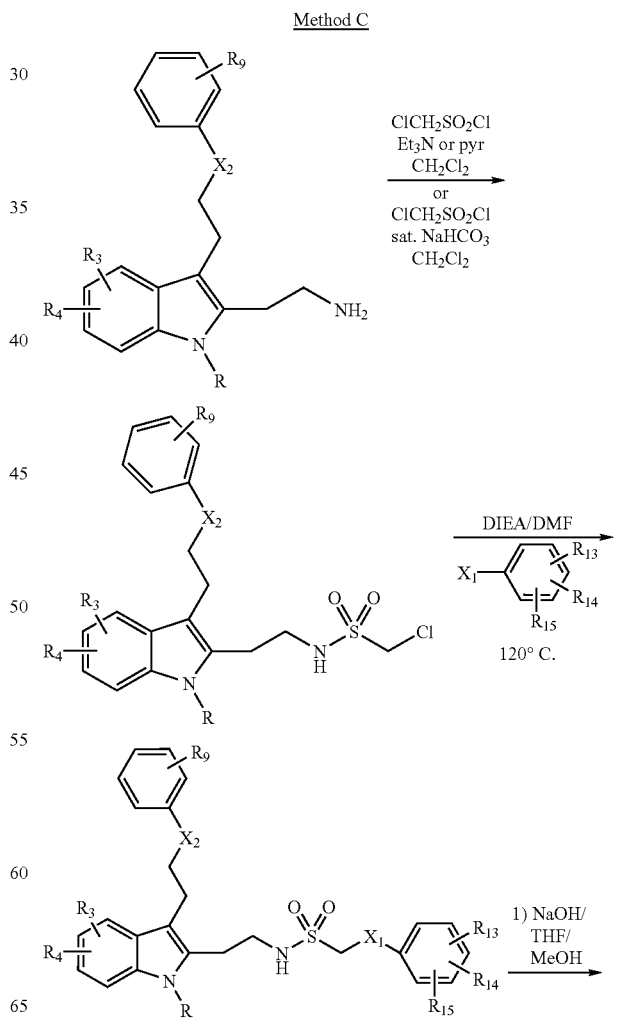

Method C

-continued

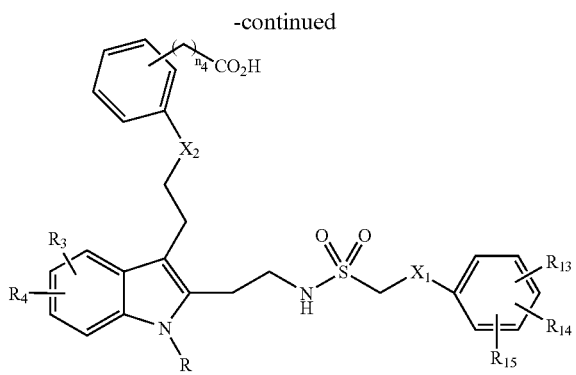

The intermediate amine, synthesized using method A, was treated with chloromethylsulfonyl chloride either under Schott and Baumman conditions or under anhydrous conditions with an organic base yielded a chloromethyl sulfonamide intermediate. This intermediate could be treated with a variety of nucleophiles in DMF with a suitable organic base, Hunigs base, triethylamine etc, and heated until the reaction was complete. The resulting intermediates where then hydrolyzed to yield the final compound.

The following examples were synthesized with method C: Examples 81–86 and 118–121.

EXAMPLE 81

4-(2-{1-benzhydryl-5-chloro-[2({[(phenylsulfanyl)-methyl]sulfonyl}amino)ethyl]-1H-indol-3-yl}ethoxy)benzoic acid The title compound was synthesized as depicted in Method C.

Step 1: To the methyl 4-{2-[2-(2-aminoethyl)-1-benzhydryl-5-chloro-1H-indol-3-yl]ethoxy}benzoate (Step 6, Example 1) was added chloromethanesulfonyl chloride according to the procedure in Example 1 Step 7 to generate the product in 99% yield.

Step 2: To methyl 4-{2-[1-benzhydryl-5-chloro-2-(2{[(chloromethyl)sulfonyl]amino}ethyl)-1H-indol-3-yl] ethoxy}benzoate (0.080M, 1.0 equiv.) and iPr$_2$NEt (3.4 equiv.) in N,N-dimethylformamide was added thiophenol (2.1–2.5 equiv.) and the mixture was stirred at 120° C. for 3.5 days. The reaction mixture was diluted with EtOAc and washed with water and brine. The combined organic phase was dried over magnesium sulfate and purified by flash chromatography.

Step 3: The ester intermediate was hydrolyzed according to Step 8 Example 1 to afford the title acid in 93% yield. m/z (M–1) 709.11. HRMS calc for [C$_{39}$H$_{35}$ClN$_2$O$_6$S$_2$–H] 709.16031. found 709.15999.

EXAMPLE 82

4-(2-{1-benzhydryl-5-chloro-2-[2-(2,6-dimethyl-phenylsulfanylmethanesulfonylamino)-ethyl]-]-1H-indol-3-yl}-ethoxy)-benzoic acid Step 1: To methyl 4-{2-[1-benzhydryl-5-chloro-2-(2-{[(chloromethyl)sulfonyl]amino}ethyl)-1H-indol-3-yl] ethoxy}benzoate, Example 81 step 1, was added 2,6-dimethylthiophenol according to the procedure in Example 81 step 2. The product was purified by the flash chromatography with 25% EtOAc/hexane in 32% yield.

Step 2: The ester intermediate was hydrolyzed according to Step 8 Example 42 to afford the title acid in 80% yield. m/z (M–1) 751.0. HRMS calc for [C$_{41}$H$_{39}$ClN$_2$O$_5$S$_2$–H] 737.19161. found 737.19128.

EXAMPLE 83

4-(2-{1-benzhydryl-5-chloro-2-[2-(2-methoxy-phenyl-sulfanylmethanesulfonylamino)-ethyl]]-1H-indol-3-yl}-ethoxy)-benzoic acid Step 1: To methyl 4-{2-[1-benzhydryl-5-chloro-2-(2-{[(chloromethyl)sulfonyl]amino}ethyl)-'1H-indol-3-yl] ethoxy}benzoate, Example 81 step 1, was added 2-methoxythiophenol according to the procedure in Example 81 step 2. The product was purified by the flash chromatography 30% EtOAc/hexane in 36% yield.

Step 2: The ester intermediate was hydrolyzed according to Step 8 Example 42 to afford the title acid in 94% yield. m/z (M–1) 753.3. HRMS calc for [C$_{40}$H$_{37}$ClN$_2$O$_6$S$_2$–H] 739.17088. found 739.17052.

EXAMPLE 84

4-(2-{1-benzhydryl-5-chloro-2-[2-(2-chloro-6-methyl-phenylsulfanylmethanesulfonylamino)-ethyl]]-1H-indol-3-yl}-ethoxy)-benzoic acid Step 1: To methyl 4-{2-[1-benzhydryl-5-chloro-2-(2-{[(chloromethyl)sulfonyl]amino)ethyl)-'1H-indol-3-yl] ethoxy}benzoate, Example 81 step 1, was added 2-chloro-6-methylthiophenol according to the procedure in Example 81 step 2. The product was purified by the flash chromatography 25% EtOAc/hexane in 46% yield.

Step 2: The ester intermediate was hydrolyzed according to Step 8 Example 42 to afford the title acid in 100% yield. m/z (M–1) 771.2. HRMS calc for [C$_{40}$H$_{36}$Cl$_2$N$_2$O$_5$S$_2$–H] 757.13699. found 757.13730.

EXAMPLE 85

4-(2-{1-benzhydryl-5-chloro-2-[2-(3,5-dichloro-phenylsulfanylmethanesulfonylamino)-ethyl]-]-1H-indol-3-yl}-ethoxy)-benzoic acid Step 1: To methyl 4-{2-[1-benzhydryl-5-chloro-2-(2-{[(chloromethyl)sulfonyl]amino}ethyl)-'1H-indol-3-yl] ethoxy}benzoate, Example 81 step 1, was added 3,5-dichlorothiophenol according to the procedure in Example 81 step 2. The product was purified by the flash chromatography 25% EtOAc/hexane in 40% yield.

Step 2: The ester intermediate was hydrolyzed according to Step 8 Example 42 to afford the title acid in 98% yield. m/z (M–1) 793.2. HRMS calc for [C$_{39}$H$_{33}$Cl$_3$N$_2$O$_5$S$_2$–H] 777.08237. found 777.08159.

EXAMPLE 86

4-(2-{1-benzhydryl-5-chloro-2-[2-(3,4-dimethoxy-phenylsulfanylmethanesulfonylamino)-ethyl]-]-1H-indol-3-yl}-ethoxy)-benzoic acid Step 1: To methyl 4-{2-[1-benzhydryl-5-chloro-2-(2-{[(chloromethyl)sulfonyl]amino}ethyl)-'1H-indol-3-yl] ethoxy}benzoate, Example 81 step 1, was added 3,4- dimethoxythiophenol according to the procedure in Example 81 step 2. The product was purified by the flash chromatography with 35% EtOAc/hexane in 40% yield.

Step 2: The ester intermediate was hydrolyzed according to Step 8 Example 42 to afford the title acid compound in 99% yield. m/z (M−1) 783.3. HRMS calc for [$C_{41}H_{39}ClN_2O_7S_2$–H] 769.18144. found 769.18120.

Method D

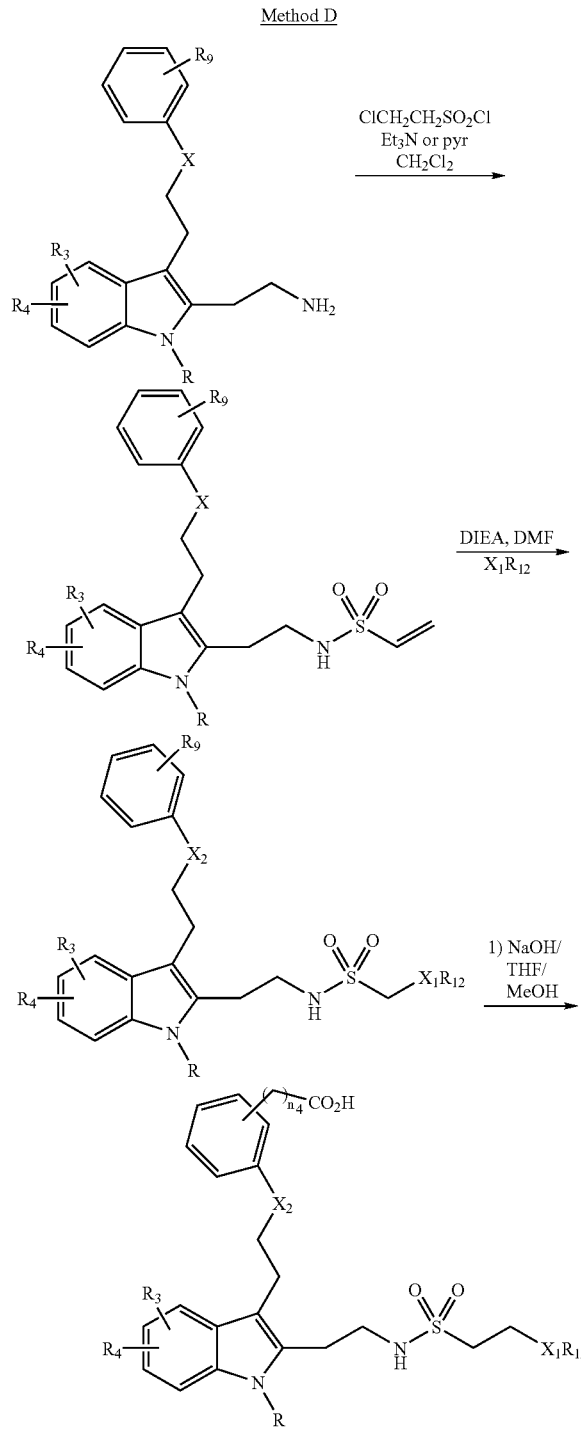

The intermediate amine, synthesized using method A, was treated with chloroethanesulfonyl chloride under anhydrous conditions with an organic base yielded a vinyl sulfonamide intermediate. This intermediate could be treated with a variety of nucleophiles in DMF with a suitable organic base, Hunigs base, triethylamine etc, and heated until the reaction was complete. The resulting intermediates were then hydrolyzed to yield the final compound.

The following examples were synthesized with Method D: Examples 87–99 and 100–105, 113–117, 122–125 and 139.

EXAMPLE 87

4-(2-{1-Benzhydryl-5-chloro-2-[2-(2-morpholin-4-ylethanesulfonylamino)-ethyl]-1H-indol-3-yl}-ethoxy)-benzoic acid The title compound was synthesis as depicted in Method D Step 1: To methyl 4-{2-[2-(2-aminoethyl)-1-benzhydryl-5-chloro-1H-indol-3-yl]ethoxy}benzoate (0.16M, 1.0 equiv.), Step 6, Example 1, and triethylamine (2.3 equiv.) in THF was added 2-chloroethanesulfonyl chloride (1.2 eq) dropwise. After 4 h the mixture was poured into brine and extracted with EtOAc. The combined organic phase was dried over magnesium sulfate and purified by column chromatography to afford 75% of the vinyl sulfonamide.

Step 2: To the product from step 1 in 1-propanol was added morpholine. After 5 h the reaction mixture was evaporated to dryness before redissolving in EtOAc. The organic phase was washed with brine, dried over magnesium sulfate, and purified by column chromatography to give the desired methyl ester in 89% yield.

Step 3: The ester intermediate was hydrolyzed according to Step 8 Example 1 to afford the title acid in 89% yield. m/z (M−1) 702.17. HRMS calc for [$C_{38}H_{40}ClN_3O_6S$–H] 700.2535. found 700.22500.

EXAMPLE 88

4-(2-{1-Benzhydryl-5-chloro-2-[2-(2-pyrazol-1-yl-ethanesulfonylamino)-ethyl]-1H-indol-3-yl}-ethoxy)-benzoic acid Step 1: The compound was prepared from the intermediate from Example 87 step 1 and 1H-pyrazole according to the procedure in Example 87 step 2 except that it was heated at 80° C. for 18 h, in 90% yield.

Step 2: The ester intermediate was hydrolyzed according to Step 8 Example 1 to afford the title acid in 61% yield. m/z (M−1) 681.24. HRMS calc for [$C_{37}H_{35}ClN_4O_5S$–H] 681.19439. found 681.19407.

EXAMPLE 89

4-(2-{1-Benzhydryl-5-chloro-2-[2-(2-phenylamino-ethanesulfonylamino)-ethyl]-1H-indol-3-yl}-ethoxy)-benzoic acid Step 1: The compound was prepared from the intermediate from Example 87 step 1 and aniline according to the procedure in Example 87 step 2 except that it was heated at 80° C. for 8 days, in 50% yield.

Step 2: The ester intermediate was hydrolyzed according to Step 8 Example 1 to afford the title acid in 98% yield. m/z (M−1) 706.26. HRMS calc for [$C_{40}H_{38}ClN_3O_5S$–H] 706.21479. found 706.21452.

EXAMPLE 90

4-(2-{1-benzhydryl-5-chloro-2-[2-({[2-(1,4-dioxa-8-azaspiro[4.5]dec-8-yl)ethyl]sulfonyl}amino)ethyl]-1H-indol-3-yl}ethoxy)benzoic acid

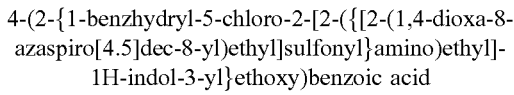

Step 1: The compound was prepared from the intermediate from Example 87 step 1 and 1,4-dioxa-8-aza-spiro[4.5]decane according to the procedure in Example 87 step 2 except that it was stirred overnight, in 82% yield.

Step 2: The ester intermediate was hydrolyzed according to Step 8 Example 1 to afford the title acid in 100% yield. m/z (M−1) 756.2. HRMS calc for [$C_{41}H_{44}ClN_3O_7S$−H] 756.25157. found 756.25142.

EXAMPLE 91

4-[2-(1-benzhydryl-5-chloro-2-{2-[({2-[4-(2-pyridinyl)-1-piperazinyl]ethyl}sulfonyl)amino]ethyl}-1H-indol-3-yl)ethoxy]benzoic acid

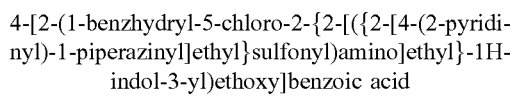

Step 1: The compound was prepared from the intermediate from Example 87 step 1 and 1-Pyridin-2-yl-piperazine according to the procedure in Example 87 step 2 except that it was stirred overnight, in 86% yield.

Step 2: The ester intermediate was hydrolyzed according to Step 8 Example 1 to afford the title acid in 100% yield. m/z (M−1) 776.2. HRMS calc for [$C_{43}H_{44}ClN_5O_5S$−H] 776.26789. found 776.26750.

EXAMPLE 92

4-(2-{1-benzhydryl-5-chloro-2-[2-(([2-(1H-1,2,4-triazol-1-yl)ethyl]sulfonyl}amino)ethyl]-1H-indol-3-yl}ethoxy)benzoic acid

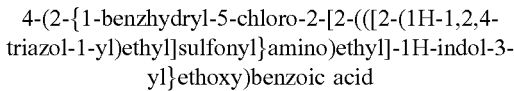

Step 1: The compound was prepared from the intermediate from Example 87 step 1 and 1H-[1,2,4]triazole according to the procedure in Example 87 step 2 except that it was refluxed for 4 days, in 64% yield Step 2: The ester intermediate was hydrolyzed according to Step 8 Example 1 to afford the title acid in 100% yield. m/z (M−1) 682.1. HRMS calc for [$C_{36}H_{34}ClN_5O_5S$−H] 682.18964. found 682.18964.

EXAMPLE 93

4-(2-{1-benzhydryl-5-chloro-2-[2-({[2-(3,5-dimethyl-1H-pyrazol-1-yl)ethyl]sulfonyl}amino)ethyl]-1H-indol-3-yl}ethoxy)benzoic acid

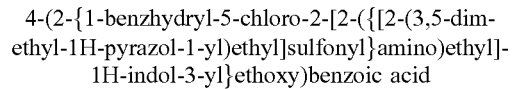

Step 1: The compound was prepared from the intermediate from Example 87 step 1 and 3,5-dimethyl-1H-pyrazole according to the procedure in Example 87 step 2 except that it was refluxed for refluxed 24 hours, in 95% yield.

Step 2: The ester intermediate was hydrolyzed according to Step 8 Example 1 to afford the title acid in 62% yield. m/z (M−1) 709.2. HRMS calc for [$C_{39}H_{39}ClN_4O_5S$−H] 709.22569. found 709.22532.

EXAMPLE 94

4-(2-{1-benzhydryl-5-chloro-2-[2-({[2-(3-methyl-1H-pyrazol-1-yl)ethyl]sulfonyl}amino)ethyl]-1H-indol-3-yl}ethoxy)benzoic acid

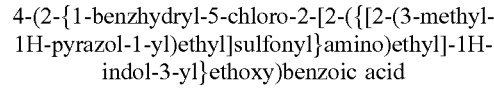

Step 1: The compound was prepared from the intermediate from Example 87 step 1 and 3-methyl-1H-pyrazole according to the procedure in Example 87 step 2 except that it was stirred overnight, in 88% yield.

Step 2: The ester intermediate was hydrolyzed according to Step 8 Example 1, except that the pH was adjusted to 4–5, to afford the title acid in 86% yield. m/z (M−1) 695.2. HRMS calc for [$C_{38}H_{37}ClN_4O_5S$−H] 695.21004. found 695.20951.

EXAMPLE 95

4-(2-{1-benzhydryl-5-chloro-2-[2-({[2-(4-methyl-1H-pyrazol-1-yl)ethyl]sulfonyl}amino)ethyl]-1H-indol-3-yl}ethoxy)benzoic acid

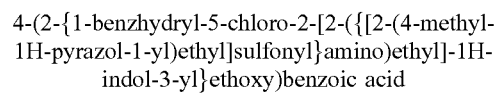

Step 1: The compound was prepared from the intermediate from Example 87 step 1 and 4-methyl-1H-pyrazole according to the procedure in Example 87 step 2 except that it was refluxed for 2 days, in 81% yield.

Step 2: The ester intermediate was hydrolyzed according to Step 8 Example 1, except that the pH was adjusted to 4–5, to afford the title acid in 93% yield. m/z (M−1) 695.2. HRMS calc for [$C_{38}H_{37}ClN_4O_5S$−H] 695.21004. found 695.20954.

EXAMPLE 96

4-[2-(1-benzhydryl-5-chloro-2-{2-[({2-[(2R,6S)-2,6-dimethyl-1-piperidinyl]ethyl}sulfonyl)amino]ethyl}-1H-indol-3-yl)ethoxy]benzoic acid

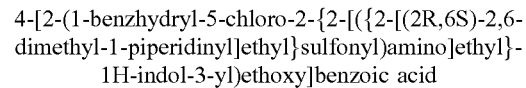

Step 1: The compound was prepared from the intermediate from Example 87 step 1 and 2,6-dimethyl-piperidine according to the procedure in Example 87 step 2 except that it was heated at 70° C. overnight, in 54% yield.

Step 2: The ester intermediate was hydrolyzed according to Step 8 Example 1, except that the pH was adjusted to 4–5, to afford the title acid in 79% yield. m/z (M−1) 726.3. HRMS calc for [$C_{41}H_{46}ClN_3O_5S$−H] 726.27739. found 726.27720.

EXAMPLE 97

4-(2-{1-benzhydryl-5-chloro-2-[2-({[2-(2-thioxo-1-imidazolidinyl)ethyl]sulfonyl}amino)ethyl]-1H-indol-3-yl}ethoxy)benzoic acid

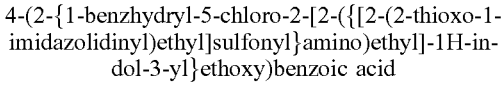

Step 1: The compound was prepared from the intermediate from Example 87 step 1 and imidazolidine-2-thione according to the procedure in Example 87 step 2 except that it was refluxed for 3 days, in 17% yield.

Step 2: The ester intermediate was hydrolyzed according to Step 8 Example 1, except that the pH was adjusted to 4–5, to afford the title acid in 88% yield. m/z (M−1) 715.3. HRMS calc for [$C_{37}H_{37}ClN_4O_5S$−H] 715.18211. found 715.18161.

EXAMPLE 98

4-(2-{1-benzhydryl-5-chloro-2-[2-(([2-(1,3-thiazolidin-3-yl)ethyl]sulfonyl}amino)ethyl]-1H-indol-3-yl}ethoxy)benzoic acid Step 1: The compound was prepared from the intermediate from Example 87 step 1 and thiazolidine according to the procedure in Example 87 step 2 except that it was refluxed overnight, in 33% yield.

Step 2: The ester intermediate was hydrolyzed according to Step 8 Example 1, except that the pH was adjusted to 4–5, to afford the title acid in 93% yield. m/z (M−1) 702.3. HRMS calc for $[C_{37}H_{38}ClN_3O_5S_2-H]$ 702.18686. found 702.18659.

EXAMPLE 99

4-(2-{1-benzhydryl-5-chloro-2-[2-(2-[1,2,3]triazol-1-yl-ethanesulfonylamino)-ethyl]-1H-indol-3-yl}ethoxy)benzoic acid Step 1: The compound was prepared from the intermediate from Example 87 step 1 and 1H-[1,2,3]triazole according to the procedure in Example 87 step 2 except that it was refluxed for 5 days, in 23% yield.

Step 2: The ester intermediate was hydrolyzed according to Step 8 Example 1, except that the pH was adjusted to 4–5, to afford the title acid in 100% yield. m/z (M−1) 682.0. HRMS calc for $[C_{36}H_{34}ClN_5O_5S-H]$ 682.18964. found 682.18933.

EXAMPLE 100

4-(3-{1-Benzhydryl-5-chloro-2-[2-(2-morpholin-4-yl-ethanesulfonylamino)-ethyl]-1H-indol-3-yl}-propyl)-benzoic acid Step 1: To methyl 4-{2-[2-(2-aminoethyl)-1-benzhydryl-5-chloro-1H-indol-3-yl]propyl}benzoate, Step 6, Example 42, (0.16M, 1.0 equiv.) and triethylamine (2.3 equiv.) in THF was added 2-chloroethanesulfonyl chloride (1.2 eq) dropwise. After 4 h the mixture was poured into brine and extracted with EtOAc. The combined organic phase was dried over magnesium sulfate and purified by column chromatography to afford the vinyl sulfonamide.

Step 2: To the product from step 1 in 1-propanol was added morpholine. After 5 h the reaction mixture was evaporated to dryness before redissolving in EtOAc. The organic phase was washed with brine, dried over magnesium sulfate, and purified by column chromatography to give the desired methyl ester in 100% yield.

Step 3: The ester intermediate was hydrolyzed according to Step 8 Example 1 to afford the title acid in 85% yield. m/z (M−1) 698.12. HRMS calc for $[C_{39}H_{42}ClN_3O_5S-H]$ 698.24609. found 698.24581.

EXAMPLE 101

4-[3-(1-Benzhydryl-5-chloro-2-{2-[2-(2,6-dimethyl-piperidin-1-yl)-ethanesulfonylamino]-ethyl}-1H-indol-3-yl)-propyl]-benzoic acid Step 1: The compound was prepared from the intermediate from Example 100 step 1 and 2,6-dimethylpiperdine according to the procedure in Example 100 step 2 except that it was refluxed for heated at 80° C. for 1 d 17 h, in 59% yield.

Step 2: The ester intermediate was hydrolyzed according to Step 8 Example 1 to afford the title acid in 86% yield. m/z (M−1) 724.20. HRMS calc for $[C_{42}H_{48}ClN_3O_4S-H]$ 724.29813. found 724.29776.

EXAMPLE 102

4-[3-(1-Benzhydryl-5-chloro-2-{2-[2-(3,5-dimethyl-pyrazol-1-yl)-ethanesulfonylamino]-ethyl}-1H-indol-3-yl)-propyl]-benzoic acid Step 1: The compound was prepared from the intermediate from Example 100 step 1 and 3,5-dimethyl-1H-pyrazole according to the procedure in Example 100 step 2 except that it was refluxed for heated at 80° C. for 1 d, in quantitative yield.

Step 2—The ester intermediate was hydrolyzed according to Step 8 Example 1 to afford the title acid in 89% yield. m/z (M−1) 707.16. HRMS calc for $[C_{40}H_{41}ClN_4O_4S-H]$ 707.24642. found 707.24597.

EXAMPLE 103 AND 104

4-(2-{1-benzhydryl-5-chloro-2-[2-(2-tetrazol-2-yl-ethanesulfonylamino)-ethyl]-1H-indol-3-yl}ethoxy)benzoic acid and 4-(2-{1-benzhydryl-5-chloro-2-[2-(2-tetrazol-1-yl-ethanesulfonylamino)-ethyl]-1H-indol-3-yl}ethoxy)benzoic acid Step 1: The mixture of 4-{2-[1-Benzhydryl-5-chloro-2-(2-ethenesulfonylamino-ethyl)-1H-indol-3-yl]-ethoxy}-benzoic acid methyl ester (0.2 M, 1.0 equiv.), 1H-tetrazole (4.0 equiv.) and iPr$_2$NEt (4.3 equiv.) in 1-propanol was refluxed overnight. It was evaporated to dryness before redissolving in EtOAc. The organic phase was washed with water and brine, dried over magnesium sulfate, purified by column chromatography to give two isomers in 41% and 52% yields, respectively.

Step 2: The ester intermediates were hydrolyzed according to Step 8 Example 1, except that the pH was adjusted to 4–5, to afford the title acids 4-(2-{1-benzhydryl-5-chloro-2-[2-(2-tetrazol-2-yl-ethanesulfonylamino)-ethyl]-1H-indol-3-yl}ethoxy)benzoic acid in 92% yield. m/z (M−1) 683.3; 4-(2-{1-benzhydryl-5-chloro-2-[2-(2-tetrazol-1-yl-ethanesulfonylamino)-ethyl]-1H-indol-3-yl}ethoxy)benzoic acid in 83% yield. m/z (M−1) 683.3. HRMS calc for $[C_{35}H_{33}ClN_6O_5S-H]$ 683.18489. found 683.18458; 4-(2-{1-benzhydryl-5-chloro-2-[2-(2-tetrazol-1-yl-ethanesulfonylamino)-ethyl]-1H-indol-3-yl}ethoxy)benzoic acid in 83% yield. HRMS calc for $[C_{35}H_{33}ClN_6O_5S-H]$ 683.18489. found 683.18435.

Method E

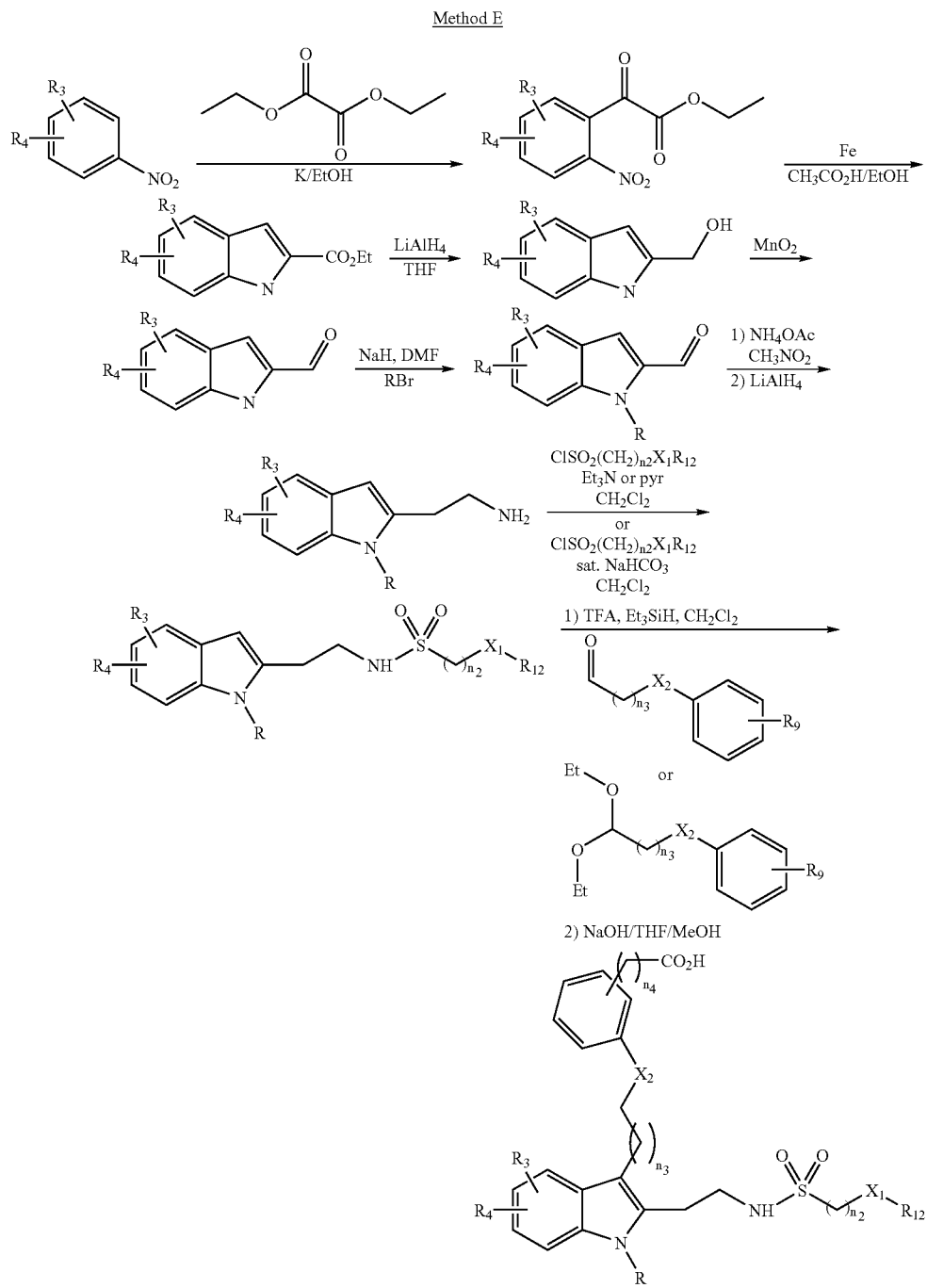

The substituted nitro aromatic was treated with ethyl oxalate in the presence of potassium or sodium in an alcoholic solvent. The resulting oxalate ester was treated with a suitable reducing agent, such as iron powder, and the resulting amine cyclized to the indole under the reaction conditions. The carboxylate was next reduced with any of a variety of reducing agents, lithium aluminum hydride, dibal etc and the resulting alcohol was oxidized using reagents such as manganese dioxide, Swern condition NMO/TPAP etc. This 2 formyl indole was next alkylated by treatment with a strong base such as Na/KHMDS, NaH, etc and then alkylated with a suitable halide. The aldehyde was next treated with nitromethane and a base such as ammonium acetate to yield a vinyl nitro intermediate that could be reduced by a variety of agents such as Lithium Aluminum Hydride or Zn(Hg) amalgam in HCl. The resulting amine was sulfonylated using a sulfonyl chloride either under biphasic Schott and Baummen conditions or anhydrous conditions with an organic base. This intermediate could be reductively alkylated at C3 using an aldehyde or an acetal under the action of a Bronsted or Lewis acid such as trifluoroacetic acid and a reducing agent such as triethylsilane. The resulting intermediate was hydrolyzed using a base, NaOH, KOH, LiOH and a mixture of solvents including an alcoholic solvent, water and tetrahydrofuran. The following Examples 105–107 were synthesized using Method E.

EXAMPLE 105

4-{2-[1-Benzhydryl-6-chloro-2-(2-phenylmethane-sulfonylamino-ethyl)-1H-indol-3-yl]-ethoxy}-benzoic acid Step 1: To potassium (6.24 g) in ether at rt were added ethanol (40 mL, in 100 mL ether), diethyl oxalate (27.85 g, in 60 mL ether), and 4-chloro-2-nitrotoluene (in 40 mL ether). The reaction mixture was stirred at rt for 15 h and followed by sonication for 7 h before pouring onto cold 1N HCl. After neutralization, the aqueous layer was extracted with EtOAc and the combined organic layers were washed with brine and dried. After evaporation, the crude 3-(4-Chloro-2-nitro-phenyl)-2-oxo-propionic acid ethyl ester was used directly in the next step without further purification.

Step 2: To crude 3-(4-chloro-2-nitro-phenyl)-2-oxo-propionic acid ethyl ester (151 mmol) in ethanol:glacial HOAc (1:1, v/v, 560 mL) at rt was added iron powder (74.4 g) and the reaction mixture was stirred at reflux for 4 h. The mixture was filtered and evaporated to give a residue which was redistributed in dichloromethane/1N HCl. The organic layer was washed with 1N HCl, NaHCO$_3$, and brine and dried. Evaporation followed by crystallization (DCM) gave 6-Chloro-1H-indole-2-carboxylic acid ethyl ester as a pale yellow solid (16.8 g, 50% over 2 steps).

Step 3: To 6-chloro-1H-indole-2-carboxylic acid ethyl ester (8.57 g) in THF at 0° C. was added lithium aluminum hydride solution (1M, in THF) dropwise and the reaction mixture was stirred for 3.5 h. The mixture was quenched with H$_2$O, 15% NaOH, and H$_2$O before it was filtered and rinsed with THF. Evaporation of the solvent gave 7.77 g of the crude (6-Chloro-1H-indol-2-yl)-methanol which was used directly in the next step.

Step 4: To (6-chloro-1H-indol-2-yl)-methanol (37.7 mmol) in THF at 0° C. was added manganese (IV) oxide and the mixture was stirred at rt for 16 h. The mixture was filtered over celite and rinsed with THF and EtOAc and evaporated to near dryness. The solid was filtered and washed with cold EtOAc/hex to give 6-Chloro-1H-indole-2-carbaldehyde (62%, 2 steps).

Step 5: To 6-chloro-1H-indole-2-carbaldehyde (1 equiv.) in DMF at 0° C. was added NaH (1.25 equiv.) portionwise followed by benzhydryl bromide (1.46 equiv.) and Bu$_4$NI (0.05 equiv.). The mixture was stirred at rt for 42 h before quenching with cold 0.4N HCl at 0° C. After neutralization, the aqueous layer was extracted with ether and the organic layer was washed with cold H$_2$O and dried. Flash chromatography on silica gel gave 1-benzhydryl-6-chloro-1H-indole-2-carbaldehyde in 40% yield.

Step 6: A solution of 1-benzhydryl-6-chloro-1H-indole-2-carbaldehyde (0.5M, 1 equiv.) and NH$_4$OAc (1 equiv.) in nitromethane was heated at 95° C. for 70 min. The mixture was diluted with EtOAc, washed with water, and dried. Evaporation of the volatiles, followed by trituration with ether/hexane produced 1-Benzhydryl-6-chloro-2-(2-nitro-vinyl)-1H-indole in 48% yield.

Step 7: To lithium aluminum hydride (1M in THF, 4 equiv.) in THF at 0° C. was added 1-benzhydryl-6-chloro-2-(2-nitro-vinyl)-1H-indole (0.1M, 1 equiv.) dropwise and the reaction mixture was stirred for 2 h. The mixture was quenched with H$_2$O, 15% NaOH, and H$_2$O, filtered through celite and rinsed with EtOAc. After evaporation, the residue was purified by column chromatography to generate 2-(1-Benzhydryl-6-chloro-1H-indol-2-yl)-ethylamine in 40% yield.

Step 8: To 2-(1-Benzhydryl-6-chloro-1H-indol-2-yl)-ethylamine was added phenylmethanesulfonyl chloride according to the procedure in Example 1 Step 7 to generate N-[2-(1-Benzhydryl-6-chloro-1H-indol-2-yl)-ethyl]-C-phenylmethanesulfonamide in 90% yield.

Step 9: To N-[2-(1-Benzhydryl-6-chloro-1H-indol-2-yl)-ethyl]-C-phenylmethanesulfonamide (0.033M, 1 equiv.) in DCM at 0° C. were added 4-(2-oxo-ethoxy)-benzoic acid methyl ester (3.3 equiv.), triethylsilane (6 equiv.), and TFA (5 equiv.). The reaction mixture was stirred at rt for 2 d 20 h before aqueous workup. Purification by silica gel chromatography followed by reverse phase HPLC gave 4-{2-[1-Benzhydryl-6-chloro-2-(2-phenylmethanesulfonylamino-ethyl)-1H-indol-3-yl]-ethoxy}-benzoic acid methyl ester in 35% yield.

Step 10: The ester intermediate from step 9 was hydrolyzed according to Step 8 Example 1 to afford the title acid in 64% yield.

EXAMPLE 106

4-(2-{1-Benzhydryl-6-chloro-2-[2-(3,4-dichloro-phenylmethanesulfonylamino)-ethyl]-1H-indol-3-yl}-ethoxy)-benzoic acid Step 1: To 2-(1-Benzhydryl-6-chloro-1H-indol-2-yl)-ethylamine, Example 105 step 7 was added (3,4-dichloro-phenyl)-methanesulfonyl chloride according to the procedure in Example 105 Step 7 to generate N-[2-(1-benzhydryl-6-chloro-1H-indol-2-yl)-ethyl]-C-(3,4-dichloro-phenyl)-methanesulfonamide in quantitative yield.

Step 2: N-[2-(1-Benzhydryl-6-chloro-1H-indol-2-yl)-ethyl]-C-(3,4-dichlorophenyl)-methanesulfonamide was reductively alkylated as described in Example 105 step 9 to give 4-(2-{1-benzhydryl-6-chloro-2-[2-(3,4-dichloro-phenylmethanesulfonylamino)-ethyl]-1H-indol-3-yl}-ethoxy)-benzoic acid methyl ester in 38% yield.

Step 3: The ester intermediate was hydrolyzed according to Step 8 Example 1 to afford the title acid in 96% yield. m/z (M−1) 747.27.

EXAMPLE 107

4-(2{1-Benzhydryl-6-chloro-2-[2-(3,5-dichloro-phenylmethanesulfonylamino)-ethyl]-1H-indol-3-yl}-ethoxy)-benzoic acid Step 1: To 2-(1-Benzhydryl-6-chloro-1H-indol-2-yl)-ethylamine, Example 105 step 7 was added (3,5-dichloro-phenyl)-methanesulfonyl chloride according to the procedure in Example 105 Step 7 to generate N-[2-(1-benzhydryl-6-chloro-1H-indol-2-yl)-ethyl]-C-(3,5-dichloro-phenyl)-methanesulfonamide in quantitative yield.

Step 2: N-[2-(1-Benzhydryl-6-chloro-1H-indol-2-yl)-ethyl]-C-(3,4-dichlorophenyl)-methanesulfonamide was reductively alkylated as described in Example 105 step 9 to give 4-(2-{1-benzhydryl-6-chloro-2-[2-(3,5-dichloro-phenylmethanesulfonylamino)-ethyl]-1H-indol-3-yl}-ethoxy)-benzoic acid methyl ester in 31% yield.

Step 3: The ester intermediate was hydrolyzed according to Step 8 Example 1 to afford the title acid in 95% yield. HRMS calc for [C$_{39}$H$_{33}$Cl$_3$N$_2$O$_5$S+Na] 769.1068. found 769.1079.

EXAMPLE 108

4-{2-[1-Benzhydryl-5-chloro-2-(2-{[(2-cyanobenzyl)sulfonyl]amino}ethyl)-1H-indol-3-yl]ethoxy}benzoic acid Step 1: The sulfonyl chloride intermediate was prepared from 2-bromomethylbenzonitrile according to the procedure in Example 18 Step 1–2 in 100% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7.

Step 3: The ester intermediate was hydrolyzed according to Step 8 Example 1 to afford the title acid in 72% overall yield. HRMS calcd. for $C_{40}H_{35}ClN_3O_5S$ (M+1): 704.1980; found: 704.1984. HRMS calcd. for $C_{40}H_{35}ClN_3O_5S$ (M+1): 704.1980; found: 704.1984.

EXAMPLE 109

4-{2-[1-Benzhydryl-5-chloro-2-(2-{[(tetrahydro-2H-pyran-2-ylmethyl)sulfonyl]amino}ethyl)-1H-indol-3-yl]ethoxy}benzoic acid Step 1: The sulfonyl chloride intermediate was prepared from 2-bromomethyl-tetrahydro-pyran according to the procedure in Example 18 Step 1–2 in 100% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7.

Step 3: The ester intermediate was hydrolyzed according to Step 8 Example 1 to afford the title acid in 20% overall yield HRMS calcd. for $C_{38}H_{38}ClN_2O_6S$ (M−1): 685.2145; found: 685.2143.

EXAMPLE 110

4-{2-[1-Benzhydryl-2-(2-{[(1,3-benzoxazol-2-ylmethyl)sulfonyl]amino}ethyl)-5-chloro-1H-indol-3-yl]ethoxy}benzoic acid Step 1: The sulfonyl chloride intermediate was prepared from 2-bromomethyl-benzooxazole according to the procedure in Example 18 Step 1–2 in 100% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7.

Step 3: The ester intermediate was hydrolyzed according to Step 8 Example 1 to afford the title acid in 26% overall yield. HRMS calcd. for $C_{40}H_{35}ClN_3O_6S$ (M+1): 720.1930; found: 720.1924.

EXAMPLE 111

4-(2-[1-Benzhydryl-5-chloro-2-(2-{[(cyanomethyl)sulfonyl]amino}ethyl)-1H-indol-3-yl]ethoxy}benzoic acid Step 1: The sulfonyl chloride intermediate was prepared from 3-bromomethyl-[1,2,4]oxadiazole according to the procedure in Example 18 Step 1–2 in 100% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7.

Step 3: The ester intermediate was hydrolyzed according to Step 8 Example 1 to afford the title acid in 59% overall yield. HRMS calcd. for $C_{34}H_{31}ClN_3O_5S$ (M+1): 628.1668; found: 628.1662.

EXAMPLE 112

4-{2-[1-Benzhydryl-5-chloro-2-(2-{[(3-thienylmethyl)sulfonyl]amino}ethyl)-1H-indol-3-yl]ethoxy}benzoic acid Step 1: The sulfonyl chloride intermediate was prepared from 3-bromomethyl 3-bromomethyl-thiophene according to the procedure in Example 18 Step 1–2 in 100% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 6, Example 1) according to the procedure in Example 1 Step 7.

Step 3: The ester intermediate was hydrolyzed according to Step 8 Example 1 to afford the title acid in 25% overall yield. HRMS calcd. for $C_{32}H_{31}ClN_2O_5S_2$ (M−1): 683.1447; found: 683.1445.

EXAMPLE 113

4-[2-(1-Benzhydryl-5-chloro-2-{2-[2-(2-methyl-pyrrolidin-1-yl)-ethanesulfonylamino]-ethyl}-1H-indol-3-yl)ethoxy]-benzoic acid Step 1: The compound was prepared from the intermediate from Example 87 step 1 and 2-methyl-pyrrolidine according to the procedure in Example 87 step 2 in 91% yield.

Step 2: The ester intermediate was hydrolyzed according to Step 8 Example 1, except that the pH was adjusted to 4–5, to afford the title acid in 99% yield. HRMS calc for $[C_{39}H_{42}ClN_3O_5S-H]$ 698.24609. found 698.24572.

EXAMPLE 114

4-[2-(1-Benzhydryl-5-chloro-2-{2-[2-(2-methyl-piperidin-1-yl)-ethanesulfonylamino]-ethyl}-1H-indol-3-yl)-ethoxy]-benzoic acid Step 1: The compound was prepared from the intermediate from Example 87 step 1 and 2-methyl-piperidine according to the procedure in Example 87 step 2 in 91% yield.

Step 2: The ester intermediate was hydrolyzed according to Step 8 Example 1, except that the pH was adjusted to 4–5, to afford the title acid in 96% yield. HRMS calc for $[C_{40}H_{44}ClN_3O_5S-H]$ 712.26174. found 712.26113.

EXAMPLE 115

4-[2-(1-Benzhydryl-5-chloro-2-{2-[2-(2,5-dimethyl-pyrrolidin-1-yl)-ethanesulfonylamino]-ethyl}-1H-indol-3-yl)-ethoxy]-benzoic acid Step 1: The compound was prepared from the intermediate from Example 87 step 1 and 2,5-dimethyl-pyrrolidine according to the procedure in Example 87 step 2 in 81% yield.

Step 2: The ester intermediate was hydrolyzed according to Step 8 Example 1, except that the pH was adjusted to 4–5,

EXAMPLE 116

4-(2-{1-Benzhydryl-5-chloro-2-[2-(2-thiomorpholin-4-yl-ethanesulfonylamino)-ethyl]-1H-indol-3-yl}-ethoxy)-benzoic acid

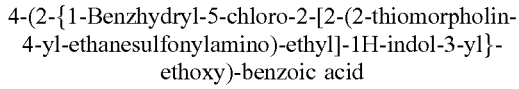

Step 1: The compound was prepared from the intermediate from Example 87 step 1 and thiomorpholine according to the procedure in Example 87 step 2 in 93% yield.

Step 2: The ester intermediate was hydrolyzed according to Step 8 Example 1, except that the pH was adjusted to 4–5, to afford the title acid in 90% yield. HRMS calc for [$C_{38}H_{40}ClN_3O_5S_2$–H] 716.20251. found 716.20217.

EXAMPLE 117

4-(2-{1-Benzhydryl-5-chloro-2-[2-(2-piperidin-1-yl-ethanesulfonylamino)-ethyl]-1H-indol-3-yl}-ethoxy)-benzoic acid

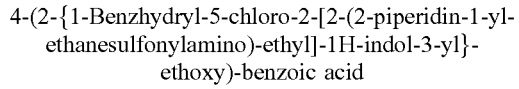

Step 1: The compound was prepared from the intermediate from Example 87 step 1 and piperidine according to the procedure in Example 87 step 2 in 99% yield.

Step 2: The ester intermediate was hydrolyzed according to Step 8 Example 1, except that the pH was adjusted to 4–5, to afford the title acid in 92% yield. HRMS calc for [$C_{39}H_{42}ClN_3O_5S$–H] 698.24609. found 698.24570.

EXAMPLE 118

4-{2-[1-benzhydryl-5-chloro-2-(2-o-tolylsulfanyl-methanesulfonylamino-ethyl)-1H-indol-3-yl]-ethoxy}-benzoic acid

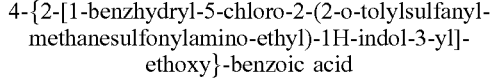

Step 1: To methyl 4-{2-[1-benzhydryl-5-chloro-2-(2-{[(chloromethyl)sulfonyl]amino}ethyl)-'1H-indol-3-yl]ethoxy}benzoate, Example 81 step 1, was added o-thiocresol according to the procedure in Example 81 step 2 and 3. The product was purified by the preparative HPLC in 45% yield.

Step 2: The ester intermediate was hydrolyzed according to Step 8 Example 42 to afford the title acid in 98% yield. m/z (M–1) 723.07. HRMS calc for [$C_{40}H_{37}ClN_2O_5S$–H] 723.17596. found 723.17596.

EXAMPLE 119

4-(2-{1-benzhydryl-5-chloro-2-[2-(2-chloro-phenyl-sulfanylmethanesulfonylamino)-ethyl]-1H-indol-3-yl}-ethoxy)-benzoic acid

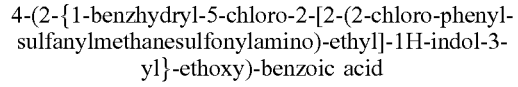

Step 1: To methyl 4-{2-[1-benzhydryl-5-chloro-2-(2-{[(chloromethyl)sulfonyl]amino}ethyl)-'1H-indol-3-yl]ethoxy}benzoate, Example 81 step 1, was added 2-chlorothiophenol according to the procedure in Example 81 step 2. The product was purified by the preparative HPLC in 53% yield.

Step 2: The ester intermediate was hydrolyzed according to Step 8 Example 42 to afford the title acid in 100% yield. m/z (M–1) 743.08. HRMS calc for [$C_{39}H_{34}Cl_2N_2O_5S_2$–H] 743.12134. found 743.12111.

EXAMPLE 120

4-(2-{1-benzhydryl-5-chloro-2-[2-(2,6-dichloro-phenylsulfanylmethanesulfonylamino)-ethyl]-1H-indol-3-yl}-ethoxy)-benzoic acid

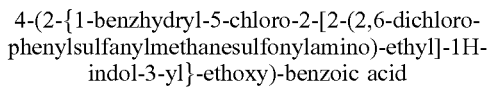

Step 1: To methyl 4-{2-[1-benzhydryl-5-chloro-2-(2-{[(chloromethyl)sulfonyl]amino}ethyl)-'1H-indol-3-yl]ethoxy}benzoate, Example 81 step 1, was added 2,6-dichlorothiophenol according to the procedure in Example 81 step 2. The product was purified by the preparative HPLC in 15.7% yield and hydrolized acid in 37%.

Step 2: The ester intermediate was hydrolyzed according to Step 8 Example 42 to afford the title acid in 98% yield. m/z (M–1) 776.93. HRMS calc for [$C_{39}H_{33}Cl_3N_2O_5S_2$–H] 777.08237. found 777.08205.

EXAMPLE 121

4-(2-{1-benzhydryl-5-chloro-2-[2-(2,5-dimethoxy-phenylsulfanylmethanesulfonylamino)-ethyl]-1H-indol-3-yl}-ethoxy)-benzoic acid

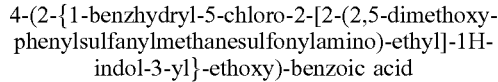

Step 1: To methyl 4-{2-[1-benzhydryl-5-chloro-2-(2-{[(chloromethyl)sulfonyl]amino}ethyl)-'1H-indol-3-yl]ethoxy}benzoate, Example 81 step 1, was added 2,5-dimethoxythiophenol according to the procedure in Example 81 step 2. The product was purified by the flash chromatography 35% EtOAc/hexane in 65% yield.

Step 2: The ester intermediate was hydrolyzed according to Step 8 Example 42 to afford the title acid in 99.5% yield. m/z (M–1) 769.18. HRMS calc for [$C_{41}H_{39}ClN_2O_7S_2$–H] 769.18144. found 769.18121.

EXAMPLE 122

4-[2-(1-benzhydryl-5-chloro-2-{2-[2-(3-hydroxy-pyrrolidine-1-yl)-ethanesulfonylamino]-ethyl}-1H-indol-3-yl)-ethoxy]-benzoic acid

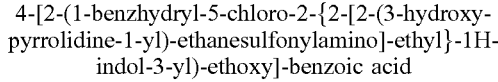

Step 1: The compound was prepared from the intermediate from Example 87 step 1 and 3-pyrrolidinol according to the procedure in Example 87 step 2 in 90% yield without the column purification.

Step 2: The ester intermediate was hydrolyzed according to Step 8 Example 1, except that the pH was adjusted to 4–5, to afford the title acid in 84% yield. m/z (M–1) 699.99. HRMS calc for [$C_{38}H_{40}ClN_3O_6S$–H] 700.22535. found 700.22490.

EXAMPLE 123

4-[2-(1-Benzhydryl-5-chloro-2-{2-[2-(4-hydroxy-piperidin-1-yl)-ethanesulfonylamino]-ethyl}-1H-indol-3-yl)-ethoxy]-benzoic acid

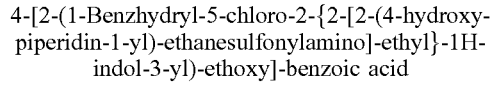

Step 1: The compound was prepared from the intermediate from Example 87 step 1 and 4-hydroxypiperidine according to the procedure in Example 87 step 2 in 95% yield without the column purification.

Step 2: The ester intermediate was hydrolyzed according to Step 8 Example 1, except that the pH was adjusted to 4–5, to afford the title acid in 42% yield. m/z (M–1) 714.03. HRMS calc for [$C_{39}H_{42}ClN_3O_6S$–H] 714.24100. found 714.24085.

EXAMPLE 124

4-[2-(1-Benzhydryl-5-chloro-2-{2-[2-(2-dimethylaminomethyl-piperidin-1-yl)-ethanesulfonylamino]-ethyl}-1H-indol-3-yl)-ethoxy]-benzoic acid Step 1: The compound was prepared from the intermediate from Example 87 step 1 and N-(2-piperidylmethyl)-dimethylamine according to the procedure in Example 87 step 2 in 90% yield without the column purification.

Step 2: The ester intermediate was hydrolyzed according to Step 8 Example 1, except that the pH was adjusted to 4–5, to afford the title acid in 71% yield. m/z (M–1) 754.94. HRMS calc for [$C_{42}H_{49}ClN_4O_5S$–H] 755.30394. found 755.30344.

EXAMPLE 125

4-(2-{1-Benzhydryl-5-chloro-2-[2-(2-imidazol-1-yl-ethanesulfonylamino)ethyl]-1H-indol-3-yl}-ethoxy)-benzoic acid Step 1: The compound was prepared from the intermediate from Example 87 step 1 and imidazole according to the procedure in Example 87 step 2 except that it was heated at 120° C. for 4.5 days, in 87% yield.

Step 2: The ester intermediate was hydrolyzed according to Step 8 Example 1, except that the pH was adjusted to 4–5, to afford the title acid in 60% yield. m/z (M–1) 681.17. HRMS calc for [$C_{37}H_{35}ClN_4O_5S$–H] 681.19439. found 681.19409.

EXAMPLE 126

4-{3-[1-benzhydryl-5-chloro-2-(2-{[(2,6-difluorobenzyl)sulfonyl]amino}ethyl)-1H-indol-3-yl]propyl}benzoic acid Step 1: The sulfonyl chloride intermediate was prepared from 2,6-difluorobenzyl bromide according to the procedure in Example 18 Step 1–2 in quantitative yield.

Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 53% yield.

Step 3: The ester intermediate was hydrolyzed according to Step 8 Example 1 to afford the title acid in 92% yield. m/z (M–1) 711.2. HRMS calc for [$C_{40}H_{35}ClF_2N_2O_4S$–H] 711.19013. found 711.18965.

EXAMPLE 127

4-{3-[1-benzhydryl-2-(2-{[(3,4-dichlorobenzyl)sulfonyl]amino}ethyl)-1H-indol-3-yl]propyl}benzoic acid Step 1: 2-methylindole was treated with the intermediate from Example 42 step 1 and the procedure from Example 42 step 2 to yield the desired product in 88%.

Step 2: The product from above was alkylated with benzhydryl bromide according to the procedure in Example 42 step 3 to yield the product in 65%.

Step 3: The product from above was oxidized using the conditions outlined in Example 42 step 4 to yield the desired 2-formyl indole in 85% yield.

Step 4: The indole from above was subjected to the nitro aldol conditions outlined in Example 42 step 6

Step 5: The vinyl nitro compound from above was reduced under the conditions outlined in Example 42 step 6 to yield the desired amino indole in 39% yield.

Step 6: The amine from step 5 was treated with (3,4-dichlorophenyl)-methyl]sulfonyl chloride according to the procedure in Example 43 Step 7 which yielded 100% of the desired product.

Step 7: The ester intermediate was hydrolyzed according to Step 8 Example 42 to afford the title acid in 24% yield. HRMS calc for [$C_{40}H_{36}ClN_2O_4S$–H] 709.1700. found 709.16951.

EXAMPLE 128

4-[3-(1-benzhydryl-2-{(2-[(benzylsulfonyl)amino]ethyl}-1H-indol-3-yl)propyl]benzoic acid Step 1: This compound was prepared from the intermediate in Example 127 step 5 □-toluenesulfonyl chloride according to the procedure in Example 43 Step 7 which yielded 83% of the desired product.

Step 2: The ester intermediate was hydrolyzed according to Step 8 Example 42 to afford the title acid in 95% yield. HRMS calc for [$C_{40}H_{38}N_2O_4S$–H] 641.24795. found 641.24761.

Method F

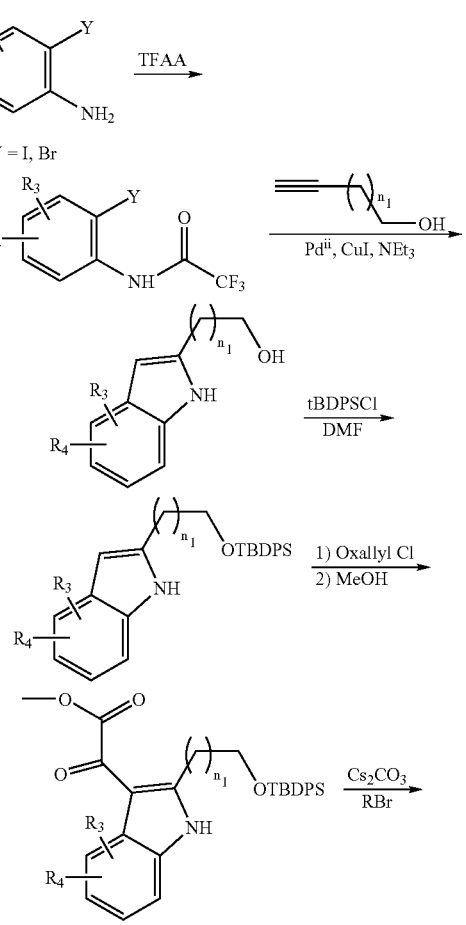

-continued
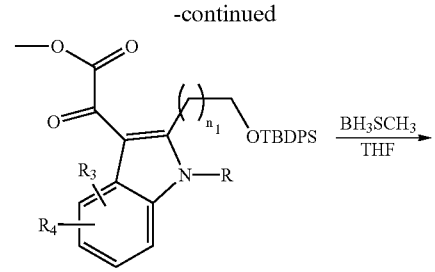
BH$_3$SCH$_3$ / THF
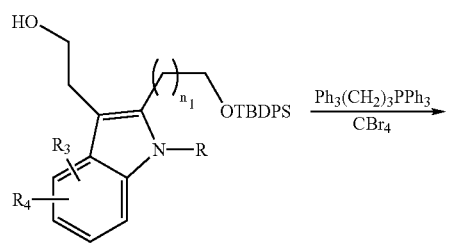
Ph$_3$(CH$_2$)$_3$PPh$_3$ / CBr$_4$
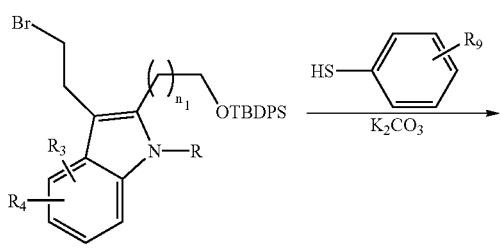
HS-C$_6$H$_4$-R$_9$ / K$_2$CO$_3$
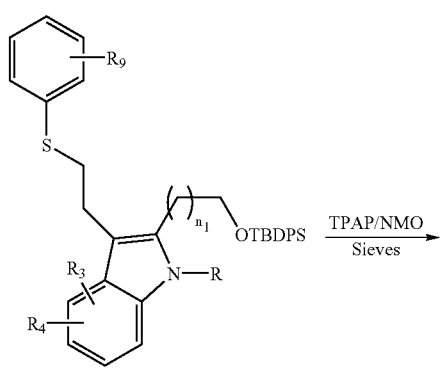
TPAP/NMO Sieves
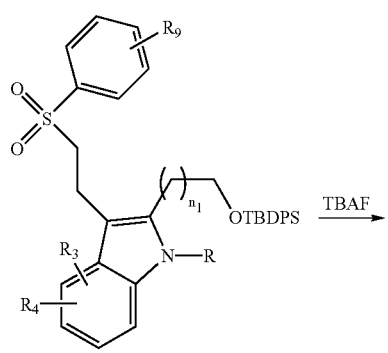
TBAF
-continued
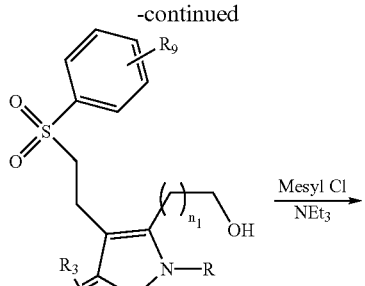
Mesyl Cl / NEt$_3$
(then) NaN$_3$ / DMF
(then) PPh$_3$ / THF
ClSO$_2$(CH$_2$)$_{n2}$X$_1$R$_{12}$
Et$_3$N or pyr
CH$_2$Cl$_2$
or
ClSO$_2$(CH$_2$)$_{n2}$X$_1$R$_{12}$
sat. NaHCO$_3$
CH$_2$Cl$_2$
1) NaOH/THF/MeOH

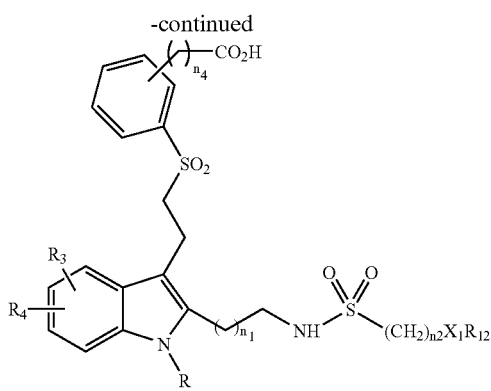

The appropriately substituted halo amine is reacted with trifluoroacetic anhydride to yield an intermediate that could be treated with a $Pd^{II}$ catalyst in the presence of a base such as triethlyamine and CuI and a suitable alkyne under heat yielded the desired indole intermediate. The primary alcohol was protected as a silyl ether using a silyl chloride such as t-Butyidiphenyl silyl chloride and a base such as imidazole. The protected indole is then treated with oxallyl chloride followed by methanol which produced the desired oxalate ester which could be alkylated using a suitable base such as cesium carbonate in refluxing acetonitrile and a halide. The oxallate could then be reduced via the action of a suitable reducing agent such as borane. The resulting primary alcohol was converted to a halide, using for example $CBr_4$ and a phosphine, which could then be a nucleophile such as a thiophenol. The resulting thioether could be oxidized by a variety of oxidizing agents including oxone and TPAP/NMO. The resulting sulfone can be deprotected via the action of a flouride source such as TBAF, CsF or HF. The resulting alcohol could be converted to a halide or mesylate, for example using methane sulfonyl chloride and an organic base, which could then be displaced by sodium azide in DMF. The resulting alkyl azide could be reduced under the action of triphenyl phosphine and wet THF. The amine could be sulfonylated by the action of a sulfonyl chloride under either biphasic Shcott and Baumman conditions, Aq. Bicarbonate and dichloromethane, or under anhydrous conditions consisting of dichloromethane and an organic base such as Hunigs base. The reulting intermediate was hydrolyzed using a base, NaOH, KOH, LiOH and a mixture of solvents including an alcoholic solvent, water and tetrahydrofuran. The following Examples 129–132 were synthesized using Method F.

EXAMPLE 129

3-[4-({2-[1-Benzhydryl-5-chloro-2-(2-{[(2-chlorobenzyl)sulfonyl]amino}ethyl)-1H-indol-3-yl]ethyl}sulfonyl)phenyl]propanoic acid Step 1: 2-Bromo-4-chloroaniline (1.0 eq) was dissolved in $CH_2Cl_2$ (0.25M), then triethylamine and triflouroacetyl anhydride (1.1 eq each) were added. The resulting mixture was stirred at room temperature for 1 hour. Solvent was then stripped-off from the reaction mixture, and the residue was purified by flash chromatography with dichloromethane as eluent to give the described product in 97% yield. m/z $(M–H)^-$ 300.0.

Step 2: N-(2-Bromo-4-chlorophenyl)-2,2,2-trifluoroacetamide (step 1, 1.0 eq) was mixed with 3-butyn-1-ol (2.0 eq), dichlorobis(triphenylphosphine)palladium(II) (2.5% eq), triethylamine (3.0 eq), CuI (5% eq) in DMF (0.2M) in a sealed vessel under $N_2$ and heated to 120° C. for 4 hours. The reaction mixture was then diluted with ethyl acetate, washed with brine and dried over $Na_2SO_4$. Furthermore, evaporate the solvent and the residue was purified by flash column chromatography with 2% $MeOH/CH_2Cl_2$ to give the described product (A) in 67% yield. m/z $(M–H)^-$ 194.09

Step 3: 2-(5-Chloro-1H-indol-2-yl)ethanol (step 2, 1.0 eq) and imidazole (2.0 eq) were dissolved in DMF (0.3M) at room temperature with stirring before tert-butylchlorodiphenylsilane (1.2 eq) was added. The resulting mixture was kept stirred overnight at room temperature before it was quenched with a saturated sodium bicarbonate aqueous solution and extracted with ethyl acetate. Organic phase was washed with water and brine and dried over $Na_2SO_4$. Solvent was removed and residue was purified with column with $CH_2Cl_2$ as eluent to give the desired product as brown gum in over 90% yield. m/z $(M–H)^-$ 433.0

Step 4: 2-({[tert-Butyl(diphenyl)silyl]oxy}ethyl)-5-chloro-1H-indole (step 3, 1.0 eq) was dissolved in ether (0.4M) and the solution was cooled to 0° C. Oxalyl chloride (1.2 eq) was added to the above cold solution with vigorous stirring. The reaction mixture was kept stirred at 0° C. for 1 hour before EtOH was added, followed by $NEt_3$. The resulting mixture was then diluted with more EtOH before it was poured into water. Extract with EtOAc. Organic phase washed with brine, dried over $Na_2SO_4$, concentrated to give the desired product as yellowish solid in 70% yield. m/z $(M–H)^-$ 533.0

Step 5: Ethyl[2-({[tert-butyl(diphenyl)silyl]oxy}ethyl)-5-chloro-1H-indol-3-yl](oxo)acetate (step 4, 1 eq), $Ph_2CHBr$ (1.5 eq) and $Cs_2CO_3$ (1.5 eq) were mixed in dry acetonitrile (0.1M). The mixture was refluxed with stirring for 2 hours. The reaction mixture was cooled to room temperature, added water and extracted with EtOAc. Organic phase was concentrated and the residue was columned with $CH_2Cl_2$ as eluent to give the desired product as orange gum in 45% yield. m/z $(M+H)^+$ 701.3

Step 6: Ethyl[1-benzhydryl-2-({[tert-butyl(diphenyl)silyl]oxy}ethyl)-5-chloro-1H-indol-3-yl](oxo)acetate (step 5, 1 eq) was dissolved in THF (0.1M), then $BH_3.Me_2S$ (2M in THF) (2 eq) was added to it. The resulting mixture was refluxed with stirring overnight under $N_2$. The reaction mixture was cooled to room temperature, then quenched slowly with 1N NaOH. Followed by EtOAc extraction, brine wash. Striping-off the solvent to give the described product in 65% yield. m/z $(M+H)^+$ 645.0

Step 7: 2-[1-Benzhydryl-2-({[tert-butyl(diphenyl)silyl]oxy}ethyl)-5-chloro-1H-indol-3-yl]ethanol (Step 6, 1 eq) was dissolved in $CH_2Cl_2$ (0.08M), then 1,3-bis(diphenylphosphino)-propane (DPPP, 0.75 eq) was added. The solution was cooled to 0° C. under $N_2$, then $CBr_4$ (1.25 eq) was added with stirring. The stirring was continued for 2 hours while the reaction temperature was allowed to return to room temperature. The solvent was stripped off, and the residue was purified by passing through a short column with $CH_2Cl_2$ as eluent to give the desired product in quantitative yield. m/z $(M+H)^+$ 708.0

Step 8: 1-Benzhydryl-3-(2-bromoethyl)-2-({[tert-butyl(diphenyl)silyl]oxy}ethyl)-5-chloro-1H-indole (Step 7, 1 eq) was mixed with methyl-3-(4-mercaptolphenyl)propionate (1.5 eq) and $K_2CO_3$ (1.5 eq) in DMF (0.1M). The resulting mixture was stirred at room temperature under $N_2$ for 2 hrs, then water was added, followed ethyl acetate extraction, brine wash, and column purification (CH$_2$Cl$_2$ as eluent) to give 80% of the desired product as brownish gum. m/z (M+H) 823.0

Step 9: Methyl 3-[4-({2-[1-benzhydryl-2-({[tert-butyl (diphenyl)silyl]oxy}ethyl)-5-chloro-1H-indol-3-yl] ethyl}sulfanyl)phenyl]propanoate (Step 8, 1 eq) was dissolved in acetonitrile (0.1M), then molecular sieve (powder, 4 A,) and 4-methylmorphorline N-oxide (NMO) (4 eq) were added under N$_2$. After 5 min, n-Pr$_4$NRuO$_4$ (TPAP) (5% eq) was added to it. The resulting mixture was heated to 40° C. with stirring and kept for 1.5 hrs. Strip-off the solvent, residue was columned with CH$_2$Cl$_2$, then 1% EtOAc/CH$_2$Cl$_2$ as eluent to give the desired product as white foam in 44% yield. m/z (M+H)$^+$ 855.1

Step 10: Methyl 3-(4-{2-[1-benzhydryl-2-({[tert-butyl (diphenyl)silyl]oxy}ethyl)-5-chloro-1H-indol-3-yl] ethoxy}phenyl)propanoate (Step 9, 1 eq) was dissolved in THF (0.1M) and cooled to 0° C., followed by nBu$_4$NF (1M in THF) (1.2 eq). The resulting mixture was stirred at 0° C. for 5', then warmed up to room temperature and stirred for 30'. Strip-off solvent. The residue was columned with EtOAc/CH$_2$Cl$_2$ (1:9 to 1:4) as eluent to give the described intermediate as white foam in 90% yield. m/z (M+H)$^+$ 616.20

Step 11: Methyl 3-[4-{2-[1-benzhydryl-5-chloro-2-(hydroxyethyl)-1H-indol-3-yl]ethyl}-sulfonyl)phenyl]propanoate (step 10, 1 eq) in dichloromethane (0.02M) was treated at 0° C. with MeSO$_2$Cl (2.0 eq) and Et$_3$N (2.5 eq) and stirred for 1 hour. The ice-bath was removed and the reaction mixture was stirred for another 1 hour at room temperature before it was diluted with CH$_2$Cl$_2$, washed with NaH$_2$PO$_4$ brine and dried over Na$_2$SO$_4$. Evaporate solvent to give the described product in quantitative yield. m/z (M+H)$^+$ 695.0

Step 11: Methyl 3-(4-{[2-(1-benzhydryl-5-chloro-2-{2-[(methylsulfonyl)oxy]ethyl}-1H-indol-3-yl)ethyl] sulfonyl}phenyl)propanoate (step 11, 1.0 eq) was dissolved in DMF (0.03M) and treated with NaN$_3$ (3.0 eq). The resulting mixture was heated to 60° C. and stirred for 2 hours, then, was added water, extracted with ethyl acetate, washed with brine and dried with Na$_2$SO$_4$. Evaporation of solvent yields quantitatively the described product. m/z (M+H)$^+$ 641.1

Step 12: Methyl 3-[4-({2-[2-(2-azidoethyl)-1-benzhydryl-5-chloro-1H-indol-3-yl]ethyl}sulfonyl)phenyl]propanoate (step 12, 1 eq) was dissolved in THF (0.1M), and treated with triphenylphosphine (1.1 eq). The reaction mixture was kept stirred for 2 days before the addition of water, then stirred overnight. Strip off solvent, residue was columned with 4% MeOH:CH$_2$Cl$_2$ as eluent to give the described product in 71% yield. m/z (M+H)$^+$ 615.2

Step 13: Methyl 3-[4-({2-[2-(2-aminoethyl)-1-benzhydryl-5-chloro-1H-indol-3-yl]ethyl}sulfonyl)phenyl]propanoate (step 12, 1 eq) and (3,4-dichlorobenzyl)sulfonyl chloride (1.1) were dissolved in CH$_2$Cl$_2$ (0.1M) at room temperature, then aqueous Na$_2$CO$_3$ solution was added with stirring. The stirring was continued for 2 hours. Then, organic phase was separated, washed with brine, dried with Na$_2$SO$_4$. Evaporate the solvent, the residue was columned with CH$_2$Cl$_2$ to 2% MeOH:CH$_2$Cl$_2$ as eluent to give 85% yield of the described product as white solid. m/z (M−H)$^−$ 834.9

Step 14: Methyl 3-[4-({2-[1-benzhydryl-5-chloro-2-(2-{[(3,4-dichlorobenzyl)sulfonyl]amino}ethyl)-1H-indol-3-yl] ethyl}sulfonyl)phenyl]propanoate (step 13, 1.0 eq) was dissolved in THF:MeOH (1:1) (0.1M), then added 1N NaOH. The mixture was kept stirred overnight at room temperature. The solvent was stripped off and the residue was dissolved in water to form a basic solution, which was neutralized with diluted HCl solution to precipitate the product. The solid was collected by filtration, washed with water, rinsed with hexane, then dried to give the desired product in 86% yield. HRMS calc for [C$_{41}$H$_{37}$Cl$_3$N$_2$O$_6$S$_2$+H] 823.12314. found 823.12292.

EXAMPLE 130

3-(4-{[2-(1-Benzhydryl-2-{2-[(benzylsulfonyl) amino]ethyl}-5-chloro-1H-indol-3-yl)ethyl] sulfonyl}phenyl)propanoic acid Step 1: The intermediate from example 129, step 12 was treated with □-toluenesulfonyl chloride according to the procedure in example 129 step 13 to yield the desired compound in 94% yield.

Step 2: The intermediate from above was treated with NaOH according to the procedure described in example 129, step 14 to yield the desired acid in 92% HRMS calc for [C$_{41}$H$_{39}$ClN$_2$O$_6$S$_2$+H] 755.20109. found 755.20201.

EXAMPLE 131

3-[4-({2-[1-benzhydryl-5-chloro-2-(2-{[(2,6-difluorobenzyl)sulfonyl]amino}ethyl)-1H-indol-3-yl] ethyl}sulfonyl)phenyl]propanoic acid Step 1: The intermediate from example 129, step 12 was treated with (2,6-Difluoro-phenyl)-methanesulfonyl chloride according to the procedure in example 129 step 13 to yield the desired compound in 42% yield.

Step 2: The intermediate from above was treated with NaOH according to the procedure described in example 129, step 14 to yield the desired acid in 83%. HRMS calc for [C$_{41}$H$_{37}$ClF$_2$N$_2$O$_6$S$_2$+H] 791.18224. found 791.18257.

EXAMPLE 132

3-[4-({2-[1-benzhydryl-5-chloro-2-(2-{[(2-fluorobenzyl)sulfonyl]amino}ethyl)-1H-indol-3-yl] ethyl}sulfonyl)phenyl]propanoic acid Step 1: The intermediate from example 129, step 12 was treated with (2-fluoro-phenyl)-methanesulfonyl chloride according to the procedure in example 129 step 13 to yield the desired compound in 42% yield.

Step 2: The intermediate from above was treated with NaOH according to the procedure described in example 129, step 14 to yield the desired acid in 86% yield. HRMS calc for [C$_{41}$H$_{38}$ClFN$_2$O$_6$S$_2$+H] 773.19166. found 773.19213.

Method G

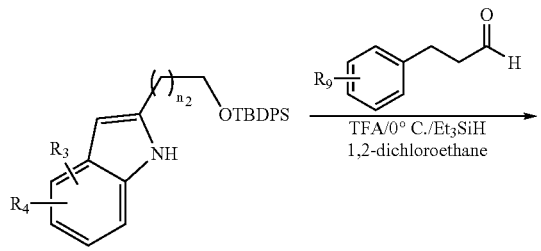

-continued

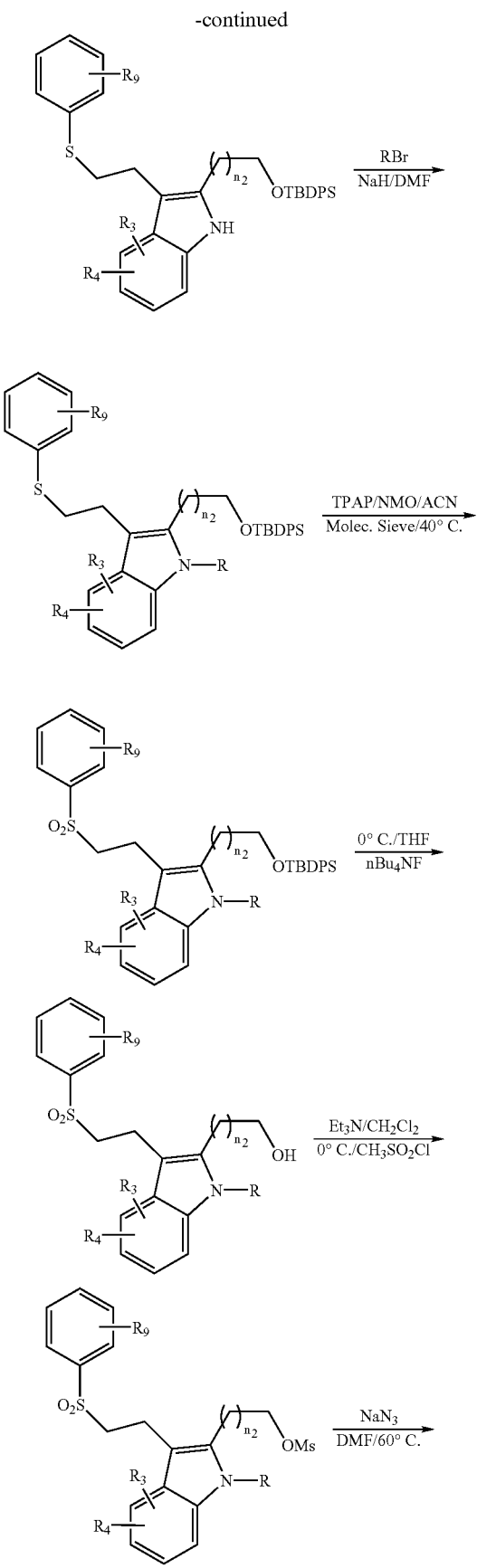

-continued

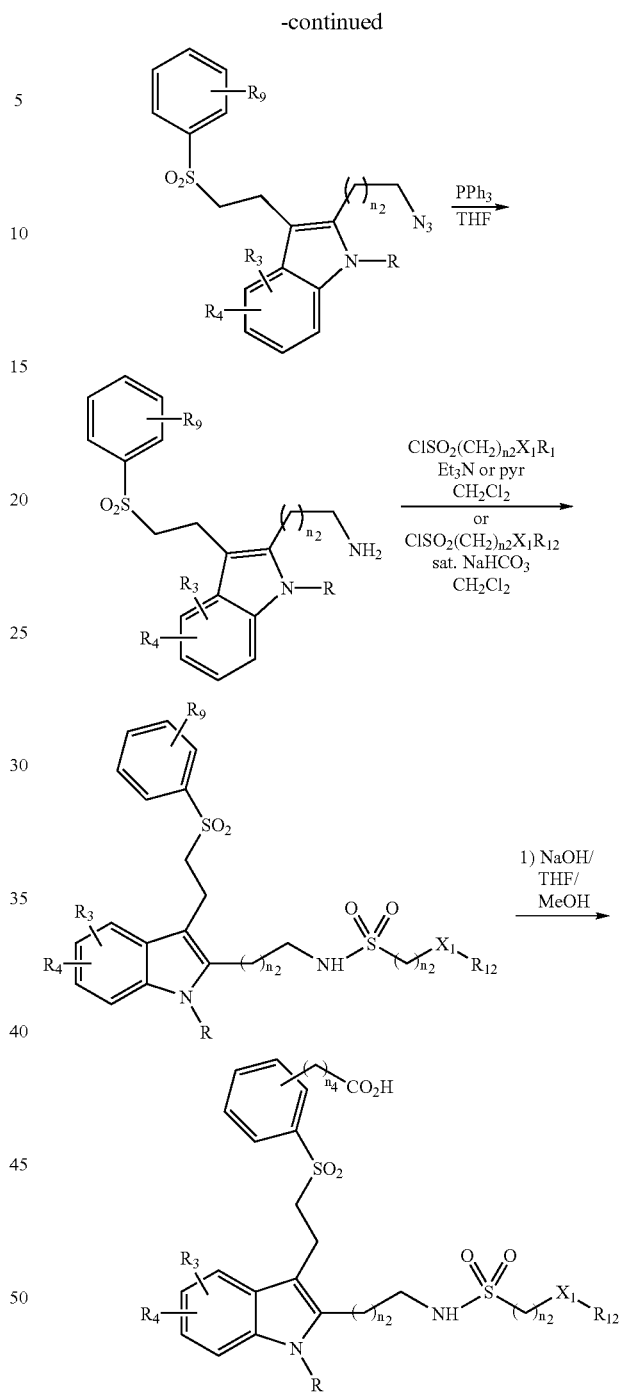

An intermediate from Method F could be alkylated at the C3 position with aldehydes or the corresponding acetals in the presence of a Lewis or Bronsted acid, such as boron triflouride etherate or trifluoroacetic acid. The indole nitrogen may then be alkylated by treatment with a strong base such as sodium bis(trimethylsilyl)amide, n-BuLi, sodium hydride or potassium hydride in a solvent such as DMF, DMSO or THF followed by exposure to the appropriate halide. The resulting thioether could be oxidized by a variety of oxidizing agents including oxone and TPAP/NMO. The resulting sulfone can be deprotected via the action of a flouride source such as TBAF, CsF or HF. The resulting alcohol could be converted to a halide or mesylate, for example using methane sulfonyl chloride and an organic base, which could then be displaced by sodium azide in DMF. The resulting alkyl azide could be reduced under the action of triphenyl phosphine and wet THF. The amine could be sulfonylated by the action of a sulfonyl chloride under either biphasic Shcott and Baumman conditions, Aq. Bicarbonate and dichloromethane, or under anhydrous conditions consisting of dichloromethane and an organic base such as Hunigs base. The reulting intermediate was hydrolyzed using a base, NaOH, KOH, LiOH and a mixture of solvents including an alcoholic solvent, water and tetrahydrofuran. The following Examples 133, 135–138 and 140–141 were synthesized by Method G.

EXAMPLE 133

3-[4-({2-[1-benzhydryl-5-chloro-2-(2-{[(2-chlorobenzyl)sulfonyl]amino}ethyl)-1H-indol-3-yl]ethyl}sulfonyl)phenyl]propanoic acid Step 1: Ethyl 4-[(2-oxoethyl)sulfanyl]propanoate (example 129 step 3, 4.2 eq) was added to a solution containing 2-({[tert-butyl(diphenyl)silyl]oxy}ethyl)-5-chloro-1H-indole (1 eq), TFA (3 eq), and 1,2-dichloroethane (0.1M) at 0° C. under $N_2$. Then $Et_3SiH$ (12 eq) was added and the reaction was allowed to return to room temperature and stirred overnight. Quenched reaction with $NaHCO_{3(aq)}$ and extracted with EtOAc and washed with brine and dried over sodium sulfate. Purified with silica gel column and 1:5 EtOAc/Hexane as eluent. Obtained ethyl 4-({2-[2-(2-{[tert-butyl(diphenyl)silyl]oxy}ethyl)-5-chloro-1H-indol-3-yl]ethyl}sulfanyl)propanoate (yellow oil) in 79% yield.

Step 2: Ethyl 4-({2-[2-(2-{[tert-butyl(diphenyl)silyl]oxy}ethyl)-5-chloro-1H-indol-3-yl]ethyl}sulfanyl)propanoate (1 eq) was added to a suspension of NaH (1.1 eq) in DMF (0.38M) at 0° C. under $N_2$. After 30 minutes $Ph_2CHBr$ was added and the reaction was warmed to room temperature. After 2.5 hours the reaction was quenched with $NH_4Cl_{(aq)}$ and extracted with EtOAc/$Et_2O$ mix and washed with water and brine and dried over sodium sulfate. Purified with silica gel column and 1:6 EtOAc/Hexane. Obtained ethyl 3-[4-({2-[1-benzhydryl-2-(2-{[tert-butyl(diphenyl)silyl]oxy}ethyl)-5-chloro-1H-indol-3-yl]ethyl}sulfanyl)phenyl]propanoate (yellow gum) in 42% yield.

Step 3: NMO (4 eq) was added to a solution/suspension containing ethyl 3-[4-({2-[1-benzhydryl-2-(2-{[tert-butyl(diphenyl)silyl]oxy}ethyl)-5-chloro-1H-indol-3-yl]ethyl}sulfanyl)phenyl]propanoate (1 eq), ACN (0.1M), and molecular sieves (1 g/mmole of propanoate) under $N_2$. After 10 minutes TPAP (0.05 eq) was added and the mixture was heated to 40° C. After 2 hours the reaction was cooled and filtered and the filtrate was collected. Purified with silica gel column and 1:4 EtOAc/Hexane. Obtained ethyl 3-[4-({2-[1-benzhydryl-2-(2-{[tert-butyl(diphenyl)silyl]oxy}ethyl)-5-chloro-1H-indol-3-yl]ethyl}sulfonyl)phenyl]propanoate (white solid) in 86% yield.

Step 4: Tetrabutylammonium fluoride (1M in THF) (1.2 eq) was added to a solution of ethyl 3-[4-({2-[1-benzhydryl-2-(2-{[tert-butyl(diphenyl)silyl]oxy}ethyl)-5-chloro-1H-indol-3-yl]ethyl}sulfonyl)phenyl]propanoate (1 eq) and THF (0.1M) at 0° C. under $N_2$. Warmed reaction to room temperature and after 30 minutes quenched with $NH_4Cl_{(aq)}$. Extracted with EtOAc and washed with brine and dried over sodium sulfate. Purified with silica gel column and 1:9 EtOAc/$CH_2Cl_2$. Obtained ethyl 3-[4-({2-[1-benzhydryl-5-chloro-2-(2-hydroxyethyl)-1H-indol-3-yl]ethyl}sulfonyl)phenyl]propanoate (white solid) in 88% yield.

Step 5: $CH_3SO_2Cl$ (2 eq) and $Et_3N$ (2.5 eq) were added to a solution of ethyl 3-[4-({2-[1-benzhydryl-5-chloro-2-(2-hydroxyethyl)-1H-indol-3-yl]ethyl}sulfonyl)phenyl]propanoate (1 eq) in $CH_2Cl_2$ (0.02M) at 0° C. under $N_2$. After 1 hour the reaction was warmed to room temperature. After an additional hour water was added and extracted with $CH_2Cl_2$ and washed with brine and dried over sodium sulfate. Removed solvent to obtain ethyl 3-(4-{[2-(1-benzhydryl-5-chloro-2-{2-[(methylsulfonyl)oxy]ethyl}-1H-indol-3-yl)ethyl]sulfonyl}phenyl)propanoate (white solid) in 98% yield.

Step 6: Ethyl 3-(4-{[2-(1-benzhydryl-5-chloro-2-{2-[(methylsulfonyl)oxy]ethyl}-1H-indol-3-yl)ethyl]sulfonyl}phenyl)propanoate (1 eq), sodium azide (5 eq), and DMF (0.05M) were placed together under $N_2$ and heated to 60° C. After 1 hour the reaction was cooled and water was added. Extracted with EtOAc/$Et_2O$ mix and washed with water and brine and dried over sodium sulfate. Removed solvent to obtain ethyl 3-[4-({2-[2-(2-azidoethyl)-1-benzhydryl-5-chloro-1H-indol-3-yl]ethyl}sulfonyl)phenyl]propanoate (light-brown solid) in 96% yield.

Step 7: Ethyl 3-[4-({2-[2-(2-azidoethyl)-1-benzhydryl-5-chloro-1H-indol-3-yl]ethyl}sulfonyl)phenyl]propanoate (1 eq), $PPh_3$ (polymer supported) (1.3 eq), and THF (0.1M) were placed together under $N_2$. After 3 days water (1 mL/1 mmole propanoate) was added and reaction was stirred overnight. Filtered and collected filtrate. Purified with silica gel column and 2% MeOH in $CH_2Cl_2$. Obtained ethyl 3-[4-({2-[2-(2-aminoethyl)-1-benzhydryl-5-chloro-1H-indol-3-yl]ethyl}sulfonyl)phenyl]propanoate (light-brown solid) in 65% yield.

Step 8: (2-chlorobenzyl)sulfonyl chloride (2.2 eq) was added to a mixture of ethyl 3-[4-({2-[2-(2-aminoethyl)-1-benzhydryl-5-chloro-1H-indol-3-yl]ethyl}sulfonyl)phenyl]propanoate (1 eq), $CH_2Cl_2$ (0.08M), water (1 mL/1 mL $CH_2Cl_2$), and $Na_2CO_3$ (2.5 eq). After 2 hours more (2-chlorobenzyl)sulfonyl chloride (1.1 eq) was added. After an additional 1.5 hours the organic layer was recovered and washed with brine and dried over sodium sulfate. Purified with silica gel preparatory plate and 2% MeOH in $CH_2Cl_2$. Obtained ethyl 3-[4-({2-[1-benzhydryl-5-chloro-2-(2-{[(2-chlorobenzyl)sulfonyl]amino}ethyl)-1H-indol-3-yl]ethyl}sulfonyl)phenyl]propanoate (light-yellow gum) in 75% yield.

Step 9: Ethyl 3-[4-({2-[1-benzhydryl-5-chloro-2-(2-{[(2-chlorobenzyl)sulfonyl]amino}ethyl)-1H-indol-3-yl]ethyl}sulfonyl)phenyl]propanoate (1 eq), THF (0.1M), MeOH (1 mL/1 mL THF), and NaOH (1N) (11 eq) were stirred together overnight. Solvents were removed and the resulting residue was taken up in water. The solution was acidified with 1N HCl and collected resulting precipitate by filtration. Obtained 3-[4-({2-[1-benzhydryl-5-chloro-2-(2-{[(2-chlorobenzyl)sulfonyl]amino}ethyl)-1H-indol-3-yl]ethyl}sulfonyl)phenyl]propanoic acid (light-brown solid) in 83% yield. HRMS calc for [$C_{39}H_{36}ClN_3O_4S$+H] 789.16211. found 789.16311.

Method H

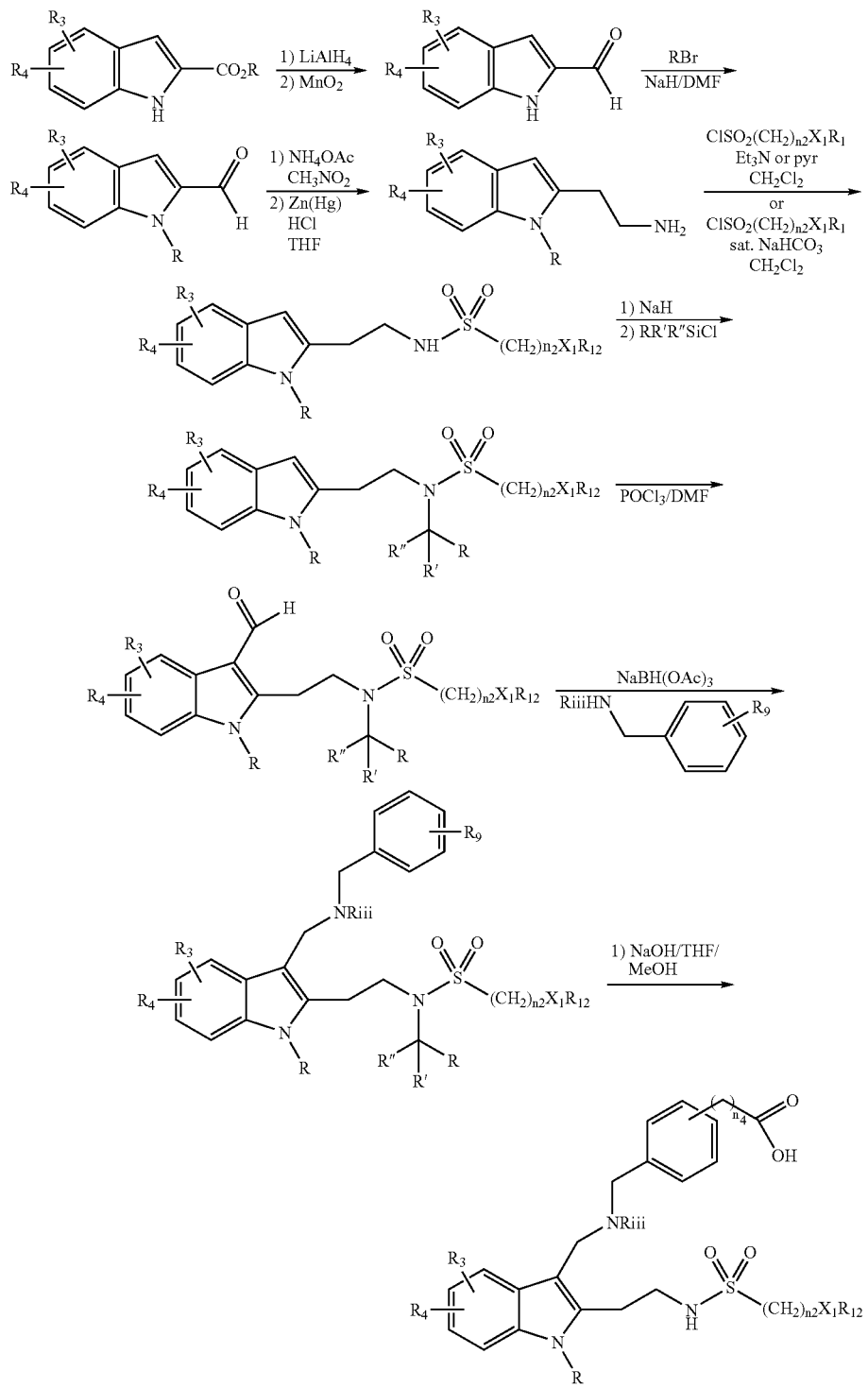

The suitably substituted indole-2-carboxylate could be reduced via a suitable reducing agent such as lithium aluminum hydride, dibal etc and then the resulting alcohol could be oxidized to the 2-formyl indole using $MnO_2$, under Swern oxidation conditions or other oxidants. The indole nitrogen may then be alkylated by treatment with a strong base such as sodium bis(trimethylsilyl)amide, n-BuLi, sodium hydride or potassium hydride in a solvent such as DMF, DMSO or THF followed by exposure to the appropriate halide. The aldehyde was next treated with nitromethane and a base such as ammonium acetate to yield a vinyl nitro intermediate that could be reduced by a variety of agents such as Lithium Aluminum Hydride or Zn(Hg) amalgam in HCl. The resulting amine was sulfonylated using a sulfonyl chloride either under biphasic Schott and Baummen conditions or anhydrous conditions with an organic base. Treatment of the the resulting sulfonamide with a strong base such as sodium bis(trimethylsilyl)amide, n-BuLi, sodium hydride or potassium hydride in a solvent such as DMF, DMSO or THF followed by exposure to a silyl chloride such as t-butyldimethyl silyl chloride to generate the protected sulfonamide. This material could be formylated at C3 using standard Vilsmeier conditions conditions of $POCl_3$/DMF. The thus formed 3-formyl indole was reductively aminated using a suitable amine, a reducing agent such as sodium triacetoxyborohydride and acid such as glacial acetic acid. The resulting intermediate was hydrolyzed using a base, NaOH, KOH, LiOH and a mixture of solvents including an alcoholic solvent, water and tetrahydrofuran. Example 134 was synthesized by Method H.

EXAMPLE 134

4-({[(1-benzhydryl-2-{2-[(benzylsulfonyl)amino] ethyl}-5-chloro-1H-indol-3-yl)methyl] amino}methyl)benzoic acid

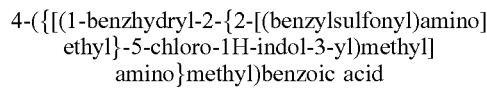

Step 1: 5-Chloro-1H-indole-2-carboxylic acid ethyl ester (1 eq.) was dissolved in THF (0.4M), flushed with a nitrogen atmosphere and then the mixture was cooled to 0° C. and LAH (3 eq of a 1M solution in THF) was slowly added. The reaction was allowed to warm slowly to room temperature and stirred until TLC analysis indicated completion. After cooling the flask to 0° C., NaOH (60 ml 3N solution) was slowly added and the reaction stirred until two layers were obtained. The layers were separated, aqueous was extracted 2× ethyl acetate, the combined organics were washed with brine and then dried over magnesium sulfate and concentrated to yield the desired alcohol that was used crude for the next step.

Step 2: The product (1 eq.) from above was dissolved in THF (0.5 M) and treated with manganese dioxide (3 eq), and stirred for 1.5 hours until TLC analysis indicated that reaction was complete. The reaction was filtered through celite, dried over magnesium sulfate, and concentrated to yield the desired crude aldehyde in 82% yield.

Step 3: To the indole from above (1.0 eq) in DMF (0.36 M) at 25° C. was added NaH (1.2 eq, 60% dispersion in oil), and the brown solution was stirred at 0 to −5° C. for 1 h and then bromodiphenylmethane was added (1.1 eq), and then the reaction mixture was stirred overnight. It was then quenched with water, diluted with ethyl acetate, washed with water and brine, dried over sodium sulfate and purified by column chromatography to yield 60% of the desired product.

Step 4: To the above aldehyde (1.0 equiv) in $CH_3NO_2$ (0.075 M) was added ammonium acetate (9 equiv) and the resulting mixture was heated to reflux overnight. The reaction mixture concentrated to a small volume and then diluted with EtOAc and washed with brine. The aqueous phase was extracted with EtOAc. The combined organic extracts were washed with brine, dried over sodium sulfate and concentrated and purification by column chromatography to the desired nitroolefin (51% yield).

Step 5: Zinc dust (20 equiv) was suspended in 5% aqueous HCl solution (8 M Zn/5% HCl). To this mixture was added $HgCl_2$ (0.28 equiv). The mixture was shaken for 10 min, the aqueous phase was decanted and replaced with fresh 5% HCl, and again the mixture was shaken for 5 min and the aqueous phase was removed. The zinc-mercury amalgam thus generated was then added to a mixture of the nitroolefin (1.0 equiv) and conc. HCl (80 equiv) in THF (0.04 M nitroolefin/THF). The mixture was maintained at a gentle reflux for 1 h. The formation of product was followed by TLC analysis. The mixture was cooled to room temperature and the solids were removed by filtration through Celite. Conc. $NH_4OH$ was added to the solution phase and the mixture was concentrated on the rotary evaporator. The residue was dissolved in $CH_2Cl_2$ and conc. $NH_4OH$. The aqueous phase was extracted with $CH_2Cl_2$, and the organic phase was washed with brine, dried over sodium sulfate, and concentrated to yield the desired crude amine (100%) that was used in the next step without purification.

Step 7: To the amine form above (1.0 equiv) and sat. $NaHCO_3$ (0.14 M) in $CH_2Cl_2$ (0.07 M) was added □-toluenesulfonyl chloride (1.0 equiv). After 1 h the mixture was poured into saturated sodium bicarbonate and extracted with $CH_2Cl_2$. The combined organic phase was washed with brine, dried over sodium sulfate and purified by column chromatography (gradient elution using 10% EtOAc-hexanes→20% EtOAc-hexanes) to afford 40% of the desired sulfonamide.

Step 8: The sulfonamide from above was dissolved in DMF (0.5 M) under nitrogen atmosphere, cooled to 0° C., treated with sodium hydride (1.05 eq of a 60 oil dispersion), stirred for 15 minutes to ensure anion generation, treated with t-butyldimethsilyl chloride (1.2 eq) and then stirred for two hours at 0° C. at which time TLC analysis indicated the reaction was complete. The reaction was worked up by partitioning between ½ saturated ammonium chloride solution and ethyl acetate, extraction of the aqueous layers with ethyl acetate (2×), washing combined organic layers with brine (1×), drying over magnesium sulfate and concentrating to yield quantitative crude yield of the desired protected sulfonamide.

Step 9: To DMF (~1 ml) was added phosporous oxychloride (1.2 eq), these reagents were stirred for 10 minutes and then a solution of the indole (1 eq) from above in DMF (0.8 M) was added. The resulting red reaction mixture is stirred for 4 hours, diluted with water and then the pH was adjusted to 8 (total volume of aqueous added about ¾ of DMF added initially) and then the reaction was refluxed for 2 hours and finally cooled, extracted with dicloromethane, aqueous layer extracted with dichloromethane (2×), combined organic layers washed with brine (1×), dried over magnesium sulfate and concentrated to yield 75% of a crude aldehyde that was used without further purification.

Step 10: To the aldehyde from above (1 eq) in THF (1.2 M) was added 4-aminomethyl-benzoic acid methyl ester (1.2 eq), sodium triacetoxyborohydride (1.5 eq) and acetic acid (glacial, 1.5 eq). The reaction was stirred overnight and then worked up by the addition of saturated sodium bicarbonate and ethyl acetate, the layers were separated, the aqueous layer extracted with dichloromethane (2×), combined organic layers washed with brine (1×), dried over magnesium sulfate and concentrated and purified via chromatography to yield 37% of the desired product.

Step 11: The resulting ester was hydrolyzed by stirring with 1N NaOH (5 equiv) in THF (0.07 M) and enough MeOH to produce a clear solution. The reaction was monitored by TLC (10% MeOH—$CH_2Cl_2$) for the disappearance of starting material. The mixture was stirred at room temperature for 72 hours. The mixture was concentrated, diluted with $H_2O$, and acidified to pH 5 using 1 M HCl. The aqueous phase was extracted with EtOAc and the organic phase was washed with brine, dried over sodium sulfate, and concentrated to afford the desired product in 83% yield. HRMS calc for [$C_{39}H_{36}ClN_3O_4S-H$] 676.20423. found 676.20397.

EXAMPLE 135

4-{[2-(1-benzhydryl-2-{2-[(benzylsulfonyl)amino]-ethyl}-5-chloro-1H-indol-3yl)ethyl]sulfonyl}benzoic acid Step 1: 2-(5-chloro-1H-indol-2-yl)ethanol (1 eq) was added to a solution (under $N_2$) containing tert-Butyldiphenylchlorosilane (1.2 eq), imidazole (2.5 eq), and DMF (1.8M). The reaction was stirred overnight. Quenched with $NaHCO_{3(aq)}$ and extracted with a $Et_2O$/EtOAc mixture. The organic layer was washed with water and brine and dried over sodium sulfate. Purified with silica gel column and 1:4 Hexane/$CH_2Cl_2$ as eluent. Obtained 2-({[tert-butyl(diphenyl)silyl]oxy}ethyl)-5-chloro-1H-indole (yellow oil) in 98% yield.

Step 2: Methyl 4-[(2-oxoethyl)sulfanyl]benzoate (3.7 eq) was added to a solution containing 2-({[tert-butyl(diphenyl)silyl]oxy}ethyl)-5-chloro-1H-indole (1 eq), TFA (3 eq), and 1,2-dichloroethane (0.1M) at 0° C. under $N_2$. Then $Et_3SiH$ (12 eq) was added and the reaction was allowed to return to room temperature and stirred overnight. Quenched reaction with $NaHCO_{3(aq)}$ and extracted with EtOAc and washed with brine and dried over sodium sulfate. Purified with silica gel column and 1:5 EtOAc/Hexane as eluent. Obtained methyl 4-({2-[2-(2-{[tert-butyl(diphenyl)silyl]oxy}ethyl)-5-chloro-1H-indol-3-yl]ethyl}sulfanyl)benzoate (yellow solid) in 79% yield.

Step 3: Methyl 4-({2-[2-(2-{[tert-butyl(diphenyl)silyl]oxy}ethyl)-5-chloro-1H-indol-3-yl]ethyl}sulfanyl)benzoate (1 eq) was added to a suspension of NaH (1.1 eq) in DMF (0.37M) at 0° C. under $N_2$. After 30 minutes $Ph_2CHBr$ (1.8 eq) was added and the reaction was warmed to room temperature. After 3 hours the reaction was quenched with $NH_4Cl_{(aq)}$ and extracted with EtOAc/$Et_2O$ mix and washed with water and brine and dried over sodium sulfate. Purified with silica gel column and 1:5 EtOAc/Hexane. Obtained methyl 3-[4-({2-[1-benzhydryl-2-(2-{[tert-butyl(diphenyl)silyl]oxy}ethyl)-5-chloro-1H-indol-3-yl]ethyl}sulfanyl)phenyl]benzoate (yellow gum) in 65% yield.

Step 4: NMO (4 eq) was added to a solution/suspension containing methyl 3-[4-({2-[1-benzhydryl-2-(2-{[tert-butyl(diphenyl)silyl]oxy}ethyl)-5-chloro-1H-indol-3-yl]ethyl}sulfanyl)phenyl]benzoate (1 eq), ACN (0.1M), and molecular sieves (1 g/mmole of benzoate) under $N_2$. After 10 minutes TPAP (0.12 eq) was added and the mixture was heated to 40° C. After 1.5 hours the reaction was cooled and filtered and the filtrate was collected. Purified with silica gel column and 1:5 EtOAc/Hexane. Obtained methyl 3-[4-({2-[1-benzhydryl-2-(2-{[tert-butyl(diphenyl)silyl]oxy}ethyl)-5-chloro-1H-indol-3-yl]ethyl}sulfonyl)phenyl]benzoate (white solid) in 71% yield.

Step 5: Tetrabutylammonium fluoride (1M in THF) (1.2 eq) was added to a solution of methyl 3-[4-({2-[1-benzhydryl-2-(2-{[tert-butyl(diphenyl)silyl]oxy}ethyl)-5-chloro-1H-indol-3-yl]ethyl}sulfonyl)phenyl]benzoate (1 eq) and THF (0.1M) at 0° C. under $N_2$. Warmed reaction to room temperature and after 1 hour quenched with $NH_4Cl_{(aq)}$. Extracted with EtOAc and washed with brine and dried over sodium sulfate. Purified with silica gel column and 1:9 EtOAc/$CH_2Cl_2$. Obtained methyl 3-[4-({2-[1-benzhydryl-5-chloro-2-(2-hydroxyethyl)-1H-indol-3-yl]ethyl}sulfonyl)phenyl]benzoate (white solid) in 86% yield.

Step 6: $CH_3SO_2Cl$ (2 eq) and $Et_3N$ (2.5 eq) were added to a solution of methyl 3-[4-({2-[1-benzhydryl-5-chloro-2-(2-hydroxyethyl)-1H-indol-3-yl]ethyl}sulfonyl)phenyl]benzoate (1 eq) in $CH_2Cl_2$ (0.02M) at 0° C. under $N_2$. After 1 hour the reaction was warmed to room temperature. After an additional hour water was added and extracted with $CH_2Cl_2$ and washed with brine and dried over sodium sulfate. Removed solvent to obtain methyl 3-(4-{[2-(1-benzhydryl-5-chloro-2-{2-[(methylsulfonyl)oxy]ethyl}-1H-indol-3-yl)ethyl]sulfonyl}phenyl)benzoate (light-yellow solid) in 99% yield.

Step 7: Methyl 3-(4-{[2-(1-benzhydryl-5-chloro-2-{2-[(methylsulfonyl)oxy]ethyl}-1H-indol-3-yl)ethyl]sulfonyl}phenyl)benzoate (1 eq), sodium azide (5 eq), and DMF (0.05M) were placed together under $N_2$ and heated to 60° C. After 1 hour the reaction was cooled and water was added. Extracted with EtOAc/$Et_2O$ mix and washed with water and brine and dried over sodium sulfate. Removed solvent to obtain methyl 3-[4-({2-[2-(2-azidoethyl)-1-benzhydryl-5-chloro-1H-indol-3-yl]ethyl}sulfonyl)phenyl]benzoate (light-yellow solid) in 99% yield.

Step 8: Methyl 3-[4-({2-[2-(2-azidoethyl)-1-benzhydryl-5-chloro-1H-indol-3-yl]ethyl}sulfonyl)phenyl]benzoate (1 eq), $PPh_3$ (2 eq), and THF (0.1M) were placed together under $N_2$ and stirred overnight. Water (1 mL/1 mmole benzoate) was added and reaction was again stirred overnight. The solution was concentrated and purified with silica gel column and 3:1 EtOAc/Hexane followed by 5% MeOH in $CH_2Cl_2$. Obtained methyl 3-[4-({2-[2-(2-aminoethyl)-1-benzhydryl-5-chloro-1H-indol-3-yl]ethyl}sulfonyl)phenyl]benzoate (light-yellow solid) in 99% yield.

Step 9: alpha-Toluene sulfonyl chloride (2 eq) was added to a mixture of methyl 3-[4-({2-[2-(2-aminoethyl)-1-benzhydryl-5-chloro-1H-indol-3-yl]ethyl}sulfonyl)phenyl]benzoate (1 eq), $CH_2Cl_2$ (0.08M), water (1 mL/1 mL $CH_2Cl_2$), and $Na_2CO_3$ (2.5 eq). After 2 hours the organic layer was recovered and washed with brine and dried over sodium sulfate. Purified with silica gel preparatory plate and 3% MeOH in $CH_2Cl_2$. Obtained methyl 4-{[2-(1-benzhydryl-2-{2-[(benzylsulfonyl)amino]ethyl}-5-chloro-1H-indol-3-yl)ethyl]sulfonyl}benzoate (off-white solid) in 94% yield.

Step 10: Methyl 4-{[2-(1-benzhydryl-2-{2-[(benzylsulfonyl)amino]ethyl}-5-chloro-1H-indol-3-yl)ethyl]sulfonyl}benzoate (1 eq), THF (0.1M), MeOH (1 mL/1 mL THF), and NaOH (1N) (11 eq) were stirred together overnight. Solvents were removed and the resulting residue was taken up in water. The solution was acidified with 1N HCl and collected resulting precipitate by filtration. Obtained 4-{[2-(1-benzhydryl-2-{2-[(benzylsulfonyl)amino]ethyl}-5-chloro-1H-indol-3-yl)ethyl]sulfonyl}benzoic acid (off-white solid) in 92% yield. HRMS calc for [$C_{39}H_{35}ClN_2O_6S_2-H$] 725.15523. found 725.15437.

EXAMPLE 136

4-({2-[1-benzhydryl-5-chloro-2-(2-{[(2-chlorobenzyl)sulfonyl]amino}ethyl)-1H-indol-3-yl]ethyl}sulfonyl)benzoic acid Step 1: (2-chlorobenzyl)sulfonyl chloride (3.4 eq) was added to a mixture of methyl 3-[4-((2-[2-(2-aminoethyl)-1-benzhydryl-5-chloro-1H-indol-3-yl]ethyl}sulfonyl)phenyl] benzoate (Example 135, Step 8, 1 eq), $CH_2Cl_2$ (0.08M), water (1 mL/1 mL $CH_2Cl_2$), and $Na_2CO_3$ (2.5 eq). After 2 hours more (2-chlorobenzyl)sulfonyl chloride (3.4 eq) was added. After an additional 1.5 hours the organic layer was recovered and washed with brine and dried over sodium sulfate. Purified with silica gel preparatory plate and 3% MeOH in $CH_2Cl_2$. Obtained methyl 3-[4-({2-[1-benzhydryl-5-chloro-2-(2-{[(2-chlorobenzyl)sulfonyl]amino}ethyl)-1H-indol-3-yl]ethyl}sulfonyl)phenyl]benzoate (orange gum) in 40% yield.

Step 2: Methyl 3-[4-({2-[1-benzhydryl-5-chloro-2-(2-{[(2-chlorobenzyl)sulfonyl]amino}ethyl)-1H-indol-3-yl]ethyl}sulfonyl)phenyl]benzoate (1 eq), THF (0.1M), MeOH (1 mL/1 mL THF), and NaOH (1N) (11 eq) were stirred together overnight. Solvents were removed and the resulting residue was taken up in water. The solution was acidified with 1N HCl and collected resulting precipitate by filtration. Obtained 4-({2-[1-benzhydryl-5-chloro-2-(2-{[(2-chlorobenzyl)sulfonyl]amino}ethyl)-1H-indol-3-yl]ethyl}sulfonyl)benzoic acid (red-orange solid) in 80% yield. HRMS calc for $[C_{39}H_{34}Cl_2N_2O_6S_2+H]$ 761.13081. found 761.13146.

EXAMPLE 137

4-({2-[1-benzhydryl-5-chloro-2-(2-{[(2,6-difluorobenzyl)sulfonyl]amino}ethyl)-1H-indol-3-yl]ethyl}sulfonyl)benzoic acid Step 1: (2,6-difluorobenzyl)sulfonyl chloride (3.4 eq) was added to a mixture of methyl 3-[4-({2-[2-(2-aminoethyl)-1-benzhydryl-5-chloro-1H-indol-3-yl]ethyl}sulfonyl)phenyl]benzoate (Example 135, Step 8, 1 eq), $CH_2Cl_2$ (0.08M), water (1 mL/1 mL $CH_2Cl_2$), and $Na_2CO_3$ (2.5 eq). After 2 hours the organic layer was recovered and washed with brine and dried over sodium sulfate. Purified with silica gel preparatory plate and 3% MeOH in $CH_2Cl_2$. Obtained methyl 4-({2-[1-benzhydryl-5-chloro-2-(2-{[(2,6-difluorobenzyl)sulfonyl]amino}ethyl)-1H-indol-3-yl]ethyl}sulfonyl)benzoate (off-white solid) in 87% yield.

Step 2: Methyl 4-({2-[1-benzhydryl-5-chloro-2-(2-{[(2,6-difluorobenzyl)sulfonyl]amino}ethyl)-1H-indol-3-yl]ethyl}sulfonyl)benzoate (1 eq), THF (0.1M), MeOH (1 mL/1 mL THF), and NaOH (1N) (11 eq) were stirred together overnight. Solvents were removed and the resulting residue was taken up in water. The solution was acidified with 1N HCl and collected resulting precipitate by filtration. Obtained 4-({2-[1-benzhydryl-5-chloro-2-(2-{[(2,6-difluorobenzyl)sulfonyl]amino}ethyl)-1H-indol-3-yl]ethyl}sulfonyl)benzoic acid (white-yellow solid) in 96% yield. HRMS calc for $[C_{39}H_{33}ClF_2N_2O_6S_2-H]$ 761.13638. found 761.13565.

EXAMPLE 138

4-({2-[1-benzhydryl-5-chloro-2-(2-{[(2-fluorobenzyl)sulfonyl]amino}ethyl)-1H-indol-3-yl]ethyl}sulfonyl)benzoic acid Step 1: (2-fluorobenzyl)sulfonyl chloride (3.4 eq) was added to a mixture of methyl 3-[4-({2-[2-(2-aminoethyl)-1-benzhydryl-5-chloro-1H-indol-3-yl]ethyl}sulfonyl)phenyl]benzoate (Example 135, Step 8, 1 eq), $CH_2Cl_2$ (0.08M), water (1 mL/1 mL $CH_2Cl_2$), and $Na_2CO_3$ (2.5 eq). After 2 hours the organic layer was recovered and washed with brine and dried over sodium sulfate. Purified with silica gel preparatory plate and 3% MeOH in $CH_2Cl_2$. Obtained methyl 4-({2-[1-benzhydryl-5-chloro-2-(2-{[(2-fluorobenzyl)sulfonyl]amino}ethyl)-1H-indol-3-yl]ethyl}sulfonyl)benzoate (off-white solid) in 82% yield.

Step 2: Methyl 4-({2-[1-benzhydryl-5-chloro-2-(2-{[(2-fluorobenzyl)sulfonyl]amino}ethyl)-1H-indol-3-yl]ethyl}sulfonyl)benzoate (1 eq), THF (0.1M), MeOH (1 mL/1 mL THF), and NaOH (1N) (11 eq) were stirred together overnight. Solvents were removed and the resulting residue was taken up in water. The solution was acidified with 1N HCl and collected resulting precipitate by filtration. Obtained 4-({2-[1-benzhydryl-5-chloro-2-(2-{[(2-fluorobenzyl)sulfonyl]amino}ethyl)-1H-indol-3-yl]ethyl}sulfonyl)benzoic acid (off-white solid) in 99% yield. HRMS calc for $[C_{39}H_{34}ClFN_2O_6S_2-H]$ 743.1458. found 743.14511.

EXAMPLE 139

4-(2-{1-Benzhydryl-5-chloro-2-[2-(2-pyrrolidin-1-yl-ethanesulfonylamino)-ethyl]-1H-indol-3-yl}-ethoxy)-benzoic acid Step 1: The compound was prepared from the intermediate from Example 87 step 1 and pyrrolidine according to the procedure in Example 87 step 2 in 92% yield without the column purification.

Step 2: The ester intermediate was hydrolyzed according to Step 8 Example 1, except that the pH was adjusted to 4–5, to afford the title acid in 92% yield. HRMS calc for $[C_{38}H_{40}ClN_3O_5S-H]$ 684.23044. found 684.23009.

EXAMPLE 140

4-({2-[1-benzhydryl-5-chloro-2-(2-{[(3,4-dichlorobenzyl)sulfonyl]amino}ethyl)1H-indol-3-yl]ethyl}sulfonyl)benzoic acid Step 1: (3,4-dichlorobenzyl)sulfonyl chloride (2.1 eq) was added to a mixture of methyl 3-[4-({2-[2-(2-aminoethyl)-1-benzhydryl-5-chloro-1H-indol-3-yl]ethyl}sulfonyl)phenyl]benzoate (Example 135, Step 8, 1 eq), $CH_2Cl_2$ (0.08M), water (1 mL/1 mL $CH_2Cl_2$), and $Na_2CO_3$ (2.5 eq). After 1 hours the organic layer was recovered and washed with brine and dried over sodium sulfate. Purified with silica gel preparatory plate and 3% MeOH in $CH_2Cl_2$. Obtained methyl 4-({2-[1-benzhydryl-5-chloro-2-(2-{[(3,4-dichlorobenzyl)sulfonyl]amino}ethyl)-1H-indol-3-yl]ethyl}sulfonyl)benzoate (white solid) in 87% yield.

Step 2: Methyl 4-({2-[1-benzhydryl-5-chloro-2-(2-{[(3,4-dichlorobenzyl)sulfonyl]amino}ethyl)-1H-indol-3-yl]ethyl}sulfonyl)benzoate (1 eq), THF (0.1M), MeOH (1 mL/1 mL THF), and NaOH (1N) (11 eq) were stirred together overnight. Solvents were removed and the resulting residue was taken up in water. The solution was acidified with 1N HCl and collected resulting precipitate by filtration. Obtained 4-({2-[1-benzhydryl-5-chloro-2-(2-{[(3,4-dichlorobenzyl)sulfonyl]amino}ethyl)-1H-indol-3-yl]ethyl}sulfonyl)benzoic acid (white-yellow solid) in 93% yield. HRMS calc for $[C_{38}H_{33}Cl_3N_2O_6S_2-H]$ 793.07728. found 793.07629

EXAMPLE 141

4-({2-[1-benzhydryl-5-chloro-2-(2-{[(2,6-dimethylbenzyl)sulfonyl]amino}ethyl)1H-indol-3-yl]ethyl}sulfonyl)benzoic acid Step 1: (2,6-methylbenzyl)sulfonyl chloride (3.0 eq, example 52, step 1) was added to a mixture of methyl 3-[4-({2-[2-(2-aminoethyl)-1-benzhydryl-5-chloro-1H-indol-3-yl]ethyl}sulfonyl)phenyl]benzoate (Example 135, Step 8, 1 eq), CH₂Cl₂ (0.08M), water (1 mL/1 mL CH₂Cl₂), and Na₂CO₃ (2.5 eq). After 2 hours the organic layer was recovered and washed with brine and dried over sodium sulfate. Purified with silica gel preparatory plate and 3% MeOH in CH₂Cl₂. Obtained methyl 4-({2-[1-benzhydryl-5-chloro-2-(2-{[(2,6-dimethylbenzyl)sulfonyl]amino}ethyl)-1H-indol-3-yl]ethyl}sulfonyl)benzoate (light-brown solid) in 81% yield.

Step 2: Methyl 4-({2-[1-benzhydryl-5-chloro-2-(2-{[(2,6-dimethylbenzyl)sulfonyl]amino}ethyl)-1H-indol-3-yl]ethyl}sulfonyl)benzoate (1 eq), THF (0.1M), MeOH (1 mL/1 mL THF), and NaOH (1N) (11 eq) were stirred together overnight. Solvents were removed and the resulting residue was taken up in water. The solution was acidified with 1N HCl and collected resulting precipitate by filtration. Obtained 4-({2-[1-benzhydryl-5-chloro-2-(2-{[(2,6-dimethylbenzyl)sulfonyl]amino}ethyl)-1H-indol-3-yl]ethyl)sulfonyl)benzoic acid (white solid) in 99% yield. HRMS calc for [C₄₁H₃₉ClN₂O₆S₂+H] 753.18653. found 753.18597.

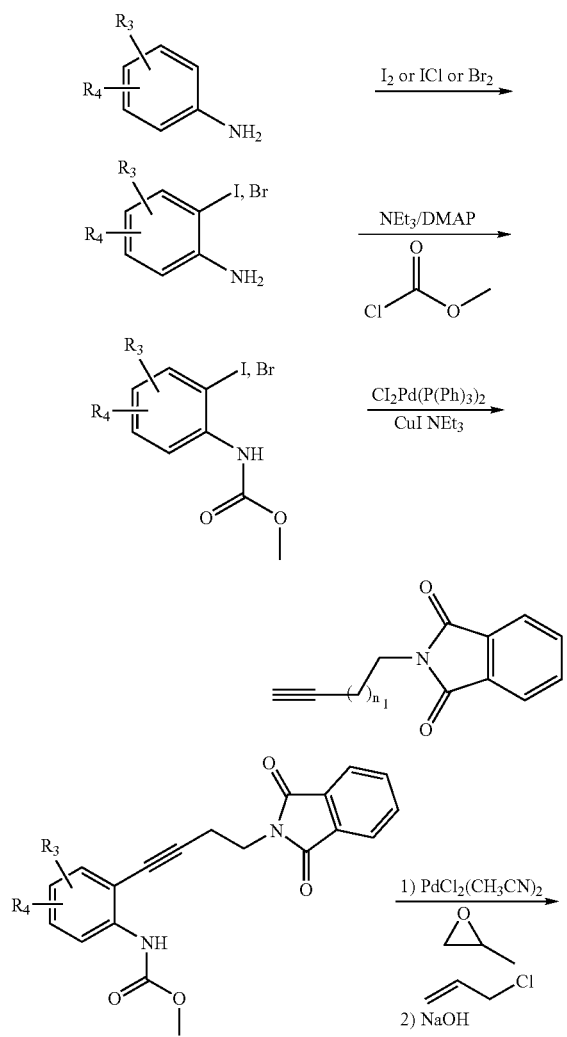

Method J

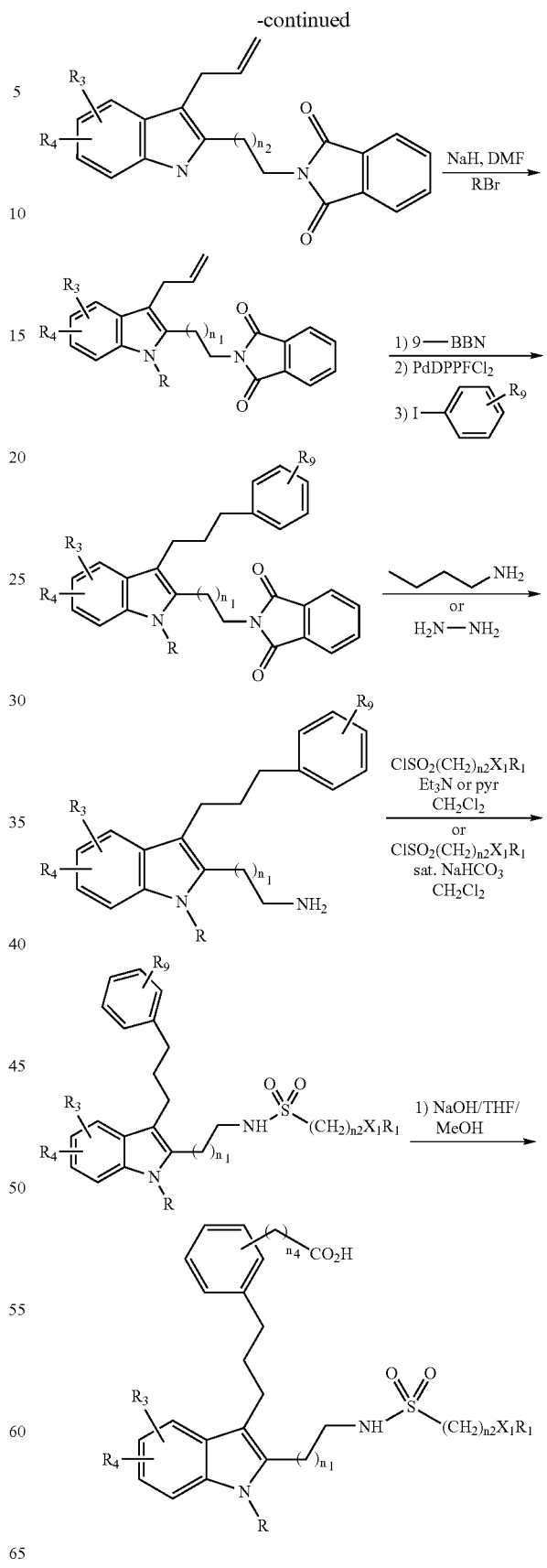

Method J provides an alternative reaction scheme to a subset of the compounds contained in this document. A suitably substituted aniline is halogenated using ICl, I₂, or Br₂ and then the amine is protected as a carbamate, using for example triethylamine and a chloroformate. This aryl halide is coupled to a suitably functionalized alkyne under the reaction of Pd and copper catalysis in the presence of a base such as triethylamine. This resulting product could be cyclized using Pd catalysis in the presence of allyl chloride and a substituted oxirane. The indole nitrogen may then be alkylated by treatment with a strong base such as sodium bis(trimethylsilyl)amide, n-BuLi, sodium hydride or potassium hydride in a solvent such as DMF, DMSO or THF followed by exposure to the appropriate halide. The allyl indole could then be treated with 9-BBN and then a palladium catalyst followed by an aryl or vinyl iodide to effect a Suzuki coupling reaction. The resulting intermediate could be deprotected using a hydrazine or an alkyl amine to yield the primary amine. This amine could then be treated with the requisite sulfonyl chloride under biphasic conditions, aqueous sodium bicarbonate/dichloromethane, or in organic solvent with the addition of a hindered organic amine base. The final hydrolysis was accomplished under basic conditions with sodium hydroxide in water and methanol and THF at room temperature or at elevated temperature. Alternatively it may be cleaved by treatment with sodium thiomethoxide in a solvent such as THF or DMF at elevated temperatures (50° C.–100° C.).

Method K

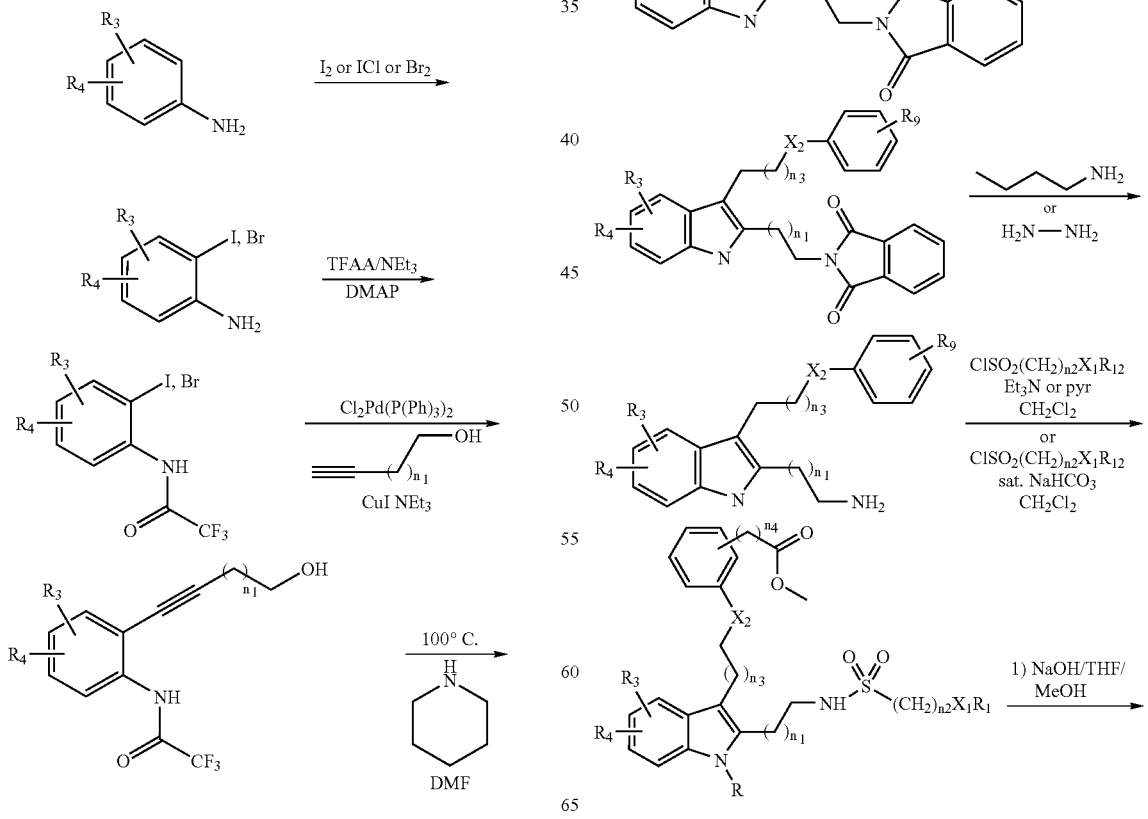

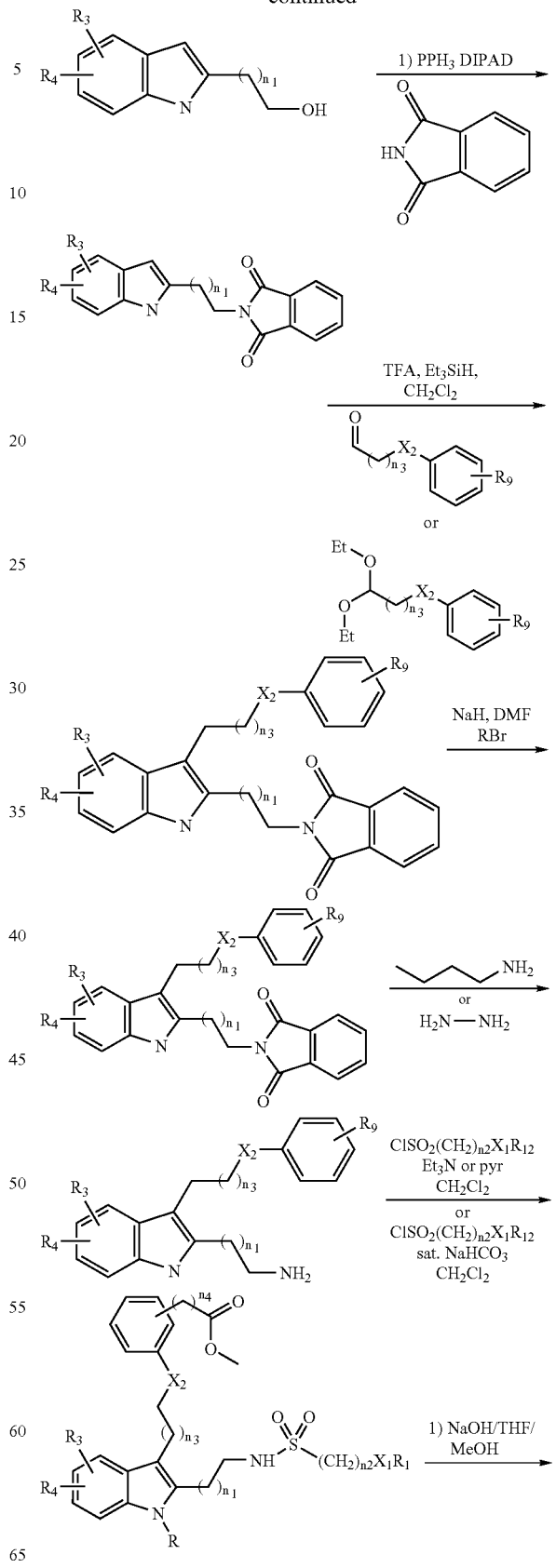

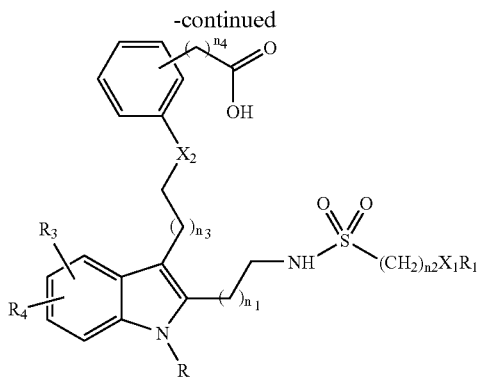

Method K provides an alternative method to prepare compounds of this invention. A suitably substituted aniline is halogenated using ICl, I$_2$, or Br$_2$ and then the amine is protected as a carbamate or amide using for example trifluoroacetic anhydride triethyamine and dimethylamino pyridine. This intermediate is then reacted with a suitably functionalized alkyne under palladium and copper catalysis in the presence of a base. The resulting aryl alkyne is cyclized to the indole by heating with an amine such as piperidine. Standard Mitsunobu reaction conditions, a phosphine, an azodicarboxylate and phthalamide are used to generate the protected amine. The indole may be alkylated at the C3 position (the indole 3-position carbon atom) with aldehydes or the corresponding acetals in the presence of a Lewis or Bronsted acid, such as boron triflouride etherate or trifluoroacetic acid. The indole nitrogen may then be alkylated by treatment with a strong base such as sodium bis(trimethylsilyl)amide, n-BuLi, sodium hydride or potassium hydride in a solvent such as DMF, DMSO or THF followed by exposure to the appropriate halide. The resulting intermediate could be deprotected using a hydrazine or an alkyl amine to yield the primary amine. This amine could then be treated with the requisite sulfonyl chloride under biphasic conditions, aqueous sodium bicarbonate/dichloromethane, or in organic solvent with the addition of a hindered organic amine base. The final hydrolysis was accomplished under basic conditions with sodium hydroxide in water and methanol and THF at room temperature or at elevated temperature. Alternatively it may be cleaved by treatment with sodium thiomethoxide in a solvent such as THF or DMF at elevated temperatures (50° C.–100° C.).

Method L

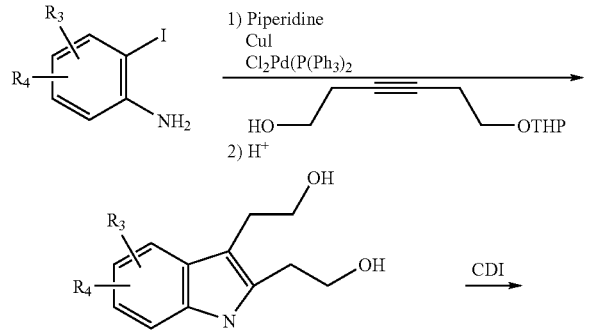

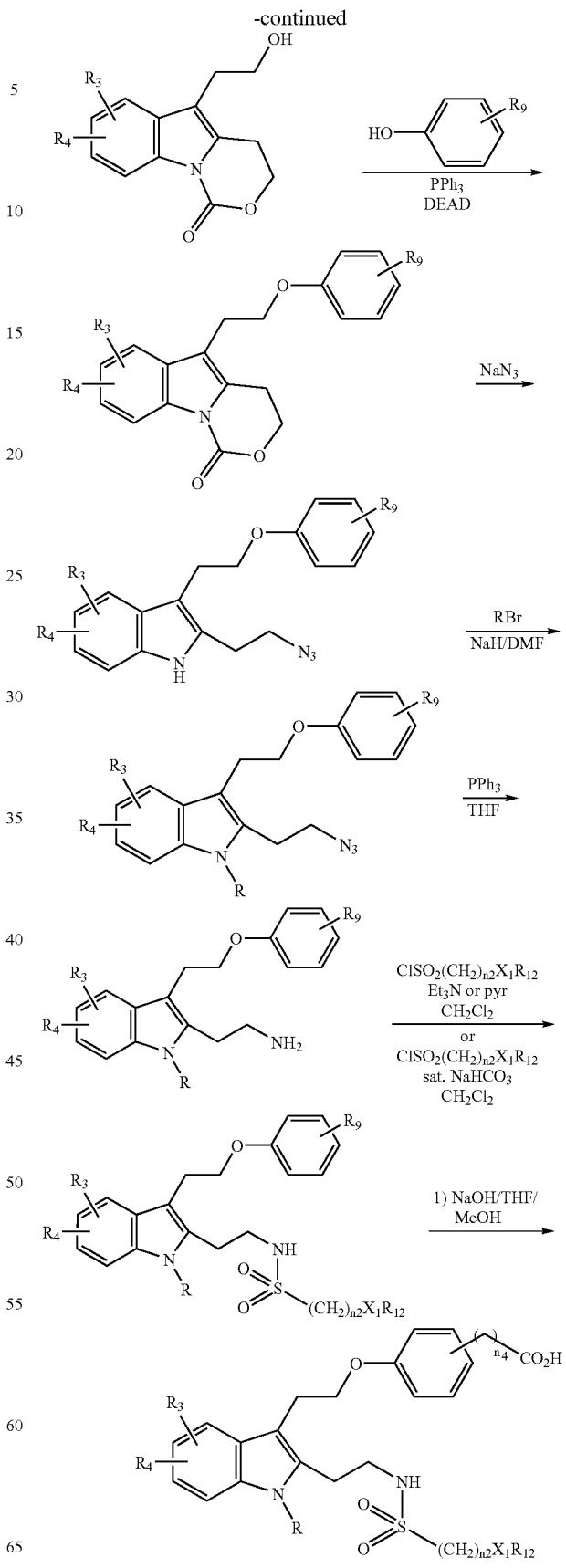

Method L provides another alternative method to prepare compounds of this invention. A suitably substituted halo aniline, see methods J and K, and a symmetric alkynol or a monoprotected alkynol, for example THP protection, are reacted in the presence of a base, copper and palladium catalysis, followed by deprotection under acidic conditions if a monoprotected substrate is used yielded the symmetrical indole diol. The diol is desymmetrized by treatment with carbonyl diimidazole in a suitable solvent and then the primary alcohol was substituted under standard Mitsunobu conditions, a phosphine, an azodicarboxylate and an alcohol were used to generated the desired ether. The carbamate could be opened up by reaction with sodium azide to yield the alkyl azide. The indole nitrogen may then be alkylated by treatment with a strong base such as sodium bis(trimethylsilyl)amide, n-BuLi, sodium hydride or potassium hydride in a solvent such as DMF, DMSO or THF followed by exposure to the appropriate halide. Treatment with triphenyl phosphine in wet THf delivered the desired alkyl amine. This amine could then be treated with the requisite sulfonyl chloride under biphasic conditions, aqueous sodium bicarbonate/dichloromethane, or in organic solvent with the addition of a hindered organic amine base. The final hydrolysis was accomplished under basic conditions with sodium hydroxide in water and methanol and THF at room temperature or at elevated temperature. Alternatively it may be cleaved by treatment with sodium thiomethoxide in a solvent such as THF or DMF at elevated temperatures (50° C.–100° C.).

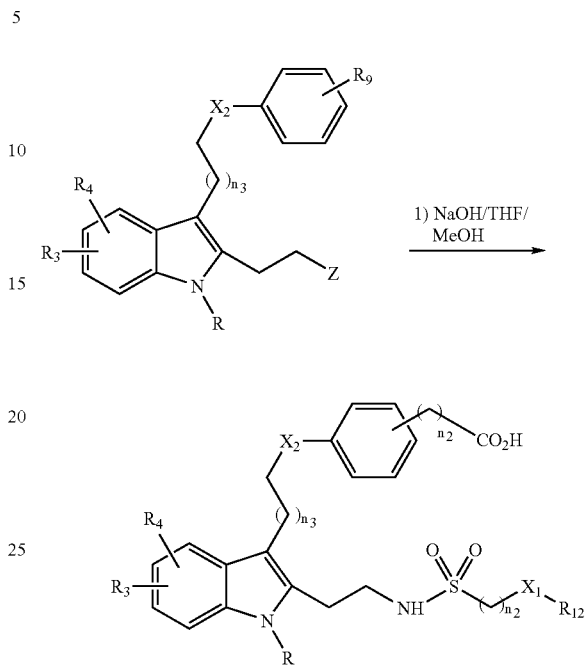

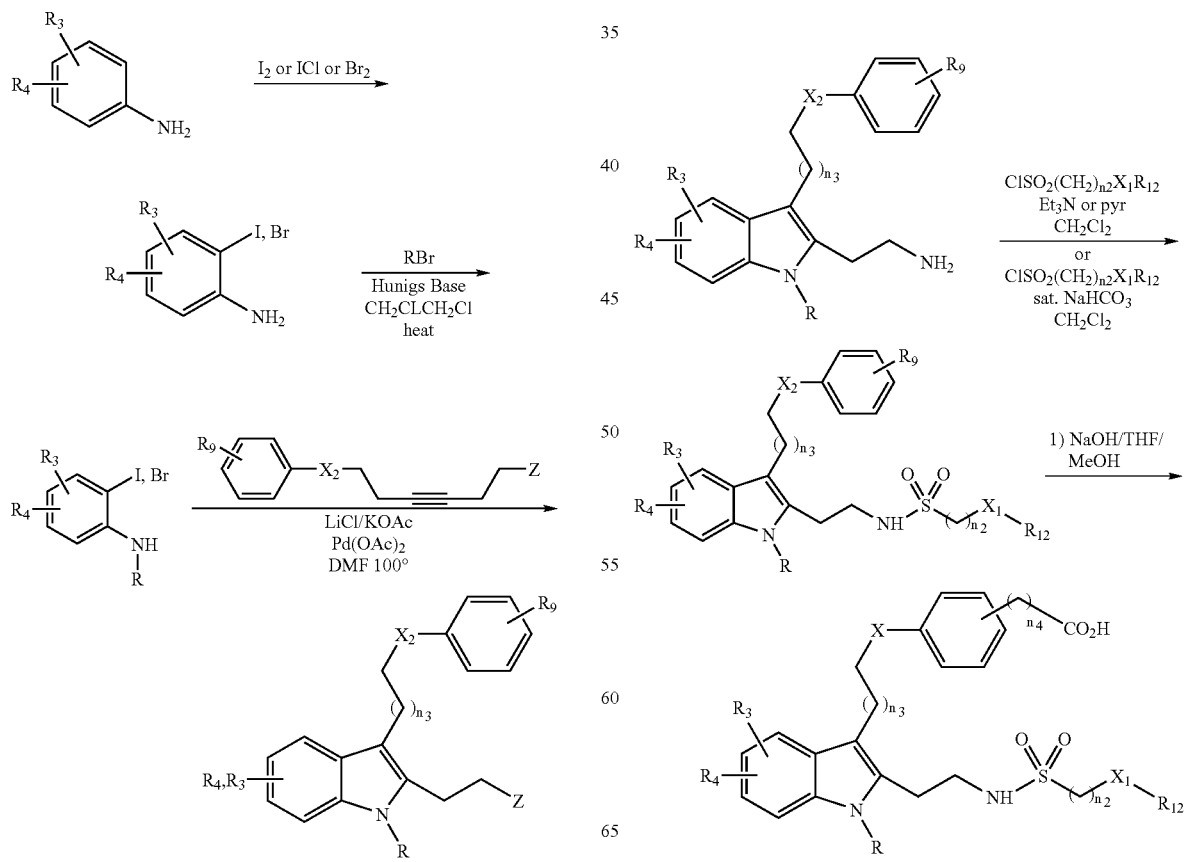

-continued

When Z = OH

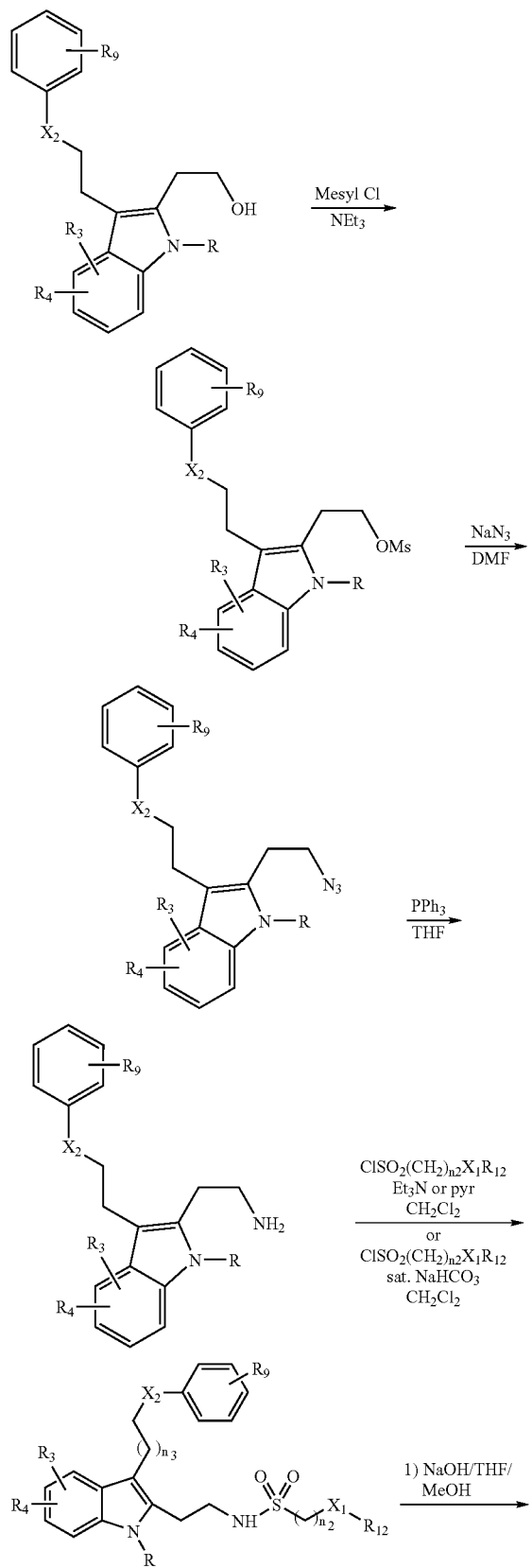

-continued

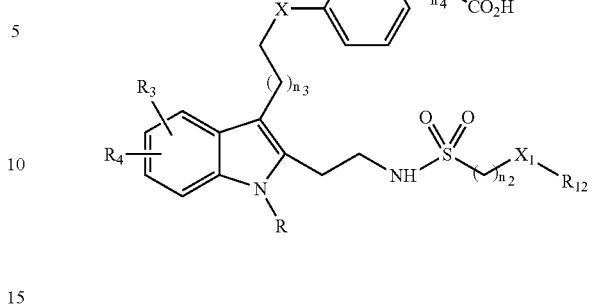

Method M provides a further strategy to furnish compounds of this invention. A suitably substituted aniline is halogenated using ICl, I$_2$, or Br$_2$ and then the amine can be alkylated using an organic base and a halide. The thus formed alkyl amine is then reacted under palladium catalyzed conditions in the presence of a chloride source a base and with or without a phsophine and the requisite alkyne to yield the indole. When the Z in the alkyne is NHSO$_2$(CH$_2$)$_{n2}$X1R1 the synthesis is finished by hydrolysis under basic conditions with sodium hydroxide in water and methanol and THF at room temperature or at elevated temperature. Alternatively it may be cleaved by treatment with sodium thiomethoxide in a solvent such as THF or DMF at elevated temperatures (50° C.–100° C.).

When Z=NH$_2$

The resulting indole can then be treated with the requisite sulfonyl chloride under biphasic conditions, aqueous sodium bicarbonate/dichloromethane, or in organic solvent with the addition of a hindered organic amine base. The final hydrolysis was accomplished under basic conditions with sodium hydroxide in water and methanol and THF at room temperature or at elevated temperature. Alternatively it may be cleaved by treatment with sodium thiomethoxide in a solvent such as THF or DMF at elevated temperatures (50° C.–100° C.).

When Z=OH

The resulting alcohol could be converted to a halide or mesylate, for example using methane sulfonyl chloride and an organic base, which could then be displaced by sodium azide in DMF. The resulting alkyl azide could be reduced under the action of triphenyl phosphine and wet THF. The amine could be sulfonylated by the action of a sulfonyl chloride under either biphasic Shcott and Baumman conditions, Aq. Bicarbonate and dichloromethane, or under anhydrous conditions consisting of dichloromethane and an organic base such as Hunigs base. The resulting intermediate was hydrolyzed using a base, NaOH, KOH, LiOH and a mixture of solvents including an alcoholic solvent, water and tetrahydrofuran.

Method N
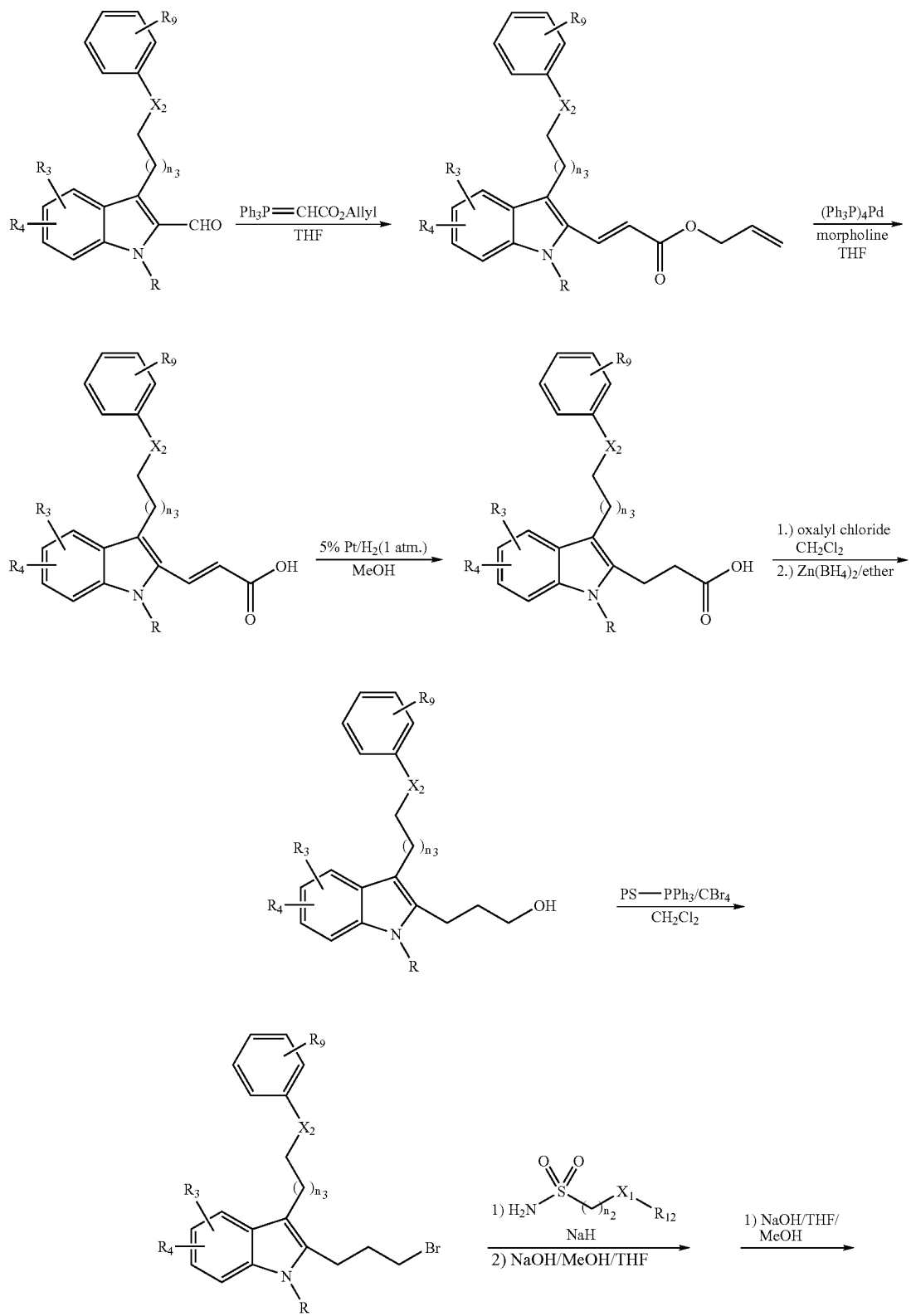

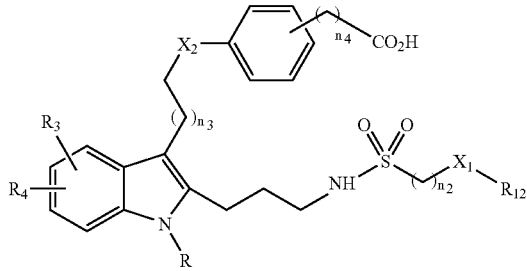

Method N provides a further strategy to furnish a subset of the compounds of this invention. The C3 functionalized-2-formyl indole (See method A) was reacted under Wittig, or other organometallic conditions, to generate an alkeneoate ester. This ester could be converted to the acid by treatment with Pd and the resulting unsaturated acid was reduced via hydrogenation. The alkyl acid was activated by conversion to the acid chloride, under the action of oxalyl chloride, or the acid flouride, via cyanuric flouride, and then treated with a suitable borohydride reducing agent to generate the alcohol. The alcohol was converted to the bromide using triphenyl phosphine and carbontetrabromide and then displaced by the anion of the sulfonmide, generated by treating the primary sulfonamide with a strong base, such as NaH, n-BuLi etc, to yield the desired secondary sulfonamide. The resulting ester intermediate was hydrolyzed using a base, NaOH, KOH, LiOH and a mixture of solvents including an alcoholic solvent, water and tetrahydrofuran.

EXAMPLE 142

4-[2-(1-benzhydryl-2-{3-[(benzylsulfonyl)amino]propyl}-5-chloro-1H-indol-3-yl)ethoxy]benzoic acid Step 1: 5.0 g of 4-[2-(1-Benzhydryl-2-formyl-1H-indol-3-yl)-ethoxy]-benzoic acid methyl ester, Step 4, Example 1, (0.0092M, 1.0 eq.) and 5.0 g of allyl(triphenylphosphoranylidene) acetate (0.0139M, 1.5 eq.) were dissolved in 250 mL of tetrahydrofuran at room temperature. The pale yellow solution was stirred for one hour. TLC indicated a new spot at □Rf of +0.5 in 1:1 hexanes/ethyl acetate and no remaining starting indole. The reaction was poured into 500 mL of ethyl acetate and washed with water (2×125 mL) and brine (2×125 mL). The organic layer was dried over magnesium sulfate and filtered. The filtrate was evaporated to a yellow oil which was dissolved in 50 ml 1:1 hexanes/ethyl acetate and filtered through a plug of silica gel to remove baseline material. This left 5.23 g of 4-{2-[2-(2-Allyloxycarbonyl-vinyl)-1-benzhydryl-5-chloro-1H-indol-3-yl]-ethoxy}-benzoic acid methyl ester as a yellow oil (91% yield).

Step 2: 6.12 g of 4-{2-[2-(2-Allyloxycarbonyl-vinyl)-1-benzhydryl-5-chloro-1H-indol-3-yl]-ethoxy}-benzoic acid methyl ester (0.098M, 1 eq.) and 1.12 g of tetrakis(triphenylphosphine) palladium (0) (0.001M, 0.1 eq.) were added to 75 mL of THF. To the reaction 8.60 ml of morpholine (0.098M, 1 eq.) was added drop-wise over 20 min. After addition was complete the reaction was stirred at room temperature for 4 hours. The reaction was poured into 250 mL of ethyl acetate and the organic solution was extracted with 1N NaOH (2×75 mL). The aqueous layers were combined and acidified with 1N HCl, the acidic solution was extracted with ethyl acetate (3×75 mL). The organic layers were combined and washed with brine (1×50 mL), dried over magnesium sulfate, filtered and evaporated to yield 4-{2-[1-Benzhydryl-2-(2-carboxy-vinyl)-5-chloro-1H-indol-3-yl]-ethoxy}-benzoic acid methyl ester as a yellow oil (5.40 g, 97% yield).

Step 3: 400 mg of 4-{2-[1-Benzhydryl-2-(2-carboxy-vinyl)-5-chloro-1H-indol-3-yl]-ethoxy}-benzoic acid methyl ester (0.0007M, 1 eq.) was dissolved in 15 mL of methanol. To the solution, 80 mg of 5% platinum on activated carbon was added as a slurry in 5 mL of methanol. The black suspension was placed under a hydrogen atmosphere via a balloon and stirred for 24 hrs. at room temperature. The hydrogen was evacuated and another 80 mg of 5% platinum on activated carbon in 5 mL of methanol was added and the reaction was again placed under a hydrogen atmosphere via a balloon and stirred for another 24 hrs. at room temperature. The reaction was monitored via NMR and at this point complete conversion was indicated. The reaction was filtered through Celite and the filtrate was evaporated to give 4-{2-[1-Benzhydryl-2-(2-carboxy-ethyl)-5-chloro-1H-indol-3-yl]-ethoxy}-benzoic acid methyl ester as a yellow-green solid (320 mg, 79% yield).

Step 4: 100 mg of 4-{2-[1-Benzhydryl-2-(2-carboxy-ethyl)-5-chloro-1H-indol-3-yl]-ethoxy}-benzoic acid methyl ester (0.0002M, 1 eq.) was dissolved in 1.0 ml of anhydrous methylene chloride. To the solution 33.5 mg of oxalyl chloride (0.0003M, 1.5 eq.) was added and the reaction stirred for one hour at room temperature. The reaction was then evaporated to dryness and the residue dissolved in 1.0 mL of anhydrous ethyl ether to which 0.027 mL of TMEDA was added. To this solution 0.35 mL of zinc borohydride solution in ether prepared by the literature method (Tet. Lett. Vol. 22, pg. 4723, 1981) was added. The reaction was stirred for 15 min. at room temperature and quenched with 1.0 mL of water. The reaction was diluted with 10 mL of ethyl ether and the water layer separated, the organic layer was dried over magnesium sulfate, filtered and evaporated to a clear oil. The oil was chromatographed with ethyl acetate/hexanes (1:9) to result in isolation of 4-{2-[1-Benzhydryl-5-chloro-2-(3-hydroxy-propyl)-1H-indol-3-yl]-ethoxy}-benzoic acid methyl ester as a white foam (81 mg, 83% yield).

Step 5: 104.0 mg of 4-{2-[1-Benzhydryl-5-chloro-2-(3-hydroxy-propyl)-1H-indol-3-yl]-ethoxy}-benzoic acid methyl ester (0.0002M, 1.0 eq.) was dissolved in 2.0 mL of anhydrous methylene chloride. To the solution 116.0 mg of polystyrene bound triphenylphosphine was added (1.61 mmol/g, 0.0002M, 1.0 eq.) followed by 125.0 mg of carbon tetrabromide (0.0004M, 2 eq.). The suspension was stirred for 2 hrs at room temperature at which point the reaction was filtered and the filtrate evaporated to an orange oil. The oil was purified via column chromatography with ethyl acetate/hexanes (2:98) to give 100 mg (86%) of 4-{2-[1-Benzhydryl-2-(3-bromo-propyl)-5-chloro-1H-indol-3-yl]-ethoxy}-benzoic acid methyl ester title as a yellow foam.

Step 6: 33.3 mg of ☐-toluene sulfonamide (0.0002M, 1.2 eq.) was dissolved in 0.5 mL of DMF and added to a slurry of 8.0 mg of 60% sodium hydride (0.0002M, 1.2 eq.) in 0.5 mL of DMF. The reaction was stirred for 30 min. at which point 100 mg of 4-{2-[1-Benzhydryl-2-(3-bromo-propyl)-5-chloro-1H-indol-3-yl]-ethoxy}-benzoic acid methyl ester (0.0002M, 1.0 eq.) in 0.5 mL of DMF was added and the solution was stirred for an additional 1 hour. The reaction was quenched with water and diluted with 10 mL of ethyl acetate. The organic layer was washed with water (2×5 mL) and brine (2×5 mL), dried over magnesium sulfate and evaporated to a yellow oil. The residue was purified via column chromatography (ethyl acetate/hexanes 5:95) to give 20 mg (17%) of 4-{2-[1-Benzhydryl-5-chloro-2-(3-phenyl-methanesulfonylaminopropyl)-1H-indol-3-yl]-ethoxy}-benzoic acid methyl ester as a clear oil.

Step 7: 20.0 mg of indole from Example 6 (0.00002M, 1 eq.) was hydrolyzed as in Example 1 Step 8 to yield the title compound (13.0 mg, 88% yield) m/z (M−1) 691.

Method O

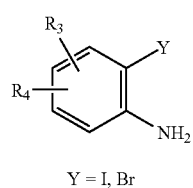

Y = I, Br

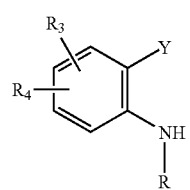

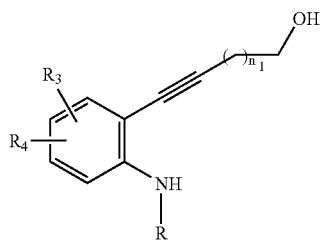

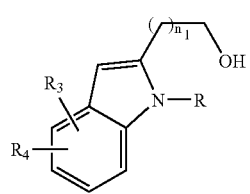

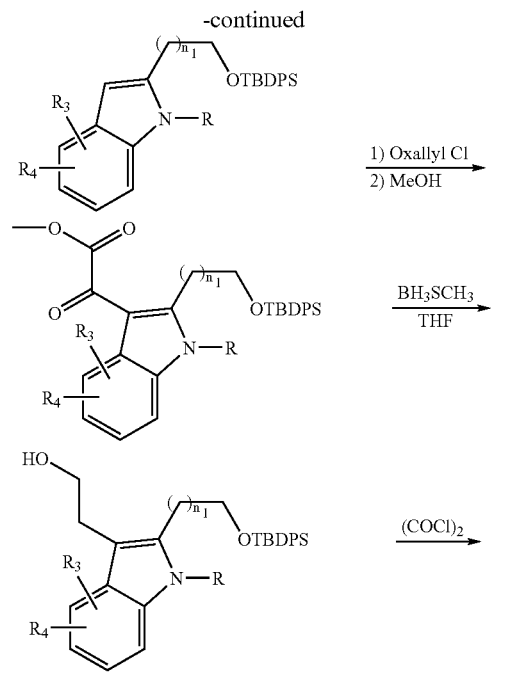

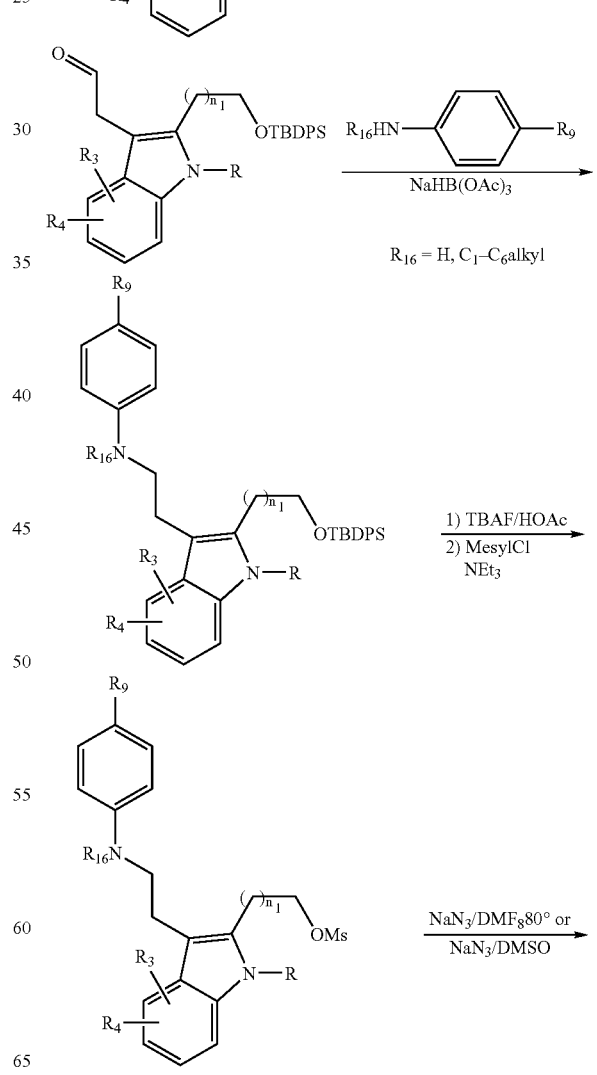

-continued

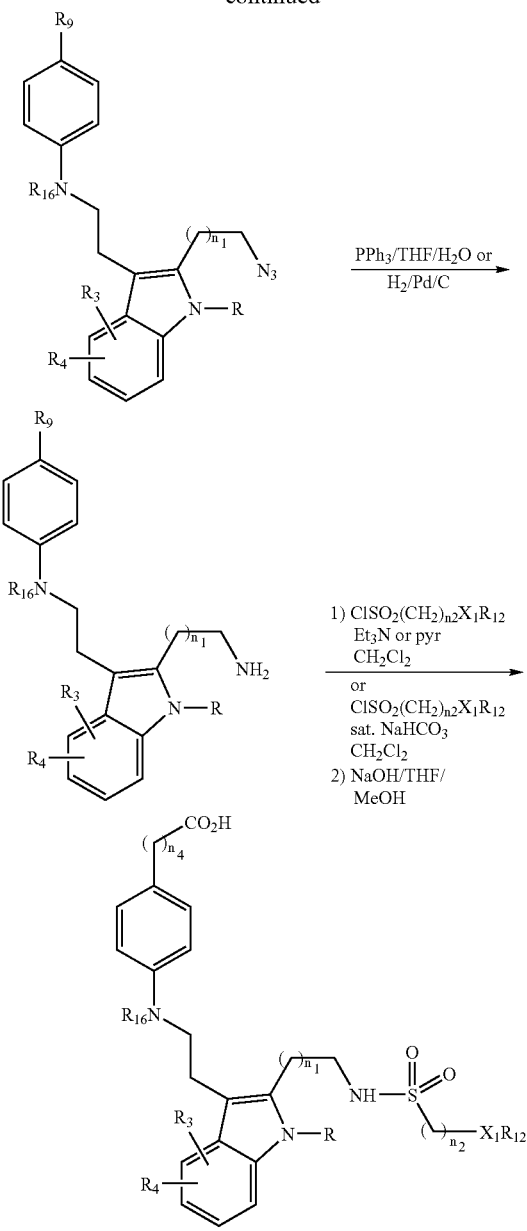

The appropriately substituted halo amine is reacted with a suitable halide and a tertiary amine base to yield an N-alkylated substrate for a Shonigishiru coupling (with an alkynol in the presence of $Pd^{ii}$ and a suitable base). This arylalkynol is cyclized to the indole under the action of a copper halide and heat. The free alcohol was protected with a silyl protecting group by reaction with a silyl chloride in the presence of a base such as imidazole. This indole was next $C_3$ acylated by reaction with a suitable acid chloride and the resulting compound reduced with most reducing agents but preferably borane or a borane complex. The primary alcohol was then oxidized to an aldehyde by any number of oxiidizing agents, including oxalyl chloride/DMSO (swern conditions) or TPAP/NMO. This aldehyde was subjected to reductive amination conditions, which include a borohydride reducing agent and in some cases a protice acid, and a primary or secondary amine. The silyl ether was then deprotected with a flouride source including CsF, TBAF, HF etc. This free alcohol was converted into a leaving group, halide with $CBr_4$ and a phosphine, or a sulfonate ester with methane sulfonyl chloride and a tertiary amine. The activated alcohol is reacted with sodium azide in either DMF or DMSO to yield the desired azide which in turn was reduced under Staudinger conditions, phosphine and $THF/H_2O$, or via hydrogenation using hydrogen and a suitable catalyst. The amine could be sulfonylated by the action of a sulfonyl chloride under either biphasic Shcott and Baumman conditions, Aq. Bicarbonate and dichloromethane, or under anhydrous conditions consisting of dichloromethane and an organic base such as Hunigs base. The resulting intermediate was hydrolyzed using a base, NaOH, KOH, LiOH and a mixture of solvents including an alcoholic solvent, water and tetrahydrofuran.

The following Examples 143–151 were synthesized with Method N.

EXAMPLE 143

4-{[2(1-benzhydryl-2-{2-[(benzylsulfonyl)amino]ethyl}-5-chloro-1H-indol-3-yl)ethyl]amino}benzoic acid Step 1: To a solution of 4-chloro-2-iodoaniline (16.5 g, 65.1 mmol) in DMF (250 mL) at rt were added □-bromo-diphenylmethane (21.5 g, 84.6 mmol) and $^iPr_2NEt$ (23 mL, 130 mmol) and the reaction mixture was heated at 45° C. overnight. After the volatile was removed under reduced pressure, the residue was dissolved in EtOAc, washed with water (3×) and brine and dried over $MgSO_4$. Purification on $SiO_2$ column chromoatography (hexanes to 5% EtOAc/hexanes) gave the desired Benzhydryl-(4-chloro-2-iodo-phenyl)-amine (26.1 g, 97% yield) as a yellowish solid.

Step 2: A mixture of benzhydryl-(4-chloro-2-iodo-phenyl)-amine (26.1 g, 62.2 mmol), $PdCl_2(PPh_3)_2$ (1.90 g, 2.67 mmol), CuI (1.2 g, 6.2 mmol), 3-butyn-1-ol, and $Et_3N$ (120 mL) was stirred at 45° C. for 20 hours. The reaction mixture was filtered through celite and rinsed with EtOAc. The filtrate was concentrated, redissolved in EtOAc, washed with water (3×) and brine, and dried over $MgSO_4$. The crude 4-[2-(Benzhydryl-amino)-5-chloro-phenyl]-but-3-yn-1-ol (25.5 g) was used in the next step directly without further purification.

Step 3: A solution of the crude 4-[2-(benzhydryl-amino)-5-chloro-phenyl]-but-3-yn-1-ol (25.5 g) and CuI (2.7 g, 14.1 mmol) in DMF (200 mL) was heated at 125° C. for 24 hours. The reaction mixture was filtered through celite and rinsed with EtOAc. The filtrate was concentrated, redissolved in EtOAc, washed with water (3×) and brine, and dried over $MgSO_4$. Silica gel column chromatography (30% EtOAc/hexanes) yielded the desired 2-(1-Benzhydryl-5-chloro-1H-indol-2-yl)-ethanol as a yellow solid (14.5 g, 73% over 2 steps).

Step 4: To a solution of 2-(1-benzhydryl-5-chloro-1H-indol-2-yl)-ethanol (15.3 g, 42.3 mmol) in $CH_2Cl_2$ (190 mL) at 0° C. were added imidazole (3.72 g, 55.0 mmol) and TBDPSCI (13.2 mL, 50.8 mmol). After stirring at the same temperature for 1.5 hours, the reaction mixture was washed with cold water (3×) and brine, and dried over $MgSO_4$. The crude silyl ether was used in the next step directly without further purification.

Step 5: To a solution of the crude silyl ether in $Et_2O$ (200 mL) at 0° C. was added oxalyl chloride (4.84 mL, 55.5 mmol) dropwise. The reaction mixture was allowed to warm to rt and stirring continued for 4 hours before $Et_3N$ (35 mL)

and MeOH (10 mL) were added. The mixture was washed with water, brine, and dried over MgSO$_4$. The crude keto ester was used directly in the next step.

Step 6: To the keto ester in THF (300 mL) was added BH$_3$.Me$_2$S (10 M, 36 mL) dropwise at rt and the reaction mixture was refluxed overnight. The mixture was cooled at 0° C. before NaOH (30%, 150 mL) was added and stirring continued for 30 min. THF was removed under reduced pressure and the reaction mixture was extracted with EtOAc, washed with water, brine, and dried over MgSO$_4$. Purification on column chromatography (15 to 20% EtOAc/hexanes) yielded the desired product as a white solid (15.9 g, 24.7 mmol, 58% over 3 steps).

Step 7: To a solution of oxalyl chloride (0.372 mL, 4.27 mmol) in CH$_2$Cl$_2$ (10 mL) at −78° C. was added DMSO (0.661 mL, 9.31 mmol) dropwise. The reaction mixture was stirred at the same temperature for 5 min before a solution of 2-{1-benzhydryl-2-[2-(tert-butyl-diphenyl-silanyloxy)-ethyl]-5-chloro-1H-indol-3-yl}-ethanol (2.50 g, 3.88 mmol) in CH$_2$Cl$_2$ (8 mL) was introduced. After additional 40 min stirring, $^i$Pr$_2$NEt (3.38 mL, 19.4 mmol) was added and the reaction was quenched with cold water (5 mL) and extracted with CH$_2$Cl$_2$. The organic layer was dried over MgSO$_4$ and evaporated. The crude {1-Benzhydryl-2-[2-(tert-butyl-diphenylsilanyloxy)-ethyl]-5-chloro-1H-indol-3-yl}-acetaldehyde was used directly in the next step.

Step 8: To a solution of the crude aldehyde (3.88 mmol) in 1,2-dichloroethane (39 mL) at 0° C. were added methyl 4-aminobenzoate (645 mg, 4.27 mmol), acetic acid (1.33 mL), and NaBH(OAc)$_3$. The reaction mixture was allowed to warm to rt overnight and quenched with cold NaHCO$_3$. An extractive workup furnished the desired 4-(2-{1-Benzhydryl-2-[2-(tert-butyl-diphenyl-silanyloxy)-ethyl]-5-chloro-1H-indol-3-yl}-ethylamino)-benzoic acid methyl ester which was used directly in the next step without further purification.

Step 9: To 4-(2-{1-benzhydryl-2-[2-(tert-butyl-diphenyl-silanyloxy)-ethyl]-5-chloro-1H-indol-3-yl}-ethylamino)-benzoic acid methyl ester (3.88 mmol) in THF (25 mL) at 0° C. was added a mixture of HOAc:1M TBAF (in THF) (2.3 mL:5.8 mL) and the reaction mixture was allowed to stir at rt for 18 h. Extractive workup followed by trituration with 5% EtOAc/hex gave the desired 4-{2-[1-Benzhydryl-5-chloro-2-(2-hydroxy-ethyl)-1H-indol-3-yl]-ethylamino}-benzoic acid methyl ester with slight impurity as an off-white solid (92%, over 3 steps).

Step 10: To a solution of 4-{2-[1-benzhydryl-5-chloro-2-(2-hydroxyethyl)-1H-indol-3-yl]-ethylamino}-benzoic acid methyl ester (1.64 g, 3.04 mmol) in CH$_2$Cl$_2$ at 0° C. were added Et$_3$N (0.636 mL, 4.56 mmol) and MsCl (0.282 mL, 3.64 mmol). After stirring at the same temperature for 35 min, the reaction mixture was quenched with cold water. An extractive workup revealed the crude mesylate as an off-white solid (1.70 g, 90%).

Step 11: A solution of the crude mesylate (1.70 g, 2.75 mmol) and NaN$_3$ (89 mg, 13.8 mmol) in DMF (14 mL) was stirred at 80° C. for 6 h. The reaction mixture was diluted with EtOAc and subjected to an aqueous workup followed by flash column chromatography to yield the desired 4-{2-[2-(2-Azido-ethyl)-1-benzhydryl-5-chloro-1H-indol-3-yl]-ethylamino}-benzoic acid methyl ester (813 mg, 52% yield).

Step 12: To 4-{2-[2-(2-azido-ethyl)-1-benzhydryl-5-chloro-1H-indol-3-yl]-ethylamino}-benzoic acid methyl ester (400 mg, 0.709 mmol) in THF (4 mL) at 0 C was added Ph$_3$P (223 mg, 0.851 mmol) in portions. The reaction mixture was stirred at rt for 11 h and 35° C. for 4 h before water (50 uL) was added and stirring continued overnight. The reaction mixture was diluted with EtOAc, dried with MgSO$_4$ and purified by flash column chromatography (EtOAc to 20% MeOH/EtOAc with 1% Et$_3$N) to give the desired 4-{2-[2-(2-Amino-ethyl)-1-benzhydryl-5-chloro-1H-indol-3-yl]-ethylamino}-benzoic acid methyl ester (201 mg, 53%) as a solid.

Step 13: The intermediate from step 8 was treated with □-toluenesulfonyl chloride according to the procedure in Example 87 step 2 to generate the desired product in 72% yield.

Step 14: The ester intermediate was hydrolyzed according to Step 8 Example 1, to afford the title acid in 87% yield. HRMS calc for [C$_{39}$H$_{36}$ClN$_3$O$_4$S+H] 678.21879. found 678.2178.

EXAMPLE 144

4-({2-[1-benzhydryl-5-chloro-2-(2-{[(2-chloro-6-methylphenyl)sulfonyl]amino}ethyl)-1H-indol-3-yl]ethyl}amino)benzoic acid Step 1: The intermediate from example 142 step 12 was treated with 2-chloro-6-methyl-benzenesulfonyl chloride according to the procedure in Example 87 step 2 to generate the desired product in 85% yield.

Step 2: The ester intermediate was hydrolyzed according to Step 8 Example 1, to afford the title acid in 96% yield. HRMS calc for [C$_{39}$H$_{35}$Cl$_2$N$_3$O$_4$S+H] 712.17981. found 712.17895.

EXAMPLE 145

4-({2-[1-benzhydryl-5-chloro-2-(2-{[(2-methoxyphenyl)sulfonyl]amino}ethyl)-1H-indol-3-yl]ethyl}amino)benzoic acid Step 1: The intermediate from example 142 step 12 was treated with 2-methoxy-benzenesulfonyl chloride according to the procedure in Example 87 step 2 to generate the desired product in 85% yield.

Step 2: The ester intermediate was hydrolyzed according to Step 8 Example 1, to afford the title acid in 92% yield. HRMS calc for [C$_{39}$H$_{36}$ClN$_3$O$_5$S+H] 694.2137. found 694.21311.

EXAMPLE 146

4-({2-[1-benzhydryl-5-chloro-2-(2-{[(2-chlorophenyl)sulfonyl]amino}ethyl)-1H-indol-3-yl]ethyl}amino)benzoic acid Step 1: The intermediate from example 142 step 12 was treated with 2-chloro-benzenesulfonyl chloride according to the procedure in Example 87 step 2 to generate the desired product in 21% yield.

Step 2: The ester intermediate was hydrolyzed according to Step 8 Example 1, to afford the title acid in 94% yield. HRMS calc for [C$_{38}$H$_{33}$Cl$_2$N$_3$O$_4$S+H] 698.16416. found 698.16365.

EXAMPLE 147

4-[[2-(1-benzhydryl-2-(2-[(benzylsulfonyl)amino]ethyl}-5-chloro-1H-indol-3-yl)ethyl](methyl)amino]benzoic acid Step 1: Crude {1-Benzhydryl-2-[2-(tert-butyl-diphenyl-silanyloxy)-ethyl]-5-chloro-1H-indol-3-yl}-acetaldehyde from step 7, example 142 was treated with 4-Methylamino-benzoic acid methyl ester according to the procedure in Example 142 step 8 to yield the desired 4-[(2-{1-Benzhydryl-2-[2-(tert-butyl-diphenyl-silanyloxy)-ethyl]-5-chloro-1H-indol-3-yl}-ethyl)-methyl-amino]-benzoic acid methyl ester in 73% yield.

Step 2: The title compound was prepared according to the procedure described for Example 142 step 9. The crude 4-({2-[1-Benzhydryl-5-chloro-2-(2-hydroxy-ethyl)-1H-indol-3-yl]-ethyl}-methyl-amino)-benzoic acid methyl ester was used in the next step directly without further purification.

Step 3–6: 4-({2-[2-(2-Azido-ethyl)-1-benzhydryl-5-chloro-1H-indol-3-yl]-ethyl}-methyl-amino)-benzoic acid methyl ester was prepared according to the procedure described for example 142 steps 10–12 in 61% yield (3 steps).

Step 7: A solution of 4-({2-[2-(2-azido-ethyl)-1-benzhydryl-5-chloro-1H-indol-3-yl]-ethyl}-methyl-amino)-benzoic acid methyl ester (410 mg, 0.709 mmol) and 10% Pd/C (155 mg) in MeOH:CH$_2$Cl$_2$ (=7 mL:1 mL) was stirred under H$_2$ atmosphere (1 atm) for 2 h 15 min. The reaction mixture was filtered through celite and rinsed with MeOH and CH$_2$Cl$_2$. Flash column chromatography (CH$_2$Cl$_2$ to 8% MeOH/CH$_2$Cl$_2$) of the residue gave the desired 4-({2-[2-(2-Amino-ethyl)-1-benzhydryl-5-chloro-1H-indol-3-yl]-ethyl}-methyl-amino)-benzoic acid methyl ester in 78% yield (305 mg).

Step 8: The intermediate from step 7 was treated with □-toluenesulfonyl chloride according to the procedure in Example 87 step 2 to generate the desired product in 83% yield.

Step 9: The ester intermediate was hydrolyzed according to Step 8 Example 1, to afford the title acid in 91% yield. HRMS calc for [C$_{39}$H$_{38}$ClN$_3$O$_4$S+H] 692.23444. found 692.23374.

EXAMPLE 148

4-[{2-[1-benzhydryl-5-chloro-2-(2-{[(3,4-dichlorobenzyl)sulfonyl]amino}ethyl)-1H-indol-3-yl]ethyl}(methyl)amino]benzoic acid Step 1: The intermediate from example 146 step 7 was treated with 3,4-dichlorophenylmethanesulfonylchloride according to the procedure in Example 87 step 2 to generate the desired product in 87% yield.

Step 2: The ester intermediate was hydrolyzed according to Step 8 Example 1, to afford the title acid in 68% yield. HRMS calc for [C$_{40}$H$_{36}$Cl$_3$N$_3$O$_4$S+H] 760.15649. found 760.1573.

EXAMPLE 149

4-[{2-[1-benzhydryl-5-chloro-2-(2-{[(2-chloro-6-methylphenyl)-sulfonyl]amino}ethyl)-1H-indol-3-yl]ethyl}(methyl)amino]benzoic acid Step 1: The intermediate from example 146 step 7 was treated with 2-chloro-6-methyl-benzenesulfonyl chloride according to the procedure in Example 87 step 2 to generate the desired product in 96% yield.

Step 2: The ester intermediate was hydrolyzed according to Step 8 Example 1, to afford the title acid in 88% yield. HRMS calc for [C$_{40}$H$_{37}$Cl$_2$N$_3$O$_4$S+H] 726.19546. found 726.19461.

EXAMPLE 150

4-[{2-[1-benzhydryl-5-chloro-2-(2-{[(2-chlorophenyl)sulfonyl]amino}ethyl)-1H-indol-3-yl]ethyl}(methyl)amino]benzoic acid Step 1: The intermediate from example 146 step 7 was treated with 2-chlorobenzenesulfonyl chloride according to the procedure in Example 87 step 2 to generate the desired product in 96% yield.

Step 2: The ester intermediate was hydrolyzed according to Step 8 Example 1, to afford the title acid in 84% yield. HRMS calc for [C$_{39}$H$_{35}$Cl$_2$N$_3$O$_4$S+H] 712.17981. found 712.17966.

EXAMPLE 151

4-[{2-[1-benzhydryl-5-chloro-2-(2-{[(2-methoxyphenyl)sulfonyl]amino}ethyl)-1H-indol-3-yl]ethyl}(methyl)amino]benzoic acid Step 1: The intermediate from example 146 step 7 was treated with 2-methoxy-benzenesulfonyl chloride according to the procedure in Example 87 step 2 to generate the desired product in 95% yield.

Step 2: The ester intermediate was hydrolyzed according to Step 8 Example 1, to afford the title acid in 73% yield. HRMS calc for [C$_{40}$H$_{38}$ClN$_3$O$_5$S+H] 708.22935. found 708.2286.

EXAMPLE 152

4-{3-[1-benzhydryl-5-chloro-2-(2-{[(2,4-dichlorophenyl)sulfonyl]-amino}ethyl)-1H-indol-3-yl]propyl}benzoic acid Step 1: To methyl 4-{2-[2-(2-aminoethyl)-1-benzhydryl-5-chloro-1H-indol-3-yl]propyl}benzoate (Step 6, Example 42) was added and 2,4-dichlorobenzenesulfonyl chloride according to the procedure in Example 1 Step 7 to generate the product in 95% yield.

Step 2: The ester intermediate was hydrolyzed according to Step 8 Example 1 to afford the title acid in 77% yield. HRMS calc for C$_{39}$H$_{33}$Cl$_3$N$_2$O$_4$S, 730.1227; found (ESI+), 731.1299.

EXAMPLE 153

4-{3-[1-benzhydryl-5-chloro-2-(2-{[(2,6-dichlorophenyl)sulfonyl]amino}ethyl)-1H-indol-3-yl]propyl}benzoic acid Step 1: To methyl 4-{2-[2-(2-aminoethyl)-1-benzhydryl-5-chloro-1H-indol-3-yl]propyl}benzoate (Step 6, Example 42) was added and 2,6-dichlorobenzenesulfonyl chloride according to the procedure in Example 1 Step 7 to generate the product in 93% yield.

Step 2: The ester intermediate was hydrolyzed according to Step 8 Example 1 to afford the title acid in 71% yield. HRMS calc for C$_{39}$H$_{33}$Cl$_3$N$_2$O$_4$S, 730.1227; found (ESI+), 731.13005.

EXAMPLE 154

4-{3-[1-benzhydryl-5-chloro-2-(2-{[(2,4,6-trichlorophenyl)sulfonyl]amino}ethyl)-1H-indol-3-yl]propyl}benzoic acid

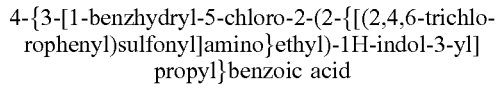

Step 1: To methyl 4-{2-[2-(2-aminoethyl)-1-benzhydryl-5-chloro-1H-indol-3-yl]propyl}benzoate (Step 6, Example 42) was added and 2,4,6-trichlorobenzenesulfonyl chloride according to the procedure in Example 1 Step 7 to generate the product in 76% yield.

Step 2: The ester intermediate was hydrolyzed according to Step 8 Example 1 to afford the title acid in 84% yield. HRMS calc for $C_{39}H_{32}Cl_4N_2O_4S$, 764.0837; found (ESI+), 765.08981.

EXAMPLE 155

4-{3-[1-benzhydryl-5-chloro-2-(2-{[(2-cyanophenyl)sulfonyl]amino}ethyl)-1H-indol-3-yl]propyl}benzoic acid

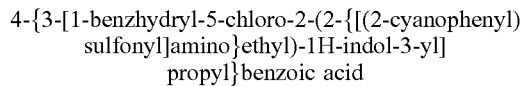

Step 1: To methyl 4-{2-[2-(2-aminoethyl)-1-benzhydryl-5-chloro-1H-indol-3-yl]propyl}benzoate (Step 6, Example 42) was added 2-cyanobenzenesulfonyl chloride according to the procedure in Example 1 Step 7 to generate the product in 87% yield.

Step 2: The ester intermediate was hydrolyzed according to Step 8 Example 1 and purified by prep HPLC to afford the title acid in 8% yield. HRMS calcd for $C_{40}H_{34}ClN_3O_4S$, 687.1959; found (ESI+), 688.2019.

EXAMPLE 156

4-(3-{2-[2-({[2-(aminomethyl)phenyl]sulfonyl}amino)ethyl]-1-benzhydryl-5-chloro-1H-indol-3-yl}propyl)benzoic acid

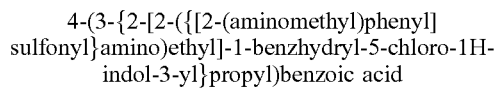

Step 1: Methyl 4-{3-[1-benzhydryl-5-chloro-2-(2-{[(2-cyanophenyl)sulfonyl]amino}ethyl)-1H-indol-3-yl]propyl}benzoate (Example 154, Step 1, 0.43 g, 0.61 mmol) was dissolved in THF (4 mL) and MeOH (12 mL). Cobalt (II) chloride (0.16 g, 1.2 mmol) and $NaBH_4$ (0.23 g, 6.1 mmol) were added. After 2 h the mixture was filtered, concentrated, and chromatographed on silica gel (MeOH—$CH_2Cl_2$) to afford the amino ester in 13% yield.

Step 2: The ester intermediate was hydrolyzed according to Step 8 Example 1 to afford the title acid in 59% yield. HRMS calcd for $C_{39}H_{36}ClN_3O_5S$, 693.2064; found (ESI+), 694.21261

EXAMPLE 157

4-[3-(1-benzhydryl-2-{2-[(1,1'-biphenyl-2-ylsulfonyl)amino]ethyl}-5-chloro-1H-indol-3-yl)propyl]benzoic acid

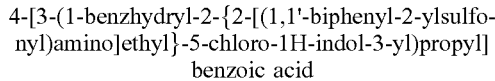

Step 1: 2-Bromobiphenyl (0.55 mL, 3.2 mmol) was dissolved in THF (10 mL) and $Et_2O$ (10 mL) and cooled at −78° C. while n-BuLi (1.3 mL of 2.5 M solution in hexanes, 3.2 mmol) was added rapidly dropwise. After 40 min, the mixture was added via cannula to a −78° C. solution of $SO_2$ (10 mL) in $Et_2O$ (20 mL). The mixture was warmed to room temperature overnight, concentrated, and triturated with $Et_2O$. The resulting white solid was suspended in hexane (40 mL) and cooled at 0° C. Sulfuryl chloride (3.4 mL of 1.0 M soln. in $CH_2Cl_2$, 3.4 mmol) was added and the mixture was stirred at room temperature for 5 h. It was then concentrated to afford 2-biphenylsulfonyl chloride in 67% yield.

Step 2: To methyl 4-{2-[2-(2-aminoethyl)-1-benzhydryl-5-chloro-1H-indol-3-yl]propyl}benzoate (Step 6, Example 42) was added 2-biphenylsulfonyl chloride according to the procedure in Example 1 Step 7 to generate the product in 83% yield.

Step 3: The ester intermediate was hydrolyzed according to Step 8 Example 1 to afford the title acid in 98% yield. HRMS calcd for $C_{45}H_{39}ClN_2O_4S$, 738.2319; found (ESI+), 739.23825.

EXAMPLE 158

4-{3-[1-benzhydryl-2-(2-{[(2-bromophenyl)sulfonyl]amino}ethyl)-5-chloro-1H-indol-3-yl]propyl}benzoic acid

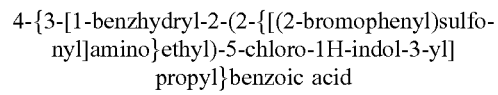

Step 1: To methyl 4-{2-[2-(2-aminoethyl)-1-benzhydryl-5-chloro-1H-indol-3-yl]propyl}benzoate (Step 6, Example 42) was added 2-bromobenzenesulfonyl chloride according to the procedure in Example 1 Step 7 to generate the product in 76% yield.

Step 2: The ester intermediate was hydrolyzed according to Step 8 Example 1 to afford the title acid in 95% yield. HRMS calcd for $C_{39}H_{34}BrClN_2O_4S$, 740.1111; found (ESI+), 741.11696.

EXAMPLE 159

4-{2-[1-benzhydryl-5-chloro-2-(2-{[(2,4-dichlorophenyl)sulfonyl]amino}ethyl)-1H-indol-3-yl]ethoxy}benzoic acid

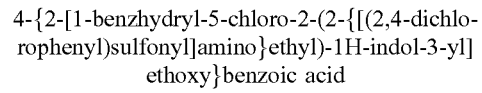

Step 1: This compound was prepared from methyl 4-{2-[2-(2-aminoethyl)-1-benzhydryl-5-chloro-1H-indol-3-yl]ethoxy}benzoate (Step 6, Example 1) and 2,4-dichlorobenzenesulfonyl chloride according to the procedure in Example 1 Step 7 in 83% yield.

Step 2: The ester intermediate was hydrolyzed according to Step 8 Example 1 to afford the title acid in 80% yield. HRMS calc for $C_{38}H_{31}Cl_3N_2O_5S$, 732.1019; found (ESI+), 733.10824.

EXAMPLE 160

4-{2-[1-benzhydryl-5-chloro-2-(2-{[(2,6-dichlorophenyl)sulfonyl]amino}ethyl)-1H-indol-3-yl]ethoxy}benzoic acid

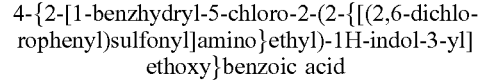

Step 1: This compound was prepared from methyl 4-{2-[2-(2-aminoethyl)-1-benzhydryl-5-chloro-1H-indol-3-yl]ethoxy}benzoate (Step 6, Example 1) and 2,6-dichlorobenzenesulfonyl chloride according to the procedure in Example 1 Step 7 in 77% yield.

Step 2: The ester intermediate was hydrolyzed according to Step 8 Example 1 to afford the title acid in 82% yield. HRMS calc for $C_{38}H_{31}Cl_3N_2O_5S$, 732.1019; found (ESI+), 733.10836.

EXAMPLE 161

4-{2-[1-benzhydryl-5-chloro-2-(2-{[(2,4,6-trichlorophenyl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2,4,6-trichlorobenzenesulfonyl chloride according to the procedure in Example 1 Step 7 in 90% yield.
Step 2: The ester intermediate was hydrolyzed according to Step 8 Example 1 to afford the title acid in 87% yield. HRMS calcd for $C_{38}H_{30}Cl_4N_2O_5S$, 766.0630; found (ESI+), 767.07063.

EXAMPLE 162

4-{2-[1-benzhydryl-5-chloro-2-(2-{[(2-cyanophenyl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-cyanobenzenesulfonyl chloride according to the procedure in Example 1 Step 7 in 82% yield.
Step 2: The ester intermediate was hydrolyzed according to Step 8 Example 1 and purified by prep HPLC to afford the title acid in 17% yield. HRMS calcd for $C_{39}H_{32}ClN_3O_5S$, 689.1751; found (ESI+), 690.18082.

EXAMPLE 163

4-(2-{2-[2-({[2-(aminomethyl)phenyl]sulfonyl}amino)ethyl]-1-benzhydryl-5-chloro-1H-indol-3-yl}ethoxy)benzoic acid Step 1: Methyl 4-{2-[1-benzhydryl-5-chloro-2-(2-{[(2-cyanophenyl)sulfonyl]amino}ethyl)-1H-indol-3-yl]ethoxy}benzoate (Example 161, Step 1, 0.31 g, 0.44 mmol) was dissolved in THF (4 mL) and MeOH (12 mL). Cobalt (II) chloride (0.11 g, 0.88 mmol) and NaBH$_4$ (0.17 g, 4.4 mmol) were added. After 2 h the mixture was filtered, concentrated, and chromatographed on silica gel (MeOH—CH$_2$Cl$_2$) to afford the amino ester in 17% yield.
Step 2: The ester intermediate was hydrolyzed according to Step 8 Example 1 to afford the title acid in 39% yield. HRMS calcd for $C_{39}H_{36}ClN_3O_5S$, 693.2064; found (ESI+), 694.21261.

EXAMPLE 164

4-[2-(1-benzhydryl-2-{2-[(1,1'-biphenyl-2-ylsulfonyl)amino]ethyl}-5-chloro-1H-indol-3-yl)ethoxy]benzoic acid Step 1: The sulfonamide was prepared from methyl 4-{2-[2-(2-aminoethyl)-1-benzhydryl-5-chloro-1H-indol-3-yl]ethoxy}benzoate (Step 6, Example 1) and 2-biphenylsulfonyl chloride (Step 1, Example 156) according to the procedure in Example 1 Step 7 in 93% yield.
Step 3: The ester intermediate was hydrolyzed according to Step 8 Example 1 to afford the title acid in 94% yield. HRMS calcd for $C_{44}H_{37}ClN_2O_5S$, 740.2112; found (ESI+), 741.21709.

EXAMPLE 165

4-{2-[1-benzhydryl-2-(2-{[(2-bromophenyl)sulfonyl]amino}ethyl)-5-chloro-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-bromobenzenesulfonyl chloride according to the procedure in Example 1 Step 7 in 90% yield.
Step 2: The ester intermediate was hydrolyzed according to Step 8 Example 1 to afford the title acid in 91% yield. HRMS calcd for $C_{38}H_{32}BrClN_2O_5S$, 742.0904; found (ESI+), 743.09697.

EXAMPLE 166

4-{3-[1-benzhydryl-5-chloro-2-(2-{[(5-chloro-2,4-difluorophenyl)sulfonyl]amino}ethyl)-1H-indol-3-yl]propyl}benzoic acid Step 1: To the methyl 4-{3-[2-(2-aminoethyl)-1-benzhydryl-5-chloro-1H-indol-3-yl]propyl}benzoate (Step 6, Example 42) was added and 5-chloro-2,4-difluorobenzenesulfonyl chloride according to the procedure in Example 1 Step 7 to generate the product in 68% yield.
Step 2: The ester intermediate was hydrolyzed according to Step 8 Example 1 to afford the title acid in 44% yield. HRMS calc for $[C_{39}H_{32}Cl_2F_2N_2O_4S+H]$ 733.15007. found 733.14978.

EXAMPLE 167

4-{3-[1-benzhydryl-5-chloro-2-(2-{[(2-methoxy-4-methylphenyl)sulfonyl]amino}ethyl)-1H-indol-3-yl]propyl}benzoic acid Step 1: To the methyl 4-{3-[2-(2-aminoethyl)-1-benzhydryl-5-chloro-1H-indol-3-yl]propyl}benzoate (Step 6, Example 42) was added and 2-methoxy-4-methylbenzenesulfonyl chloride according to the procedure in Example 1 Step 7 to generate the product in 86% yield.
Step 2: The ester intermediate was hydrolyzed according to Step 8 Example 1 to afford the title acid in 39% yield. HRMS calc for $[C_{41}H_{39}ClN_2O_5S+H]$ 707.2341. found 707.23407.

EXAMPLE 168

4-{3-[1-benzhydryl-5-chloro-2-(2-{[(4-chloro-2,5-difluorophenyl)sulfonyl]amino}ethyl)-1H-indol-3-yl]propyl}benzoic acid Step 1: To the methyl 4-{3-[2-(2-aminoethyl)-1-benzhydryl-5-chloro-1H-indol-3-yl]propyl}benzoate (Step 6, Example 42) was added and 4-chloro-2,5-difluorobenzenesulfonyl chloride according to the procedure in Example 1 Step 7 to generate the product in 79% yield.
Step 2: The ester intermediate was hydrolyzed according to Step 8 Example 1 to afford the title acid in 63% yield. HRMS calc for $[C_{39}H_{32}Cl_2F_2N_2O_4S+H]$ 733.15007. found 733.14882.

EXAMPLE 169

4-{2-[1-Benzhydryl-5-chloro-2-(2-{[(5-chloro-2,4-difluorophenyl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 5-chloro-2,4-difluorobenzenesulfonyl chloride according to the procedure in Example 1 Step 7 in 38% yield.

Step 2: The ester intermediate was hydrolyzed according to Step 8 Example 1 to afford the title acid in 31% yield. HRMS calc for $[C_{38}H_{30}Cl_2F_2N_2O_5.S+H]$ 735.12933. found 735.12824.

EXAMPLE 170

4-{2-[1-benzhydryl-5-chloro-2-(2-{[(4-chloro-2,5-difluorophenyl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 4-chloro-2,5-difluorobenzenesulfonyl chloride according to the procedure in Example 1 Step 7 in 79% yield.

Step 2: The ester intermediate was hydrolyzed according to Step 8 Example 1 to afford the title acid in 63% yield. HRMS calc for $[C_{38}H_{30}Cl_2F_2N_2O_5.S+H]$ 735.12933. found 735.12913.

EXAMPLE 171

4-{2-[1-benzhydryl-5-chloro-2-(2-{[(2-methoxy-4-methylphenyl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-methoxy-2-methylbenzenesulfonyl chloride according to the procedure in Example 1 Step 7.

Step 2: The crude ester intermediate was hydrolyzed according to Step 8 Example 1 to afford 407 mg of the title acid in quantitative yield. HRMS calc for $[C_{40}H_{37}ClN_2O_6.S+H]$ 709.21337. found 709.21194.

EXAMPLE 172

4-{3-[1-benzhydryl-5-chloro-2-(2-{[(7-chloro-2,1,3-benzoxadiazol-4-yl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 42) was added 4-chloro-7-chlorosulfonyl-2,1,3-benzoxadiazole according to the procedure in Example 1 Step 7 to generate the product in 43% yield.

Step 2: The ester intermediate was hydrolyzed according to Step 8 Example 1 to afford the title acid in 26% yield after HPLC separation. HRMS calc for $[C_{39}H_{32}Cl_2N_4O_5S+H]$ 739.15433. found 739.1537.

EXAMPLE 173

4-{3-[1-benzhydryl-5-chloro-2-(2-{[(7-methoxy-2,1,3-benzoxadiazol-4-yl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 42) was added 4-chloro-7-chlorosulfonyl-2,1,3-benzoxadiazole according to the procedure in Example 1 Step 7 to generate the product in 43% yield.

Step 2: The ester intermediate was hydrolyzed according to Step 8 Example 1 to afford the title acid in 36% yield after HPLC separation. HRMS calc for $[C_{40}H_{35}ClN_4O_6S+H]$ 735.2046. found 735.2029.

EXAMPLE 174

4-{2-[1-benzhydryl-5-chloro-2-(2-{[(7-chloro-2,1,3-benzoxadiazol-4-yl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 4-chloro-7-chlorosulfonyl-2,1,3-benzoxadiazole according to the procedure in Example 1 Step 7 in 56% yield.

Step 2: The ester intermediate was hydrolyzed according to Step 8 Example 1 to afford the title acid in 30% yield after HPLC separation. HRMS calc for $[C_{36}H_{30}Cl_2N_4O_6.S+H]$ 741.1343. found 741.1328.

EXAMPLE 175

4-{2-[1-benzhydryl-5-chloro-2-(2-{[(7-methoxy-2,1,3-benzoxadiazol-4-yl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 4-chloro-7-chlorosulfonyl-2,1,3-benzoxadiazole according to the procedure in Example 1 Step 7 in 56% yield.

Step 2: The ester intermediate was hydrolyzed according to Step 8 Example 1 to afford the title acid in 36% yield after HPLC separation. HRMS calc for $[C_{39}H_{33}ClN_4O_7.S+H]$ 737.1838. found 737.1819.

EXAMPLE 176

4-(3-{1-benzhydryl-5-chloro-2-[2-({[5-(2-methyl-1,3-thiazol-4-yl)thien-2-yl]sulfonyl}amino)ethyl]-1H-indol-3-yl}propyl)benzoic acid Step 1: To the methyl 4-{2-[2-(2-aminoethyl)-1-benzhydryl-5-chloro-1H-indol-3-yl]propyl}benzoate (Step 6, Example 42) was added 5-(2-methyl-1,3-thiazol-4-yl)-thiophene-2-sulfonyl chloride according to the procedure in Example 1 Step 7 to generate the product in 90% yield.

Step 2: The ester intermediate was hydrolyzed according to Step 8 Example 1 to afford the title acid in 100% yield. HRMS calc for $[C_{41}H_{36}ClN_3O_4S_3+H]$ 766.1636. found 766.1629.

EXAMPLE 177

4-(2-{1-benzhydryl-5-chloro-2-[2-({[5-(2-methyl-1,3-thiazol-4-yl)thien-2-yl]sulfonyl}amino)ethyl]-1H-indol-3-yl}ethoxy)benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 5-(2-methyl-1,3-thiazol-4-yl)-thiophene-2-sulfonyl chloride according to the procedure in Example 1 Step 7 in 100% yield.

Step 2: The ester intermediate was hydrolyzed according to Step 8 Example 1 to afford the title acid in 92% yield. HRMS calc for $[C_{40}H_{34}ClN_3O_5.S_3-H]$ 767.1269. found 766.1259.

EXAMPLE 178

4-[2-(1-benzhydryl-5-chloro-2-{2-[(thien-3-ylsulfonyl)amino]ethyl}-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 3-thiophenesulfonyl chloride according to the procedure in Example 1 Step 7 in 91% yield.

Step 2: The ester intermediate was hydrolyzed according to Step 8 Example 1 to afford the title acid in 96% yield. HRMS calc for $[C_{36}H_{31}ClN_2O_5.S_2+H]$ 671.14357. found 671.1428.

EXAMPLE 179

4-{2-[1-benzhydryl-5-chloro-2-(2-{[(6-morpholin-4-ylpyridin-3-yl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 6-morpholino-3-pyridinesulfonyl chloride according to the procedure in Example 1 Step 7 in 91% yield.

Step 2: The ester intermediate was hydrolyzed according to Step 8 Example 1 to afford the title acid in 92% yield. HRMS calc for $[C_{41}H_{39}ClN_4O_6.S+H]$ 751.23516. found 751.2345.

EXAMPLE 180

4-[3-(1-benzhydryl-5-chloro-2-{2-[(thien-3-ylsulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added 3-thiophenesulfonyl chloride according to the procedure in Example 1 Step 7 to generate the product in 87% yield.

Step 2: The ester intermediate was hydrolyzed according to Step 8 Example 1 to afford the title acid in 99% yield. HRMS calc for $[C_{37}H_{33}ClN_2O_4S_2+H]$ 669.16431. found 669.1629.

EXAMPLE 181

4-{3-[1-benzhydryl-5-chloro-2-(2-{[(6-morpholin-4-ylpyridin-3-yl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 42) was added 6-morpholino-3-pyridinesulfonyl chloride according to the procedure in Example 1 Step 7 to generate the product in 79% yield.

Step 2: The ester intermediate was hydrolyzed according to Step 8 Example 1 to afford the title acid in 89% yield. HRMS calc for $[C_{42}H_{41}ClN_4O_5S+H]$ 749.2559. found 749.255.

EXAMPLE 182

4-(2-{1-Benzhydryl-2-[2-(benzo[1,2,5]oxadiazole-4-sulfonylamino)-ethyl]-5-chloro-1H-indol-3-yl}-ethoxy)benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and benzofuran-4-sulfonyl chloride according to the procedure in Example 1 Step 7 in 88% yield.

Step 2: The ester intermediate was hydrolyzed according to Step 8 Example 1 to afford the title acid in 94% yield. HRMS calc for $[C_{38}H_{31}ClN_4O_6S+H]$ 707.17256. found 707.1719.

EXAMPLE 183

4-(3-{1-Benzhydryl-2-[2-(benzo[1,2,5]oxadiazole-4-sulfonylamino)-ethyl]-5-chloro-1H-indol-3-yl}-propyl)benzoic acid Step 1: To the methyl 4-{2-[2-(2-aminoethyl)-1-benzhydryl-5-chloro-1H-indol-3-yl]propyl}benzoate (Step 6, Example 42) was added benzofuran-4-sulfonyl chloride according to the procedure in Example 1 Step 7 to generate the product in 69% yield.

Step 2: The ester intermediate was hydrolyzed according to Step 8 Example 1 to afford the title acid in 93% yield. HRMS calc for $[C_{39}H_{33}ClN_4O_5S+H]$ 705.1933. found 705.1931.

EXAMPLE 184

4-(2-{1-Benzhydryl-2-[2-(2-benzyloxy-benzenesulfonylamino)-ethyl]-5-chloro-1H-indol-3-yl}-ethoxy)benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-benzyloxy-benzenesulfonyl chloride according to the procedure in Example 1 Step 7 in 87% yield.

Step 2: The ester intermediate was hydrolyzed according to Step 8 Example 1 to afford the title acid in 95% yield. HRMS calc for $[C_{45}H_{39}ClN_2O_6S-H]$ 769.21446. found 769.2129.

EXAMPLE 185

4-(2-{1-Benzhydryl-5-chloro-2-[2-(2-isopropoxy-benzenesulfonylamino)-ethyl]-1H-indol-3-yl}-ethoxy)benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-isopropoxybenzenesulfonyl chloride according to the procedure in Example 1 Step 7 in 88% yield.

Step 2: The ester intermediate was hydrolyzed according to Step 8 Example 1 to afford the title acid in 74% yield after trturation with ethylether. HRMS calc for $[C_{41}H_{39}ClN_2O_6S+H]$ 723.22902. found 723.2284.

EXAMPLE 186

4-(3-{1-Benzhydryl-5-chloro-2-[2-(2-isopropoxy-benzenesulfonylamino)-ethyl]-1H-indol-3-yl}-propyl)benzoic acid Step 1: To the methyl 4-{2-[2-(2-aminoethyl)-1-benzhydryl-5-chloro-1H-indol-3-yl]propyl}benzoate (Step 6, Example 42) was added 2-isopropoxybenzenesulfonyl chloride according to the procedure in Example 1 Step 7 to generate the product in 71% yield.

Step 2: The ester intermediate was hydrolyzed according to Step 8 Example 1 to afford the title acid in 82% yield after HPLC purification. HRMS calc for $[C_{42}H_{41}ClN_2O_5S+H]$ 721.24975. found 721.2490.

EXAMPLE 187

4-(3-{1-Benzhydryl-2-[2-(2-benzyloxy-benzene-sulfonylamino)-ethyl]-5-chloro-1H-indol-3-yl}-propyl)benzoic acid Step 1: To the methyl 4-{2-[2-(2-aminoethyl)-1-benzhydryl-5-chloro-1H-indol-3-yl]propyl}benzoate (Step 6, Example 42) was added 2-benzyloxy-benzenesulfonyl chloride according to the procedure in Example 1 Step 7 to generate the product in 57% yield.

Step 2: The ester intermediate was hydrolyzed according to Step 8 Example 1 to afford the title acid in 97% yield after HPLC purification. HRMS calc for $[C_{46}H_{41}ClN_2O_5S+H]$ 769.2505. found 769.2494.

EXAMPLE 188

4-(3-{1-Benzhydryl-2-[2-(2-hydroxy-benzenesulfonylamino)-ethyl]-1H-indol-3-yl}-propyl)-benzoic acid Step 1: The benzyl group from step 1 Example 186 was removed by hydrogenolysis. The crude was purified on silica gel column with $CH_2Cl_2$-5% EtOAc/$CH_2Cl_2$, to get a mixture which was further purified by HPLC to obtain 4-(3-{1-Benzhydryl-2-[2-(2-hydroxy-benzenesulfonylamino)-ethyl]-1H-indol-3-yl}-propyl)benzoic acid methyl ester (7%) and 4-(3-{1-Benzhydryl-5-chloro-2-[2-(2-hydroxy-benzenesulfonylamino)-ethyl]-1H-indol-3-yl}-propyl)benzoic acid methyl ester (18%)

Step 2: The 4-(3-{1-Benzhydryl-2-[2-(2-hydroxy-benzenesulfonylamino)-ethyl]-1H-indol-3-yl}-propyl)benzoic acid methyl ester intermediate was hydrolyzed according to Step 8 Example 1 to afford the title acid in 81% yield. HRMS calc for $[C_{39}H_{36}N_2O_5S+H]$ 645.2418. found 645.2423.

EXAMPLE 189

4-(3-{1-Benzhydryl-5-chloro-2-[2-(2-hydroxy-benzenesulfonylamino)-ethyl]-1H-indol-3-yl}-propyl)benzoic acid Step 1: 4-(3-{1-Benzhydryl-5-chloro-2-[2-(2-hydroxy-benzenesulfonylamino)-ethyl]-1H-indol-3-yl}-propyl)benzoic acid methyl ester intermediate from step 1 of Example 187 was hydrolyzed according to Step 8 Example 1 to afford the title acid in 86% yield. HRMS calc for $[C_{39}H_{35}ClN_2O_5S+H]$ 679.2028. found 679.2038.

EXAMPLE 190

4-(2-{1-Benzhydryl-5-chloro-2-[2-(2-chloro-benzenesulfonylamino)-ethyl]-1H-indol-3-yl}-ethoxy)-2-fluoro-benzoic acid Step 1: To a solution of Ph3P (698 mg, 2.7 mmole, 2.0 equiv.) in THF (10 ml) was slowly introduced diisopropylazodicarboxylate (0.55 ml, 2.7 mmole, 2.0 equiv.) at 0° C. under $N_2$. It was allowed to stir for 15 min. A solution of 2-{1-Benzhydryl-2-[2-(tert-butyl-diphenyl-silanyloxy)-ethyl]-5-chloro-1H-indol-3-yl}-ethanol (859 mg, 1.3 mmole, 1.0 equiv. Step 6, Example 142) in THF (5 ml) was transferred to Mitsunobu reagents, followed by 2-fluoro-4-hydroxy-benzoic acid methyl ester (340 mg, 2.0 mmole, 1.5 equiv.). The resulted solution was stirred overnight. THF was removed. The residues were partitioned between EtOAc and water. The organic phase was washed with water and brine, dried over $MgSO_4$. The product was purified on silica gel column with 8% EtOAc/hexane. 0.95 g (90%) of product was obtained as a white solid.

Step 2: The 4-(2-{1-Benzhydryl-2-[2-(tert-butyl-diphenyl-silanyloxy)-ethyl]-5-chloro-1H-indol-3-yl}-ethoxy)-2-fluoro-benzoic acid methyl ester was deprotected according to the procedure in Example 142, step 9 to yield 4-{2-[1-Benzhydryl-5-chloro-2-(2-hydroxy-ethyl)-1H-indol-3-yl]-ethoxy}-2-fluoro-benzoic acid methyl ester in 89% yield.

Step 3: 4-{2-[1-Benzhydryl-5-chloro-2-(2-hydroxy-ethyl)-1H-indol-3-yl]-ethoxy}-2-fluoro-benzoic acid methyl ester was activated by conversion to the mesylate following the procedure in Step 10 Example 142 and the resulting product was used crude in the next step.

Step 4: The mesylate from above was displaced with azide as described in Step 11 Example 142 to generate 4-{2-[2-(2-Azido-ethyl)-1-benzhydryl-5-chloro-1H-indol-3-yl]-ethoxy}-2-fluoro-benzoic acid methyl ester in 97% yield (over two steps).

Step 5: The 4-{2-[2-(2-Azido-ethyl)-1-benzhydryl-5-chloro-1H-indol-3-yl]-ethoxy}-2-fluoro-benzoic acid methyl ester was reduced under Staudinger conditions to yield methyl 4-{2-[2-(2-amino-ethyl)-1-benzhydryl-5-chloro-1H-indol-3-yl]-ethoxy}-2-fluoro-benzoate in 93% yield.

Step 6: The methyl 4-{2-[2-(2-amino-ethyl)-1-benzhydryl-5-chloro-1H-indol-3-yl]-ethoxy}-2-fluoro-benzoate from above and 2-chloro-benzenesulfonyl chloride were reacted according to the procedure in Example 1 Step 7 to generate the desired product in 73% yield.

Step 7: The ester intermediate was hydrolyzed according to Step 8 Example 1 to afford the title acid in 96% yield. HRMS calc for [$C_{38}H_{31}Cl_2FN_2O_5S+H$] 717.13876. found 717.1365.

EXAMPLE 191

4-(2-{1-Benzhydryl-5-chloro-2-[2-(2-chloro-6-methyl-benzenesulfonylamino)-ethyl]-1H-indol-3-yl}-ethoxy)-2-fluoro-benzoic acid Step 2: This compound was prepared from methyl 4-{2-[2-(2-amino-ethyl)-1-benzhydryl-5-chloro-1H-indol-3-yl]-ethoxy}-2-fluoro-benzoate (Step 5, Example 189) and 2-chloro-6-methyl-benzenesulfonyl chloride according to the procedure in Example 1 Step 7 in 66% yield.

Step 3: The ester intermediate was hydrolyzed according to Step 8 Example 1 to afford the title acid in 95% yield HRMS calc for [$C_{39}H_{33}Cl_2FN_2O_5S+H$] 731.15441. found 731.1532.

EXAMPLE 192

N-[2-(1-benzhydryl-5-chloro-3-{2-[4-(2H-tetraazol-5-yl)phenoxy]ethyl}-1H-indol-2-yl)ethyl]-1-(3,4-dichlorophenyl)methanesulfonamide Step 1: The 2-{1-Benzhydryl-2-[2-(tert-butyl-diphenyl-silanyloxy)-ethyl]-5-chloro-1H-indol-3-yl}-ethanol (Step 6, Example 142) was coupled with 4-Hydroxy-benzonitrile according to the conditions described in Example 189, Step 1 to yield 4-(2-{1-Benzhydryl-2-[2-(tert-butyl-diphenyl-silanyloxy)-ethyl]-5-chloro-1H-indol-3-yl}-ethoxy)-benzonitrile in 85% yield.

Step 2: The silyl ether from above was deprotected following the Example 142, step 9 to yield 4-{2-[1-Benzhydryl-5-chloro-2-(2-hydroxy-ethyl)-1H-indol-3-yl]-ethoxy}-benzonitrile in 93% yield.

Step 3: The alcohol from above was activated by conversion to the mesylate as described in Step 10 Example 142 to yield the desired mesylate which was used without purification in the next step.

Step 4: The mesylate from above was treated under the conditions described in Step 11 Example 142 to generate 4-{2-[2-(2-Azido-ethyl)-1-benzhydryl-5-chloro-1H-indol-3-yl]-ethoxy}-benzonitrile in 91% yield (2 steps).

Step 5: 4-{2-[2-(2-Azido-ethyl)-1-benzhydryl-5-chloro-1H-indol-3-yl]-ethoxy}-benzonitrile was reduced under Staudinger conditions as detailed in Step 12, example 142 to yield 4-{2-[2-(2-amino-ethyl)-1-benzhydryl-5-chloro-1H-indol-3-yl]-ethoxy}benzonitrile in 92% yeild.

Step 6: The 4-{2-[2-(2-amino-ethyl)-1-benzhydryl-5-chloro-1H-indol-3-yl]-ethoxy}benzonitrile from above and (3,4-dichloro-phenyl)-methanesulfonyl chloride were reacted according to the procedure in Example 1 Step 7 to yield the desired product in 92% yield.

Step 7: The mixture of nitrile (1.0 equiv.), azidotrimethylsilane (2.0 equiv.), dibutyltin oxide (0.1 equiv.) and toluene (3.3 ml/mmole) in a sealed tube was heated at 120° C. for 20 hours. It was acidified with 1 N HCl at room temperature, then diluted with EtOAc. The organic phase was washed with water and brine, dried over $MgSO_4$. The crude tetrazole was chromatographed with 50% EtOAc/hexanes–80% EtOAc/hexanes plus 0.5% of acetic acid to afford the title product in 58% yield HRMS calc for [$C_{39}H_{33}Cl_3N_6O_3S+H$] 771.14732. found 771.1475.

EXAMPLE 193

N-[2-(1-benzhydryl-5-chloro-3-{2-[4-(2H-tetrazol-5-yl)-phenoxy]-ethyl}-1H-indol-2-yl)-ethyl]-2-chlorobenzenesulfonamide Step 1: 4-{2-[2-(2-amino-ethyl)-1-benzhydryl-5-chloro-1H-indol-3-yl]-ethoxy}benzonitrile (Step 5, Example 191) and 2-chloro-benzenesulfonyl chloride were reacted according to the procedure in Example 1 Step 7 to yield the desired product in 77% yield.

Step 2: The nitrile from above was converted to tetrazole according to Step 7 of Example 191 to afford the title product in 45% yield. HRMS calc for [$C_{38}H_{32}Cl_2N_6O_3S+H$] 723.17065. found 723.1711.

EXAMPLE 194

N-[2-(1-benzhydryl-5-chloro-3-{2-[4-(2H-tetraazol-5-yl)phenoxy]ethyl}-1H-indol-2-yl)ethyl]butane-1-sulfonamide Step 1: The 4-{2-[2-(2-amino-ethyl)-1-benzhydryl-5-chloro-1H-indol-3-yl]-ethoxy}benzonitrile (Step 5, Example 191) and 1-butanesulfonyl chloride where reacted according to the procedure in Example 1 Step 7 to yield the product in 79% yield.

Step 2: The nitrile was converted to tetrazole according to Step 7 of Example 191 to afford the title product in 91% yield HRMS calc for [$C_{36}H_{37}ClN_6O_3S+H$] 669.24092. found 669.2409.

EXAMPLE 195

N-[2-(1-benzhydryl-5-chloro-3-{2-[4-(2H-tetraazol-5-yl)phenoxy]ethyl}-1H-indol-2-yl)ethyl]-2,2,2-trifluoroethanesulfonamide Step 1: The 4-{2-[2-(2-amino-ethyl)-1-benzhydryl-5-chloro-1H-indol-3-yl]-ethoxy}benzonitrile (Step 5, Example 191) and 2,2,2-trifluoro-ethanesulfonyl chloride where reacted according to the procedure in Example 1 Step 7 to yield the desired product in 64% yield.

Step 2: The nitrile was converted to tetrazole according to Step 7 of Example 191 to afford the title product in 77% yield HRMS calc for [$C_{34}H_{30}ClF_3N_6O_3S+H$] 695.18135. found 695.1807.

EXAMPLE 196

4-(2-{1-Benzhydryl-5-chloro-2-[2-(2,4,6-trifluoro-benzenesulfonylamino)-ethyl]-1H-indol-3-yl}-ethoxy)-benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2,4,6-trifluorobenzenesulfonyl chloride according to the procedure in Example 1 Step 7 in 92% yield.

Step 2: The ester intermediate was hydrolyzed according to Step 8 Example 1 to afford the title acid in 92% yield. HRMS calc for [$C_{38}H_{30}ClFN_2O_3S+H$] 719.15889. found 719.15843.

EXAMPLE 197

4-(2-{1-Benzhydryl-5-chloro-2-[2-(4-methoxy-2-nitro-benzenesulfonylamino)-ethyl]-1H-indol-3-yl}-ethoxy)-benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 4-methoxy-2-nitrobenzenesulfonyl chloride according to the procedure in Example 1 Step 7 in 74% yield.

Step 2: The ester intermediate was hydrolyzed according to Step 8 Example 1 to afford the title acid in 94% yield. HRMS calc for $[C_{39}H_{34}ClN_3O_8S+H]$ 740.1828. found 740.1834.

EXAMPLE 198

4-(2-{1-Benzhydryl-5-chloro-2-[2-(3-trifluoromethoxy-benzenesulfonylamino)-ethyl]-1H-indol-3-yl}-ethoxy)-benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 3-(trifluoromethoxy)benzenesulfonyl chloride according to the procedure in Example 1 Step 7 in 61% yield.

Step 2: The ester intermediate was hydrolyzed according to Step 8 Example 1 to afford the title acid in 86% yield. HRMS calc for $[C_{39}H_{32}ClF_3N_2O_6S+H]$ 771.1514. found 771.1512.

EXAMPLE 199

4-(3-{1-Benzhydryl-5-chloro-2-[2-(2,4,6-trifluoro-benzenesulfonylamino)-ethyl]-1H-indol-3-yl}-propyl)-benzoic acid Step 1: To the methyl 4-{2-[2-(2-aminoethyl)-1-benzhydryl-5-chloro-1H-indol-3-yl]propyl}benzoate (Step 6, Example 42) was added and 2,4,6-trifluorobenzenesulfonyl chloride according to the procedure in Example 1 Step 7 to generate the product in 61% yield.

Step 2: The ester intermediate was hydrolyzed according to Step 8 Example 1 to afford the title acid in 97% yield. HRMS calc for $[C_{39}H_{32}ClF_3N_2O_4S+H]$ 717.17962. found 717.17913.

EXAMPLE 200

4-(3-{1-Benzhydryl-5-chloro-2-[2-(4-methoxy-2-nitrobenzenesulfonylamino)-ethyl]-1H-indol-3-yl}-propyl)-benzoic acid Step 1: To the methyl 4-{2-[2-(2-aminoethyl)-1-benzhydryl-5-chloro-1H-indol-3-yl]propyl}benzoate (Step 6, Example 42) was added 4-methoxy-2-nitrobenzenesulfonyl chloride according to the procedure in Example 1 Step 7 to generate the product in 81% yield.

Step 2: The ester intermediate was hydrolyzed according to Step 8 Example 1 to afford the title acid in 95% yield. HRMS calc for $[C_{40}H_{36}ClN_3O_7S+H]$ 738.2035. found 738.2028.

EXAMPLE 201

4-(3-{1-Benzhydryl-5-chloro-2-[2-(3-trifluoromethoxy-benzenesulfonylamino)-ethyl]-1H-indol-3-yl}-propyl)-benzoic acid Step 1: To the methyl 4-{2-[2-(2-aminoethyl)-1-benzhydryl-5-chloro-1H-indol-3-yl]propyl}benzoate (Step 6, Example 42) was added 4-methoxy-2-nitrobenzenesulfonyl chloride according to the procedure in Example 1 Step 7 to generate the product in 83% yield.

Step 2: The ester intermediate was hydrolyzed according to Step 8 Example 1 to afford the title acid in 91% yield. HRMS calc for $[C_{40}H_{34}ClF_3N_2O_5S+H]$ 747.19019. found 747.18996.

EXAMPLE 202

4-{2-[1-Benzhydryl-5-chloro-2-{2-[({4-methysulfonylbenzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added 4-methysulfonybenzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for $[C_{40}H_{37}ClN_2O_6S_2+H]$ 741.18544. found 741.18421.

EXAMPLE 203

4-[2-(1-Benzhydryl-2-{2-[(4-methylsulfonylbenzene)amino]-ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 4-methylsulfonylbenzenesulfonyl chloride according to the procedure in Example 1 Step 7 in 61% yield.

Step 2: The ester intermediate was hydrolyzed according to Step 8 Example 1 to afford the title acid in 90% yield. HRMS calc for $[C_{39}H_{.35}ClN_2O_7S_2-H]$ 741.15014. found 741.14842.

EXAMPLE 204

4-{2-[1-Benzhydryl-5-chloro-2-{2-[({2-methylsulfonylbenzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 2-methylsulfonybenzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for $[C_{40}H_{37}ClN_2O_6S_2+H]$ 741.18544. found 741.18425.

EXAMPLE 205

4-[2-(1-Benzhydryl-2-{2-[(2-methylsulfonylbenzene)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-methylbenzenesulfonyl chloride according to the procedure in Example 1 Step 7 in 61% yield.

Step 2: The ester intermediate was hydrolyzed according to Step 8 Example 1 to afford the title acid in 90% yield. HRMS calc for $[C_{39}H_{35}ClN_2O_7S_2+H]$ 743.16470. found 743.16431.

EXAMPLE 206

4-{2-[1-Benzhydryl-5-chloro-2-{2-[({3-phenylsulfonylbenzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 3-phenylbenzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for $[C_{45}H_{39}ClN_2O_4S+H]$ 739.23919. found 739.23896.

EXAMPLE 207

4-[2-(1-Benzhydryl-2-{2-[(3-phenylsulfonylbenzene)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 3-phenylbenzenesulfonyl chloride according to the procedure in Example 1 Step 7 in 61% yield.

Step 2: The ester intermediate was hydrolyzed according to Step 8 Example 1 to afford the title acid in 90% yield. HRMS calc for $[C_{44}H_{37}ClN_2O_5S+H]$ 741.21845. found 741.21879.

EXAMPLE 208

4-{2-[1-Benzhydryl-5-chloro-2-{2-[({2-trifluoromethylsulfonylbenzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 2-trifluoromethylsulfonybenzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for $[C_{40}H_{34}F_3ClN_2O_5S+H]$ 731.19527. found 731.19591.

EXAMPLE 209

4-[2-(1-Benzhydryl-2-{2-[(2-trifluoromethylsulfonylbenzene)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-trifluoromethylbenzenesulfonyl chloride according to the procedure in Example 1 Step 7 in 61% yield.

Step 2: The ester intermediate was hydrolyzed according to Step 8 Example 1 to afford the title acid in 90% yield. HRMS calc for $[C_{40}H_{34}F_3ClN_2O_4S_2+H]$ 733.17454. found 733.17439.

EXAMPLE 210

4-{3-[1-benzhydryl-5-chloro-2-(2-{[(5-methyl-1-phenyl-1H-pyrazol-4-yl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 42) was added 5-Methyl-1-phenyl-1H-pyrazole-4-sulfonyl chloride according to the procedure in Example 1 Step 7 to generate the product in 93% yield.

Step 2: The ester intermediate was hydrolyzed according to Step 8 Example 1 to afford the title acid in 99% yield. HRMS calc for $[C_{43}H_{39}ClN_4O_4S+H]$ 743.24533. found 743.24506.

EXAMPLE 211

4-{2-[1-benzhydryl-5-chloro-2-(2-{[(5-methyl-1-phenyl-1H-pyrazol-4-yl)sulfonyl]amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 6, Example 1) was added 5-Methyl-1-phenyl-1H-pyrazole-4-sulfonyl chloride according to the procedure in Example 1 Step 7 to generate the product in 88% yield.

Step 2: The ester intermediate was hydrolyzed according to Step 8 Example 1 to afford the title acid in 100% yield. HRMS calc for $[C_{42}H_{37}ClN_4O_5S+H]$ 745.2246. found 745.22362.

EXAMPLE 212

4-{3-[1-benzhydryl-5-chloro-2-(2-{[(1,3,5-trimethyl-1H-pyrazol-4-yl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 42) was added 1,5-Dimethyl-1H-pyrazole-4-sulfonyl chloride according to the procedure in Example 1 Step 7 to generate the product in 92% yield.

Step 2: The ester intermediate was hydrolyzed according to Step 8 Example 1 to afford the title acid in 92% yield. HRMS calc for $[C_{39}H_{39}ClN_4O_4S+H]$ 695.24533. found 695.24453.

EXAMPLE 213

4-{2-[1-benzhydryl-5-chloro-2-(2-{[(1,3,5-trimethyl-1H-pyrazol-4-yl)sulfonyl]amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 6, Example 1) was 1,5-Dimethyl-1H-pyrazole-4-sulfonyl chloride according to the procedure in Example 1 Step 7 to generate the product in 100% yield.

Step 2: The ester intermediate was hydrolyzed according to Step 8 Example 1 to afford the title acid in 74% yield. HRMS calc for $[C_{38}H_{37}ClN_4O_5S+H]$ 697.2246. found 697.2241.

EXAMPLE 214

4-{3-[1-benzhydryl-5-chloro-2-(2-{[(2,3-dichlorophenyl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 42) was added 2,3-Dichloro-benzenesulfonyl chloride according to the procedure in Example 1 Step 7 to generate the product in 85% yield.

Step 2: The ester intermediate was hydrolyzed according to Step 8 Example 1 to afford the title acid in 96% yield. HRMS calc for $[C_{39}H_{33}Cl_3N_2O_4S-H]$ 729.1154. found 729.1135.

EXAMPLE 215

4-{2-[1-benzhydryl-5-chloro-2-(2-{[(2,3-dichlorophenyl)sulfonyl]amino}ethyl)-1H-indol-3-yl]ethoxy}benzoic acid Step 1: To the 4-{2-[2-(2-aminoethyl)-1-benzhydryl-5-chloro-1H-indol-3-yl]ethoxy)benzoate (Step 6, Example 1) was added 2,3-Dichloro-benzenesulfonyl chloride according to the procedure in Example 1 Step 7 to generate the product in 79% yield.

Step 2: The ester intermediate was hydrolyzed according to Step 8 Example 1 to afford the title acid in 97% yield. HRMS calc for $[C_{38}H_{31}Cl_3N_2O_5S-H]$ 731.0947. found 731.0930.

EXAMPLE 216

4-{3-[1-benzhydryl-5-chloro-2-(2-{[(4'-fluoro-1,1'-biphenyl-4-yl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 42) was added and 4'-fluorophenyl-4-benzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for $[C_{45}H_{38}ClFN_2O_4S+H]$ 757.22976. found 757.22874.

EXAMPLE 217

4-{2-[1-benzhydryl-5-chloro-2-(2-{[(4'-fluoro-1,1'-biphenyl-4-yl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 4'-fluorophenyl-4-benzenesulfonyl chloride according to the procedure in Example 1 Step 7 in 61% yield.

Step 2: The ester intermediate was hydrolyzed according to Step 8 Example 1 to afford the title acid in 90% yield. HRMS calc for $[C_{44}H_{36}ClFN_2O_5S+H]$ 759.20903. found 759.20745.

EXAMPLE 218

4-{2-[1-Benzhydryl-5-chloro-2-{2-[({3-trifluoromethylbenzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 3-trifluoromethylbenzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for $[C_{40}H_{37}ClF_3N_2O_4S+H]$ 731.19527. found 731.19582.

EXAMPLE 219

4-[2-(1-Benzhydryl-2-{2-[(3-trifluoromethylbenzene)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 3-trifluoromethylbenzenesulfonyl chloride according to the procedure in Example 1 Step 7 in 61% yield.

Step 2: The ester intermediate was hydrolyzed according to Step 8 Example 1 to afford the title acid in 90% yield. HRMS calc for $[C_{39}H_{35}ClF3N_2O_5S+H]$ 733.17454. found 733.17431.

EXAMPLE 220

4-[2-(1-benzhydryl-5-chloro-2-{2-[({[(3,4-dichlorophenyl)thio]methyl}sulfonyl)amino]ethyl}-1H-indol-3-yl)ethoxy]benzoic acid Step 1: To methyl 4-{2-[1-benzhydryl-5-chloro-2-(2-chloromethanesulfonylamino-ethyl)-1H-indol-3-yl]-ethoxy}-benzoate, Example 81 step 1, was added 3,4-dichlorothiophenol according to the procedure in Example 81 step 2. The crude was purified by the preperative HPLC in 24% yield of ester and 14% of acid.

Step 2: The ester intermediate was hydrolyzed according to Step 8 Example 1 to afford the title acid in 97% yield. m/z (M−1) 779.01.

EXAMPLE 221

4-[2-(1-benzhydryl-5-chloro-2-{2-[({[(3-chloro-4-fluorophenyl)thio]methyl}sulfonyl)amino]ethyl}-1H-indol-3-yl)ethoxy]benzoic acid Step 1: To methyl 4-{2-[1-benzhydryl-5-chloro-2-(2-chloromethanesulfonylamino-ethyl)-1H-indol-3-yl]-ethoxy}-benzoate, Example 81 step 1, was added 3-chloro-4-flurothiophenol according to the procedure in Example 81 step 2. The product was purified by flash column with 30% EtOAc/hexanes in 70% yield.

Step 2: The ester intermediate was hydrolyzed according to Step 8 Example 1 to afford the title acid in 89% yield. m/z (M−1) 760.94.

EXAMPLE 222

4-{2-[1-Benzhydryl-5-chloro-2-{2-[({2-fluorobenzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 2-fluorobenzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for [$C_{39}H_{34}ClFN_2O_4S$+H] 681.19846. found 681.19854.

EXAMPLE 223

4-[2-(1-Benzhydryl-2-{2-[(2-fluorobenzene)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-fluorobenzenesulfonyl chloride according to the procedure in Example 1 Step 7 in 61% yield.

Step 2: The ester intermediate was hydrolyzed according to Step 8 Example 1 to afford the title acid in 90% yield. HRMS calc for [$C_{38}H_{33}ClFN_2O_5S$+H] 683.17773. found 683.17694.

EXAMPLE 224

4-{2-[1-Benzhydryl-5-chloro-2-{2-[({2,6-difluorobenzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 2,6-difluorobenzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for [$C_{39}H_{33}ClF_2N_2O_4S$+H] 699.18904. found 699.18850.

EXAMPLE 225

4-[2-(1-Benzhydryl-2-{2-[(2,6-difluorobenzene)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2,6-difluorobenzenesulfonyl chloride according to the procedure in Example 1 Step 7 in 61% yield.

Step 2: The ester intermediate was hydrolyzed according to Step 8 Example 1 to afford the title acid in 90% yield. HRMS calc for [$C_{38}H_{32}ClF_2N_2O_5S$+H] 701.16831. found 701.16849.

EXAMPLE 226

4-{2-[1-Benzhydryl-5-chloro-2-{2-[({2-chloro-6-methylbenzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 2-chloro-6-methylbenzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for [$C_{40}H_{36}Cl_2N_2O_4S$+H] 711.18456. found 711.18404.

EXAMPLE 227

4-[2-(1-Benzhydryl-2-{2-[(2-chloro-6-methylbenzene)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-chloro-6-methylbenzenesulfonyl chloride according to the procedure in Example 1 Step 7 in 61% yield.

Step 2: The ester intermediate was hydrolyzed according to Step 8 Example 1 to afford the title acid in 90% yield. HRMS calc for [$C_{39}H_{34}Cl_2N_2O_5S$+H] 713.16383. found 713.16269.

EXAMPLE 228

4-(2-[1-Benzhydryl-5-chloro-2-{2-[({4-trifluoromethylbenzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 4-trifluoromethylbenzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for [$C_{40}H_{37}ClF_3N_2O_4S$+H] 731.19527. found 731.19580.

EXAMPLE 229

4-[2-(1-Benzhydryl-2-{2-[(4-trifluoromethylbenzene)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 4-trifluoromethylbenzenesulfonyl chloride according to the procedure in Example 1 Step 7 in 61% yield.

Step 2: The ester intermediate was hydrolyzed according to Step 8 Example 1 to afford the title acid in 90% yield. HRMS calc for [$C_{39}H_{35}ClF_3N_2O_5S+H$] 733.17454. found 733.17432.

EXAMPLE 230

4-{2-[1-Benzhydryl-5-chloro-2-{2-[({2-trifluoromethoxybenzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 2-trifluoromethoxybenzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for [$C_{40}H_{37}ClF_3N_2O_5S+H$] 747.19019. found 747.18848.

EXAMPLE 231

4-[2-(1-Benzhydryl-2-(2-[(2-trifluoromethoxybenzene)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-trifluoromethoxybenzenesulfonyl chloride according to the procedure in Example 1 Step 7 in 61% yield.

Step 2: The ester intermediate was hydrolyzed according to Step 8 Example 1 to afford the title acid in 90% yield. HRMS calc for [$C_{39}H_{35}ClF_3N_2O_6S+H$] 749.16945. found 749.16813.

EXAMPLE 232

4-{2-[1-Benzhydryl-5-chloro-2-{2-[({2-methylbenzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 2-methylbenzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for [$C_{40}H_{37}ClN_2O_4S+H$] 677.22354. found 677.22244.

EXAMPLE 233

4-[2-(1-Benzhydryl-2-{2-[(2-methylbenzene)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-methylbenzenesulfonyl chloride according to the procedure in Example 1 Step 7 in 61% yield.

Step 2: The ester intermediate was hydrolyzed according to Step 8 Example 1 to afford the title acid in 90% yield. HRMS calc for [$C_{39}H_{35}ClN_2O_5S+H$] 679.20280. found 679.20197.

EXAMPLE 234

4-{2-[1-Benzhydryl-5-chloro-2-{2-[({2-methoxybenzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 2-methoxybenzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for [$C_{40}H_{37}ClN_2O_5S+H$] 693.2185. found 693.21852.

EXAMPLE 235

4-[2-(1-Benzhydryl-2-(2-[(2-methoxybenzene)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-methoxybenzenesulfonyl chloride according to the procedure in Example 1 Step 7 in 61% yield.

Step 2: The ester intermediate was hydrolyzed according to Step 8 Example 1 to afford the title acid in 90% yield. HRMS calc for [$C_{39}H_{35}ClN_2O_6S+H$] 695.19722. found 695.19701.

EXAMPLE 236

4-{2-[1-Benzhydryl-5-chloro-2-{2-[({2-tert-butylbenzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 2-tert-butylbenzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for [$C_{43}H_{43}ClN_2O_4S+H$] 719.27049. found 719.27057.

EXAMPLE 237

4-[2-(1-Benzhydryl-2-{2-[(2-tert-butylbenzene)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-tert-butylbenzenesulfonyl chloride according to the procedure in Example 1 Step 7 in 61% yield.

Step 2: The ester intermediate was hydrolyzed according to Step 8 Example 1 to afford the title acid in 90% yield. HRMS calc for [$C_{42}H_{41}ClN_2O_5S$+H] 721.24975. found 721.24907.

EXAMPLE 238

4-{2-[1-Benzhydryl-5-chloro-2-{2-[({2-methylthiobenzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 2-methylthiobenzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for [$C_{40}H_{37}ClN_2O_4S_2$+H] 709.19561. found 709.19504.

EXAMPLE 239

4-[2-(1-Benzhydryl-2-{2-[(2-methylthiobenzene)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-methylthiobenzenesulfonyl chloride according to the procedure in Example 1 Step 7 in 61% yield.

Step 2: The ester intermediate was hydrolyzed according to Step 8 Example 1 to afford the title acid in 90% yield. HRMS calc for [$C_{39}H_{35}ClN_2O_5S_2$+H] 711.17487. found 711.17518.

EXAMPLE 240

4-{2-[1-Benzhydryl-5-chloro-2-{2-[({3-chloro-2-methylbenzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 3-chloro-2-methylbenzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for [$C_{40}H_{36}Cl_2N_2O_4S$+H] 711.18456. found 711.18465.

EXAMPLE 241

4-[2-(1-Benzhydryl-2-{2-[(3-chloro-2-methylbenzene)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 3-chloro-2-methylbenzenesulfonyl chloride according to the procedure in Example 1 Step 7 in 61% yield.

Step 2: The ester intermediate was hydrolyzed according to Step 8 Example 1 to afford the title acid in 90% yield. HRMS calc for [$C_{39}H_{34}Cl_2N_2O_5S$+H] 713.16383. found 713.16296.

EXAMPLE 242

4-[2-(2-{2-[2-(4-Acetyl-piperazin-1-yl)-ethanesulfonylamino]-ethyl}-1-benzhydryl-5-chloro-1H-indol-3-yl)-ethoxy]-benzoic acid Step 1: The compound was prepared from the intermediate from Example 100 step 1 and 1-acetylpiperazine according to the procedure in Example 100 step 2 except that it was heated at 60° C. for 19 h in 91% yield.

Step 2: The ester intermediate was hydrolyzed according to Step 8 Example 1 to the title acid in 19% yield. m/z (M−1) 741.2

EXAMPLE 243

4-[2-(1-Benzhydryl-5-chloro-2-{2-[2-(3,5-dimethyl-piperazin-1-yl)-ethanesulfonylamino]-ethyl}-1H-indol-3-yl)-ethoxy]-benzoic acid Step 1: The compound was prepared from the intermediate from Example 100 step 1 and cis-2,6-dimethylpiperazine according to the procedure in Example 100 step 2 except that it was heated at 60° C. for 19 h in 97% yield.

Step 2: The ester intermediate was hydrolyzed according to Step 8 Example 1 to the title acid in 39% yield. m/z (M−1) 727.2

EXAMPLE 244

4-[2-(2-{2-[2-(4-Acetyl-3,5-dimethyl-piperazin-1-yl)-ethanesulfonylamino]-ethyl}-1-benzhydryl-5-chloro-1H-indol-3-yl)-ethoxy]-benzoic acid Step 1: To a solution of 4-[2-(1-benzhydryl-5-chloro-2-{2-[2-(3,5-dimethyl-piperazin-1-yl)-ethanesulfonylamino]-ethyl}-1H-indol-3-yl)-ethoxy]-benzoic acid methyl ester (Step 1, Example above) (31 mg, 0.042 mmol) in $CH_2Cl_2$ (1 mL) at 0° C. were added $Et_3N$ (0.10 mL) and $Ac_2O$ (60 uL) and the reaction mixture was stirred at rt for 4 h. Aqueous workup followed by silica gel chromatography (3.5% MeOH/MeOH) gave the desired ester intermediate (17 mg, 52% yield).

Step 2: The ester intermediate was hydrolyzed according to Step 8 Example 1 to the title acid in 96% yield. m/z (M−1) 771.2.

EXAMPLE 245

4-(2-{1-benzhydryl-5-chloro-2-[2-({[2-(4-methylpi-peridin-1-yl)ethyl]sulfonyl}amino)ethyl]-1H-indol-3-yl}ethoxy)benzoic acid Step 1: The compound was prepared from the intermediate from Example 100 step 1 and 1-acetylpiperazine 4-methylpiperidine according to the procedure in Example 100 step 2. The product was purified by the flash column with 50–60% EtOAc/hexane in 87% yield.

Step 2: The ester intermediate was hydrolyzed according to Step 8 Example 1, except that the pH was adjusted to 4–5, to afford the title acid in 91% yield. m/z (M−1) 712.3.

EXAMPLE 246

4-(2-(1-benzhydryl-5-chloro-2-[2-({[2-(3-methylpi-peridin-1-yl)ethyl]sulfonyl}amino)ethyl]-1H-indol-3-yl}ethoxy)benzoic acid Step 1: The compound was prepared from the intermediate from Example 100 step 1 and 3-methylpiperidine according to the procedure in Example 100 step 2. The product was purified by the flash column with 50–60% EtOAc/hexane in 94% yield.

Step 2: The ester intermediate was hydrolyzed according to Step 8 Example 1, except that the pH was adjusted to 4–5, to afford the title acid in 87% yield. HRMS calc for $[C_{40}H_{44}ClN_3O_5S+H]$ 714.2763. found 714.2765.

EXAMPLE 247

4-[2-(1-Benzhydryl-2-{2-[2-(2-carbamoyl-pyrroli-din-1-yl)-ethanesulfonylamino]-ethyl}-5-chloro-1H-indol-3-yl)-ethoxy]-benzoic acid Step 1: The compound was prepared from the intermediate from Example 100 step 1 and L-prolinamide according to the procedure in Example 100 step 2. The product was purified by the flash column with EtOAc in 86% yield.

Step 2: The ester intermediate was hydrolyzed according to Step 8 Example 1, except that the pH was adjusted to 4–5, to afford the title acid in 43% yield after preparative HPLC purification. HRMS calc for $[C_{39}H_{41}ClN_4O_6S+H]$ 729.2508. found 729.251.

EXAMPLE 248

4-[2-(1-benzhydryl-5-chloro-2-{2-[({2-[(2S)-2-(methoxymethyl)pyrrolidin-1-yl]ethyl}sulfonyl)amino]ethyl}-1H-indol-3-yl)ethoxy]benzoic acid Step 1: The compound was prepared from the intermediate Example 100 step 1 and (S)-(+)-2-(methoxymethyl)pyrrolidine according to the procedure Example 100 step 2. The product was purified by the flash column with 80% EtOAc/hexane in 87% yield.

Step 2: The ester intermediate was hydrolyzed according to Step 8 Example 1, except that the pH was adjusted to 4–5, to afford the title acid in 87% yield. HRMS calc for $[C_{40}H_{44}ClN_3O_6S+H]$ 730.2712. found 730.2709.

EXAMPLE 249

4-(2-{1-benzhydryl-5-chloro-2-[2-({[2-(2-ethylpip-eridin-1-yl)ethyl]sulfonyl}amino)ethyl]-1H-indol-3-yl}ethoxy)benzoic acid Step 1: The compound was prepared from the intermediate from Example 100 step 1 and 2-ethylpiperidine according to the procedure in Example 100 step 2. The product was purified by the flash column with 50–60% EtOAc/hexane in 73% yield.

Step 2: The ester intermediate was hydrolyzed according to Step 8 Example 1, except that the pH was adjusted to 4–5, to afford the title acid in 38% yield after preparative HPLC purification. HRMS calc for $[C_{41}H_{46}ClN_3O_5S+H]$ 728.292. found 728.2925.

EXAMPLE 250

4-[2-(1-benzhydryl-5-chloro-2-{2-[({2-[(3R,5S)-3,5-dimethylmorpholin-4-yl]ethyl}sulfonyl)amino]ethyl}-1H-indol-3-yl)ethoxy]benzoic acid Step 1: The compound was prepared from the intermediate from Example 100 step 1 and cis-2,6-dimethylmorpholine according to the procedure Example 100 step 2. The product was purified by the flash column with 50% EtOAc/hexane in 79% yield.

Step 2: The ester intermediate was hydrolyzed according to Step 8 Example 1, except that the pH was adjusted to 4–5, to afford the title acid in 94% yield. m/z (M−1) 729.4

EXAMPLE 251

4-(2-{1-benzhydryl-5-chloro-2-[2-({[2-(2-oxa-5-azabicyclo[2.2.1]hept-5-yl)ethyl]sulfonyl}amino)ethyl]-1H-indol-3-yl}ethoxy)benzoic acid Step 1: The compound was prepared from the intermediate from Example 100 step 1 and (1S, 4S)-(+)-2-aza-5-oxabicyclo-[2.2.1]-heptane hydrochloride according to the procedure in Example 100 step 2. The product was purified on the CombiFlash with 1–7% MeOH/CH$_2$Cl$_2$ in 85% yield.

Step 2: The ester intermediate was hydrolyzed according to Step 8 Example 1, except that the pH was adjusted to 4–5, to afford the title acid in 100% yield. HRMS calc for $[C_{39}H_{40}ClN_3O_6S+H]$ 714.2399. found 714.2397.

EXAMPLE 252

4-(2-{1-benzhydryl-5-chloro-2-[2-({[2-(2-isopropy-lpyrrolidin-1-yl)ethyl]sulfonyl}amino)ethyl]-1H-indol-3-yl}ethoxy)benzoic acid Step 1: The compound was prepared from the intermediate from Example 100 step 1 and 2-(methylethyl)-pyrrolidine hydrochloride according to the procedure Example 100 step 2. The product was purified on the CombiFlash with 1–5% MeOH/CH$_2$Cl$_2$ in 61% yield.

Step 2: The ester intermediate was hydrolyzed according to Step 8 Example 1, except that the pH was adjusted to 4–5, to afford the title acid in 97% yield. HRMS calc for $[C_{41}H_{46}ClN_3O_5S+H]$ 728.292. found 728.293.

EXAMPLE 253

4-(2-{1-benzhydryl-5-chloro-2-[2-({[2-(2-methyl-3-oxopiperazin-1-yl)ethyl]sulfonyl}amino)ethyl]-1H-indol-3-yl}ethoxy)benzoic acid Step 1: The compound was prepared from the intermediate from Example 100 step 1 and 3-methyl-2-piperazinone according to the procedure in Example 100 step 2. The product was purified by the flash column with 5% MeOH/$CH_2Cl_2$ in 80% yield.

Step 2: The ester intermediate was hydrolyzed according to Step 8 Example 1, except that the pH was adjusted to 4–5, to afford the title acid in 29% yield after preparative HPLC purification. HRMS calc for $[C_{39}H_{41}ClN_4O_6S+H]$ 729.2508. found 729.2501.

EXAMPLE 254

4-{3-[1-benzhydryl-5-chloro-2-(2-{[(2-chlorophenyl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 1) was added 2-chlorobenzenesulfonyl chloride according to the procedure in Example 1, Step 7 to generate the product in 66% yield. $^1$H NMR (400 MHz, $CDCl_3$) δ ppm 1.94 (m, 2H), 2.74 (m, 6H), 2.97 (m, 2H), 3.91 (s, 3H), 4.94 (t, J=6.32 Hz, 1H), 6.48 (d, J=9.09 Hz, 1H), 6.79 (dd, J=8.84, 2.02 Hz, 1H), 6.83 (s, 1H), 7.03 (m, 4H), 7.26 (m, 9H), 7.39 (d, J=2.02 Hz, 1H), 7.44 (d, J=3.54 Hz, 2H), 7.90 (d, J=7.58 Hz, 1H), 7.96 (d, J=8.34 Hz, 2H)

Step 2: The ester intermediate was hydrolyzed according to Step 8, Example 1 to afford, after flash chromatography, the title acid in 84% yield. $^1$H NMR (400 MHz, $CDCl_3$) δ ppm 1.96 (m, 2H), 2.76 (m, 6H), 2.98 (m, 2H), 5.00 (t, J=6.32 Hz, 1H), 6.79 (dd, J=8.84, 2.02 Hz, 1H), 6.84 (s, 1H), 7.04 (m, 4H), 7.28 (m, 10H), 7.40 (d, J=1.77 Hz, 1H), 7.45 (d, J=3.79 Hz, 2H), 7.90 (d, J=7.58 Hz, 1H), 8.02 (d, J=8.34 Hz, 2H). HRMS calc for $C_{39}H_{34}Cl_2N_2O_4S$: Na, 719.1514; found (ESI−), 695.15363

EXAMPLE 255

4-{2-[1-benzhydryl-5-chloro-2-(2-{[(2-chlorophenyl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate and 2-chlorobenzenesulfonyl chloride according to the procedure in Example 1, Step 7 in 86% yield. $^1$H NMR (400 MHz, DMSO-D6) δ ppm 2.93 (m, 2H), 3.02 (m, 2H), 3.11 (t, J=6.57 Hz, 2H), 3.81 (s, 3H), 4.19 (t, J=6.57 Hz, 2H), 6.49 (d, J=8.84 Hz, 1H), 6.80 (dd, J=8.84, 2.02 Hz, 1H), 6.96 (d, J=8.84 Hz, 2H), 7.01 (s, 1H), 7.04 (dd, J=6.95, 2.40 Hz, 4H), 7.34 (m, 5H), 7.40 (m, 1H), 7.60 (m, 3H), 7.80 (dd, J=7.83, 1.52 Hz, 1H), 7.86 (d, J=8.84 Hz, 2H), 8.11 (t, J=5.81 Hz, 1H).

Step 2: The ester intermediate was hydrolyzed according to Step 8, Example 1. The crude material was purified via flash chromatography to afford the title acid in 74% yield. $^1$H NMR (400 MHz, $CDCl_3$) δ ppm 2.89 (m, 2H), 3.18 (t, J=6.57 Hz, 2H), 4.20 (t, J=6.57 Hz, 2H), 5.09 (t, J=6.32 Hz, 1H), 6.53 (d, J=8.84 Hz, 1H), 6.82 (m, 3H), 6.90 (s, 1H), 7.05 (m, 4H), 7.26 (m, 7H), 7.45 (m, 2H), 7.52 (d, J=2.02 Hz, 1H), 7.90 (m, 1H), 8.00 (d, J=8.84 Hz, 2H). HRMS calc for $C_{38}H_{32}Cl_2N_2O_5S$, 698.1409; found (ESI+), 699.14786. Anal. Calcd for $C_{38}H_{32}Cl_2N_2O_5S$: C, 65.23; H, 4.61; N, 4.00. Found: C, 65.02; H, 4.44; N, 3.94.

EXAMPLE 256

4-({2-[1-benzhydryl-5-chloro-2-(2-{[(2-chlorophenyl)sulfonyl]amino}ethyl)-1H-indol-3-yl]ethyl}sulfonyl)benzoic acid Step 1: This compound was prepared from 4-{2-[2-(2-amino-ethyl)-1-benzhydryl-5-chloro-1H-indol-3-yl]-ethanesulfonyl}-benzoic acid methyl ester and 2-chlorosulfonyl chloride according to the procedure in Example 1, Step 7 in 48% yield. $^1$H NMR (400 MHz, $CDCl_3$) δ ppm 2.88 (q, J=7.07 Hz, 2H), 3.03 (t, J=7.33 Hz, 2H), 3.20 (m, 2H), 3.43 (m, 2H), 3.97 (s, 3H), 5.18 (t, J=6.44 Hz, 1H), 6.46 (d, J=8.84 Hz, 1H), 6.78 (dd, J=8.97, 2.15 Hz, 1H), 6.84 (s, 1H), 7.04 (dd, J=6.69, 2.40 Hz, 4H), 7.21 (d, J=2.02 Hz, 1H), 7.31 (m, 7H), 7.48 (d, J=3.79 Hz, 2H), 7.91 (d, J=7.58 Hz, 1H), 8.08 (d, J=8.59 Hz, 2H), 8.24 (m, 2H).

Step 2: The ester intermediate was hydrolyzed according to Step 8, Example 1 to afford the title acid in 97% yield. $^1$H NMR (400 MHz, $CDCl_3$) δ ppm 2.88 (q, J=6.91 Hz, 2H), 3.04 (t, J=7.20 Hz, 2H), 3.22 (m, 2H), 3.45 (m, 2H), 5.25 (t, J=6.44 Hz, 1H), 6.47 (d, J=9.09 Hz, 1H), 6.78 (dd, J=8.84, 2.02 Hz, 1H), 6.84 (s, 1H), 7.04 (dd, J=6.57, 2.53 Hz, 4H), 7.22 (d, J=2.02 Hz, 1H), 7.31 (m, 7H), 7.48 (d, J=3.79 Hz, 2H), 7.92 (d, J=7.83 Hz, 1H), 8.12 (d, J=8.59 Hz, 2H), 8.28 (d, J=8.34 Hz, 2H).

EXAMPLE 257

4-{3-[1-benzhydryl-5-chloro-2-(2-{[(1,2-dimethyl-1H-imidazol-4-yl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate was added 1,2-dimethylimidazole-4-sulfonyl chloride according to the procedure in Example 1, Step 7 to generate the product in 80% yield. $^1$H NMR (400 MHz, DMSO-D6) δppm 1.86 (m, 2H), 2.18 (s, 3H), 2.71 (m, 4H), 2.94 (m, 4H), 3.49 (s, 3H), 3.83 (s, 3H), 6.42 (d, J=8.84 Hz, 1H), 6.76 (dd, J=8.84, 2.02 Hz, 1H), 7.06 (m, 4H), 7.36 (m, 8H), 7.44 (d, J=2.02 Hz, 1H), 7.49 (s, 1H), 7.59 (s, 1H), 7.87 (d, J=8.08 Hz, 2H).

Step 2: The ester intermediate was hydrolyzed according to Step 8, Example 1 to afford the title acid in 61% yield. $^1$H NMR (400 MHz, DMSO-D6) δ ppm 1.87 (m, 2H), 2.18 (s, 3H), 2.70 (t, J=7.58 Hz, 4H), 2.95 (m, 4H), 3.49 (s, 3H), 6.42 (d, J=8.84 Hz, 1H), 6.76 (dd, J=8.84, 2.02 Hz, 1H), 7.06 (m, 5H), 7.35 (m, 8H), 7.44 (d, J=2.02 Hz, 1H), 7.49 (s, 1H), 7.59 (t, J=4.93 Hz, 1H), 7.85 (d, J=8.34 Hz, 2H). HRMS: calcd for $C_{38}H_{37}ClN_4O_4S$, 680.2224; found (ESI+), 681.22879

EXAMPLE 258

4-{2-[1-benzhydryl-5-chloro-2-(2-{[(1,2-dimethyl-1H-imidazol-4-yl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate and 1,2-dimethylimidazole-4-sulfonyl chloride according to the procedure in Example 1, Step 7 in 84% yield. $^1$H NMR (400 MHz, CDCl$_3$) δ ppm 2.25 (s, 3H), 3.07 (m, 2H), 3.13 (m, 2H), 3.18 (t, J=6.82 Hz, 2H), 3.39 (s, 3H), 3.88 (s, 3H), 4.17 (t, J=6.69 Hz, 2H), 5.30 (m, J=2.78 Hz, 1H), 6.47 (d, J=9.09 Hz, 1H), 6.79 (dd, J=8.84, 2.02 Hz, 1H), 6.83 (d, J=8.84 Hz, 2H), 6.93 (s, 1H), 7.08 (m, 5H), 7.29 (m, 6H), 7.51 (d, J=2.02 Hz, 1H), 7.94 (d, J=8.84 Hz, 2H).

Step 2: The ester intermediate was hydrolyzed according to Step 8, Example 1 to afford the title acid in 55% yield. $^1$H NMR (400 MHz, DMSO-D6) δ ppm 2.17 (s, 3H), 3.02 (m, J=9.10 Hz, 4H), 3.14 (t, J=6.57 Hz, 2H), 3.47 (s, 3H), 4.21 (t, J=6.69 Hz, 2H), 6.47 (d, J=8.84 Hz, 1H), 6.79 (dd, J=8.84, 2.27 Hz, 1H), 6.96 (d, J=8.84 Hz, 2H), 7.07 (m, 5H), 7.36 (m, 6H), 7.49 (s, 1H), 7.63 (m, 2H), 7.84 (d, J=8.84 Hz, 2H). HRMS: calcd. for C$_{37}$H$_{35}$ClN$_4$O$_5$S, 682.2017; found (ESI+), 683.20812.

EXAMPLE 259

3-[4-({2-[1-benzhydryl-5-chloro-2-(2-{[(2-chlorophenyl)sulfonyl]amino)ethyl)-1H-indol-3-yl]ethyl}sulfonyl)phenyl]propanoic acid Step 1: This compound was prepared from 3-(4-{2-[2-(2-Amino-ethyl)-1-benzhydryl-5-chloro-1H-indol-3-yl]-ethanesulfonyl}-phenyl)-propionic acid ethyl ester and 2-chlorosulfonyl chloride according to the procedure in Example 1, Step 7 in 78% yield. $^1$H NMR (400 MHz, CDCl$_3$) δ ppm 1.25 (m, 3H), 2.66 (t, J=7.58 Hz, 2H), 2.88 (q, J=6.48 Hz, 2H), 3.07 (m, 6H), 3.34 (m, 2H), 4.12 (q, J=7.07 Hz, 2H), 5.31 (t, J=6.32 Hz, 1H), 6.45 (d, J=8.84 Hz, 1H), 6.77 (dd, J=8.84, 2.02 Hz, 1H), 6.85 (s, 1H), 7.04 (m, 4H), 7.16 (d, J=1.77 Hz, 1H), 7.30 (m, 7H), 7.46 (m, 4H), 7.91 (m, 3H).

Step 2: The ester intermediate was hydrolyzed according to Step 8, Example 1 to afford, after flash chromatography, the title acid in 41% yield. $^1$H NMR (400 MHz, CDCl$_3$) δ ppm 2.74 (s, 4H), 2.86 (t, J=6.69 Hz, 2H), 2.93 (m, 2H), 3.08 (t, J=6.57 Hz, 2H), 3.29 (m, 2H), 6.43 (d, J=8.84 Hz, 1H), 6.61 (s, 1H), 6.78 (m, 2H), 7.00 (m, 4H), 7.25 (m, 7H), 7.36 (d, J=1.77 Hz, 1H), 7.45 (m, 2H), 7.50 (d, J=8.34 Hz, 2H), 7.80 (d, J=7.58 Hz, 1H), 7.93 (d, J=8.34 Hz, 2H). HRMS: calcd. for C$_{40}$H$_{36}$Cl$_2$N$_2$O$_6$S$_2$ (M–H) 773.1319. found 773.13107.

EXAMPLE 260

4-{2-[1-benzhydryl-5-chloro-2-(2-{[(3-chloro-4-methylphenyl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate and 3-chloro-4-methylbenzenesulfonyl chloride according to the procedure in Example 1, Step 7 in 100% yield. $^1$H NMR (400 MHz, CDCl$_3$) δ ppm 2.38 (s, 3H), 2.92 (q, J=6.99 Hz, 2H), 3.09 (t, J=7.58 Hz, 2H), 3.18 (t, J=6.44 Hz, 2H), 3.88 (s, 3H), 4.21 (t, J=6.44 Hz, 2H), 4.42 (t, J=6.44 Hz, 1H), 6.54 (d, J=8.84 Hz, 1H), 6.79 (m, 2H), 6.83 (dd, J=8.84, 2.02 Hz, 1H), 6.88 (s, 1H), 7.04 (m, 4H), 7.20 (d, J=8.08 Hz, 1H), 7.29 (m, 6H), 7.40 (dd, J=7.96, 1.89 Hz, 1H), 7.52 (d, J=2.02 Hz, 1H), 7.66 (d, J=1.77 Hz, 1H), 7.93 (m, 2H).

Step 2: The ester intermediate was hydrolyzed according to Step 8, Example 1. The crude product was purified using flash chromatography to afford the title acid in 69% yield. $^1$H NMR (400 MHz, CDCl$_3$) δ ppm 2.38 (s, 3H), 2.93 (m, 2H), 3.10 (t, J=7.45 Hz, 2H), 3.19 (t, J=6.44 Hz, 2H), 4.23 (t, J=6.44 Hz, 2H), 4.52 (s, 1H), 6.54 (d, J=8.84 Hz, 1H), 6.83 (m, 3H), 6.89 (s, 1H), 7.04 (m, 4H), 7.20 (d, J=8.08 Hz, 1H), 7.29 (m, 6H), 7.40 (dd, J=8.08, 1.77 Hz, 1H), 7.53 (d, J=2.02 Hz, 1H), 7.67 (d, J=2.02 Hz, 1H), 7.98 (d, J=8.84 Hz, 2H). HRMS: calcd. for C$_{39}$H$_{34}$Cl$_2$N$_2$O$_5$S, 712.1565; found (ESI+), 713.16268. Anal. Calcd for C$_{39}$H$_{34}$Cl$_2$N$_2$O$_5$S: C, 65.64; H, 4.80; N, 3.93. Found: C, 65.62; H, 4.52; N, 3.73.

EXAMPLE 261

4-{3-[1-benzhydryl-5-chloro-2-(2-{[(3-chloro-4-methylphenyl)sulfonyl]amino}ethyl)-1H-indol-3-yl]propyl}benzoic acid Step 1: To the methyl 4-[(2-[2-(2-aminoethyl)-1-benzhydryl-5-chloro-1H-indol-3-yl]propyl}benzoate was added 3-chloro-4-methylbenzenesulfonyl chloride according to the procedure in Example 1, Step 7 to generate the product in 98% yield. $^1$H NMR (400 MHz, CDCl$_3$) δ ppm 1.95 (m, 2H), 2.40 (s, 3H), 2.72 (q, J=8.25 Hz, 4H), 2.82 (q, J=6.74 Hz, 2H), 2.96 (t, J=7.33 Hz, 2H), 3.91 (s, 3H), 4.27 (t, J=6.44 Hz, 1H), 6.49 (d, J=8.84 Hz, 1H), 6.80 (dd, J=8.97, 2.15 Hz, 1H), 6.82 (s, 1H), 7.02 (m, 4H), 7.26 (m, 9H), 7.38 (dd, J=7.96, 1.89 Hz, 1H), 7.40 (d, J=2.02 Hz, 1H), 7.66 (d, J=1.77 Hz, 1H), 7.96 (d, J=8.34 Hz, 2H).

Step 2: The ester intermediate was hydrolyzed according to Step 8, Example 1 to afford, after flash chromatography, the title acid in 40% yield. $^1$H NMR (400 MHz, CDCl$_3$) δ ppm 1.96 (m, 2H), 2.40 (s, 3H), 2.73 (m, 4H), 2.83 (m, 2H), 2.98 (t, J=7.33 Hz, 2H), 4.33 (t, J=6.32 Hz, 1H), 6.49 (d, J=8.84 Hz, 1H), 6.80 (dd, J=8.84, 2.27 Hz, 1H), 6.83 (s, 1H), 7.02 (m, 4H), 7.21 (d, J=7.83 Hz, 1H), 7.29 (m, 8H), 7.39 (m, 2H), 7.66 (d, J=1.77 Hz, 1H), 8.00 (d, J=8.08 Hz, 2H). HMRS: calcd. for C$_{40}$H$_{36}$Cl$_2$N$_2$O$_4$S, 710.1773; found (ESI+), 711.18411. Anal. Calcd for C$_{40}$H$_{36}$Cl$_2$N$_2$O$_4$S: C, 67.51; H, 5.10; N, 3.94. Found: C, 67.67; H, 5.27; N, 3.81.

EXAMPLE 262

4-{2-[1-benzhydryl-5-chloro-2-(2-{[(3-chloro-5-fluoro-2-methylphenyl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate and 3-chloro-5-fluoro-2-methylbenzenesulfonyl chloride according to the procedure in Example 1, Step 7 in 100% yield. $^1$H NMR (400 MHz, CDCl$_3$) δ ppm 2.26 (s, 3H), 2.99 (m, 2H), 3.10 (m, 2H), 3.18 (t, J=6.57 Hz, 2H), 3.88 (s, 3H), 4.21 (t, J=6.57 Hz, 2H), 4.71 (t, J=6.32 Hz, 1H), 6.52 (d, J=8.84 Hz, 1H), 6.81 (m, 3H), 6.88 (s, 1H), 7.04 (m, 4H), 7.14 (d, J=9.60 Hz, 1H), 7.29 (m, 6H), 7.52 (d, J=2.02 Hz, 1H), 7.58 (d, J=7.58 Hz, 1H), 7.94 (m, 2H).

Step 2: The ester intermediate was hydrolyzed according to Step 8, Example 1 to afford the title acid in 69% yield. $^1$H NMR (400 MHz, CDCl$_3$) δ ppm 2.26 (s, 3H), 2.99 (m, 2H), 3.11 (m, 2H), 3.19 (t, J=6.44 Hz, 2H), 4.23 (t, J=6.44 Hz, 2H), 4.79 (t, J=6.32 Hz, 1H), 6.52 (d, J=8.84 Hz, 1H), 6.83 (m, 3H), 6.88 (s, 1H), 7.04 (m, 4H), 7.15 (d, J=9.60 Hz, 1H), 7.29 (m, 6H), 7.52 (d, J=2.02 Hz, 1H), 7.59 (d, J=7.58 Hz, 1H), 7.99 (d, J=8.84 Hz, 2H). HRMS: calcd. for C$_{39}$H$_{33}$Cl$_2$FN$_2$O$_5$S, 730.1471; found (ESI+), 731.1532.

EXAMPLE 263

4-{3-[1-benzhydryl-5-chloro-2-(2-{[(3-chloro-5-fluoro-2-methylphenyl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate added and 3-chloro-5-fluoro-2-methylbenzenesulfonyl chloride according to the procedure in Example 1, Step 7 to generate the product in 75% yield. $^1$H NMR (400 MHz, CDCl$_3$) δ ppm 1.95 (m, 2H), 2.27 (s, 3H), 2.72 (q, J=7.58 Hz, 4H), 2.89 (t, J=6.82 Hz, 2H), 2.97 (m, 2H), 3.91 (s, 3H), 4.59 (t, J=6.19 Hz, 1H), 6.47 (d, J=8.84 Hz, 1H), 6.80 (dd, J=8.97, 2.15 Hz, 1H), 6.82 (s, 1H), 7.03 (dd, J=6.82, 2.53 Hz, 4H), 7.13 (d, J=9.60 Hz, 1H), 7.24 (d, J=8.34 Hz, 2H), 7.29 (m, 6H), 7.40 (d, J=2.02 Hz, 1H) 7.58 (d, J=7.58 Hz, 1H), 7.96 (d, J=8.34 Hz, 2H).

Step 2: The ester intermediate was hydrolyzed according to Step 8, Example 1 to afford the title acid in 96% yield. $^1$H NMR (400 MHz, CDCl$_3$) δ ppm 1.96 (m, 2H), 2.28 (s, 3H), 2.74 (m, 4H), 2.89 (m, 2H), 2.99 (m, 2H), 4.65 (q, J=6.32 Hz, 1H), 6.47 (d, J=8.84 Hz, 1H), 6.80 (dd, J=8.97, 2.15 Hz, 1H), 6.82 (s, 1H), 7.03 (m, 4H), 7.14 (d, J=9.60 Hz, 1H), 7.30 (m, 8H), 7.40 (d, J=2.02 Hz, 1H), 7.58 (d, J=7.58 Hz, 1H), 8.01 (d, J=8.08 Hz, 2H) HMRS: calcd. for C$_{40}$H$_{35}$Cl$_2$FN$_2$O$_4$S, 728.1679; found (ESI+), 729.17441. Anal. Calcd for C$_{40}$H$_{35}$Cl$_2$FN$_2$O$_4$S: C, 65.84; H, 4.83; N, 3.84. Found: C, 65.49; H, 5.02; N, 3.72.

EXAMPLE 264

4-{3-[1-benzhydryl-5-chloro-2-(2-{[(2-nitrophenyl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 1) was added and 2-nitrobenzenesulfonyl chloride according to the procedure in Example 1, Step 7 to generate the product in 74% yield. $^1$H NMR (400 MHz, CDCl$_3$) δ ppm 1.97 (m, 2H), 2.73 (q, J=8.08 Hz, 4H), 2.91 (m, 2H), 3.04 (m, 2H), 3.91 (s, 3H), 5.33 (t, J=6.06 Hz, 1H), 6.52 (d, J=8.84 Hz, 1H), 6.80 (dd, J=8.84, 2.02 Hz, 1H), 6.90 (s, 1H), 7.06 (dd, J=6.57, 2.53 Hz, 4H), 7.24 (d, J=8.34 Hz, 2H), 7.29 (m, 6H), 7.39 (d, J=2.02 Hz, 1H), 7.50 (td, J=7.71, 1.26 Hz, 1H), 7.65 (td, J=7.77, 1.39 Hz, 1H), 7.75 (dd, J=7.83, 1.26 Hz, 1H), 7.80 (dd, J=7.96, 1.14 Hz, 1H), 7.96 (d, J=8.08 Hz, 2H).

Step 2: The ester intermediate was hydrolyzed according to Step 8, Example 1 to afford the title acid in 100% yield. $^1$H NMR (400 MHz, CDCl$_3$) δ ppm 1.98 (m, 2H), 2.75 (m, 4H), 2.92 (m, 2H), 3.06 (m, 2H), 5.35 (t, J=6.06 Hz, 1H), 6.52 (d, J=8.84 Hz, 1H), 6.81 (dd, J=8.84, 2.02 Hz, 1H), 6.91 (s, 1H), 7.07 (dd, J=6.82, 2.53 Hz, 4H), 7.29 (m, 8H), 7.40 (d, J=2.02 Hz, 1H), 7.51 (m, 1H), 7.66 (m, 1H), 7.76 (dd, J=7.83, 1.26 Hz, 1H), 7.81 (dd, J=7.96, 1.14 Hz, 1H), 8.01 (d, J=8.34 Hz, 2H) HMRS: calcd for C$_{39}$H$_{34}$ClN$_3$O$_6$S, 707.18568; found (ESI+), 708.19296.

EXAMPLE 265

4-{2-[1-benzhydryl-5-chloro-2-(2-{[(2-nitrophenyl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate and 2-nitrosulfonyl chloride according to the procedure in Example 1, Step 7 in 63% yield. $^1$H NMR (400 MHz, CDCl$_3$) δ ppm 2.99 (m, 2H), 3.19 (m, 4H), 3.88 (s, 3H), 4.21 (t, J=6.57 Hz, 2H), 5.40 (t, J=6.19 Hz, 1H), 6.57 (d, J=8.84 Hz, 1H), 6.82 (m, 3H), 6.96 (s, 1H), 7.08 (m, 4H), 7.29 (m, 6H), 7.49 (td, J=7.71, 1.26 Hz, 1H), 7.52 (d, J=1.77 Hz, 1H), 7.65 (td, J=7.71, 1.26 Hz, 1H), 7.80 (m, 2H), 7.93 (d, 2H).

Step 2: The ester intermediate was hydrolyzed according to Step 8, Example 1 to afford the title acid in 90% yield. $^1$H NMR (400 MHz, CDCl$_3$) δ ppm 2.99 (m, 2H), 3.20 (m, 4H), 4.23 (t, J=6.57 Hz, 2H), 5.40 (t, J=6.19 Hz, 1H), 6.57 (d, J=8.84 Hz, 1H), 6.84 (m, 3H), 6.95 (s, 1H), 7.08 (m, J=5.68, 3.66 Hz, 4H), 7.29 (m, 6H), 7.50 (m, 2H), 7.65 (td, J=7.77, 1.39 Hz, 1H), 7.80 (m, 2H), 7.98 (d, 2H). HRMS: calcd for C$_{38}$H$_{32}$ClN$_3$O$_7$S, 709.16495; found (ESI+), 710.17059.

EXAMPLE 266

4-[2-(1-benzhydryl-5-chloro-2-{2-[(mesitylsulfonyl)amino]ethyl}-1H-indol-2-yl)ethoxy]benzoic acid Step 1: This compound was prepared from methyl 4-{2-[2-(2-aminoethyl)-1-benzhydryl-5-chloro-1H-indol-3-yl]ethoxy}benzoate and 2-mestitylenesulfonyl chloride according to the procedure in Example 1, Step 7 in 89% yield. $^1$H NMR (400 MHz, CDCl$_3$) δ ppm 2.24 (s, 3H), 2.48 (s, 6H), 2.90 (m, 2H), 3.05 (m, 2H), 3.16 (t, J=6.69 Hz, 2H), 3.89 (s, 3H), 4.17 (t, J=6.69 Hz, 2H), 4.48 (t, J=6.44 Hz, 1H), 6.52 (d, J=8.84 Hz, 1H)

Step 2: The ester intermediate was hydrolyzed according to Step 8, Example 1 to afford the title acid in 68% yield. $^1$H NMR (400 MHz, CDCl$_3$) δ ppm 2.24 (s, 3H), 2.48 (s, 6H), 2.90 (q, J=6.99 Hz, 2H), 3.06 (m, 2H), 3.17 (t, J=6.69 Hz, 2H), 4.19 (t, J=6.57 Hz, 2H), 4.59 (s, 1H), 6.52 (d, J=8.84 Hz, 1H), 6.82 (m, 6H), 7.02 (m, 4H), 7.29 (m, 6H), 7.52 (d, J=2.02 Hz, 1H), 7.98 (d, J=8.84 Hz, 2H). HRMS: calcd. for C$_{41}$H$_{39}$ClN$_2$O$_5$S, 706.22682; found (ESI+), 707.23370.

EXAMPLE 267

4-(3-{1-Benzhydryl-5-chloro-2-[2-(2,4,6-trimethyl-benzenesulfonylamino)-ethyl]-1H-indol-3-yl}-propyl)-benzoic acid Step 1: To the methyl 4-{2-[2-(2-aminoethyl)-1-benzhydryl-5-chloro-1H-indol-3-yl]propyl}benzoate (Step 6, Example 1) was added 2-mesitylenebenzenesulfonyl chloride according to the procedure in Example 1, Step 7 to generate the product in 83% yield. $^1$H NMR (400 MHz, CHLOROF CDCl$_3$) δ ppm 1.93 (m, 2H), 2.26 (s, 3H), 2.47 (s, 6H), 2.70 (m, 4H), 2.82 (m, 2H), 2.91 (m, 2H), 3.91 (s, 3H), 4.36 (t, J=6.44 Hz, 1H), 6.46 (d, J=8.84 Hz, 1H), 6.75 (s, 1H), 6.79 (dd, J=8.84, 2.27 Hz, 1H), 6.88 (s, 2H), 7.00 (m, 4H), 7.22 (d, J=8.34 Hz, 2H), 7.28 (m, 6H), 7.39 (d, J=2.02 Hz, 1H), 7.95 (d, J=8.34 Hz, 2H).

Step 2: The ester intermediate was hydrolyzed according to Step 8, Example 1 to afford the title acid in 84% yield. $^1$H NMR (400 MHz, CDCl$_3$) δ ppm 1.94 (m, 2H), 2.26 (s, 3H), 2.47 (s, 6H), 2.71 (m, 4H), 2.83 (m, 2H), 2.93 (m, 2H), 4.45 (t, J=5.81 Hz, 1H), 6.46 (d, J=8.84 Hz, 1H), 6.75 (s, 1H), 6.79 (dd, J=8.97, 2.15 Hz, 1H), 6.88 (s, 2H), 7.00 (m, 4H), 7.27 (m, 8H), 7.40 (d, J=2.02 Hz, 1H), 8.01 (d, J=8.34 Hz, 2H). HMRS: calcd. for $C_{42}H_{41}ClN_2O_4S$, 704.24756; found (ESI+), 705.25452.

EXAMPLE 268

4-(3-{1-benzhydryl-5-chloro-2-[2-({[2-fluoro-6-(trifluoromethyl)phenyl]sulfonyl}amino)ethyl]-1H-indol-3-yl}propyl)benzoic acid Step 1: 2-bromo-1-fluoro-3-trifluoromethylbenzene (1.0 eq.) was taken up in tetrahydrofuran (0.5 M) and diethyl ether (0.5 M) and cooled to −78° C. n-butyllithium (2.5M, 1.0 eq.) was added dropwise and the reaction stirred for 40 minutes. A volume of sulfur dioxide equal to the volume of THF was condensed and diluted with two volumes of ether. The lithium salt of the benzene was canulated into the sulfur dioxide and the reaction was allowed to slowly warm to room temperature. The solvent was removed and the resulting salt was washed with ether then taken up in hexanes (1.0M) and cooled in and ice bath. Sulfuryl chloride (1.06 eq.) was added and the reaction warmed to room temperature and stirred for 5 hours. The solvent was removed to give 2-fluoro-6-trifluoromethylbenznesulfonyl chloride as a white, oily solid in 65% yield. The product was used crude. $^1$H NMR (400 MHz, DMSO-D6) □ ppm 7.46 (m, 1H), 7.52 (m, 2H).

Step 2: To methyl 4-{2-[2-(2-aminoethyl)-1-benzhydryl-5-chloro-1H-indol-3-yl]propyl}benzoate was added 2-fluoro-6-trifluoromethylbenzenesulfonyl chloride according to the procedure in Example 1, Step 7 to generate the product in 62% yield. $^1$H NMR (400 MHz, CDCl$_3$) □ ppm 1.94 (m, 2H), 2.73 (m, 4H), 2.91 (m, 2H), 2.99 (m, 2H), 3.91 (s, 3H), 4.87 (t, J=5.81 Hz, 1H), 6.50 (d, J=8.84 Hz, 1H), 6.81 (dd, J=8.97, 2.15 Hz, 2H), 7.03 (m, 4H), 7.24 (d, J=8.34 Hz, 2H), 7.30 (m, 7H), 7.41 (d, J=2.02 Hz, 1H), 7.62 (m, 2H), 7.95 (d, J=8.34 Hz, 2H).

Step 3: The ester intermediate was hydrolyzed according to Step 8, Example 1 to afford the title acid in 56% yield. $^1$H NMR (400 MHz, CDCl$_3$) □ ppm 1.96 (m, 2H), 2.75 (m, 4H), 2.92 (m, 2H), 3.00 (m, 2H), 4.93 (t, J=5.94 Hz, 1H), 6.51 (d, J=8.84 Hz, 1H), 6.82 (m, 2H), 7.03 (m, 4H), 7.28 (m, 8H), 7.32 (d, J=10.61 Hz, 1H), 7.41 (d, J=2.02 Hz, 1H,) 7.63 (m, 2H), 8.01 (d, J=8.08 Hz, 2H). HRMS calc for [$C_{40}H_{33}ClF_4N_2O_4S$+H] 749.18585. found 749.18578.

EXAMPLE 269

4-(2-{1-benzhydryl-5-chloro-2-[2-({[2-fluoro-6-(trifluoromethyl)phenyl]sulfonyl}amino)ethyl]-1H-indol-3-yl}ethoxy)benzoic acid Step 1: To methyl 4-{2-[2-(2-aminoethyl)-1-benzhydryl-5-chloro-1H-indol-3-yl]ethoxy}benzoate was added 2-fluoro-6-trifluoromethylbenzenesulfonyl chloride according to the procedure in Example 1, Step 7 to afford product in 89% yield. $^1$H NMR (400 MHz, CDCl$_3$) δ ppm 3.00 (m, 2H), 3.12 (m, 2H), 3.20 (t, J=6.44 Hz, 2H), 3.88 (s, 3H), 4.20 (t, J=6.44 Hz, 2H), 4.99 (t, J=6.06 Hz, 1H), 6.54 (d, J=8.84 Hz, 1H), 6.79 (d, J=8.84 Hz, 2H), 6.84 (dd, J=8.97, 2.15 Hz, 1H), 6.88 (s, 1H), 7.04 (dd, J=6.82, 2.53 Hz, 4H), 7.28 (m, 6H), 7.33 (m, 1H), 7.54 (d, J=2.02 Hz, 1H), 7.60 (m, 2H), 7.93 (d, J=9.10 Hz, 2H).

Step 2: The ester intermediate was hydrolyzed according to Step 8, Example 1 to afford the title acid in 36% yield. $^1$H NMR (400 MHz, CDCl$_3$) □ ppm 3.01 (m, 2H), 3.13 (m, 2H), 3.21 (t, J=6.44 Hz, 2H), 4.22 (t, J=6.44 Hz, 2H), 5.07 (t, J=6.06 Hz, 1H), 6.55 (d, J=8.84 Hz, 1H), 6.83 (m, 3H), 6.88 (s, 1H), 7.04 (m, 4H), 7.28 (m, 6H), 7.32 (m, 1H), 7.55 (d, J=2.02 Hz, 1H), 7.61 (m, 2H), 7.98 (d, J=8.84 Hz, 2H). HRMS calc for [$C_{39}H_{31}ClF_4N_2O_5S$+H] 751.16511. found 751.16431.

EXAMPLE 270

4-{3-[1-benzhydryl-5-chloro-2-(2-{[(2,6-dimethylphenyl)sulfonyl]amino}ethyl)-1H-indol-3-yl]propyl}benzoic acid Step 1: 2,6-Dimethylbenzenesulfonyl chloride was prepared from 2-bromo-1,3-dimethylbenzene according to the procedure in Example 18, Step 1–2. The reaction gave product as a white solid in 84% yield. $^1$H NMR (400 MHz, DMSO-D6) □ ppm 2.54 (s, 6H), 6.94 (d, J=7.33 Hz, 2H), 7.02 (m, 1H).

Step 2: To methyl 4-{2-[2-(2-aminoethyl)-1-benzhydryl-5-chloro-1H-indol-3-yl]propyl}benzoate was added 2,6-dimethylbenzenesulfonyl chloride according to the procedure in Example 1, Step 7 to generate the product in 66% yield. $^1$H NMR (400 MHz, CDCl$_3$) □ ppm 1.93 (m, 2H), 2.50 (s, 6H), 2.70 (m, 4H), 2.82 (m, 2H), 2.93 (m, 2H), 3.91 (s, 3H), 4.40 (t, J=6.32 Hz, 1H), 6.47 (d, J=8.84 Hz, 1H), 6.77 (s, 1H), 6.80 (dd, J=8.97, 2.15 Hz, 1H), 7.00 (m, 4H), 7.07 (d, J=7.58 Hz, 2H), 7.22 (d, J=8.08 Hz, 2H), 7.27 (m, 7H), 7.40 (d, J=2.02 Hz, 1H), 7.95 (d, J=8.08 Hz, 2H).

Step 3: The ester intermediate was hydrolyzed according to Step 8, Example 1 to afford the title acid in 96% yield. $^1$H NMR (400 MHz, DMSO-D6) □ ppm 1.81 (m, 2H,) 2.50 (s, 6H), 2.65 (m, 4H), 2.81 (m, 2H), 2.87 (m, 2H), 6.45 (d, J=8.84 Hz, 1H), 6.77 (dd, J=8.84, 2.27 Hz, 1H), 6.94 (s, 1H), 7.02 (m, 4H), 7.17 (d, J=7.58 Hz, 2H), 7.28 (d, J=8.34 Hz, 2H), 7.33 (m, 6H), 7.43 (d, J=2.27 Hz, 1H), 7.70 (t, J=5.81 Hz, 1H), 7.85 (d, J=8.08 Hz, 2H). HRMS calc for [$C_{41}H_{39}ClN_2O_4S$+H] 691.23919. found 691.23872.

EXAMPLE 271

4-(2-[1-benzhydryl-5-chloro-2-(2-{[(2,6-dimethylphenyl)sulfonyl]amino}ethyl)-1H-indol-3-yl]ethoxy}benzoic acid Step 1: To methyl 4-{2-[2-(2-aminoethyl)-1-benzhydryl-5-chloro-1H-indol-3-yl]ethoxy}benzoate was added 2,6-dimethylbenzenesulfonyl chloride (Example 266, Step 1) according to the procedure in Example 1, Step 7 to afford product in 88% yield. $^1$H NMR (400 MHz, CDCl$_3$) □ ppm 2.51 (s, 6H), 2.90 (m, 2H), 3.06 (m, 2H), 3.16 (t, J=6.69 Hz, 2H), 3.89 (s, 3H), 4.17 (t, J=6.57 Hz, 2H), 4.50 (t, J=6.19 Hz, 1H), 6.53 (d, J=8.84 Hz, 1H), 6.79 (d, J=9.10 Hz, 2H), 6.83 (m, 2H), 7.02 (m, 4H), 7.06 (d, J=7.58 Hz, 2H), 7.23 (m, 1H), 7.28 (m, 6H), 7.53 (d, J=2.02 Hz, 1H), 7.93 (d, J=8.84 Hz, 2H).

Step 2: The ester intermediate was hydrolyzed according to Step 8, Example 1 to afford the title acid in 79% yield. $^1$H NMR (400 MHz, DMSO-D7) □ ppm 2.48 (s, 6H), 2.85 (m, 2H), 2.95 (m, 2H), 3.08 (t, J=6.57 Hz, 2H), 4.15 (t, J=6.69 Hz, 2H), 6.48 (d, J=8.84 Hz, 1H), 6.79 (dd, J=8.84, 1.77 Hz, 1H), 6.90 (d, J=8.84 Hz, 2H), 6.95 (s, 1H), 7.01 (m, 4H), 7.14 (d, J=7.58 Hz, 2H), 7.29 (m, 6H), 7.63 (d, J=2.02 Hz, 1H), 7.73 (t, J=5.94 Hz, 1H), 7.82 (d, J=8.84 Hz, 2H). HRMS calc for [C$_{40}$H$_{37}$ClN$_2$O$_5$S+H] 693.21845. found 693.21791.

EXAMPLE 272

4-{2-[1-benzhydryl-5-chloro-2-(2-{[(2,6-diethylphenyl)sulfonyl]amino}ethyl)-1H-indol-3-yl]ethoxy}benzoic acid Step 1: 2,6-Diethylbenzenesulfonyl chloride was prepared from 2-bromo-1,3-diethylbenzne according to the procedure in Example 18, Step 1–2. The reaction gave product as a pale yellow, oily solid in 36% yield. $^1$H NMR (400 MHz, DMSO-D6) □ ppm 1.13 (t, J=7.33 Hz, 6H), 3.08 (q, J=7.33 Hz, 4H), 6.96 (d, J=7.58 Hz, 2H), 7.10 (m, 1H).

Step 2: To methyl 4-{2-[2-(2-aminoethyl)-1-benzhydryl-5-chloro-1H-indol-3-yl]ethoxy}benzoate was added 2,6-diethylbenzenesulfonyl chloride according to the procedure in Example 1, Step 7 to afford product in 72% yield. $^1$H NMR (400 MHz, DMSO-D6) □ ppm 1.10 (t, J=7.33 Hz, 6H), 2.91 (m, 6H), 2.99 (m, 2H), 3.11 (t, J=6.69 Hz, 2H), 3.81 (s, 3H), 4.18 (t, J=6.69 Hz, 2H), 6.49 (d, J=8.84 Hz, 1H), 6.80 (dd, J=8.84, 2.02 Hz, 1H), 6.93 (d, J=8.84 Hz, 2H), 6.97 (s, 1H), 7.02 (m, 4H), 7.17 (d, J=7.58 Hz, 2H), 7.32 (m, 5H), 7.38 (t, J=7.71 Hz, 1H), 7.65 (d, J=2.02 Hz, 1H), 7.74 (t, J=5.94 Hz, 1H), 7.85 (d, J=8.84 Hz, 2H).

Step 3: The ester intermediate was hydrolyzed according to Step 8, Example 1 to afford the title acid in 88% yield. $^1$H NMR (400 MHz, DMSO-D6) □ ppm 1.10 (t, J=7.33 Hz, 6H), 2.91 (m, 6H), 2.98 (d, J=7.83 Hz, 2H), 3.10 (t, J=6.57 Hz, 2H), 4.17 (t, J=6.69 Hz, 2H), 6.49 (d, J=8.84 Hz, 1H), 6.80 (dd, J=8.84, 2.02 Hz, 1H), 6.91 (d, J=9.09 Hz, 2H), 6.97 (s, 1H), 7.02 (m, 4H), 7.17 (d, J=7.58 Hz, 2H), 7.32 (m, 5H), 7.38 (t, J=7.58 Hz, 1H), 7.65 (d, J=2.27 Hz, 1H), 7.74 (t, J=5.81 Hz, 1H), 7.83 (d, J=8.84 Hz, 2H). HRMS calc for [C$_{42}$H$_{41}$ClN$_2$O$_5$S+H] 721.24975. found 721.24876.

EXAMPLE 273

4-{3-[1-benzhydryl-5-chloro-2-(2-{[(2,6-diethylphenyl)sulfonyl]amino}ethyl)-1H-indol-3-yl]propyl}benzoic acid Step 1: To methyl 4-{2-[2-(2-aminoethyl)-1-benzhydryl-5-chloro-1H-indol-3-yl]propyl}benzoate was added 2,6-diethylbenzenesulfonyl chloride (Example 268, Step 1) according to the procedure in Example 1, Step 7 to generate the product in 71% yield. $^1$H NMR (400 MHz, DMSO-D6) □ ppm 1.11 (t, J=7.33 Hz, 6H), 1.81 (m, 2H), 2.65 (m, 4H), 2.84 (m, 2H), 2.90 (m, 6H), 3.84 (s, 3H), 6.44 (d, J=8.84 Hz, 1H), 6.77 (dd, J=8.84, 2.02 Hz, 1H), 6.94 (s, 1H), 7.02 (m, 4H), 7.19 (d, J=7.58 Hz, 2H), 7.33 (m, 7H), 7.40 (t, J=7.71 Hz, 1H), 7.43 (d, J=2.02 Hz, 1H), 7.70 (t, J=5.68 Hz, 1H), 7.86 (d, J=8.34 Hz, 2H).

Step 2: The ester intermediate was hydrolyzed according to Step 8, Example 1 to afford the title acid in 85% yield. $^1$H NMR (400 MHz, DMSO-D6) □ ppm 1.11 (t, J=7.33 Hz, 6H), 1.81 (m, 2H), 2.65 (m, 4H), 2.84 (m, 2H), 2.91 (m, 6H), 6.45 (d, J=8.84 Hz, 1H), 6.77 (dd, J=8.84, 2.02 Hz, 1H), 6.95 (s, 1H), 7.02 (m, 4H), 7.19 (d, J=7.58 Hz, 2H), 7.28 (d, J=8.34 Hz, 2H), 7.33 (m, 5H), 7.40 (m, 1H), 7.43 (d, J=2.27 Hz, 1H), 7.70 (t, J=5.68 Hz, 1H), 7.84 (d, J=8.34 Hz, 2H). HRMS calc for [C$_{43}$H$_{43}$ClN$_2$O$_4$S+H] 719.27049. found 719.27028.

EXAMPLE 274

4-(2-[1-benzhydryl-5-chloro-2-(2-{[(2,6-dimethoxyphenyl)sulfonyl]amino}ethyl)-1H-indol-3-yl]ethoxy}benzoic acid Step 1: 1,3-dimethoxybenzene (1.0 eq) was taken up in diethy ether (0.2M) and n-butyllithium (1.0 eq.) was added dropwise. The reaction was heated to reflux for three hours. It was cooled to room temperature then it was placed in a dry ice acetone bath and cooled to −50° C. Bromide (0.98 eq.) was added and the reaction was allowed to warm slowly to room temperature. The reaction was quenched with saturated sodium thiosulfate and the aqueous layer was extracted with ether. The organic extracts were washed with brine, dried over sodium sulfate and concetrated to give a brown solid. The solid was recrystalized from hexanes to give the product as a white solid in 27% yield. $^1$H NMR (400 MHz, DMSO-D6) □ ppm 3.83 (s, 6H), 6.73 (d, J=8.34 Hz, 2H), 7.30 (t, J=8.34 Hz, 1H).

Step 2: 2,6-Dimethoxybenzenesulfonyl chloride was prepared from 2-bromo-1,3-dimethoxybenzne according to the procedure in Example 1, Step 1. The reaction gave a mixture of sulfonyl chloride and another product as a white solid.

Step 3. To methyl 4-[(2-[2-(2-aminoethyl)-1-benzhydryl-5-chloro-1H-indol-3-yl]ethoxy}benzoate was added 2,6-dimethoxybenzenesulfonyl chloride according to the procedure in Example 1, Step 7 to afford product in 72% yield. 1H NMR (400 MHz, CDCl$_3$) □ ppm 3.08 (m, 2H), 3.14 (m, 2H), 3.20 (t, J=6.69 Hz, 2H), 3.64 (s, 6H), 3.88 (s, 3H), 4.18 (t, J=6.69 Hz, 2H), 5.41 (t, J=5.68 Hz, 1H), 6.42 (d, J=8.84 Hz, 1H), 6.52 (d, J=8.59 Hz, 2H), 6.79 (m, 3H), 6.91 (s, 1H), 7.02 (m, 4H), 7.25 (m, 6H), 7.36 (t, J=8.46 Hz, 1H, 7.54 (d, J=2.02 Hz, 1H), 7.93 (d, J=8.84 Hz, 2H). m/z (M−) 737.

Step 4. The ester intermediate was hydrolyzed according to Step 8, Example 1 to afford the title acid in 100% yield. 1H NMR (400 MHz, CDCl$_3$) □ ppm 3.08 (m, 2H), 3.15 (m, 2H), 3.21 (t, J=6.69 Hz, 2H), 3.64 (s, 6H), 4.20 (t, J=6.57 Hz, 2H), 5.44 (m, 1H), 6.42 (d, J=8.84 Hz, 1H), 6.53 (d, J=8.59 Hz, 2H), 6.79 (dd, J=8.84, 2.02 Hz, 1H), 6.83 (d, J=8.84 Hz, 2H), 6.91 (s, 1H), 7.02 (m, 4H), 7.25 (m, 6H), 7.36 (t, J=8.46 Hz, 1H), 7.54 (d, J=2.02 Hz, 1H), 7.98 (d, J=8.84 Hz, 2H). HRMS calc for [C$_{40}$H$_{37}$ClN$_2$O$_7$S+H] 725.20729. found 719.27028.

EXAMPLE 275

4-{3-[1-benzhydryl-5-chloro-2-(2-{[(2,6-dimethoxyphenyl)sulfonyl]amino}ethyl)-1H-indol-3-yl]propyl}benzoic acid Step 1: To methyl 4-{2-[2-(2-aminoethyl)-1-benzhydryl-5-chloro-1H-indol-3-yl]propyl}benzoate was added 2,6-dimethoxybenzenesulfonyl chloride (Example 270, Step 1) according to the procedure in Example 1, Step 7 to generate the product in 80% yield. $^1$H NMR (400 MHz, CDCl$_3$) □ ppm 1.94 (m, 2H), 2.72 (m, 4H), 3.01 (m, 4H), 3.59 (s, 6H), 3.91 (s, 3H), 5.37 (m, 1H), 6.37 (d, J=8.84 Hz, 1H), 6.53 (d, J=8.59 Hz, 2H), 6.76 (dd, J=8.97, 2.15 Hz, 1H), 6.84 (s, 1H), 6.98 (m, 4H), 7.21 (d, J=8.34 Hz, 2H), 7.26 (m, 6H), 7.38 (m, 2H), 7.94 (d, J=8.34 Hz, 2H). m/z (M+) 737.

Step 2: The ester intermediate was hydrolyzed according to Step 8, Example 1 to afford the title acid in 91% yield. $^1$H NMR (400 MHz, CDCl$_3$) □ ppm 1.95 (m, 2H), 2.74 (m, 4H), 3.02 (m, 4H), 3.60 (s, 6H), 5.41 (s, 1H), 6.37 (d, J=8.84 Hz, 1H), 6.53 (d, J=8.59 Hz, 2H), 6.76 (dd, J=8.84, 2.27 Hz, 1H), 6.84 (s, 1H), 6.99 (m, 4H), 7.25 (m, 8H), 7.37 (t, J=8.46

Hz, 1H), 7.40 (d, J=2.02 Hz, 1H), 7.99 (d, J=8.34 Hz, 2H). HRMS calc for [C₄₁H₃₉ClN₂O₆S+H] 723.22902. found 723.22893.

EXAMPLE 276

4-{2-[1-Benzhydryl-5-nitro-2-(3-phenylmethane-sulfonyl-propyl)-1H-indol-3-yl]-ethoxy}-benzoic acid Step 1: 4-Nitroaniline (1.0 eq.) was taken up in water (0.8 M) and concetrated HCl (10.8 M). Iodine monochloride (1 eq.) was added to a 4 to 1 solution of water and concetrated HCl (1.3 M) and cooled to 0° C. The ICl solution was added to the aniline solution and the reaction sat at room temperature for 20 hours. The reaction was filtered to give the iodinated product as a yellow solid in 97.3% yield. ¹H NMR (300 MHz, DMSO-D6) δ ppm 6.75 (d, J=9.07 Hz, 1H), 7.98 (dd, J=9.07, 2.47 Hz, 1H), 8.40 (d, J=2.47 Hz, 1H). MS m/z 263 (M–H).

Step 2. To the 2-iodo-4-nitroaniline (1 eq.) and benzhydrylbromide (1.3 eq were taken up in dichloroethane (0.8 M). Diisopropylethylamine (1.1 eq.) was added and the reaction heated to 50° C. for 20 hours. The reaction mixture was cooled and washed with 1 N HCl, dried over Na₂SO₄ and concentrated. Purification using flash chromatography (10% ethyl acetate in hexanes) gave the alkylated product in 81% yield. ¹H NMR (400 MHz, CDCl₃) δ ppm 5.56 (d, J=4.80 Hz, 1H), 5.67 (d, J=5.05 Hz, 1H), 6.36 (d, J=9.10 Hz, 1H), 7.32 (m, 6H), 7.38 (m, 4H), 7.99 (dd, J=9.09, 2.53 Hz, 1H) 8.61 (d, J=2.53 Hz, 1H).

Step 3. Benzhydryl-(4-nitro-2-iodo-phenyl)-amine (1 eq.), 4-(6-hydroxy-hex-3-ynyloxy)-benzoic acid methyl ester (1.5 eq.), LiCl (1 eq.) KOAc (5 eq.) and palladium (II) acetate (0.04 eq.) were added to a roundbottom containing 10 mL of DMF that had been degassed with argon. The reaction heated to 100° C. 7.5 hours. It was then cooled, diluted with ethyl acetate, washed with water and brine, dried over Na₂SO₄ and concentrated to give a brown solid. Purification by flash chromatography gave two products, 4-{2-[1-benzhydryl-5-nitro-2-(2-hydroxy-ethyl)-1H-indol-3-yl]-ethoxy}-benzoic acid methyl ester and the desired, 4-{2-[1-benzhydryl-5-nitro-3-(2-hydroxy-ethyl)-1H-indol-2-yl]-ethoxy}-benzoic acid methyl ester in an overall yield of 71%. The products were not seperable by flash chromatography and were both carried on to the next step. ¹H NMR (400 MHz, CDCl₃) ppm 1.66 (t, J=5.56 Hz, 1H), 1.80 (t, J=5.18 Hz, 1H), 3.14 (m, 4H), 3.35 (m, 4H), 3.81 (m, 2H), 3.87 (m, J=1.52 Hz, 6H), 3.97 (q, J=6.32 Hz, 2H), 4.10 (t, J=6.82 Hz, 2H), 4.31 (t, J=6.19 Hz, 2H), 6.58 (d, J=4.04 Hz, 1H), 6.60 (d, J=4.04 Hz, 1H), 6.67 (d, J=9.10 Hz, 2H), 6.89 (d, J=8.84 Hz, 2H), 7.10 (m, 9H), 7.20 (s, 1H), 7.32 (m, 12H), 7.75 (m, 2H), 7.90 (d, J=8.84 Hz, 2H), 7.95 (d, J=9.09 Hz, 2H), 8.52 (d, J=2.27 Hz, 1H), 8.59 (d, J=2.27 Hz, 1H).

Step 4. The regiosiomers (1.0 eq.) from the previous step were taken up in THF. Triethylamine (1.2 eq.) and methanesulfonyl chloride (1.2 eq.) were added. The reaction stirred until the starting material was consumed as monitored but TLC. The reaction was diluted with dichloromethane and washed with water and brine. It was dried over Na₂SO₄ and concentrated. The reaction gave an inseperable mixture of isomers in 100% yield. ¹H NMR (400 MHz, CDCl₃) ppm 2.81 (s, 3H), 2.90 (s, 3H), 3.35 (m, 8H), 3.87 (m, J=1.52 Hz, 6H), 4.07 (t, J=6.19 Hz, 2H), 4.14 (t, J=7.20 Hz, 2H), 4.30 (t, J=6.06 Hz, 2H), 4.49 (t, J=6.69 Hz, 2H), 6.62 (d, J=6.57 Hz, 1H), 6.65 (d, J=6.57 Hz, 1H), 6.69 (d, J=8.84 Hz, 2H), 6.88 (d, J=9.09 Hz, 2H), 7.02 (s, 1H), 7.10 (dd, J=7.71, 4.67 Hz, 8H), 7.23 (s, 1H), 7.34 (m, 12H), 7.79 (m, 2H), 7.91 (d, J=8.84 Hz, 2H), 7.96 (d, J=8.84 Hz, 2H), 8.49 (d, J=2.27 Hz, 1H), 8.62 (d, J=2.02 Hz, 1H).

Step 5. The mixture of crude mesylates (1 eq.) from above and sodium azide (2.2 eq.) were taken up in DMSO (0.05 M). The reaction stirred at room temperature until the starting material was consumed as monitered by TLC. The reaction was diluted with ethyl acetate, washed with water and brine, dried over Na₂SO₄ and concentrated to give the desired azides in quantitative yield. ¹H NMR (400 MHz, CDCl₃) ppm 3.12 (m, 4H), 3.33 (m, 6H), 3.64 (t, J=6.82 Hz, 2H), 3.88 (m, J=1.52 Hz, 6H), 4.05 (t, J=6.32 Hz, 2H), 4.29 (t, J=6.19 Hz, 2H), 6.65 (m, 4H), 6.87 (d, J=8.84 Hz, 2H), 7.02 (s, 1H), 7.10 (m, 8H), 7.21 (s, 1H), 7.34 (m, 12H), 7.78 (m, 2H), 7.91 (d, J=8.84 Hz, 2H), 7.96 (d, J=8.84 Hz, 2H), 8.49 (d, J=2.27 Hz, 1H), 8.61 (d, J=2.27 Hz, 1H).

Step 6. The mixture of inseperable azides (1.0 eq.) from Step 5 and triphenylphosphine (1.1 eq.) were taken up in THF and stirred at room temperature until the starting material was consumed giving a product with a higher Rf by TLC. 1 ml of water was added to the reaction and it continued to stir at room temperature until TLC showed the disapperance of the higher Rf intermediate. The THF was removed in vacuo and the resulting solid was taken up in ethyl acetate, washed with water and brine, dried over Na₂SO₄ and concentrated. Purification by flash chromatography gave 43% overall yield of reduced products. The regioisomers where separated using flash chromatography (gradient elution 0.25% methanol in dichloromethane to 10% methanol in dichloromethane.) The regioisomers were identified by NMR and the desired compound, 4-{2-[2-(2-Amino-ethyl)-1-benzhydryl-5-nitro-1H-indol-3-yl]-ethoxy}-benzoic acid methyl ester, was taken on to the next step. 1H NMR (400 MHz, CDCl₃) δ ppm 3.30 (m, 6H), 3.88 (s, 3H), 4.27 (t, J=6.57 Hz, 2H), 6.56 (d, J=9.35 Hz, 1H), 6.88 (d, J=9.10 Hz, 2H), 7.10 (dd, J=6.44, 2.65 Hz, 4H), 7.32 (m, 7H), 7.72 (dd, J=9.09, 2.27 Hz, 1H), 7.95 (d, J=8.84 Hz, 2H), 8.60 (d, J=2.27 Hz, 1H). MS m/z 550 (M+).

Step 7. To 4-{2-[2-(2-Amino-ethyl)-1-benzhydryl-5-nitro-1H-indol-3-yl]-ethoxy}-benzoic acid methyl ester was added α-toluenesulfonyl chloride according to the procedure in Example 1, Step 7 to generate the product in 61% yield. ¹H NMR (400 MHz, CDCl₃) δ ppm 2.89 (m, 2H) 3.09 (m, 2H), 3.25 (t, J=6.06 Hz, 2H), 3.88 (s, 3H), 4.09 (s, 2H), 4.15 (m, 1H), 4.25 (t, J=6.06 Hz, 2H), 6.61 (d, J=9.35 Hz, 1H), 6.84 (d, J=8.84 Hz, 2H), 6.97 (s, 1H), 7.07 (m, 4H), 7.20 (m, J=8.08, 1.52 Hz, 2H), 7.32 (m, 9H), 7.77 (dd, J=9.10, 2.27 Hz, 1H), 7.95 (d, J=9.10 Hz, 2H), 8.59 (d, J=2.27 Hz, 1H). MS m/z 703 (M–H).

Step 8: The ester intermediate was hydrolyzed according to Step 8, Example 1 to afford the title acid in 75% yield. ¹H NMR (400 MHz, CDCl₃) δ ppm 2.90 (m, 2H), 3.10 (m, 2H), 3.26 (t, J=6.06 Hz, 2H), 4.10 (s, 2H), 4.26 (t, J=6.06 Hz, 2H), 4.37 (t, J=6.19 Hz, 1H), 6.61 (d, J=9.35 Hz, 1H), 6.85 (d, J=9.09 Hz, 2H), 6.97 (s, 1H), 7.07 (m, 4H), 7.20 (m, 2H), 7.32 (m, 9H), 7.76 (dd, J=9.10, 2.27 Hz, 1H), 7.97 (d, J=8.84 Hz, 2H), 8.58 (d, J=2.27 Hz, 1H). HRMS: calcd. for C₃₉H₃₅N₃O₇S, 689.2196; found (ESI+) 690.22581.

EXAMPLE 277

4-{2-[1-Benzhydryl-5-chloro-2-{2-[({242-chloro-1-methylethyl)benzene}-sulfonyl)amino]ethyl}-1H-indol-3-yl)propyl]benzoic acid Step 1: To the methyl 4-{2-[2-(2-aminoethyl)-1-benzhydryl-5-chloro-1H-indol-3-yl]propyl}benzoate (Step 6, Example 42) was added and 2-(2-chloro1-methylethyl)benzenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for $[C_{42}H_{40}Cl_2N_2O_4S+H]$ 739.21586. found 739.21611.

EXAMPLE 278

4-[2-(1-Benzhydryl-2-{2-[(2-(2-chloro-1-methylethyl)benzene)amino]ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2-(2-chloro-1-methylethyl)benzenesulfonyl chloride according to the procedure in Example 1 Step 7 in 61% yield.

Step 2: The ester intermediate was hydrolyzed according to Step 8 Example 1 to afford the title acid in 90% yield. m/z (M−1)=739.3

EXAMPLE 279

4-{2-[1-benzhydryl-5-chloro-2-(2-{[(2,6-dimethylbenzyl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 2,6-dimethylbenzylsulfonyl chloride according to the procedure in Example 1 Step 7 in 45% yield.

Step 2: The ester intermediate was hydrolyzed according to Step 8 Example 1 to afford the title acid in 88% yield. m/z (M−1)=738.2

EXAMPLE 280

4-[3-(1-benzhydryl-5-chloro-2-{2-[(cyclopropylsulfonyl)amino]-ethyl}-1H-indol-3-yl)propyl]benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and cyclopropanesulfonyl chloride according to the procedure in Example 1 Step 7 in 83% yield.

Step 2: The ester intermediate was hydrolyzed according to Step 8 Example 1 to afford the title acid in 80% yield. HRMS calc for $C_{36}H_{35}ClN_2O_4S$, 626.2006; found (ESI+), 627.20734.

EXAMPLE 281

4-{3-[1-benzhydryl-5-chloro-2-(2-{[(2-phenylethyl)sulfonyl]amino}ethyl)-1H-indol-3-yl]propyl}benzoic acid Step 1: To methyl 4-{2-[2-(2-aminoethyl)-1-benzhydryl-5-chloro-1H-indol-3-yl]propyl}benzoate (Step 6, Example 42) was added and □-phenylethanesulfonyl chloride (prepared following a procedure in *J. Org. Chem.* 1984, 49, 5124–5131) according to the procedure in Example 1 Step 7 to generate the product in 77% yield.

Step 2: The ester intermediate was hydrolyzed according to Step 8 Example 1 to afford the title acid in 82% yield. HRMS calc for $C_{41}H_{39}ClN_2O_4S$, 690.2313; found (ESI+), 691.2383.

EXAMPLE 282

4-{2-[1-benzhydryl-5-chloro-2-(2-{[(2-phenylethyl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and □-phenylethanesulfonyl chloride according to the procedure in Example 1 Step 7 in 81% yield.

Step 2: The ester intermediate was hydrolyzed according to Step 8 Example 1 to afford the title acid in 85% yield. HRMS calcd for $C_{40}H_{37}ClN_2O_5S$, 692.2115; found (ESI+), 693.2185.

EXAMPLE 283

2-{2-[1-Benzhydryl-5-chloro-2-(2-phenylmethanesulfonylamino-ethyl)-1H-indol-3-yl]-ethoxy}-benzoic acid Step 1: Crude 2-{11-Benzhydryl-2-[2-(tert-butyl-diphenyl-silanyloxy)-ethyl]-5-chloro-1H-indol-3-yl}-ethanol from step 6, example 142 was treated with 3-Hydroxy-benzoic acid methyl ester according to the procedure in Example 142 step 8 to yield the desired 3-(2-{1-Benzhydryl-2-[2-(tert-butyl-diphenyl-silanyloxy)-ethyl]-5-chloro-1H-indol-3-yl}-ethoxy)-benzoic acid methyl ester in 85% yield.

Step 2: The deprotected compound was prepared according to the procedure described for Example 142 step 9. The crude 3-{2-[1-Benzhydryl-5-chloro-2-(2-hydroxy-ethyl)-1H-indol-3-yl]-ethoxy}-benzoic acid methyl ester was used in the next step directly without further purification.

Step 3–5: 3-{2-[2-(2-Amino-ethyl)-1-benzhydryl-5-chloro-1H-indol-3-yl]-ethoxy}-benzoic acid methyl ester was prepared according to the procedure described for example 146 steps 3–7 in 57% (3 steps).

Step 6: To 3-{2-[2-(2-amino-ethyl)-1-benzhydryl-5-chloro-1H-indol-3-yl]-ethoxy}-benzoic acid methyl ester was added □-toluenesulfonyl chloride according to the procedure in Example 1 Step 7 to generate the product in 73% yield.

Step 7: The ester intermediate was hydrolyzed according to Step 8 Example 1 to afford the title acid in 88% yield. HRMS calc for $[C_{39}H_{35}ClN_2O_5S+H]$ 679.2028. found 679.2029.

EXAMPLE 284

2-(2-{1-Benzhydryl-5-chloro-2-[2-(3,4-dichlorophenylmethanesulfonylamino)-ethyl]-1H-indol-3-yl}-ethoxy)-benzoic acid Step 1: To 3-{2-[2-(2-amino-ethyl)-1-benzhydryl-5-chloro-1H-indol-3-yl]-ethoxy}-benzoic acid methyl ester (Step 5, Example 279) was added 3,4-dichlorophenyl-methanesulfonyl chloride according to the procedure in Example 1 Step 7 to generate the product in 84% yield.

Step 2: The ester intermediate was hydrolyzed according to Step 8 Example 1 to afford the title acid in 91% yield. HRMS calc for $[C_{39}H_{33}Cl_3N_2O_5S+H]$ 747.12486. found 747.12423.

EXAMPLE 285

3-{2-[1-Benzhydryl-5-chloro-2-(2-phenylmethane-sulfonylamino-ethyl)-1H-indol-3-yl]-ethoxy}-benzoic acid Step 1: Crude 2-{1-Benzhydryl-2-[2-(tert-butyl-diphenyl-silanyloxy)-ethyl]-5-chloro-1H-indol-3-yl}-ethanol from step 6, example 142 was treated with 2-Hydroxy-benzoic acid methyl ester according to the procedure in Example 142 step 8 to yield the desired 2-(2-{1-Benzhydryl-2-[2-(tert-butyl-diphenyl-silanyloxy)-ethyl]-5-chloro-1H-indol-3-yl}-ethoxy)-benzoic acid methyl ester in 60% yield.

Step 2: The deprotected compound was prepared according to the procedure described for Example 142 step 9. The crude 2-{2-[1-Benzhydryl-5-chloro-2-(2-hydroxy-ethyl)-1H-indol-3-yl]-ethoxy}-benzoic acid methyl ester was used in the next step directly without further purification.

Step 3–5: 2-{2-[2-(2-Amino-ethyl)-1-benzhydryl-5-chloro-1H-indol-3-yl]-ethoxy}-benzoic acid methyl ester was prepared according to the procedure described for example 146 steps 3–7 in 60% (3 steps).

Step 6: To 2-{2-[2-(2-amino-ethyl)-1-benzhydryl-5-chloro-1H-indol-3-yl]-ethoxy}-benzoic acid methyl ester was added □-toluenesulfonyl chloride according to the procedure in Example 1 Step 7 to generate the product in 90% yield.

Step 2: The ester intermediate was hydrolyzed according to Step 8 Example 1 to afford the title acid in 90% yield. HRMS calc for $[C_{39}H_{35}ClN_2O_5S+H]$ 679.2028. found 679.20358.

EXAMPLE 286

3-(2-{1-Benzhydryl-5-chloro-2-[2-(3,4-dichlorophenylmethanesulfonylamino)-ethyl]-1H-indol-3-yl}-ethoxy)-benzoic acid Step 1: To 2-{2-[2-(2-amino-ethyl)-1-benzhydryl-5-chloro-1H-indol-3-yl]-ethoxy}-benzoic acid methyl ester (Step 5, Example 281) was added 3,4-dichlorophenyl-methanesulfonyl chloride according to the procedure in Example 1 Step 7 to generate the product in 84% yield.

Step 2: The ester intermediate was hydrolyzed according to Step 8 Example 1 to afford the title acid in 89% yield. HRMS calc for $[C_{39}H_{33}Cl_3N_2O_5S+H]$ 747.12486. found 747.12457.

EXAMPLE 287

4-[2-(1-benzhydryl-5-chloro-2-{2-[({[(2,4-dichlorophenyl)sulfanyl]methyl}sulfonyl)amino]ethyl}-1H-indol-3-yl)ethoxy]benzoic acid Step 1: To methyl 4-{2-[1-benzhydryl-5-chloro-2-(2-chloromethanesulfonylamino-ethyl)-1H-indol-3-yl]-ethoxy}-benzoate, Example 81 step 1, was added 2,4-dichlorothiophenol according to the procedure in Example 81 step 2. The crude was purified by the preperative HPLC in 50% yield.

Step 2: The ester intermediate was hydrolyzed according to Step 8 Example 1 to afford the title acid in 100% yield. m/z (M−1) 776.92.

EXAMPLE 288

4-[2-(1-benzhydryl-5-chloro-2-{2-[({[(2,4-difluorophenyl)thio]methyl}sulfonyl)amino]ethyl}-1H-indol-3-yl)ethoxy]benzoic acid Step 1: To methyl 4-{2-[1-benzhydryl-5-chloro-2-(2-chloromethanesulfonylamino-ethyl)-1H-indol-3-yl]-ethoxy}-benzoate, Example 81 step 1, was added 2,4-difluorothiophenol according to the procedure in Example 81 step 2. The crude was purified by the preperative HPLC in 27% yield.

Step 2: The ester intermediate was hydrolyzed according to Step 8 Example 1 to afford the title acid in 100% yield. m/z (M−1) 744.97.

EXAMPLE 289

4-[2-(1-benzhydryl-5-chloro-2-{2-[({[(3,4-dichlorophenyl)sulfinyl]methyl}sulfonyl)amino]ethyl}-1H-indol-3-yl)ethoxy]benzoic acid Step 1: The methyl 4-[2-(1-benzhydryl-5-chloro-2-{2-[({[(3,4-dichlorophenyl)thio]methyl}sulfonyl)amino]ethyl}-1H-indol-3-yl)ethoxy]benzoate (Step 1 Example 219) in THF was oxidized with mCPBA (1.1 equiv.) The crude was purified by the flash column with 30% EtOAc/hexane in 42% yield.

Step 2: The ester intermediate was hydrolyzed according to Step 8 Example 1 to afford the title acid in 93% yield. m/z (M−1) 795.14.

EXAMPLE 290

4-{2-[1-benzhydryl-5-chloro-2-(2-{[(2-hydroxyphenyl)sulfonyl]amino}ethyl)-1H-indol-3-yl]ethoxy}benzoic acid Step 1: 4-[2-(1-Benzhydryl-5-chloro-2-{2-[2-(2-methyl-penta-2,4-dienyloxy)-benzenesulfonylamino]-ethyl}-1H-indol-3-yl)-ethoxy]-benzoic acid (0.55 g, 0.70 mmole), (Step 1, Example 183) and 10% Pd/C (55 mg) in MeOH (30 ml) and EtOH (20 ml) was hydrogenated. The resulting mixture was filtered through Celite and concentrated. The residue was chromatographed with 35–40% EtOAC/hexane to give the desired product (0.50 g, 95%).

Step 2: The ester intermediate was hydrolyzed according to Step 8 Example 1 to afford the title acid in 90% yield. HRMS: calcd for $C_{38}H_{33}ClN_2O_6S$, 680.1748; found (ESI+), 681.18118

EXAMPLE 291

N-{2-[1-benzhydryl-5-chloro-3-(2-{4-[(Z)-(2,4-dioxo-1,3-thiazolidin-5-ylidene)methyl]phenoxy}ethyl)-1H-indol-2-yl]ethyl}-1-(3,4-dichlorophenyl)methanesulfonamide Step 1: The 2-{1-Benzhydryl-2-[2-(tert-butyl-diphenyl-silanyloxy)-ethyl]-5-chloro-1H-indol-3-yl}-ethanol (Step 6, Example 142) was coupled with 4-Hydroxy-benzaldehyde according to the conditions described in Example 189, Step 1 to yield 4-(2-{1-Benzhydryl-2-[2-(tert-butyl-diphenyl-silanyloxy)-ethyl]-5-chloro-1H-indol-3-yl}-ethoxy)-benzaldehyde in 70% yield.

Step 2: The silyl ether from above was deprotected following the Example 142, step 9 to yield 4-{2-[1-Benzhydryl-5-chloro-2-(2-hydroxy-ethyl)-1#H!-indol-3-yl]-ethoxy}-benzaldehyde in 90% yield.

Step 3: The alcohol from above was activated by conversion to the mesylate as described in Step 10 Example 142 to yield the desired mesylate which was used without purification in the next step.

Step 4: The mesylate from above was treated under the conditions described in Step 11 Example 142 to generate 4-{2-[2-(2-Azido-ethyl)-1-benzhydryl-5-chloro-1H-indol-3-yl]-ethoxy}-benzaldehyde in 98% yield (2 steps).

Step 5: The mixture of 4-{2-[2-(2-Azido-ethyl)-1-benzhydryl-5-chloro-1H-indol-3-yl]-ethoxy}-benzaldehyde (1.29 g, 2.41 mmole, 1.0 equiv.), 2,4-thiazolidine dione (0.41 g, 3.13 mmole, 1.3 equiv.) and piperidine (0.12 ml, 1.21 mmole, 0.5 equiv.) in EtOH (125 ml) was refluxed overnight. EtOH was removed on vacuo. The residue was diluted in EtOAc and washed with water, then brine. The organic layer was dried over $MgSO_4$ and concentrated, and the residue was chromatographed with 30–35% EtOAc/hexane to obtain 5-(4-{2-[2-(2-Azido-ethyl)-1-benzhydryl-5-chloro-1H-indol-3-yl]-ethoxy}-benzylidene)-thiazolidine-2,4-dione (1.33 g, 87%).

Step 6: To a solution of the product from step 5 in THF (80 ml) was added $Ph_3P$ in small portions. The mixture was stirred for 1 day. 3 ml of water was added, and stirred for an additional 2 days. The produced solid, which was identified as triphenyl phosphine imine of the above azide, (60%) by LC/MS, was filtered.

Step 7: The imine (250 mg, 0.29 mmole, 1.0 equiv.) from step 6, and (3,4-dichlorophenyl)methylsulfonyl chloride in $CH_2Cl_2$ (10 ml) and saturated $NaHCO_3$ (5 ml) was stirred overnight according to the procedure in Example 1 Step 7 to generate the product in 7% yield. m/z (M−1) 830.45

EXAMPLE 292

N-[2-(1-Benzhydryl-5-chloro-3-(2-[4-(2,4-dioxo-thiazolidin-5-ylidenemethyl)-phenoxy]-ethyl)-1H-indol-2-yl)-ethyl]-2-methyl-benzenesulfonamide Step 1: The mixture of triphenylphosphine imine (300 mg, 0.35 mmole, 1.0 equiv.) from Step 6, Example 287 and 2-methyl-benzenesulfonyl chloride in $CH_2Cl_2$ (15 ml) and saturated $NaHCO_3$ (5 ml) was stirred overnight according to the procedure in Example 1 Step 7 to generate the product in 3% yield. HRMS calc for $[C_{42}H_{36}ClN_3O_5S-H]$ 760.1723. found 760.1728.

EXAMPLE 293

4-{3-[1-Benzhydryl-5-chloro-2-(2-{[(1-methyl-1H-imidazol-2-yl)sulfonyl]amino}ethyl)-1H-indol-3-yl]propyl}benzoic acid Step 1: To the methyl 4-{3-[2-(2-aminoethyl)-1-benzhydryl-5-chloro-1H-indol-3-yl]propyl}benzoate (Step 6, Example 42) was added 1-Methyl-1H-imidazole-2-sulfonyl chloride according to the procedure in Example 1 Step 7 to generate the product in 70% yield.

Step 2: The ester intermediate was hydrolyzed according to Step 8 Example 1 to afford the title acid in 92% yield. HRMS calc for $[C_{37}H_{35}ClN_4O_4S+H]$ 667.2141. found 667.2137.

EXAMPLE 294

4-{2-[1-benzhydryl-5-chloro-2-(2-{[(1-methyl-1H-imidazol-2-yl)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 6, Example 1) and 1-Methyl-1H-imidazole-2-sulfonyl chloride according to the procedure in Example 1 Step 7 in 76% yield.

Step 2: The ester intermediate was hydrolyzed according to Step 8 Example 1 to afford the title acid in 87% yield. HRMS calc for $[C_{36}H_{33}ClN_4O_5.S+H]$ 669.1933. found 669.1933.

EXAMPLE 295

4-{3-[1-benzhydryl-2-(2-{[(2-chlorophenyl)sulfonyl]amino}ethyl)-1H-indol-3-yl]propyl}benzoic acid Step 1: A mixture of methyl-4-iodobenzoate (5.3 g, 20.2 mmol), allyl alcohol (1.78 g, 30.3 mmol), $NaHCO_3$ (4.24 g, 50.5 mmol), $Pd(OAc)_2$ (0.14 g, 0.60 mmol), $(n-Bu)_4NBr$ (6.55 g, 20.2 mmol) and 4-A molecular Sieves (4.1 g) in anhydrous DMF (69 mL) was stirred at room temperature for 4 days. The reaction mixture was filtered through celite and the filtrate poured onto water and extracted with EtOAc. Organic layer was washed with brine, dried ($Na_2SO_4$), and concentrated under vacuum. Flash chromatography (silica gel, 10–20% EtOAc-hexanes) gave 2.11 g (85% based on the recovered starting material) of the desired 4-(3-Oxo-propyl)-benzoic acid methyl ester as a clear oil.

Step 2: To a solution of 2-Methyl-1H-indole (0.86 g, 5.2 mmol) and 4-(3-Oxo-propyl)-benzoic acid methyl ester (1.0 g, 5.2 mmol) in methylene chloride (50 mL), was added TFA (1.78 g, 15.6 mmol), followed by triethylsilane (1.81 g, 15.6 mmol). The reaction mixture was stirred overnight, quenched with sat. $NaHCO_3$ solution (50 mL), and the organic layer was washed with sat. $NaHCO_3$ solution, water, brine, and dried ($Na_2SO_4$). Solvent was removed under reduced pressure, and the residue was purified by flash column chromatography with 10–20% EtOAc/hexanes to yield the desired 4-[3-(2-Methyl-1H-indol-3-yl)-propyl]-benzoic acid methyl ester in 88% (1.67 g) yield.

Step 3: To a solution of the product from step 2 (1.66 g, 4.86 mmol) in DMF (20 mL) was added NaH (60% in mineral oil, 0.24 g, 5.83 mmol) under $N_2$ atmosphere. The mixture was stirred for 1 h at room temperature, followed by the dropwise addition of benzhydryl bromide (1.8 g, 7.29 mmol) in DMF (5 mL). This reaction mixture was stirred overnight at room temperature. Water (500 mL) was added to reaction mixture, it was extracted with EtOAc, washed with brine, dried ($Na_2SO_4$), and concentrated under reduced pressure to a brown syrup, which was purified by silica-gel chromatography using 10% EtOAc/hexanes as eluent to isolate 4-[3-(1-Benzhydryl-2-methyl-1H-indol-3-yl)-propyl]-benzoic acid methyl ester as a white solid in 76% (1.47 g) yield.

Step 4: The product from above (1.46 g, 2.87 mmol) was dissolved in $CCl_4$ (14.5 mL), followed by the addition of NBS (1.02 g, 5.73 mmol) and benzoyl peroxide (2 mg). The reaction mixture was heated to reflux for 1 h (until all the starting material disappeared). This mixture was cooled to room temperature, filtered and the solid was washed with $CCl_4$. The filtrate was evaporated to a brown residue, which was dissolved in acetone (40 mL) and water (4 mL), Ag$_2$CO$_3$ (1.75 g, 3.16 mmol) was then added to this solution and after being stirred overnight at room temperature, it was filtered through celite, the solvent was evaporated under reduced pressure, and water was added to the residue. It was extracted with EtOAc, washed with brine, dried (Na$_2$SO$_4$), and evaporated to a syrup, which was purified by 10% EtOAc/hexanes to isolate the 4-[3-(1-Benzhydryl-2-formyl-1H-indol-3-yl)-propyl]-benzoic acid methyl ester (1.13 g) in 85% yield. Alternatively the dibromide from the reaction with NBS could be poured into DMSO (10–20% concentration by weight) and stirred for 30 minutes at room temperature. When the reaction was deemed complete it was poured into water and the resulting precipitate was isolated by filtration, the cake was washed with water and dried to yield an essentially quantitative yield.

Step 5: To a solution of the indole from above (0.52 g, 1 mmol) in CH$_3$NO$_2$ (6.2 mL) was added NH$_4$OAC (0.077 g, 1 mmol), the mixture was heated to reflux for 1 h, NH$_4$OAc (0.077 g, 1 mmol) was then added, heating at reflux was continued for an additional 1 h, NH$_4$Oac (0.077 g, 1 mmol) was added again and the heating continued for further 1 h. The reaction mixture was allowed to attain room temperature, EtOAc (50 mL) was added, followed by the addition of 100 mL water. The aqueous layer was extracted with EtOAc, and the combined organic layers were washed with brine, dried (Na$_2$SO$_4$), and evaporated to a yellow foam, which was subjected to chromatographic purification using 10% EtOAc/hexanes as an eluent to yield 4-{3-[1-Benzhydryl-2-(2-nitro-vinyl)-1H-indol-3-yl]-propyl}-benzoic acid methyl ester as a yellow foam in 75% yield (0.38 g).

Step 6: Zn(Hg) was made by adding HgCl$_2$ (3.4 g, 7.2 mmol) to a mixture of Zn-dust (34.68 g, 530.35 mmol) and 5% HCl (38 mL) in a 100 mL beaker, this mixture was stirred vigorously for 10 min. Aqueous phase was decanted and added 38 mL of 5% HCl again and the mixture was stirred for 10 min. Aqueous phase was decanted. This solid was added to the vinyl nitro compound 6 (15 g, 26.57 mmol) in THF (660 mL) and conc. HCl (64.5 mL). This mixture was stirred at room temperature for 1 h, then at reflux for 15 min. The reaction mixture was cooled to room temperature and filtered through celite. Aq. NH$_4$OH solution (200 mL) was added to the filtrate, stirred for 15 min and THF was removed under reduced pressure. The aqueous layer was extracted with CH$_2$Cl$_2$, combined organic layer was washed with brine, dried (Na2SO4) and concentrated to a brown foam, which was purified by column chromatography by eluting the column with CHCl$_3$ in the beginning to remove non-polar impurities then with 2% MeOH/CHCl$_3$ to isolate the desired 4-{3-[2-(2-Amino-ethyl)-1-benzhydryl-1H-indol-3-yl]-propyl}-benzoic acid methyl ester in 40% yield (6.1 g)

Step 7: To the amine (1.0 equiv.) and sat. NaHCO$_3$ (0.14 M) in CH$_2$Cl$_2$ (0.07 M) was added 2-Chloro-benzenesulfonyl chloride (1.0 equiv.). After 1 h the mixture was poured into saturated sodium bicarbonate and extracted with CH$_2$Cl$_2$. The combined organic phase was washed with brine, dried over sodium sulfate and purified by column chromatography to afford 92% of the desired 4-(3-{1-Benzhydryl-2-[2-(2-chloro-benzenesulfonylamino)-ethyl]-1H-indol-3-yl}-propyl)-benzoic acid methyl ester.

Step 8: The resulting ester was hydrolyzed by stirring with 1N NaOH (5 equiv.) in THF (0.07 M) and enough MeOH to produce a clear solution. The reaction was monitored by TLC (10% MeOH—CH$_2$Cl$_2$) for the disappearance of starting material. The mixture was stirred overnight at room temperature and then concentrated, diluted with H$_2$O, and acidified to pH 2–4 using 1 M HCl. The aqueous phase was extracted with EtOAc and the organic phase was washed with brine, dried over sodium sulfate, and concentrated to afford the title compound in 56% yield. m/z (M–1) 663.2

EXAMPLE 296

4-{2-[1-benzhydryl-5-chloro-2-(2-{[(3,4-dichlorobenzyl)sulfonyl]amino}ethyl)-1H-indol-3-yl]ethoxy}-2-fluorobenzoic acid Step 1: [(3,4-dichlorophenyl)methyl]sulfonyl chloride (0.07 g, 0.24 mmol) was added to a mixture of ethyl 4-{2-[2-(2-Aminoethyl)-1-benzhydryl-5-chloro-1H-indol-3-yl]-ethoxy}-2-fluoro-benzoate (Step 6, Example 190, 0.17 g, 0.2 mmol) and K$_2$CO$_3$ (0.055 g, 0.4 mmol) in CH$_2$Cl$_2$ (2 mL) and water (0.7 mL) with stirring. After 2 hour at room temperature, the mixture was extracted with CH$_2$Cl$_2$ (10 mL) and the extract was washed with 0.5 N NaOH, and brine and dried over sodium sulfate. The CH$_2$Cl$_2$ solution was filtered through silica gel and the filtrate was evaporated. The resulting residue was triturated with a mixture of ether and hexanes to give 0.15 g of ethyl 4-{2-[1-benzhydryl-5-chloro-2-(2-{[(3,4-dichlorobenzyl)sulfonyl]amino)-ethyl)-1H-indol-3-yl]ethoxy}-2-fluorobenzoate as a white solid; mp 83–85° C.; HRMS: calcd for C$_{41}$H$_{36}$Cl$_3$FN$_2$O$_5$S, 792.1395; found (ESI+), 793.14729.

Step 2: Ethyl 4-{2-[1-benzhydryl-5-chloro-2-(2-{[(3,4-dichlorobenzyl)sulfonyl]amino)-ethyl)-1H-indol-3-yl]ethoxy}-2-fluorobenzoate (0.11 g, 0.14 mmol), THF (0.5 mL), MeOH (0.5 mL), and 1N NaOH (0.5 mL) were stirred together overnight. Solvents were removed and the resulting residue was taken up in water. The solution was acidified with 1N HCl and extracted with ethyl acetate. The extract was dried over sodium sulfate, and evaporated. The resulting residue was triturated with a mixture of ether and hexanes to give 0.10 g of 4-{2-[1-benzhydryl-5-chloro-2-(2-{[(3,4-dichlorobenzyl)sulfonyl]amino}ethyl)-1H-indol-3-yl]ethoxy}-2-fluorobenzoic acid as a white solid; mp 117–119° C.; HRMS: calcd for C$_{39}$H$_{32}$Cl$_3$FN$_2$O$_5$S, 764.1082; found (ESI+), 787.09794

EXAMPLE 297

4-{2-[1-benzhydryl-5-chloro-2-(2-{[(2-chlorobenzyl)sulfonyl]amino}ethyl)-1H-indol-3-yl]ethoxy}-2-fluorobenzoic acid Step 1: [(2-chlorophenyl)methyl]sulfonyl chloride (0.14 g, 0.6 mmol) was added to a mixture of ethyl 4-{2-[2-(2-Aminoethyl)-1-benzhydryl-5-chloro-1H-indol-3-yl]-ethoxy}-2-fluoro-benzoate (Step 6, Example 190, 0.12 g, 0.2 mmol) and K$_2$CO$_3$ (0.11 g, 0.8 mmol) in CH$_2$Cl$_2$ (2 mL) and water (1 mL) with stirring. After 2 hour at room temperature, the mixture was extracted with CH$_2$Cl$_2$ (10 mL) and the extract was washed with 0.5 N NaOH, and brine and dried over sodium sulfate. The CH$_2$Cl$_2$ solution was filtered through silica gel and the filtrate was evaporated. The resulting residue was triturated with a mixture of ether and hexanes to give 0.07 g of ethyl 4-{2-[1-benzhydryl-5-chloro-2-(2-{[(2-chlorobenzyl)sulfonyl]amino}ethyl)-1H-indol-3-yl]ethoxy}-2-fluorobenzoate as a white solid.

Step 2: Ethyl 4-{2-[1-benzhydryl-5-chloro-2-(2-{[(2-chlorobenzyl)sulfonyl]amino}ethyl)-1H-indol-3-yl]ethoxy}-2-fluorobenzoate (0.06 g, 0.1 mmol), THF (0.5 mL), MeOH (0.5 mL), and 1N NaOH (0.5 mL) were stirred together overnight. Solvents were removed and the resulting residue was taken up in water. The solution was acidified with 1N HCl and extracted with ethyl acetate. The extract was dried over sodium sulfate, and evaporated. The resulting residue was triturated with a mixture of ether and hexanes to give 0.06 g of 4-{2-[1-benzhydryl-5-chloro-2-(2-{[(2-chlorobenzyl)sulfonyl]amino}ethyl)-1H-indol-3-yl]ethoxy}-2-fluorobenzoic acid as an off-white solid; mp 132–135° C.; MS (ESI) m/z 729.74 ((M–H)–); HRMS: calcd for $C_{39}H_{33}Cl_2FN_2O_5S$, 730.1471; found (ESI+), 731.15514.

EXAMPLE 298

3-[4-({2-[1-benzhydryl-5-chloro-2-(2-{[(3,4-dichlorobenzyl)sulfonyl]amino}ethyl)-1H-indol-3-yl]ethyl}sulfonyl)phenyl]-2,2-dimethylpropanoic acid Step 1: [(3,4-chlorophenyl)methyl]sulfonyl chloride (0.06 g, 0.2 mmol) was added to a mixture of ethyl 3-(4-{2-[2-(2-aminoethyl)-1-benzhydryl-5-chloro-1H-indol-3-yl]-ethanesulfonyl}-phenyl)-2,2-dimethyl-propionate (0.09 g, 0.14 mmol) and $K_2CO_3$ (0.04 g, 0.28 mmol) in $CH_2Cl_2$ (2 mL) and water (0.7 mL) with stirring. After 2 hour at room temperature, the mixture was extracted with $CH_2Cl_2$ (10 mL) and the extract was washed with 0.5 N NaOH, and brine and dried over sodium sulfate. The $CH_2Cl_2$ solution was filtered through silica gel and the filtrate was evaporated. The resulting residue was triturated with a mixture of ether and hexanes to give 0.04 g of ethyl 3-[4-({2-[1-benzhydryl-5-chloro-2-(2-{[(3,4-dichlorobenzyl)sulfonyl]amino}ethyl)-1H-indol-3-yl]ethyl}sulfonyl)phenyl]-2,2-dimethylpropanoate as a white solid.

Step 2: Ethyl 3-[4-({2-[1-benzhydryl-5-chloro-2-(2-{[(3,4-dichlorobenzyl)sulfonyl]amino)-ethyl)-1H-indol-3-yl]ethyl}sulfonyl)phenyl]-2,2-dimethylpropanoate (0.04 g, 0.05 mmol), THF (0.5 mL), MeOH (0.5 mL), and 1N NaOH (0.5 mL) were stirred together overnight. Solvents were removed and the resulting residue was taken up in water. The solution was acidified with 1N HCl and extracted with ethyl acetate. The extract was dried over sodium sulfate, and evaporated. The resulting residue was triturated with a mixture of ether and hexanes to give 0.04 g of 3-[4-({2-[1-benzhydryl-5-chloro-2-(2-{[(3,4-dichlorobenzyl)sulfonyl]amino}ethyl)-1H-indol-3-yl]ethyl}sulfonyl)phenyl]-2,2-dimethylpropanoic acid as a white solid; mp 207–208° C.; MS (ESI) m/z 849.1 (M–H); HRMS: calcd for $C_{43}H_{41}Cl_3N_2O_6S_2$, 850.1472; found (ESI+), 851.1545.

EXAMPLE 299

4-{2-[1-benzhydryl-5-chloro-2-(2-{[(3,4-dichlorobenzyl)sulfonyl]amino}ethyl)-1H-indol-3-yl]ethoxy}-2-methoxybenzoic acid Step 1: 2,4-Dihydroxy-benzoic acid methyl ester (11.76 g, 70 mmol) was dissolved in $Et_2O$ (175 mL). Then $Et_3N$ (10.78 mL, 77 mmol), $Ac_2O$ (7.28 mL, 77 mmol), and DMAP (catalytic amount) were added. The reaction solution was then stirred for one hour at room temperature. Then the reaction solution was concentrated by rotary evaporation and the resulting residue was purified with a silica gel column and dichloromethane as eluent. Obtained 3.44 g 4-Acetoxy-2-hydroxy-benzoic acid methyl ester in 23% yield.

Step 2: MeOH (0.3 mL, 7.4 mmol) was added to the product from step 1 (0.962 g, 4.6 mmol), $Ph_3P$ (1.79 g, 6.8 mmol), and dichloromethane (10 mL). Then DEAD (1.32 mL, 8.4 mmol) was added to the reaction. Reaction was stirred at room temperature for 4 days. Reaction solution was concentrated by rotary evaporation and the resulting residue was purified with silica gel prep plates and 1:3 EtOAc/Hexane as eluent. Obtained 1.10 g of 4-Acetoxy-2-methoxy-benzoic acid methyl ester in quantitative yield.

Step 3: 0.1N NaOH (10 mL, 1 mmol) was added to a solution of the product of step 2 (1.10 g, 4.9 mmol) in THF (1 mL) and MeOH (1 mL). Reaction was stirred for three days at room temperature. Reaction solution was concentrated by rotary evaporation and resulting residue was dissolved in water. The solution was neutralized with 1N HCl and a precipitate formed. Collected precipitate and washed with water and hexane. Obtained 0.29 g of 4-Hydroxy-2-methoxy-benzoic acid methyl ester in 33% yield.

Step 4: 2-{1-Benzhydryl-2-[2-(tert-butyl-diphenyl-silanyloxy)-ethyl]-5-chloro-1H-indol-3-yl)-ethanol (Step 6, Example 142, 0.503 g, 0.78 mmol) was added to a mixture of Hydroxy-2-methoxy-benzoic acid methyl ester (0.29 g, 1.6 mmol), $Ph_3P$ (0.312 g, 1.2 mmol), and dichloromethane (10 mL). Then DEAD (0.2 mL, 1.3 mmol) was added to the reaction. Reaction was stirred at room temperature overnight. Reaction solution was concentrated by rotary evaporation and the resulting residue was purified with silica gel prep plates and dichloromethane as eluent. Obtained 0.25 g of 4-(2-{1-Benzhydryl-2-[2-(tert-butyl-diphenyl-silanyloxy)-ethyl]-5-chloro-1H-indol-3-yl}-ethoxy)-2-methoxy-benzoic acid methyl ester in 40% yield.

Step 5: TBAF (1M in THF) (0.37 mL, 0.37 mmol) was added to a solution of 4-(2-{1-Benzhydryl-2-[2-(tert-butyl-diphenyl-silanyloxy)-ethyl]-5-chloro-1H-indol-3-yl}-ethoxy)-2-methoxy-benzoic acid methyl ester (0.25 g, 0.31 mmol) in THF (4 mL). Reaction was stirred at room temperature for 30 minutes. Reaction solution was concentrated by rotary evaporation and the resulting residue was purified with silica gel prep plates and 1:9 EtOAc/dichloromethane as eluent. Obtained 0.11 g of 4-{2-[1-Benzhydryl-5-chloro-2-(2-hydroxy-ethyl)-1H-indol-3-yl]-ethoxy}-2-methoxy-benzoic acid methyl ester (white solid) in 62% yield.

Step 6: $MeSO_2Cl$ (0.03 mL, 0.39 mmol) and $Et_3N$ (0.07 mL, 0.48 mmol) were added to a solution of the alcohol from step 5 (0.11 g, 0.19 mmol) in dichloromethane (8 mL) at 0° C. Reaction was stirred at 0° C. for one hour and then warmed to room temperature and stirred an additional hour. Reaction solution was concentrated by rotary evaporation. Obtained 0.123 g of 4-{2-[1-Benzhydryl-5-chloro-2-(2-methanesulfonyloxy-ethyl)-1H-indol-3-yl]-ethoxy}-2-methoxy-benzoic acid methyl ester in quantitative yield.

Step 7: The mesylate from above (0.123 g, 0.19 mmol) was dissolved in DMF (5 mL). $NaN_3$ (0.065 g, 1.0 mmol) was added and the mixture was heated to 60° C. and stirred for three hours. Reaction was cooled to room temperature and water was added. Extracted with EtOAc and washed organic layer with brine. Dried organics over sodium sulfate and filtered and concentrated by rotary evaporation. Dried further under a strong vacuum. Obtained 0.110 g of 4-{2-[2-(2-Azido-ethyl)-1-benzhydryl-5-chloro-1H-indol-3-yl]-ethoxy}-2-methoxy-benzoic acid methyl ester in 97% yield.

Step 8: $Ph_3P$ (polymer support: 3 mmol $Ph_3P$/gram) (0.110 g, 0.33 mmol) was added to a solution of the azide from step 7 (0.110 g, 0.18 mmol) in THF (2 mL). Reaction was stirred at room temperature for 24 hours. Then water (0.5 mL) was added and reaction was stirred at room temperature overnight. Reaction solution was filtered and the filtrate was concentrated by rotary evaporation. The resulting residue was purified with silica gel prep plates and 2% MeOH in dichloromethane as eluent. Obtained 0.012 g of 4-{2-[2-(2-Amino-ethyl)-1-benzhydryl-5-chloro-1H-indol-3-yl]-ethoxy}-2-methoxy-benzoic acid methyl ester in 12% yield.

Step 9: An aqueous, saturated solution of Na$_2$CO$_3$ (2 mL) was added to a solution of the amine from step 8 (0.012 g, 0.021 mmol) and [(3,4-dichlorophenyl)methyl]sulfonyl chloride (0.010 g, 0.039 mmol) in dichloromethane (2 mL). Reaction was stirred at room temperature for two hours. The reaction solution was then separated and the organic phase was collected and washed with brine and dried over sodium sulfate. Filtered and concentrated the organic solution by rotary evaporation. The resulting residue was purified with silica gel prep plates and 2% MeOH in dichloromethane as eluent. Obtained 0.016 g of the desired sulfonamide (white solid) in 96% yield. m/z (M+1) 793

Step 10: 1N NaOH (1 mL) was added to a solution of the ester from step 9 (0.016 g, 0.020 mmol) in THF (1 mL) and MeOH (1 mL). Reaction was stirred at room temperature for five days. The THF and MeOH were removed by rotary evaporation. Extracted with dichloromethane and separated and collected the aqueous layer. Neutralized the aqueous layer with 1N HCl and collected the resulting precipitate. Obtained 0.013 g of the title acid (yellow solid) in 84% yield. m/z (M−1) 777

EXAMPLE 300

4-{2-[1-benzhydryl-5-chloro-2-(2-{[(3,4-dichlorobenzyl)sulfonyl]amino}ethyl)-1H-indol-3-yl]ethoxy}-2-isopropoxybenzoic acid Step 1: Isopropanol (0.63 mL, 8.2 mmol) was added to a mixture of 4-Acetoxy-2-methoxy-benzoic acid methyl ester (Step 1, Example 299, 1.18 g, 5.6 mmol), Ph$_3$P (1.84 g, 7.0 mmol), and dichloromethane (15 mL). Then DEAD (1.12 mL, 7.1 mmol) was added to the reaction. Reaction was stirred at room temperature for two days. Reaction solution was concentrated by rotary evaporation and the resulting residue was purified with silica gel prep plates and 1:5 EtOAc/Hexane as eluent. Obtained 1.11 g of 4-Acetoxy-2-isopropoxy-benzoic acid methyl ester in 79% yield.

Step 2: 0.1N NaOH (10 mL, 1 mmol) was added to a solution of 4-Acetoxy-2-isopropoxy-benzoic acid methyl ester (0.910 g, 3.6 mmol) in THF (1 mL) and MeOH (1 mL). Reaction was stirred for three days at room temperature. Reaction solution was concentrated by rotary evaporation and resulting residue was dissolved in water. The solution was neutralized with 1N HCl and a precipitate formed. Collected precipitate and washed with water and hexane. Obtained 0.870 g of 4-Hydroxy-2-isopropoxy-benzoic acid methyl ester in quantitative yield.

Step 3: 2-{1-Benzhydryl-2-[2-(tert-butyl-diphenyl-silanyloxy)-ethyl]-5-chloro-1H-indol-3-yl}-ethanol (Step 6, Example 142, 0.500 g, 0.78 mmol) was added to a mixture of 4-Hydroxy-2-isopropoxy-benzoic acid methyl ester (0.328 g, 1.6 mmol), Ph$_3$P (0.312 g, 1.2 mmol), and dichloromethane (10 mL). Then DEAD (0.2 mL, 1.3 mmol) was added to the reaction. Reaction was stirred at room temperature overnight. Reaction solution was concentrated by rotary evaporation and the resulting residue was purified with silica gel prep plates and dichloromethane as eluent. Obtained 0.20 g of 4-(2-{1-Benzhydryl-2-[2-(tert-butyl-diphenyl-silanyloxy)-ethyl]-5-chloro-1H-indol-3-yl}-ethoxy)-2-isopropoxy-benzoic acid methyl ester in 31% yield.

Step 4: TBAF (1M in THF) (0.29 mL, 0.29 mmol) was added to a solution of the silyl ether from step 3 (0.20 g, 0.24 mmol) in THF (4 mL). Reaction was stirred at room temperature for 30 minutes. Reaction solution was concentrated by rotary evaporation and the resulting residue was purified with silica gel prep plates and 1:9 EtOAc/dichloromethane as eluent. Obtained 0.10 g of 4-{2-[1-Benzhydryl-5-chloro-2-(2-hydroxy-ethyl)-1H-indol-3-yl]-ethoxy}-2-isopropoxy-benzoic acid methyl ester (brown solid) in 70% yield.

Step 5: Methane sulfonyl chloride (0.03 mL, 0.39 mmol) and Et$_3$N (0.06 mL, 0.43 mmol) were added to a solution of the alcohol from Step 4 (0.10 g, 0.17 mmol) in dichloromethane (8 mL) at 0° C. Reaction was stirred at 0° C. for one hour and then warmed to room temperature and stirred an additional hour. Reaction solution was concentrated by rotary evaporation. Obtained 0.115 g of 4-(2-[1-Benzhydryl-5-chloro-2-(2-methanesulfonyloxy-ethyl)-1H-indol-3-yl]-ethoxy}-2-isopropoxy-benzoic acid methyl ester in quantitative yield.

Step 6: The mesylate from Step 5 (0.115 g, 0.17 mmol) was dissolved in DMF (5 mL). NaN$_3$ (0.065 g, 1.0 mmol) was added and the mixture was heated to 60° C. and stirred for three hours. Reaction was cooled to room temperature and water was added. Extracted with EtOAc and washed organic layer with brine. Dried organics over sodium sulfate and filtered and concentrated by rotary evaporation. Dried further under a strong vacuum. Obtained 0.100 g of 4-{2-[2-(2-Azido-ethyl)-1-benzhydryl-5-chloro-1H-indol-3-yl]-ethoxy}-2-isopropoxy-benzoic acid methyl ester in 94% yield.

Step 7: Ph$_3$P (polymer support: 3 mmol Ph$_3$P/gram) (0.100 g, 0.30 mmol) was added to a solution of the azide from Step 6 (0.100 g, 0.16 mmol) in THF (2 mL). Reaction was stirred at room temperature for 24 hours. Then water (0.5 mL) was added and reaction was stirred at room temperature overnight. Reaction solution was filtered and the filtrate was concentrated by rotary evaporation. The resulting residue was purified with silica gel prep plates and 2% MeOH in dichloromethane as eluent. Obtained 0.020 g of 4-{2-[2-(2-Amino-ethyl)-1-benzhydryl-5-chloro-1H-indol-3-yl]-ethoxy}-2-isopropoxy-benzoic acid methyl ester in 21% yield.

Step 8: An aqueous, saturated solution of Na$_2$CO$_3$ (2 mL) was added to a solution of the amine from Step 7 (0.020 g, 0.034 mmol) and [(3,4-dichlorophenyl)methyl]sulfonyl chloride (0.015 g, 0.058 mmol) in dichloromethane (2 mL). Reaction was stirred at room temperature for two hours. The reaction solution was then separated and the organic phase was collected and washed with brine and dried over sodium sulfate. Filtered and concentrated the organic solution by rotary evaporation. The resulting residue was purified with silica gel prep plates and 2% MeOH in dichloromethane as eluent. Obtained 0.022 g of the desired sulfonamide (white solid) in 79% yield. m/z (M+1) 821

Step 9: 1N NaOH (1 mL) was added to a solution of the ester from Step 8 (0.022 g, 0.027 mmol) in THF (1 mL) and MeOH (1 mL). Reaction was stirred at room temperature for five days. The THF and MeOH were removed by rotary evaporation. Extracted with dichloromethane and separated and collected the aqueous layer. Neutralized the aqueous layer with 1N HCl and collected the resulting precipitate. Obtained 0.021 g of the title acid (yellow solid) in 96% yield. m/z (M−1) 805

Activity Assay

Coumarine Assay 7-hydroxycoumarinyl 6-heptenoate was used as a monomeric substrate for cPLA2 as reported previously (Huang, Z.

et al., 1994, Nalytical Biochemistry 222, 110–115). Inhibitors were mixed with 200 μL assay buffer (80 mM Heped, pH 7.5, 1 mM EDTA) containing 60 μM 7-hydroxycoumarinyl 6-heptenoate. The reaction was initiated by adding 4 μg cPLA2 in 50 μL assay buffer. Hydrolysis of the 7-hydroxycounarimyl 6-heptenoate ester was monitored in a fluorometer by exciting at 360 nm and monitoring emission at 460 nm. Enzyme activity is proportional to the increase in emission at 460 nm per minute. In the presence of a cPLA2 inhibitor, the rate of increase is less.

| Example # | Coumarin IC$_{50}$ (uM) |
| --- | --- |
| Example 1 | 0.42 |
| Example 2 | 2 |
| Example 3 | 2.5 |
| Example 4 | 56 |
| Example 5 | 3 |
| Example 6 | 2.0 |
| Example 7 | 0.55 |
| Example 8 | 2 |
| Example 9 | 0.7 |
| Example 10 | 0.57 |
| Example 11 | 0.45 |
| Example 12 | 150 |
| Example 13 | 0.64 |
| Example 14 | 0.8 |
| Example 15 | 0.63 |
| Example 16 | 0.98 |
| Example 17 | 0.2 |
| Example 18 | 0.4 |
| Example 19 | 0.31 |
| Example 20 | 1.1 |
| Example 21 | 1.1 |
| Example 22 | 1.8 |
| Example 23 | 1.5 |
| Example 24 | 0.34 |
| Example 25 | 3.4 |
| Example 26 | 1.1 |
| Example 27 | 0.8 |
| Example 28 | 0.95 |
| Example 29 | 0.19 |
| Example 30 | 0.15 |
| Example 31 | 0.15 |
| Example 32 | 0.085 |
| Example 33 | 2.9 |
| Example 35 | 0.33 |
| Example 36 | 0.5 |
| Example 37 | 0.37 |
| Example 38 | 0.5 |
| Example 39 | 0.32 |
| Example 40 | 0.73 |
| Example 41 | 0.2 |
| Example 42 | 0.18 |
| Example 43 | 0.2 |
| Example 44 | 0.25 |
| Example 45 | 4.7 |
| Example 46 | 4.8 |
| Example 47 | 0.58 |
| Example 48 | 2.35 |
| Example 49 | 1.1 |
| Example 50 | 0.69 |
| Example 51 | 2.2 |
| Example 52 | 0.13 |
| Example 53 | 0.37 |
| Example 54 | 0.31 |
| Example 55 | 0.26 |
| Example 56 | 0.13 |
| Example 57 | 0.28 |
| Example 58 | 0.36 |
| Example 59 | 0.29 |
| Example 60 | 0.15 |
| Example 61 | 0.34 |
| Example 62 | 0.38 |
| Example 63 | 0.30 |
| Example 64 | 0.12 |

-continued

| Example # | Coumarin IC$_{50}$ (uM) |
| --- | --- |
| Example 65 | 0.13 |
| Example 66 | 0.15 |
| Example 67 | 0.14 |
| Example 68 | 0.16 |
| Example 69 | 0.15 |
| Example 70 | 0.18 |
| Example 71 | 0.45 |
| Example 72 | 0.28 |
| Example 73 | 0.30 |
| Example 74 | 0.28 |
| Example 75 | 0.4 |
| Example 76 | 0.4 |
| Example 77 | 0.48 |
| Example 78 | 0.34 |
| Example 79 | 0.15 |
| Example 80 | 3.7 |
| Example 81 | 0.47 |
| Example 82 | 0.5 |
| Example 83 | 0.45 |
| Example 84 | 0.5 |
| Example 85 | 0.4 |
| Example 86 | 0.6 |
| Example 87 | 1.2 |
| Example 88 | <7.4 |
| Example 89 | 0.38 |
| Example 90 | 0.65 |
| Example 91 | 0.5 |
| Example 92 | 1.0 |
| Example 93 | 0.56 |
| Example 94 | 0.8 |
| Example 95 | 0.85 |
| Example 96 | 0.95 |
| Example 97 | 0.95 |
| Example 98 | 1.1 |
| Example 99 | 1.0 |
| Example 100 | 0.12 |
| Example 101 | 0.1 |
| Example 102 | 0.19 |
| Example 103 | 1.1 |
| Example 104 | 1.1 |
| Example 105 | 0.65 |
| Example 106 | 0.22 |
| Example 107 | 0.33 |
| Example 108 | 0.15 |
| Example 109 | 0.4 |
| Example 110 | 0.5 |
| Example 111 | 1.0 |
| Example 112 | 1.2 |
| Example 113 | 1.3 |
| Example 114 | 1.1 |
| Example 115 | 0.9 |
| Example 116 | 1.2 |
| Example 117 | 1.6 |
| Example 118 | 0.4 |
| Example 119 | 0.4 |
| Example 120 | 0.4 |
| Example 121 | 0.46 |
| Example 122 | 2.5 |
| Example 123 | 1.5 |
| Example 124 | 0.8 |
| Example 125 | 1.4 |
| Example 126 | 0.2 |
| Example 127 | 0.2 |
| Example 128 | 0.32 |
| Example 129 | 0.13 |
| Example 130 | 0.17 |
| Example 131 | 0.2 |
| Example 132 | 0.2 |
| Example 133 | 0.09 |
| Example 134 | >1 |
| Example 135 | 0.2 |
| Example 136 | 0.18 |
| Example 137 | NT |
| Example 138 | 0.2 |
| Example 139 | 1.7 |
| Example 140 | 0.2 |

-continued

| Example # | Coumarin IC$_{50}$ (uM) |
|---|---|
| Example 141 | 0.17 |
| Example 142 | NT |
| Example 143 | NT |
| Example 144 | NT |
| Example 145 | NT |
| Example 146 | NT |
| Example 147 | NT |
| Example 148 | NT |
| Example 149 | NT |
| Example 150 | NT |
| Example 151 | NT |
| Example 152 | 0.32 |
| Example 153 | 0.16 |
| Example 154 | 0.35 |
| Example 155 | 0.45 |
| Example 156 | 0.16 |
| Example 157 | 0.2 |
| Example 158 | 0.2 |
| Example 159 | 0.65 |
| Example 160 | 0.19 |
| Example 161 | 0.32 |
| Example 162 | 1.0 |
| Example 163 | 0.3 |
| Example 164 | 0.2 |
| Example 165 | 0.53 |
| Example 166 | 0.4 |
| Example 167 | 0.19 |
| Example 168 | 0.27 |
| Example 169 | 0.46 |
| Example 170 | 0.95 |
| Example 171 | 0.36 |
| Example 172 | 0.35 |
| Example 173 | 0.4 |
| Example 174 | 1.1 |
| Example 175 | 0.37 |
| Example 176 | 0.4 |
| Example 177 | 0.9 |
| Example 178 | 0.65 |
| Example 179 | 0.9 |
| Example 180 | 0.23 |
| Example 181 | 0.32 |
| Example 182 | 0.6 |
| Example 183 | 0.17 |
| Example 184 | 0.35 |
| Example 185 | 0.17 |
| Example 186 | 0.1 |
| Example 187 | 0.2 |
| Example 188 | NT |
| Example 189 | NT |
| Example 190 | 0.53 |
| Example 191 | 0.2 |
| Example 192 | <3.7 |
| Example 193 | 1.8 |
| Example 194 | 1 |
| Example 195 | 1 |
| Example 196 | 0.56 |
| Example 197 | 0.4 |
| Example 198 | 0.7 |
| Example 199 | 0.45 |
| Example 200 | 0.35 |
| Example 201 | 0.35 |
| Example 202 | 0.3 |
| Example 203 | 0.69 |
| Example 204 | 0.2 |
| Example 205 | 0.37 |
| Example 206 | 0.5 |
| Example 207 | 1.4 |
| Example 208 | 0.24 |
| Example 209 | 0.35 |
| Example 210 | 0.15 |
| Example 211 | 0.4 |
| Example 212 | 0.18 |
| Example 213 | 0.45 |
| Example 214 | NT |
| Example 215 | NT |
| Example 216 | NT |

-continued

| Example # | Coumarin IC$_{50}$ (uM) |
|---|---|
| Example 217 | 2.6 |
| Example 218 | 0.14 |
| Example 219 | 0.4 |
| Example 220 | 0.4 |
| Example 221 | 0.5 |
| Example 222 | 0.19 |
| Example 223 | 0.6 |
| Example 224 | 0.25 |
| Example 225 | 0.4 |
| Example 226 | 0.14 |
| Example 227 | 0.16 |
| Example 228 | 0.4 |
| Example 229 | 0.5 |
| Example 230 | 0.15 |
| Example 231 | 0.25 |
| Example 232 | 0.13 |
| Example 233 | 0.34 |
| Example 234 | 0.23 |
| Example 235 | 0.18 |
| Example 236 | 0.085 |
| Example 237 | 0.2 |
| Example 238 | 0.25 |
| Example 239 | 0.48 |
| Example 240 | 0.32 |
| Example 241 | 0.54 |
| Example 242 | 1.3 |
| Example 243 | 0.75 |
| Example 244 | 1.3 |
| Example 245 | 0.9 |
| Example 246 | 1.2 |
| Example 247 | 1.2 |
| Example 248 | 1.2 |
| Example 249 | 0.67 |
| Example 250 | 2.1 |
| Example 251 | 1.5 |
| Example 252 | 0.73 |
| Example 253 | 0.75 |
| Example 254 | 0.26 |
| Example 255 | 0.5 |
| Example 256 | 0.6 |
| Example 257 | 0.5 |
| Example 258 | 0.8 |
| Example 259 | 0.2 |
| Example 260 | 0.37 |
| Example 261 | 0.25 |
| Example 262 | 0.53 |
| Example 263 | 0.32 |
| Example 264 | 0.4 |
| Example 265 | 0.37 |
| Example 266 | 0.16 |
| Example 267 | 0.074 |
| Example 268 | 0.09 |
| Example 269 | 0.15 |
| Example 270 | 0.14 |
| Example 271 | 0.15 |
| Example 272 | 0.1 |
| Example 273 | 0.11 |
| Example 274 | NT |
| Example 275 | 0.24 |
| Example 276 | 0.32 |
| Example 277 | 0.6 |
| Example 278 | 1.9 |
| Example 279 | 0.16 |
| Example 280 | 0.35 |
| Example 281 | NT |
| Example 282 | NT |
| Example 283 | 0.5 |
| Example 284 | 0.4 |
| Example 285 | NT |
| Example 286 | NT |
| Example 287 | 0.42 |
| Example 288 | 0.4 |
| Example 289 | 0.9 |
| Example 290 | NT |
| Example 291 | NT |
| Example 292 | NT |

-continued

| Example # | Coumarin IC$_{50}$ (uM) |
|---|---|
| Example 293 | NT |
| Example 294 | NT |
| Example 295 | 0.55 |
| Example 296 | 0.32 |
| Example 297 | 0.3 |
| Example 298 | 0.19 |
| Example 299 | 1.0 |
| Example 300 | >2 |

The compounds of the invention inhibit cPLA2 activity that is required for supplying arachidonic acid substrate to cyclooxygenase-1 or 2 and 5-lipoxygenase, which in turn initiate the production of prostaglandins and leukotrienes respectively. In addition, cPLA2 activity is essential for producing the lyso-phospholipid that is the precursor to PAF. Thus these compounds are useful in the treatment and prevention of disease states in which leukotrienes, prostaglandins or PAF are involved. Moreover, in diseases where more than one of these agents plays a role, a cPLA2 inhibitor would be expected to be more efficacious than leukotriene, prostaglandin or PAF receptor antagonists and also more effective than cyclooxygenase or 5-lipoxygenase inhibitors.

Therefore, the compounds, pharmaceutical compositions and regimens of the present invention are useful in treating and preventing the disorders treated by cyclooxygenase-2, cycloxygenase-1, and 5-lipoxygenase inhibitors and also antagonists of the receptors for PAF, leukotrienes or prostaglandins. Diseases treatable by compounds of this invention include but are not limited to: pulmonary disorders including diseases such as asthma, chronic bronchitis, and related obstructive airway diseases; allergies and allergic reactions such as allergic rhinitis, contact dermatitis, allergic conjunctivitis, and the like; inflammation such as arthritis or inflammatory bowel diseases, skin disorders such as psoriasis, atopic eczema, acne, UV damage, burns and dermatitis; cardiovascular disorders such as atherosclerosis, angina, myocardial ischaemia, hypertension, platelet aggregation, and the like; and renal insufficiency induced by immunological or chemical. The drugs may also be cytoprotective, preventing damage to the gastrointestinal mucosa by noxious agents. The compounds will also be useful in the treatment of adult respiratory distress syndrome, endotoxin shock and ischeamia induced injury including myocardial or brain injury.

This invention further provides a method of alleviation, inhibition, relief or treatment of arthritic and rheumatic disorders in a mammal, the method comprising administering to a mammal in need thereof a pharmaceutically effective amount of a chemical inhibitor of phospholipase enzymes, particularly phospholipase A$_2$ enzymes, as defined herein and a pharmaceutically effective amount of an anti-rheumatic agent.

Combinations for the treatment of arthritic disorders may include commercially available anti-rheumatic agents such as, but not limited to, naproxen, which is commercially available in the form of EC-NAPROSYN® delayed release tablets, NAPROSYN®, ANAPROX® and ANAPROX® DS tablets and NAPROSYN® suspension from Roche Labs, CELEBREX® brand of celecoxib tablets, VIOXX® brand of rofecoxib, CELESTONE® brand of betamethasone, CUPRAMINE® brand penicillamine capsules, DEPEN® brand titratable penicillamine tablets, DEPO-MEDROL brand of methylprednisolone acetate injectable suspension, ARAVA™ leflunomide tablets, AZULFIDIINE EN-tabs® brand of sulfasalazine delayed release tablets, FELDENE® brand piroxicam capsules, CATAFLAM® diclofenac potassium tablets, VOLTAREN® diclofenac sodium delayed release tablets, VOLTAREN®-XR diclofenac sodium extended release tablets, ENBREL® etanerecept products, and other commercially available antirheumatic agents.

Also useful are GENGRAF™ brand cyclosprine capsules, NEORAL® brand cyclosprine capsules or oral solution, IMURAN® brand azathioprine tablets or IV injection, INDOCIN® brand indomethacin capsules, oral suspension and suppositories, PEDIAPED® prednisolone sodium phosphate oral solution, PLAQUENIL® brand hydroxychloroquine sulfate, PRELONE® brand prednisolone syrup, REMICADE® infliximab recombinant for IV injection, and SOLU-MEDROL® methylprednisolone sodium succinate for injection.

Also useful in the combinations of this invention are gold compounds and products useful in the treatment of arthritis and rheumatic conditions, such as auranofin or MYOCHRISYINE® gold sodium thiomalate injection.

Such compositions are also useful in the treatment of menstrual cramps, preterm labor, tendonitis, bursitis, allergic neuritis, cytomegalovirus infection, apoptosis, including HIV-induced apoptosis, lumbago, liver disease including hepatitis.

The compounds of this invention may also be used in comparable veterinary methods of treatment for arthritic and rheumatic conditions, particularly for the veterinary treatment, inhibition or alleviation of inflammation and pain. These methods will be understood to be of particular interest for companion mammals, such as dogs and cats, and for use in farm mammals, such as cattle, horses, mules, donkeys, goats, hogs, sheep, etc. These methods may be used to treat the types of inflammation and pain experienced in veterinary medicine including, but not limited to, pain and inflammation associated with arthritis, joint imperfections, developmental joint defects, such as hip dysplasia, elbow dysplasia, tendonitis, suspensary ligament inflammation, laminitis, curb and bursitis, or pain or inflammation associated with surgery, accident, trauma or disease, such as Lyme Disease. These compounds may also be used in the treatment of inflammation of the air passages, such as in conditions of asthma, laryngitis, tracheitis, bronchitis, rhinitis and pharyngitis.

The compounds of this invention may also be administered in the methods of this invention with analgesic and anti-inflammatory agents such as NSAIDs and aspirin and other salicylates. Examples of useful agents include ibuprofen (MOTRIN®, ADVIL®), naproxen (NAPROSYN®), sulindac (CLINORIL®), diclofenac (VOLTAREN®), piroxicam (FELDENE®) ketoprofen (ORUDIS®), diflunisal (DOLOBID®), nabumetone (RELAFEN®), etodolac (LODINE®), oxaprozin (DAYPRO®), indomethacin (INDOCIN®), melicoxam (MOBICOX®), valdecoxib and eterocoxib. Aspirin is anti-inflammatory when given in high doses, otherwise it is just a pain killer like acetaminophen (TYLENOL®).

Suitable cyclooxygenase 2 (COX-2) inhibitors for use with the methods of this invention include, but are not limited to, 2-(4-ethoxy-phenyl)-3-(4-methanesulfonyl-phenyl)-pyrazolo[1,5-b]pyridazine, CDC-501, celecoxib, COX-189, 4-(2-oxo-3-phenyl-2,3-dihydrooxazol-4-yl)benzenesulfonamide, CS-179, CS-502, D-1367, darbufelone, DFP, DRF-4367, flosulide, JTE-522 (4-(4-cyclohexyl-2-methyl-5-oxazolyl)-2-fluorobenzenesulfonamide), L-745337, L-768277, L-776967, L-783003, L-791456, L-804600, meloxicam, MK663 (etoricoxib), nimesulide, NS-398, parecoxib, 1-Methylsulfonyl-4-(1,1-dimethyl-4-(4-fluorophenyl)cyclopenta-2,4-dien-3-yl)benzene, 4-(1,5-Dihydro-6-fluoro-7-methoxy-3-(trifluoromethyl)-(2)-benzothiopyrano(4,3-c)pyrazol-1-yl)benzenesulfonamide, 4,4-dimethyl-2-phenyl-3-(4-methylsulfonyl)phenyl) cyclobutenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzo-furanyl)-4-cyclopropyl butan-1-one, Pharmaprojects No. 6089 (Kotobuki Pharmaceutical), RS-113472, RWJ-63556, S-2474, S-33516, SC-299, SC-5755, valdecoxib, UR-8877, UR-8813, UR-8880. Further suitable COX-2 inhibitors for use according to the invention include parecoxib, MK663, 4-(4-cyclohexyl-2-methyl-5-oxazolyl)-2-fluorobenzenesulfonamide (JTE-522), nimesulide, flosulide, DFP and 2-(4-ethoxy-phenyl)-3-(4-methanesulfonyl-phenyl)-pyrazolo[1,5-b]pyridazine, and their physiologically acceptable salts, esters or solvates.

Each of the methods of this invention comprises administering to a mammal in need of such treatment a pharmaceutically or therapeutically effective amount of a compound of this invention. In the instances of combination therapies described herein, it will be understood the administration further includes a pharmaceutically or therapeutically effective amount of the second pharmaceutical agent in question. The second or additional pharmacological agents described herein may be administered in the doses and regimens known in the art.

The compounds of this invention may be used for human or veterinary methods in conjunction with other medicaments or dietary supplements known in the art for the treatment, inhibition or alleviation of inflammation or pain. These may include aspirin (including buffered aspirin, aspirin with Maalox and enteric coated aspirin), COX-2 inhibitors, such as celecoxib, non-acetylated carboxylic acids, such as magnesium salicylate, salicylamide or sodium salicylate, acetic acids, such as doclofenac or etodolac, propionic acids, such as ibuprofen, naproxen (available in NAPROSYN® and EQUIPROXEN® brands), ketoprofen, RIMADYL® (carprofen), flunixin meglumine, fenamic acids, such as tolfenamic acid, mefanamic acid, meclofenamic acid (ARQUEL®) or niflumic acid, enolic acids, such as oxyphenbutazone, phenylbutazone, piroxicam or dipyrone, or non-acidic compounds like nabumetone. Also used in veterinary applications are dimethylsulfoxide (DMSO), orgotein (such as PALOSEIN® brand of orgotein), polysulfated glycosaminoglycans or PS-GAGs (such as ADEQUAN® brand polysulfated glycosaminoglycan), hyaluronic acid and its natural and synthetic analogues, Ketorolac trimethamine (such as the TORADOL® brand), FELDEN® (piroxicam), or METACAM® (meloxicam).

Dietary supplements used in human or veterinary applications include glucosamines, chondroitin sulfate, methylsulfonylmethane (MSM), and omega 3 fatty acids and other cold water fish oils. The compounds and methods of this invention may also be used in conjunction with human or veterinary physical therapy, massage, chiropractic and accupuncture treatments and regimens. Each of these medicaments and dietary supplements may be administered to the mammal in question using regimens and effective dosages known in the art.

What is claimed is:
1. A method of treatment of arthritic and rheumatic disorders in a mammal, the method comprising administering to a mammal in need thereof a pharmaceutically effective amount of a compound of the formula:

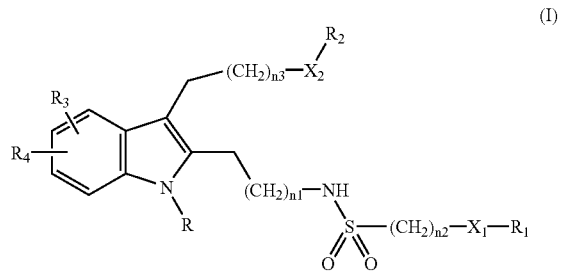

wherein:
R is selected from the formulae $-(CH_2)_n-A$, $-(CH_2)_n-S-A$, or $-(CH_2)_n-O-A$, wherein A is selected from the moieties:

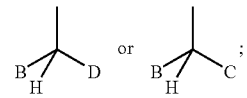

wherein
D is $C_1-C_6$ lower alkyl, $C_1-C_6$ lower alkoxy, $C_3-C_6$ cylcoalkyl, $-CF_3$ or $-(CH_2)_{1-3}-CF_3$;
B and C are independently selected from phenyl, pyridinyl, pyrimidinyl, furyl, thienyl or pyrrolyl groups, each optionally substituted by from 1 to 3, preferably 1 to 2, substituents selected independently from H, halogen, $-CN$, $-CHO$, $-CF_3$, $-OCF_3$, $-OH$, $-C_1-C_6$ alkyl, $C_1-C_6$ alkoxy, $-NH_2$, $-N(C_1-C_6)_2$, $-NH(C_1-C_6)$, $-N-C(O)-(C_1-C_6)$, $-NO_2$, or by a 5- or 6-membered heterocyclic or heteroaromatic ring containing 1 or 2 heteroatoms selected from O, N or S; or
n is an integer from 0 to 3;
$n_1$ is an integer from 1 to 3;
$n_2$ is an integer from 0 to 4;
$n_3$ is an integer from 0 to 3;
$n_4$ is an integer from 0 to 2;
$X_1$ is selected from a chemical bond, $-S-$, $-O-$, $-S(O)-$, $-S(O)_2-$, $-NH-$, $-NHC(O)-$, $-C=C-$,

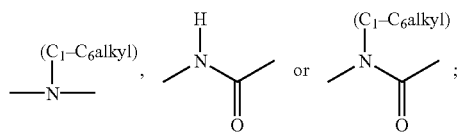

$R_1$ is selected from $C_1-C_6$ alkyl, $C_1-C_6$ fluorinated alkyl, $C_3-C_6$ cycloalkyl, tetrahydropyranyl, camphoryl, adamantyl, CN, $-N(C_1-C_6$ alkyl$)_2$, phenyl, pyridinyl, pyrimidinyl, furyl, thienyl, napthyl, morpholinyl, triazolyl, pyrazolyl, piperidinyl, pyrrolidinyl, imidazolyl, piperizinyl, thiazolidinyl, thiomorpholinyl, tetrazole, indole, benzoxazole, benzofuran, imidazolidine-2-thione, 7,7,dimethyl-bicyclo[2.2.1]heptan-2-one, Benzo[1,2,5]oxadiazole, 2-Oxa-5-aza-bicyclo[2.2.1]heptane, Piperazin-2-one or pyrrolyl groups, each optionally substituted by from 1 to 3, preferably 1 to 2, substituents independently selected from H, halogen, $-CN$, $-CHO$, $-CF_3$, $OCF_3$, $-OH$, $-C_1-C_6$ alkyl, $C_1-C_6$ alkoxy, $-NH_2$, $-N(C_1-C_6)_2$, $-NH(C_1-C_6)$, —N—C(O)—(C$_1$–C$_6$), —NO$_2$, —SO$_2$(C$_1$–C$_3$ alkyl), —SO$_2$NH$_2$, —SO$_2$NH(C$_1$–C$_3$ alkyl), —SO$_2$N(C$_1$–C$_3$ alkyl)$_2$, —COOH, —CH$_2$—COOH, —CH$_2$—N(C$_1$–C$_6$ alkyl), —CH$_2$—N(C$_1$–C$_6$ alkyl)$_2$, —CH$_2$—NH$_2$, pyridine, 2-Methyl-thiazole, morpholino, 1-Chloro-2-methyl-propyl, —C$_1$–C$_6$thioalkyl, phenyl (further optionally substituted with halogens), benzyloxy, (C$_1$–C$_3$ alkyl)C(O)CH$_3$, (C$_1$–C$_3$ alkyl)OCH$_3$, C(O)NH$_2$, or

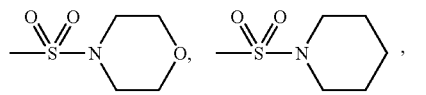

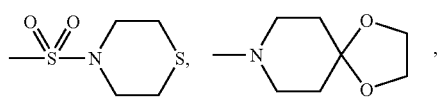

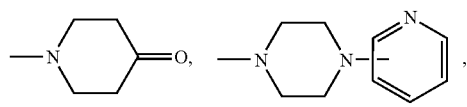

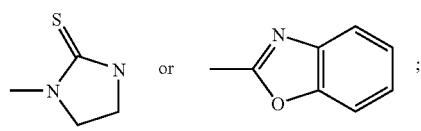

X$_2$ is selected from —O—, —CH$_2$—, —S—, —SO—, —SO$_2$—, —NH—, —C(O)—,

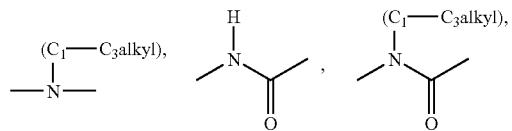

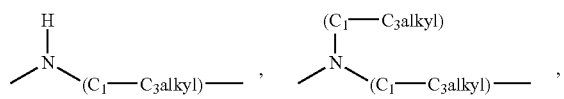

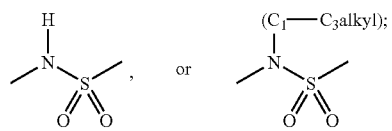

R$_2$ is a ring moiety selected from phenyl, pyridinyl, pyrimidinyl, furyl, thienyl or pyrrolyl groups, the ring moiety being substituted by a group of the formula —(CH$_2$)$_{n4}$—CO$_2$H or a pharmaceutically acceptable acid mimic or mimetic; and also optionally substituted by 1 or 2 additional substituents independently selected from H, halogen, —CN, —CHO, —CF$_3$, —OCF$_3$, —OH, —C$_1$–C$_6$ alkyl, C$_1$–C$_6$ alkoxy, C$_1$–C$_6$ thioalkyl, —NH$_2$, —N(C$_1$–C$_6$)$_2$, —NH(C$_1$–C$_6$), —N—C(O)—(C$_1$–C$_6$), or —NO$_2$;

R$_3$ is selected from H, halogen, —CN, —CHO, —CF$_3$, —OCF$_3$, —OH, —C$_1$–C$_6$ alkyl, C$_1$–C$_6$ alkoxy, C$_1$–C$_6$ thioalkyl, —NH$_2$, —N(C$_1$–C$_6$)$_2$, —NH(C$_1$–C$_6$), —N—C(O)—(C$_1$–C$_6$), or —NO$_2$;

R$_4$ is selected from H, halogen, —CN, —CHO, —CF$_3$, —OCF$_3$, —OH, —C$_1$–C$_6$ alkyl, C$_1$–C$_6$ alkoxy, C$_1$–C$_6$ thioalkyl, —NH$_2$, —N(C$_1$–C$_6$)$_2$, —NH(C$_1$–C$_6$), —N—C(O)—(C$_1$–C$_6$), —NO$_2$, —N—C(O)—N(C$_1$–C$_3$ alkyl)$_2$, —N—C(O)—NH(C$_1$–C$_3$ alkyl), —N—C(O)—O—(C$_1$–C$_3$ alkyl), —SO$_2$—C$_1$–C$_6$ alkyl, —S—C$_3$–C$_6$ cycloalkyl, —S—CH$_2$—C$_3$–C$_6$ cycloalkyl, —SO$_2$—C$_3$–C$_6$ cycloalkyl, —SO$_2$—CH$_2$—C$_3$–C$_6$ cycloalkyl, C$_3$–C$_6$ cycloalkyl, —CH$_2$—C$_3$–C$_6$ cycloalkyl, —O—C$_3$–C$_6$ cycloalkyl, —O—CH$_2$—C$_3$–C$_6$ cycloalkyl, phenyl, benzyl, benzyloxy, morpholino or other heterocycles such as pyrrolidino, piperidine, piperizine furan, thiophene, imidazole, tetrazole, pyrazine, pyrazolone, pyrazole, imidazole, oxazole or isoxazole, the rings of each of these R$_4$ groups each being optionally substituted by from 1 to 3 substituents selected from the group of H, halogen, —CN, —CHO, —CF$_3$, —OH, —C$_1$–C$_6$ alkyl, C$_1$–C$_6$ alkoxy, —NH$_2$, —N(C$_1$–C$_6$)$_2$, —NH(C$_1$–C$_6$), —N—C(O)—(C$_1$–C$_6$), —NO$_2$, —SO$_2$(C$_1$–C$_3$ alkyl), —SO$_2$NH(C$_1$–C$_3$ alkyl), —SO$_2$N(C$_1$–C$_3$ alkyl)$_2$, or OCF$_3$;

or a pharmaceutically acceptable salt form thereof.

2. A method of claim 1 wherein the pharmaceutically acceptable acid mimics or mimetics include those wherein R$_2$ is selected from the group consisting of:

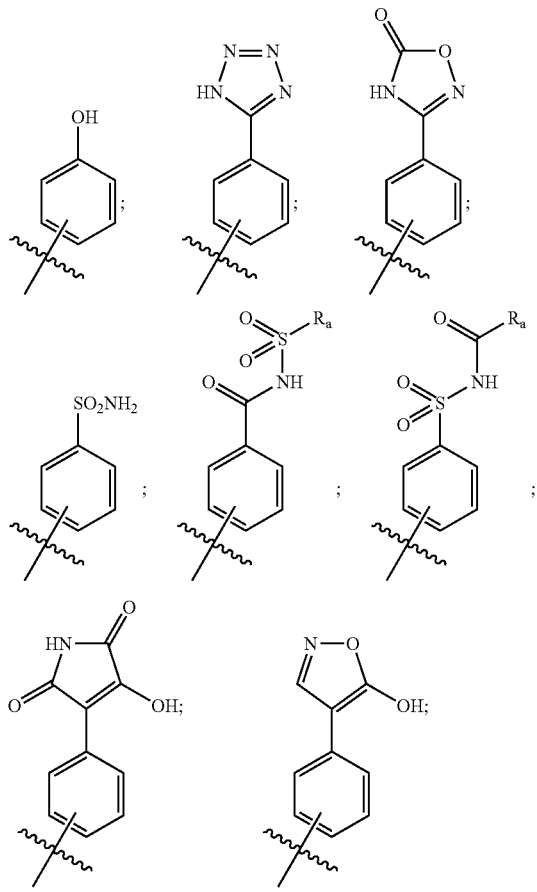

-continued

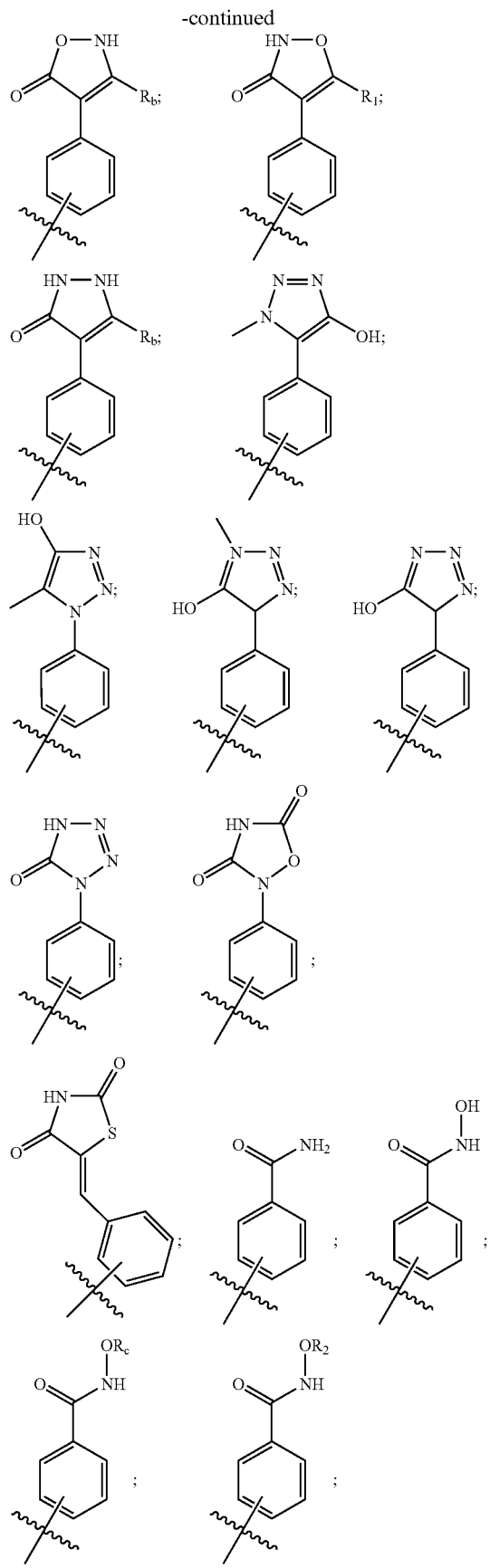

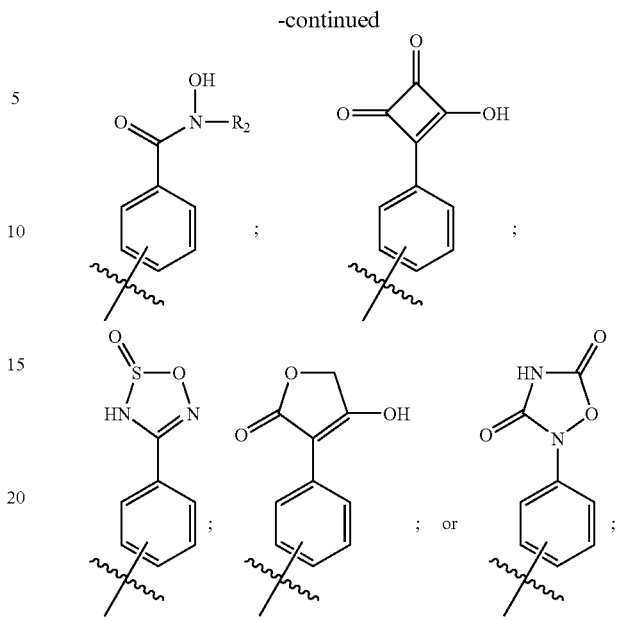

wherein $R_a$ is selected from —$CF_3$, —$CH_3$, phenyl, or benzyl, with the phenyl or benzyl groups being optionally substituted by from 1 to 3 groups selected from $C_1$–$C_6$ alkyl, $C_1$–$C_6$ alkoxy, $C_1$–$C_6$ thioalkyl, —$CF_3$, halogen, —OH, or —COOH; $R_b$ is selected from —$CF_3$, —$CH_3$, —$NH_2$, phenyl, or benzyl, with the phenyl or benzyl groups being optionally substituted by from 1 to 3 groups selected from $C_1$–$C_6$ alkyl, $C_1$–$C_6$ alkoxy, $C_1$–$C_6$ thioalkyl, —$CF_3$, halogen, —OH, or —COOH; and $R_c$ is selected from —$CF_3$ or $C_1$–$C_6$ alkyl.

3. A method of claim 1 wherein A is the moiety:

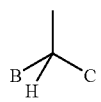

and B, C, n, n1, n2, n3, n4, R, $X_1$, $X_2$, $R_1$, $R_2$, $R_3$, and $R_4$ are as defined in claim 1.

4. A method of claim 3 wherein B and C are unsubstituted phenyl, pyridinyl, pyrimidinyl, furyl, thienyl or pyrrolyl groups and R, n, n1, n2, n3, n4, $R_1$, $X_1$, $X_2$, $R_2$, $R_3$, and $R_4$ are as defined in claim 1.

5. A method of claim 1 wherein A is the moiety:

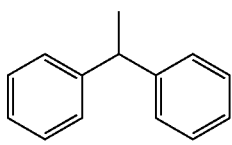

and n, n1, n2, n3, n4, R, $X_1$, $X_2$, $R_1$, $R_2$, $R_3$, and $R_4$ are as defined in claim 1.

6. A method of treatment of arthritic and rheumatic disorders in a mammal, the method comprising administering to a mammal in need thereof a pharmaceutically effective amount of a compound of formulae (II) or (III):

(II)

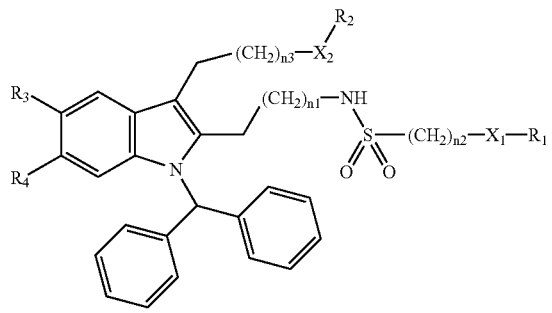

or (III)

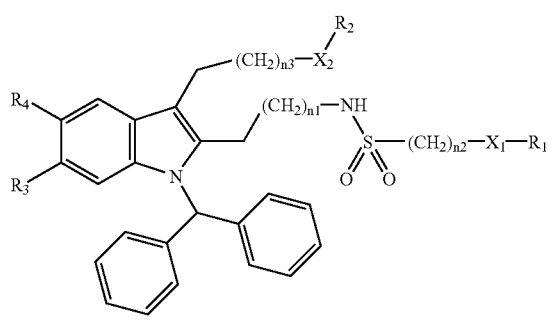

wherein n1, n2, n3, n4, $X_1$, $X_2$, $R_1$, $R_2$, $R_3$, and $R_4$ are as defined in claim 1, or a pharmaceutically acceptable salt thereof.

7. A method of claim 6 wherein n3=1, and n, n1, n2, n4, $X_1$, $X_2$, $R_1$, $R_2$, $R_3$, and $R_4$ are as defined in claim 6, or a pharmaceutically acceptable salt thereof.

8. A method of claim 6 wherein $R_2$ is phenyl substituted by a group of the formula $—(CH_2)_{n4}—CO_2H$; and optionally substituted by 1 or 2 additional substituents independently selected from H, halogen, —CN, —CHO, —$CF_3$, —OH, —$C_1$-$C_6$ alkyl, $C_1$-$C_6$ alkoxy, $C_1$-$C_6$ thioalkyl, —$NH_2$, —$N(C_1$-$C_6)_2$, —$NH(C_1$-$C_6)$, —N—C(O)—($C_1$-$C_6$), or —NO; and n1, n2, n4, $R_1$, $X_1$, $X_2$, $R_2$, $R_3$, and $R_4$ are as defined in claim 6, or a pharmaceutically acceptable salt thereof.

9. A method of treatment of arthritic and rheumatic disorders in a mammal, the method comprising administering to a mammal in need thereof a pharmaceutically effective amount of a compound of formulae (IV) or (V):

(IV)

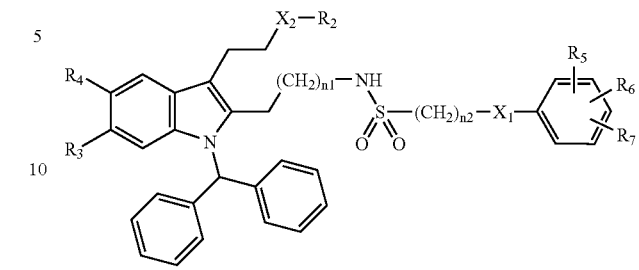

or

-continued (V)

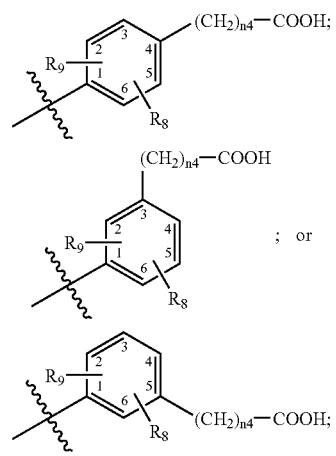

$n_1$ is an integer from 1 to 3;
$n_2$ is an integer from 1 to 3;
$R_5$, $R_6$ and $R_7$ are independently selected from H, halogen, —CN, —CHO, —$CF_3$, —OH, —$C_1$-$C_6$ alkyl, $C_1$-$C_6$ alkoxy, —$NH_2$, —$N(C_1$-$C_6)_2$, —$NH(C_1$-$C_6)$, —N—C(O)—($C_1$-$C_6$), or —$NO_2$;
$X_1$ is selected from a chemical bond, —S—, —O—, —NH— or —$N(C_1$-$C_3$ alkyl)-;
$X_2$ is selected from —O—, —$SO_2$— or —$CH_2$—;
$R_2$ is a moiety selected from the group of:

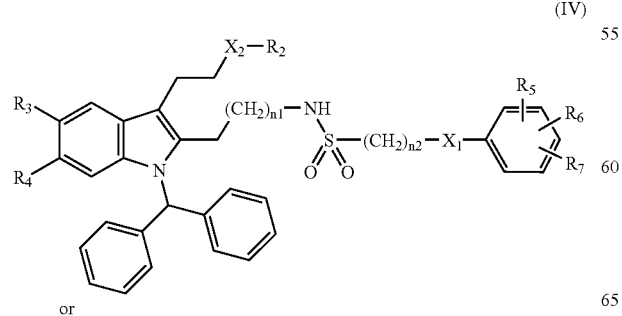

$R_8$ and $R_9$ are independently selected from H, halogen, —CN, —CHO, —$CF_3$, —OH, —$C_1$-$C_6$ alkyl, $C_1$-$C_6$ alkoxy, —$NH_2$, —$N(C_1$-$C_6)_2$, —$NH(C_1$-$C_6)$, —N—C(O)—($C_1$-$C_6$), or —$NO_2$;
$n_4$ is an integer from 0 to 2;
$R_3$ is selected from H, halogen, —CN, —CHO, —$CF_3$, —OH, —$C_1$-$C_6$ alkyl, $C_1$-$C_6$ alkoxy, $C_1$-$C_6$ thioalkyl, —$NH_2$, —$N(C_1$-$C_6)_2$, —$NH(C_1$-$C_6)$, —N—C(O)—($C_1$-$C_6$), or —$NO_2$; and
$R_4$ is selected from H, halogen, —CN, —CHO, —$CF_3$, —OH, —$C_1$-$C_6$ alkyl, $C_1$-$C_6$ alkoxy, $C_1$-$C_6$ thioalkyl, —$NH_2$, —$N(C_1$-$C_6)_2$, —$NH(C_1$-$C_6)$, —N—C(O)—($C_1$-$C_6$), —$NO_2$, morpholino or other heterocycles such as pyrrolidino, piperidine, piperizine furan, thiophene, imidazole, tetrazole, pyrazine, pyrazolone, pyrazole, imidazole, oxazole or isoxazole;
or a pharmaceutically acceptable salt form thereof.

10. A method of treatment of arthritic and rheumatic disorders in a mammal, the method comprising administering to a mammal in need thereof a pharmaceutically effective amount of a compound of the formulae (VI) or (VII):

(VI)

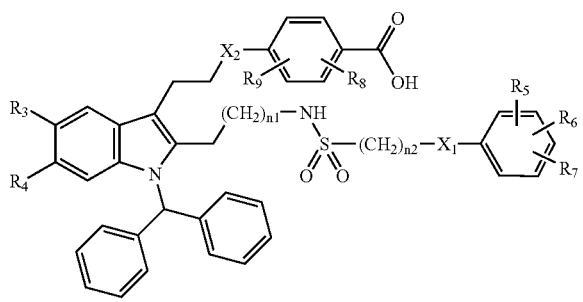

(VII)

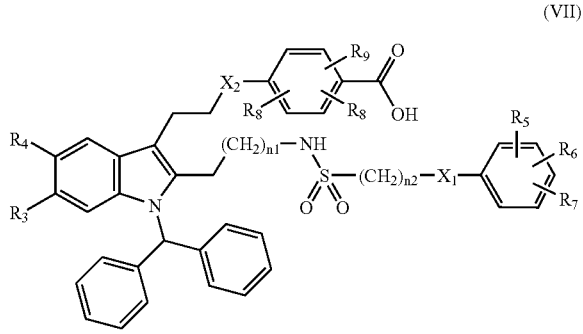

wherein:
X$_1$ is selected from a chemical bond, —S—, —O—, —NH— or —N(C$_1$–C$_3$ alkyl)-;
X$_2$ is selected from —O—, —SO$_2$—, or —CH$_2$—;
R$_3$ is selected from H, halogen, —CN, —CHO, —CF$_3$, —OH, —C$_1$–C$_6$ alkyl, C$_1$–C$_6$ alkoxy, C$_1$–C$_6$ thioalkyl, —NH$_2$, —N(C$_1$–C$_6$)$_2$, —NH(C$_1$–C$_6$), —N—C(O)—(C$_1$–C$_6$), or —NO$_2$; and
R$_4$ is selected from H, halogen, —CN, —CHO, —CF$_3$, —OH, —C$_1$–C$_6$ alkyl, C$_1$–C$_6$ alkoxy, C$_1$–C$_6$ thioalkyl, —NH$_2$, —N(C$_1$–C$_6$)$_2$, —NH(C$_1$–C$_6$), —N—C(O)—(C$_1$–C$_6$), —NO$_2$, morpholino or other heterocycles such as pyrrolidino, piperidine, piperizine furan, thiophene, imidazole, tetrazole, pyrazine, pyrazolone, pyrazole, imidazole, oxazole or isoxazole;
n$_1$ is an integer from 1 to 2;
n$_2$ is an integer from 1 to 2;
R$_5$, R$_6$ and R$_7$ are independently selected from H, halogen, —CN, —CHO, —CF$_3$, OCF$_3$, —OH, —C$_1$–C$_6$ alkyl, C$_1$–C$_6$ alkoxy, —NH$_2$, —N(C$_1$–C$_6$)$_2$, —NH(C$_1$–C$_6$), —N—C(O)—(C$_1$–C$_6$), or —NO$_2$;
R$_8$ and R$_9$ are independently selected from H, halogen, —CN, —CHO, —CF$_3$, —OH, —C$_1$–C$_6$ alkyl, C$_1$–C$_6$ alkoxy, —NH$_2$, —N(C$_1$–C$_6$)$_2$, —NH(C$_1$–C$_6$), —N—C(O)—(C$_1$–C$_6$), or —NO$_2$;
or a pharmaceutically acceptable salt form thereof.

11. A method of claim 10 of formulae (VI) or (VII) wherein: n$_1$ is 1; n$_2$ is 1; and X$_1$, X$_2$, R$_3$, R$_4$, R$_5$, R$_6$, R$_7$, R$_8$ and R$_9$ are as defined in claim 10, or a pharmaceutically acceptable salt form thereof.

12. A method of claim 1, wherein X$_1$ is a chemical bond and n$_1$, n$_2$, X$_2$, R$_3$, R$_4$, R$_5$, R$_6$, R$_7$, R$_8$ and R$_9$ are as defined in claim 1, or a pharmaceutically acceptable salt form thereof.

13. A method of claim 1, wherein X$_1$ is a chemical bond and B, C, n, n$_1$, n$_2$, n$_3$, n$_4$, R, X$_1$, X$_2$, R$_1$, R$_2$, R$_3$, R$_4$, R$_5$, R$_6$, R$_7$, R$_8$ and R$_9$ are as defined in claim 1, or a pharmaceutically acceptable salt form thereof.

14. A method of claim 6 of formulae (II) or (III) wherein: X$_1$ is a chemical bond and n$_1$, n$_2$, n$_3$, n$_4$, X$_1$, X$_2$, R$_1$, R$_2$, R$_3$ and R$_4$ are as defined in claim 1, or a pharmaceutically acceptable salt form thereof.

15. A method of claim 9 of formulae (IV) or (V) wherein: X$_1$ is a chemical bond and n$_1$, n$_2$, n$_4$, X$_1$, X$_2$, R$_2$, R$_3$ and R$_4$, R$_5$, R$_6$, R$_7$, R$_8$, R$_9$ are as defined in claim 9, or a pharmaceutically acceptable salt form thereof.

16. A method of claim 10, wherein X$_1$ is a chemical bond and n$_1$, n$_2$, X$_2$, R$_3$, R$_4$, R$_5$, R$_6$, R$_7$, R$_8$ and R$_9$ are as defined in claim 10, or a pharmaceutically acceptable salt form thereof.

17. A method of claim 1 wherein the compound is selected from the group consisting of:
4-[2-(1-Benzhydryl-2-{2-[(benzylsulfonyl)amino]ethyl}-5-chloro-1H-indol-3-yl)ethoxy]benzoic acid;
4-[2-(1-Benzhydryl-5-chloro-2-{2-[(isopropylsulfonyl)amino]ethyl}-1H-indol-3-yl)ethoxy]benzoic acid;
4-[2-(1-Benzhydryl-2-{2-[(butylsulfonyl)amino]ethyl}-5-chloro-1H-indol-3-yl)ethoxy]benzoic acid;
4-{2-[1-Benzhydryl-5-chloro-2-(2-{[(1-methyl-1H-imidazol-4-yl)sulfonyl]amino}ethyl)-1H-indol-3-yl]ethoxy}benzoic acid; and
4-{2-[1-Benzhydryl-2-(2-{[(5-bromo-6-chloro-3-pyridinyl)sulfonyl]amino}ethyl)-5-chloro-1H-indol-3-yl]ethoxy}benzoic acid;
and a pharmaceutically acceptable salt form thereof.

18. A method of claim 1 wherein the compound is selected from the group consisting of:
4-[2-(1-Benzhydryl-5-chloro-2-{2-[({[(1R)-7,7-dimethyl-2-oxobicyclo[2.2.1]hept-1-yl]methyl}sulfonyl)amino]ethyl}-1H-indol-3-yl)ethoxy]benzoic acid;
4-(2-{1-Benzhydryl-5-chloro-2-[2-({[(methylsulfonyl)methyl]sulfonyl}amino)ethyl]-1H-indol-3-yl}ethoxy)benzoic acid;
4-(2-{1-Benzhydryl-5-chloro-2-[2-({[(2-(1-naphthyl)ethyl]sulfonyl}amino)ethyl]-1H-indol-3-yl}ethoxy)benzoic acid;
4-{2-[1-Benzhydryl-5-chloro-2-{2-[({2-nitrobenzyl}-sulfonyl)amino]ethyl}-1H-indol-3-yl)ethoxy]benzoic acid; and
4-{2-[1-Benzhydryl-5-chloro-2-(2-{[(3,4-dichlorobenzyl)sulfonyl]amino}-ethyl)-1H-indol-3-yl]ethoxy}benzoic acid;
and a pharmaceutically acceptable salt form thereof.

19. A method of claim 1 wherein the compound is selected from the group consisting of:
4-{2-[1-Benzhydryl-5-chloro-2-(2-{[(3,5-dichlorobenzyl)sulfonyl]amino}-ethyl)-1H-indol-3-yl]ethoxy}benzoic acid;
4-(2-{1-Benzhydryl-5-chloro-2-(2-({[(3-(trifluoromethyl)benzyl]sulfonyl}-amino)ethyl]-1H-indol-3-yl}ethoxy)benzoic acid;
4-(2-{1-Benzhydryl-5-chloro-2-(2-({[(4-(trifluoromethyl)benzyl]sulfonyl}-amino)ethyl]-1H-indol-3-yl}ethoxy)benzoic acid;
4-{2-[1-Benzhydryl-5-chloro-2-(2-{[(4-fluorobenzyl)sulfonyl]amino}-ethyl)-1H-indol-3-yl]ethoxy}benzoic acid; and
4-{2-[1-Benzhydryl-5-chloro-2-(2-{[(4-chlorobenzyl)sulfonyl]amino}-ethyl)-1H-indol-3-yl]ethoxy}benzoic acid;
and a pharmaceutically acceptable salt form thereof.

20. A method of claim 1 wherein the compound is selected from the group consisting of:

2-(2-{[(2-Aminobenzyl)sulfonyl]amino}ethyl)-4-{2-[1-benzhydryl-5-chloro-1H-indol-3-yl]ethoxy}benzoic acid;

4-{2-[1-Benzhydryl-5-chloro-2-(2-{[(dimethylamino)sulfonyl]amino}ethyl)-1H-indol-3-yl]ethoxy}benzoic acid;

4-{2-[1-Benzhydryl-5-chloro-2-(2-{[(3,4-difluorobenzyl)sulfonyl]amino}-ethyl)-1H-indol-3-yl]ethoxy}benzoic acid;

4-{2-[1-benzhydryl-5-chloro-2-(2-{[(2-naphthylmethyl)sulfonyl]amino}ethyl)-1H-indol-3-yl]ethoxy}benzoic acid; and 3-({[(2-{1-benzhydryl-3-[2-(4-carboxyphenoxy)ethyl]-5-chloro-1H-indol-2-yl}ethyl)amino]sulfonyl}methyl)benzoic acid;

and a pharmaceutically acceptable salt form thereof.

21. A method of claim 1 wherein the compound is selected from the group consisting of:

4-(2-{1-benzhydryl-5-chloro-2-[2-({[(E)-2-phenylethenyl]sulfonyl}amino)ethyl'1H-indol-3-yl}ethoxy)benzoic acid;

4-{2-[1-benzhydryl-5-chloro-2-(2-{[(trifluoromethyl)sulfonyl)amino}ethyl)-1H-indol-3-yl]ethoxy}benzoic acid;

4-[2-(1-benzhydryl-5-chloro-2-{2-[(cyclopropylsulfonyl)amino]ethyl}-1H-indol-3-yl)ethoxy]benzoic acid;

4-(2-{1-benzhydryl-2-[2-({[3,5-bis(trifluoromethyl)benzyl]sulfonyl}amino)ethyl]-5-chloro-1H-indol-3-yl}ethoxy)benzoic acid; and 2-{[(2-{1-benzhydryl-3-[2-(4-carboxyphenoxy)ethyl]-5-chloro-1H-indol-2-yl}ethyl)amino]sulfonyl}benzoic acid;

and a pharmaceutically acceptable salt form thereof.

22. A method of claim 1 wherein the compound is selected from the group consisting of:

4-[2-(1-benzhydryl-5-chloro-242-[(2-naphthylsulfonyl)amino]ethyl}-1H-indol-3-yl)ethoxy]benzoic acid;

4-{2-[1-benzhydryl-5-chloro-2-(2-{[(3,5-dichlorophenyl)sulfonyl]amino}ethyl)-1H-indol-3-yl]ethoxy}benzoic acid;

4-{2-[1-benzhydryl-5-chloro-2-(2-{[(3,4-dichlorophenyl)sulfonyl]amino}ethyl)-1H-indol-3-yl]ethoxy}benzoic acid;

4-{2-[1-benzhydryl-5-chloro-2-(2-{[(2,3-dichlorobenzyl)sulfonyl]amino}ethyl)-1H-indol-3-yl]ethoxy}benzoic acid; and 4-{2-[1-benzhydryl-5-chloro-2-(2-{[(2,4-dichlorobenzyl)sulfonyl]amino}ethyl)-1H-indol-3-yl]ethoxy}benzoic acid;

and a pharmaceutically acceptable salt form thereof.

23. A method of claim 1 wherein the compound is selected from the group consisting of:

4-{2-[1-benzhydryl-5-chloro-2-(2-{[(2,4-dichlorobenzyl)sulfonyl]amino}ethyl)-1H-indol-3-yl]ethoxy}benzoic acid;

4-{2-[1-benzhydryl-5-chloro-2-(2-{[(4-chloro-2-nitrobenzyl)sulfonyl]amino}ethyl)-1H-indol-3-yl]ethoxy}benzoic acid;

4-[2-(1-benzhydryl-2-{2-[(benzylsulfonyl)amino]ethyl}-5-morpholin-4-yl-1H-indol-'3-yl)ethoxy]benzoic acid;

4-{2-[1-Benzhydryl-5-chloro-2-(2-{[(2-cyanobenzyl)sulfonyl]amino}ethyl)-1H-indol-3-yl]ethoxy}benzoic acid; and 4-{2-[1-Benzhydryl-5-chloro-2-(2-{[(2-cyanobenzyl)sulfonyl]amino}ethyl)-1H-indol-3-yl]ethoxy}benzoic acid;

and a pharmaceutically acceptable salt form thereof.

24. A method of claim 1 wherein the compound is selected from the group consisting of:

4-{2-[1-Benzhydryl-5-chloro-2-(2-{[(3-cyanobenzyl)sulfonyl]amino}ethyl)-1H-indol-3-yl]ethoxy}benzoic acid;

4-{2-[1-Benzhydryl-5-chloro-2-(2-{[(4-cyanobenzyl)sulfonyl]amino}ethyl)-1H-indol-3-yl]ethoxy}benzoic acid;

4-(2-{1-Benzhydryl-5-chloro-2-[2-({[4-(1piperidinylsulfonyl)benzyl]sulfonyl}amino)ethyl]-1H-indol-3-yl}ethoxy)benzoic acid;

4-(2-{2-[2-({[4-(Aminosulfonyl)benzyl]sulfonyl}amino)ethyl]-1-benzhydryl-5-chloro-1H-indol-3-yl}ethoxy)benzoic acid; and 4-(2-{1-Benzhydryl-5-chloro-2-[2-(4-methanesulfonylphenylmethanesulfonylamino)-ethyl]-1H-indol-3-yl}-ethoxy)-benzoic acid;

and a pharmaceutically acceptable salt form thereof.

25. A method of claim 1 wherein the compound is selected from the group consisting of:

4-(2-{1-Benzhydryl-5-chloro-2-[2-(4-diethylsulfamoylphenylmethanesulfonylamino)-ethyl]-1H-indol-3-yl}-ethoxy)-benzoic acid;

4-{3-[1-Benzhydryl-5-chloro-2-(2-phenylmethanesulfonylamino-ethyl)-1H-indol-3-yl]-propyl}-benzoic acid;

4-{3-[1-benzhydryl-5-chloro-2-(2-{[(3,5-dichlorobenzyl)sulfonyl]amino}ethyl)-1H-indol-3-yl]propyl}benzoic acid;

4-{3-[1-benzhydryl-5-chloro-2-(2-{[(3,4-dichlorobenzyl)sulfonyl]amino}ethyl)-1H-indol-3-yl]propyl}benzoic acid;

4-[2-(1-benzhydryl-5-chloro-2-(2-[(methylsulfonyl)amino]ethyl)-1H-indol-3-yl]ethoxy}benzoic acid;

and a pharmaceutically acceptable salt form thereof.

26. A method of claim 1 wherein the compound is selected from the group consisting of:

4-[2-(1-benzhydryl-5-chloro-2-{2-[(phenylsulfonyl)amino]ethyl}-1H-indol-3-yl)ethoxy}benzoic acid;

4-(2-{1-benzhydryl-5-chloro-2-[2-({[3-(trifluoromethyl)benzyl]sulfonyl}amino)ethyl]-1H-indol-3-yl}ethoxy)benzoic acid;

2-{((2-{([(2-{1-benzhydryl-3-[2-(4-carboxyphenoxy)ethyl]-5-chloro-1H-indol-2-yl}ethyl)amino]sulfonyl}ethyl)amino]carbonyl}benzoic acid;

4-{2-[{1-benzhydryl-5-chloro-2-(2-{[(3-(pyridinylmethyl)sulfonyl]amino}ethyl)-1H-indol-3-yl]ethoxy}benzoic acid; and 4-{2-[{1-benzhydryl-5-chloro-2-(2-{[(4-(pyridinylmethyl)sulfonyl]amino}ethyl)-1H-indol-3-yl]ethoxy}benzoic acid;

and a pharmaceutically acceptable salt form thereof.

27. A method of claim 1 wherein the compound is selected from the group consisting of:

4-{2-[{1-benzhydryl-5-chloro-2-(2-{[(2-(pyridinylmethyl)sulfonyl]amino}ethyl)-1H-indol-3-yl]ethoxy}benzoic acid;

4-{3-[1-benzhydryl-5-chloro-2-(2-{[(2,6-dimethylbenzyl)sulfonyl]amino}ethyl)-1H-indoly-3-yl]propyl}benzoic acid;

4-{2-[1-benzhydryl-5-chloro-2-(2-{[(cyclohexylmethyl)sulfonyl]amino}ethyl)-1H-indol-3-yl]ethoxy}benzoic acid;

4-{2-[1-Benzhydryl-5-chloro-2-(2-{[(4-nitrobenzyl)sulfonyl]amino}ethyl)-1H-indol-3-yl]ethoxy}benzoic acid; and 4-{2-[1-benzhydryl-5-chloro-2-(2-{[(3-nitrobenzyl)sulfonyl]amino}ethyl)-1H-indol-3-yl]ethoxy}benzoic acid;

and a pharmaceutically acceptable salt form thereof.

28. A method of claim 1 wherein the compound is selected from the group consisting of:

4-{2-[1-Benzhydryl-5-chloro-2-{2-[({2-nitrobenzyl}-sulfonyl)amino]ethyl}-1H-indol-3-yl) propyl]benzoic acid;

4-{3-[1-benzhydryl-5-chloro-2-(2-{[(4-fluorobenzyl)sulfonyl]amino}ethyl)-1H-indol-3-yl]propyl}benzoic acid;

4-(3-{1-benzhydryl-5-chloro-2-[2-({[4-(trifluoromethyl)benzyl]sulfonylamino)ethyl]-1H-indol-3-yl}propyl) benzoic acid;

4-(3-{1-benzhydryl-5-chloro-2-[2-({[3-(trifluoromethyl)benzyl]sulfonyl}amino)ethyl]-1H-indol-3-yl}propyl) benzoic acid; and 4-{3-[1-benzhydryl-5-chloro-2-(2-{[(4-chlorobenzyl)sulfonyl]amino}ethyl)-1H-indol-3-yl]propyl}benzoic acid;

and a pharmaceutically acceptable salt form thereof.

29. A method of claim 1 wherein the compound is selected from the group consisting of:

4-{3-[1-benzhydryl-5-chloro-2-(2-{[(2-pyridinylmethyl)sulfonyl]amino}ethyl)-1H-indol-3-yl]propyl}benzoic acid;

4-{3-[1-benzhydryl-5-chloro-2-(2-{[(3-pyridinylmethyl)sulfonyl]amino}ethyl)-1H-indol-3-yl]propyl}benzoic acid;

4-{3-[1-benzhydryl-5-chloro-2-(2-{[(4-pyridinylmethyl)sulfonyl]amino}ethyl)-1H-indol-3-yl]propyl}benzoic acid;

4-{3-[1-benzhydryl-5-chloro-2-(2-{[(2-chlorobenzyl)sulfonyl]amino}ethyl)-1H-indol-3-yl]propyl)benzoic acid; and 4-{3-[1-benzhydryl-5-chloro-2-(2-{[(3-nitrobenzyl)sulfonyl]amino}ethyl)-1H-indol-3-yl]propyl}benzoic acid;

and a pharmaceutically acceptable salt form thereof.

30. A method of claim 1 wherein the compound is selected from the group consisting of:

4-(3-(1-benzhydryl-5-chloro-2-(2-{[(3-chlorobenzyl)sulfonyl]amino}ethyl)-1H-indol-3-yl]propyl}benzoic acid;

4-{3-[1-benzhydryl-5-chloro-2-(2-{[(2,5-dichlorobenzyl)sulfonyl]amino}ethyl)-1H-indol-3-yl]propyl}benzoic acid;

4-{3-[1-benzhydryl-5-chloro-2-(2-{[(3-methoxybenzyl)sulfonyl]amino}ethyl)-1H-indol-3-yl]propyl}benzoic acid;

4-{3-[2-(2-{[(2-aminobenzyl)sulfonyl]amino}ethyl)-1-benzhydryl-5-chloro-1H-indol-3-yl]propyl}benzoic acid; and 4-{3-[1-Benzhydryl-5-chloro-2-(2-{[(2-methylbenzyl)sulfonyl]amino}ethyl)-1H-indol-3-yl]propyl}benzoic acid;

and a pharmaceutically acceptable salt form thereof.

31. A method of claim 1 wherein the compound is selected from the group consisting of:

4-{2-[1-Benzhydryl-5-chloro-2-(2-{[(4-trifluorometoxybenzyl)sulfonyl]amino}ethyl)-1H-indol-3-yl]ethoxy}benzoic acid;

4-{2-[1-Benzhydryl-5-chloro-2-(2-{[(2-fluoro-6-nitrobenzyl)sulfonyl]amino}ethyl)-1H-indol-3-yl]ethoxy}benzoic acid;

4-{2-[1-Benzhydryl-5-chloro-2-(2-{[(2-dichlorobenzyl)sulfonyl]amino}ethyl)-1H-indol-3-yl]ethoxy}benzoic acid;

4-{2-[1-Benzhydryl-5-chloro-2-(2-{[(2,6-difluorobenzyl)sulfonyl]amino}ethyl)-1H-indol-3-yl]ethoxy}benzoic acid; and 4-(2-{1-benzhydryl-5-chloro-2-[2-({[(6-chloro-3-pyridinyl)methyl]sulfonyl}amino)ethyl]-1H-indol-3-yl}ethoxy)benzoic acid;

and a pharmaceutically acceptable salt form thereof.

32. A method of claim 1 wherein the compound is selected from the group consisting of:

4-(2-{1-benzhydryl-5-chloro-2-[2-({[(5,6-dichloro-2-[pyridinyl)methyl]sulfonylamino)ethyl]-1H-indol-3-yl}ethoxy)benzoic acid;

4-{2-[1-Benzhydryl-5-chloro-2-(2-{[(3-methoxybenzyl)sulfonyl]amino}ethyl)-1H-indol-3-yl]ethoxy}benzoic acid;

4-{2-[1-Benzhydryl-5-chloro-2-(2-{[(3,5-dimethylbenzyl)sulfonyl]amino}ethyl)-1H-indol-3-yl]ethoxy}benzoic acid;

4-{2-[1-Benzhydryl-5-chloro-2-(2-{[(2-methylbenzyl)sulfonyl]amino}ethyl)-1H-indol-3-yl]ethoxy}benzoic acid; and 4-{2-[1-Benzhydryl-5-chloro-2-(2-{[(2,6-dichlorobenzyl)sulfonyl]amino}ethyl)-1H-indol-3-yl]ethoxy}benzoic acid;

and a pharmaceutically acceptable salt form thereof.

33. A method of claim 1 wherein the compound is selected from the group consisting of:

4-(2-{1-benzhydryl-5-chloro2[2-({[(phenylsulfanyl)methyl]sulfonyl}amino)ethyl]-1H-indol-3-yl}ethoxy) benzoic acid;

4-(2-{1-benzhydryl-5-chloro-2-[2-(2,6-dimethyl-phenylsulfanylmethanesulfonylamino)-ethyl]-]-1H-indol-3-yl}-ethoxy)-benzoic acid;

4-(2-{1-benzhydryl-5-chloro-2-[2-(2-methoxy-phenylsulfanylmethanesulfonylamino)-ethyl]-]-1H-indol-3-yl}-ethoxy)-benzoic acid;

4-(2-{1-benzhydryl-5-chloro-2-[2-(2-chloro-6-methyl-phenylsulfanylmethanesulfonylamino)-ethyl]-]-1H-indol-3-yl}-ethoxy)-benzoic acid; and 4-(2-{1-benzhydryl-5-chloro-2-[2-(3,5-dichloro-phenylsulfanylmethanesulfonylamino)-ethyl]-]-1H-indol-3-yl}-ethoxy)-benzoic acid;

and a pharmaceutically acceptable salt form thereof.

34. A method of claim 1 wherein the compound is selected from the group consisting of:

4-(2-{1-benzhydryl-5-chloro-2-[2-(3,4-dimethoxy-phenylsulfanylmethanesulfonylamino)-ethyl]-]-1H-indol-3-yl}-ethoxy)-benzoic acid;

4-(2-{1-Benzhydryl-5-chloro-2-[2-(2-morpholin-4-ylethanesulfonylamino)-ethyl]-1H-indol-3-yl}-ethoxy)-benzoic acid;

4-(2-{1-Benzhydryl-5-chloro-2-[2-(2-pyrazol-1-ylethanesulfonylamino)-ethyl]-1H-indol-3-yl}-ethoxy)-benzoic acid;

4-(2-{1-Benzhydryl-5-chloro-2-[2-(2-phenylaminoethanesulfonylamino)-ethyl]-1H-indol-3-yl}-ethoxy)-benzoic acid; and 4-(2-{1-benzhydryl-5-chloro-2-[2-({[2-(1,4-dioxa-8-azaspiro[4.5]dec-8-yl)ethyl]sulfonyl}amino)ethyl]-1H-indol-3-yl}ethoxy)benzoic acid;

and a pharmaceutically acceptable salt form thereof.

35. A method of claim 1 wherein the compound is selected from the group consisting of:

4-[2-(1-benzhydryl-5-chloro-2-{2-[({2-[4-(2-pyridinyl)-1-piperazinyl]ethyl}sulfonyl)amino]ethyl}-1H-indol-3-yl)ethoxy]benzoic acid;

4-(2-{1-benzhydryl-5-chloro-2-[2-({[2-(1H-1,2,4-triazol-1-yl)ethyl]sulfonyl}amino)ethyl]-1H-indol-3-yl}ethoxy)benzoic acid;

4-(2-{1-benzhydryl-5-chloro-2-[2-({[2-(3,5-dimethyl-1H-pyrazol-1-yl)ethyl]sulfonyl}amino)ethyl]-1H-indol-3-yl}ethoxy)benzoic acid;

4-(2-{1-benzhydryl-5-chloro-2-[2-({[2-(3-methyl-1H-pyrazol-1-yl)ethyl]sulfonyl}amino)ethyl]-1H-indol-3-yl}ethoxy)benzoic acid; and 4-(2-{1-benzhydryl-5-chloro-2-[2-({[2-(4-methyl-1H-pyrazol-1-yl)ethyl]sulfonyl}amino)ethyl]-1H-indol-3-yl}ethoxy)benzoic acid;

and a pharmaceutically acceptable salt form thereof.

36. A method of claim 1 wherein the compound is selected from the group consisting of:

4-[2-(1-benzhydryl-5-chloro-2-{2-[({2-[(2R,6S)-2,6-dimethyl-1-piperidinyl]ethyl}sulfonyl)amino]ethyl}-1H-indol-3-yl)ethoxy]benzoic acid;

4-(2-{1-benzhydryl-5-chloro-2-[2-({[2-(2-thioxo-1-imidazolidinyl)ethyl]sulfonyl}amino)ethyl]-1H-indol-3-yl}ethoxy)benzoic acid;

4-(2-{1-benzhydryl-5-chloro-2-[2-({[2-(1,3-thiazolidin-3-yl)ethyl]sulfonyl}amino)ethyl]-1H-indol-3-yl}ethoxy)benzoic acid;

4-(2-{1-benzhydryl-5-chloro-2-[2-(2-[1,2,3]triazol-1-yl-ethanesulfonylamino)-ethyl]-1H-indol-3-yl}ethoxy)benzoic acid; and 4-(3-{1-Benzhydryl-5-chloro-2-[2-(2-morpholin-4-yl-ethanesulfonylamino)-ethyl]-1H-indol-3-yl}-propyl)-benzoic acid;

and a pharmaceutically acceptable salt form thereof.

37. A method of claim 1 wherein the compound is selected from the group consisting of:

4-[3-(1-Benzhydryl-5-chloro-2-{2-[2-(2,6-dimethyl-piperidin-1-yl)-ethanesulfonylamino]-ethyl)-1H-indol-3-yl)-propyl]-benzoic acid;

4-[3-(1-Benzhydryl-5-chloro-2-{2-[2-(3,5-dimethyl-pyrazol-1-yl)-ethanesulfonylamino]-ethyl}-1H-indol-3-yl)-propyl]-benzoic acid;

4-(2-{1-benzhydryl-5-chloro-2-[2-(2-tetrazol-2-yl-ethanesulfonylamino)-ethyl]-1H-indol-3-yl}ethoxy)benzoic acid;

4-(2-{1-benzhydryl-5-chloro-2-[2-(2-tetrazol-1-yl-ethanesulfonylamino)-ethyl]-1H-indol-3-yl}ethoxy)benzoic acid; and 4-{2-[1-Benzhydryl-6-chloro-2-(2-phenylmethanesulfonylamino-ethyl)-1H-indol-3-yl]-ethoxy}-benzoic acid;

and a pharmaceutically acceptable salt form thereof.

38. A method of claim 1 wherein the compound is selected from the group consisting of:

4-(2-{1-Benzhydryl-6-chloro-2-[2-(3,4-dichloro-phenylmethanesulfonylamino)-ethyl]-1H-indol-3-yl}-ethoxy)-benzoic acid;

4-(2-{1-Benzhydryl-6-chloro-2-[2-(3,5-dichloro-phenylmethanesulfonylamino)-ethyl]-1H-indol-3-yl}-ethoxy)-benzoic acid;

4-{2-[1-Benzhydryl-5-chloro-2-(2-{[(2-cyanobenzyl)sulfonyl]amino}ethyl)-1H-indol-3-yl]ethoxy}benzoic acid;

4-{2-[1-Benzhydryl-5-chloro-2-(2-{[(tetrahydro-2H-pyran-2-ylmethyl)sulfonyl]amino}ethyl)-1H-indol-3-yl]ethoxy}benzoic acid; and 4-{2-[1-Benzhydryl-2-(2-{f[(1,3-benzoxazol-2-ylmethyl)sulfonyl]amino}ethyl)-5-chloro-1H-indol-3-yl]ethoxy}benzoic acid;

and a pharmaceutically acceptable salt form thereof.

39. A method of claim 1 wherein the compound is selected from the group consisting of:

4-{2-[1-Benzhydryl-5-chloro-2-(2-{[(cyanomethyl)sulfonyl]amino}ethyl)-1H-indol-3-yl]ethoxy}benzoic acid;

4-{2-[1-Benzhydryl-5-chloro-2-(2-{[(3-thienylmethyl)sulfonyl]amino}ethyl)-1H-indol-3-yl]ethoxy}benzoic acid;

4-[2-(1-Benzhydryl-5-chloro-2-{2-[2-(2-methyl-pyrrolidin-1-yl)-ethanesulfonylamino]-ethyl}-1H-indol-3-yl)-ethoxy]-benzoic acid;

4-[2-(1-Benzhydryl-5-chloro-2-{2-[2-(2-methyl-piperidin-1-yl)-ethanesulfonylamino]-ethyl}-1H-indol-3-yl)-ethoxy]-benzoic acid; and 4-[2-(1-Benzhydryl-5-chloro-2-{2-[2-(2,5-dimethyl-pyrrolidin-1-yl)-ethanesulfonylamino]-ethyl}-1H-indol-3-yl)-ethoxy]-benzoic acid;

and a pharmaceutically acceptable salt form thereof.

40. A method of claim 1 wherein the compound is selected from the group consisting of:

4-(2-{1-Benzhydryl-5-chloro-2-[2-(2-thiomorpholin-4-yl-ethanesulfonylamino)-ethyl]-1H-indol-3-yl}-ethoxy)-benzoic acid;

4-(2-{1-Benzhydryl-5-chloro-2-[2-(2-piperidin-1-yl-ethanesulfonylamino)-ethyl]-1H-indol-3-yl}-ethoxy)-benzoic acid;

4-{2-[1-benzhydryl-5-chloro-2-(2-o-tolylsulfanyl-methanesulfonylamino-ethyl)-1H-indol-3-yl]-ethoxy)-benzoic acid;

4-(2-{1-benzhydryl-5-chloro-2-[2-(2-chloro-phenylsulfanylmethane-sulfonylamino)-ethyl]-1H-indol-3-yl}-ethoxy)-benzoic acid; or 4-(2-{1-benzhydryl-5-chloro-2-[2-(2,6-dichloro-phenylsulfanylmethane-sulfonylamino)-ethyl]-1H-indol-3-yl}-ethoxy)-benzoic acid;

and a pharmaceutically acceptable salt form thereof.

41. A method of claim 1 wherein the compound is selected from the group consisting of:

4-(2-{1-benzhydryl-5-chloro-2-[2-(2,5-dimethoxy-phenylsulfanylmethanesulfonylamino)-ethyl]-1H-indol-3-yl)-ethoxy)-benzoic acid;

4-[2-(1-benzhydryl-5-chloro-2-{2-[2-(3-hydroxy-pyrrolidine-1-yl)-ethanesulfonylamino]-ethyl}-1H-indol-3-yl)-ethoxy]-benzoic acid;

4-[2-(1-Benzhydryl-5-chloro-2-{2-[2-(4-hydroxy-piperidin-1-yl)-ethanesulfonylamino]-ethyl}-1H-indol-3-yl)-ethoxy]-benzoic acid;

4-(2-{1-Benzhydryl-5-chloro-2-[2-(2-pyrrolidin-1-yl-ethanesulfonylamino)-ethyl]-1H-indol-3-yl}-ethoxy)-benzoic acid; and 4-[2-(1-Benzhydryl-5-chloro-2-{2-[2-(2-dimethylaminomethyl-piperidin-1-yl)-ethanesulfonylamino]-ethyl}-1H-indol-3-yl)-ethoxy]-benzoic acid;

and a pharmaceutically acceptable salt form thereof.

42. A method of claim 1 wherein the compound is selected from the group consisting of:

4-(2-{1-Benzhydryl-5-chloro-2-[2-(2-imidazol-1-yl-ethanesulfonylamino)-ethyl]-1H-indol-3-yl}-ethoxy)-benzoic acid;

4-{3-[1-benzhydryl-5-chloro-2-(2-{[(2,6-difluorobenzyl)sulfonyl]amino}ethyl)-1H-indol-3-yl]propyl}benzoic acid;

4-{3-[1-benzhydryl-2-(2-{[(3,4-dichlorobenzyl)sulfonyl]amino}ethyl)-1H-indol-3-yl]propyl}benzoic acid;

3-[4-({2-[1-Benzhydryl-5-chloro-2-(2-{[(2-chlorobenzyl)sulfonyl]amino}ethyl)-1H-indol-3-yl]ethyl}sulfonyl)phenyl]propanoic acid; and 3-(4-{[2-(1-Benzhydryl-2-{2-[(benzylsulfonyl)amino]ethyl}-5-chloro-1H-indol-3-yl)ethyl]sulfonyl}phenyl)propanoic acid;

and a pharmaceutically acceptable salt form thereof.

43. A method of claim 1 wherein the compound is selected from the group consisting of:

3-[4-({2-[1-benzhydryl-5-chloro-2-(2-{[(2,6-difluorobenzyl)sulfonyl]amino}ethyl)-1H-indol-3-yl]ethyl}sulfonyl)phenyl]propanoic acid;

3-[4-({2-[1-benzhydryl-5-chloro-2-(2-{[(2-fluorobenzyl)sulfonyl]amino}ethyl)-1H-indol-3-yl]ethyl}sulfonyl)phenyl]propanoic acid;

3-[4-({2-[1-benzhydryl-5-chloro-2-(2-{[(2-chlorobenzyl)sulfonyl]amino}ethyl)-1H-indol-3-yl]ethyl}sulfonyl)phenyl]propanoic acid;

4-({[(1-benzhydryl-2-{2-[(benzylsulfonyl)amino]ethyl}-5-chloro-1H-indol-3-yl)methyl]amino}methyl)benzoic acid; and 4-{[2-(1-benzhydryl-2-{2-[(benzylsulfonyl)amino]ethyl}-5-chloro-1H-indol-3yl)ethyl]sulfonyl}benzoic acid;

and a pharmaceutically acceptable salt form thereof.

44. A method of claim 1 wherein the compound is selected from the group consisting of:

4-({2-[1-benzhydryl-5-chloro-2-(2-{[(2-chlorobenzyl)sulfonyl]amino}ethyl)-1H-indol-3-yl]ethyl}sulfonyl)benzoic acid;

4-({2-[1-benzhydryl-5-chloro-2-(2-{[(2,6-difluorobenzyl)sulfonyl]amino}ethyl)-1H-indol-3-yl]ethyl}sulfonyl)benzoic acid;

4-({2-[1-benzhydryl-5-chloro-2-(2-{[(2-fluorobenzyl)sulfonyl]amino}ethyl)-1H-indol-3-yl]ethyl}sulfonyl)benzoic acid; and 4-(2-{1-Benzhydryl-5-chloro-2-[2-(2-pyrrolidin-1-yl-ethanesulfonylamino)-ethyl]-1H-indol-3-yl}-ethoxy)-benzoic acid;

and a pharmaceutically acceptable salt form thereof.

45. A method of claim 1 wherein the compound is selected from the group consisting of:

4-((2-[1-benzhydryl-5-chloro-2-(2-{[(3,4-dichlorobenzyl)sulfonyl]amino}ethyl)1H-indol-3-yl]ethyl}sulfonyl)benzoic acid;

4-({2-[1-benzhydryl-5-chloro-2-(2-{[(2,6-dimethylbenzyl)sulfonyl]amino}ethyl)1H-indol-3-yl]ethyl}sulfonyl)benzoic acid; and 4-[2-(1-benzhydryl-2-{3-[(benzylsulfonyl)amino]propyl}-5-chloro-1H-indol-3-yl)ethoxy]benzoic acid;

and a pharmaceutically acceptable salt form thereof.

46. A method of claim 1 wherein the disorder is rheumatoid arthritis.

47. A method of claim 1 wherein the disorder is osteoarthritis.

48. A method of claim 1 wherein the disorder is juvenile arthritis.

* * * * *